US012534462B2

(12) United States Patent
Li

(10) Patent No.: US 12,534,462 B2
(45) Date of Patent: Jan. 27, 2026

(54) SUBSTITUTED HETEROARYLS AS THERMALLY ASSISTED DELAYED FLUORESCENT MATERIALS

(71) Applicant: Arizona Board of Regents on behalf of Arizona State University, Scottsdale, AZ (US)

(72) Inventor: Jian Li, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 367 days.

(21) Appl. No.: 18/169,289

(22) Filed: Feb. 15, 2023

(65) Prior Publication Data

US 2023/0192695 A1 Jun. 22, 2023

Related U.S. Application Data

(63) Continuation of application No. 17/066,965, filed on Oct. 9, 2020, now Pat. No. 11,603,370, which is a continuation of application No. 16/552,585, filed on Aug. 27, 2019, now Pat. No. 10,851,106, which is a continuation of application No. 15/984,102, filed on May 18, 2018, now Pat. No. 10,392,387.

(60) Provisional application No. 62/508,555, filed on May 19, 2017.

(51) Int. Cl.

| | |
|---|---|
| ***C07D 221/18*** | (2006.01) |
| ***C07D 471/04*** | (2006.01) |
| ***C07D 471/14*** | (2006.01) |
| ***C07D 471/22*** | (2006.01) |
| ***C07D 493/22*** | (2006.01) |
| ***C07D 495/14*** | (2006.01) |
| ***C07D 495/22*** | (2006.01) |
| ***C09K 11/06*** | (2006.01) |
| ***H10K 85/60*** | (2023.01) |
| *H10K 50/11* | (2023.01) |
| *H10K 101/10* | (2023.01) |

(52) U.S. Cl.

CPC ......... *C07D 471/14* (2013.01); *C07D 471/04* (2013.01); *C07D 471/22* (2013.01); *C07D 493/22* (2013.01); *C07D 495/14* (2013.01); *C07D 495/22* (2013.01); *C09K 11/06* (2013.01); *H10K 85/636* (2023.02); *H10K 85/657* (2023.02); *H10K 85/6572* (2023.02); *C09K 2211/1018* (2013.01); *H10K 50/11* (2023.02); *H10K 2101/10* (2023.02)

(58) Field of Classification Search

CPC .................................................... C07D 221/18
USPC ........................................ 546/30, 33, 41, 71
See application file for complete search history.

(56) References Cited

U.S. PATENT DOCUMENTS

| | | | |
|---|---|---|---|
| 4,769,292 | A | 9/1988 | Tang |
| 5,707,745 | A | 1/1998 | Forrest |
| 5,844,363 | A | 12/1998 | Gu |
| 6,303,238 | B1 | 10/2001 | Thompson |
| 7,279,704 | B2 | 10/2007 | Walters |
| 8,106,199 | B2 | 1/2012 | Jabbour |
| 8,389,725 | B2 | 3/2013 | Li |
| 8,669,364 | B2 | 3/2014 | Li |
| 8,816,080 | B2 | 8/2014 | Li |
| 8,846,940 | B2 | 9/2014 | Li |
| 8,927,713 | B2 | 1/2015 | Li |
| 8,946,417 | B2 | 2/2015 | Li |
| 9,012,599 | B2 | 4/2015 | Stoessel |
| 9,076,974 | B2 | 7/2015 | Li |
| 9,082,989 | B2 | 7/2015 | Li |
| 9,203,039 | B2 | 12/2015 | Li |
| 9,221,857 | B2 | 12/2015 | Li |
| 9,224,963 | B2 | 12/2015 | Li |
| 9,238,668 | B2 | 1/2016 | Li |
| 9,312,502 | B2 | 4/2016 | Li |
| 9,318,725 | B2 | 4/2016 | Li |
| 9,324,957 | B2 | 4/2016 | Li |
| 9,382,273 | B2 | 7/2016 | Li |
| 9,385,329 | B2 | 7/2016 | Li |
| 9,425,415 | B2 | 8/2016 | Li |
| 9,502,671 | B2 | 11/2016 | Li |
| 9,550,801 | B2 | 1/2017 | Li |
| 9,598,449 | B2 | 3/2017 | Li |
| 9,617,291 | B2 | 4/2017 | Li |
| 9,673,409 | B2 | 6/2017 | Li |

(Continued)

FOREIGN PATENT DOCUMENTS

| | | | |
|---|---|---|---|
| CN | 108148088 | A | 6/2018 |
| CN | 108794539 | A | 11/2018 |

(Continued)

OTHER PUBLICATIONS

Bachowska, B. Monatshefte fuer Chemie, 126(2), 1995, 227-231.*

(Continued)

*Primary Examiner* — Douglas M Willis
(74) *Attorney, Agent, or Firm* — Riverside Law LLP

(57) ABSTRACT

Thermally assisted delayed fluorescent materials with triad-type materials for use in full color displays and lighting applications with the following generic structures are provided:

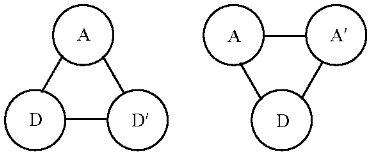

10 Claims, 8 Drawing Sheets

(56) References Cited

U.S. PATENT DOCUMENTS

| | | | |
|---|---|---|---|
| 9,698,359 | B2 | 7/2017 | Li |
| 9,711,739 | B2 | 7/2017 | Li |
| 9,711,741 | B2 | 7/2017 | Li |
| 9,711,742 | B2 | 7/2017 | Li |
| 9,755,163 | B2 | 9/2017 | Li |
| 9,818,959 | B2 | 11/2017 | Li |
| 9,865,825 | B2 | 1/2018 | Li |
| 9,879,039 | B2 | 1/2018 | Li |
| 9,882,150 | B2 | 1/2018 | Li |
| 9,899,614 | B2 | 2/2018 | Li |
| 9,920,242 | B2 | 3/2018 | Li |
| 9,923,155 | B2 | 3/2018 | Li |
| 9,941,479 | B2 | 4/2018 | Li |
| 9,947,881 | B2 | 4/2018 | Li |
| 9,985,224 | B2 | 5/2018 | Li |
| 10,020,455 | B2 | 7/2018 | Li |
| 10,033,003 | B2 | 7/2018 | Li |
| 10,056,564 | B2 | 8/2018 | Li |
| 10,056,567 | B2 | 8/2018 | Li |
| 10,158,091 | B2 | 12/2018 | Li |
| 10,177,323 | B2 | 1/2019 | Li |
| 10,211,411 | B2 | 2/2019 | Li |
| 10,211,414 | B2 | 2/2019 | Li |
| 10,263,197 | B2 | 4/2019 | Li |
| 10,294,417 | B2 | 5/2019 | Li |
| 10,392,387 | B2 | 8/2019 | Li |
| 10,411,202 | B2 | 9/2019 | Li |
| 10,414,785 | B2 | 9/2019 | Li |
| 10,516,117 | B2 | 12/2019 | Li |
| 10,566,553 | B2 | 2/2020 | Li |
| 10,566,554 | B2 | 2/2020 | Li |
| 10,615,349 | B2 | 4/2020 | Li |
| 10,622,571 | B2 | 4/2020 | Li |
| 10,727,422 | B2 | 7/2020 | Li |
| 10,745,615 | B2 | 8/2020 | Li |
| 10,790,457 | B2 | 9/2020 | Li |
| 10,793,546 | B2 | 10/2020 | Li |
| 10,804,476 | B2 | 10/2020 | Li |
| 10,822,363 | B2 | 11/2020 | Li |
| 10,836,785 | B2 | 11/2020 | Li |
| 10,851,106 | B2 | 12/2020 | Li |
| 10,886,478 | B2 | 1/2021 | Li |
| 10,930,865 | B2 | 2/2021 | Li |
| 10,937,976 | B2 | 3/2021 | Li |
| 10,944,064 | B2 | 3/2021 | Li |
| 10,964,897 | B2 | 3/2021 | Li |
| 10,991,897 | B2 | 4/2021 | Li |
| 10,995,108 | B2 | 5/2021 | Li |
| 11,011,712 | B2 | 5/2021 | Li |
| 11,063,228 | B2 | 7/2021 | Li |
| 11,101,435 | B2 | 8/2021 | Li |
| 11,114,626 | B2 | 9/2021 | Li |
| 11,121,328 | B2 | 9/2021 | Li |
| 11,145,830 | B2 | 10/2021 | Li |
| 2005/0139810 | A1 | 6/2005 | Kuehl |
| 2007/0160905 | A1 | 7/2007 | Morishita |
| 2007/0252140 | A1 | 11/2007 | Limmert |
| 2008/0269491 | A1 | 10/2008 | Jabbour |
| 2009/0136779 | A1 | 5/2009 | Cheng |
| 2009/0167167 | A1 | 7/2009 | Aoyama |
| 2010/0288362 | A1 | 11/2010 | Hatwar |
| 2011/0028723 | A1 | 2/2011 | Li |
| 2011/0066763 | A1 | 3/2011 | Minot |
| 2011/0301351 | A1 | 12/2011 | Li |
| 2012/0095232 | A1 | 4/2012 | Li |
| 2012/0108806 | A1 | 5/2012 | Li |
| 2012/0146012 | A1 | 6/2012 | Limmert |
| 2012/0202997 | A1 | 8/2012 | Parham |
| 2012/0215001 | A1 | 8/2012 | Li |
| 2012/0264938 | A1 | 10/2012 | Li |
| 2012/0302753 | A1 | 11/2012 | Li |
| 2013/0137870 | A1 | 5/2013 | Li |
| 2013/0203996 | A1 | 8/2013 | Li |
| 2013/0237706 | A1 | 9/2013 | Li |
| 2014/0066628 | A1 | 3/2014 | Li |
| 2014/0073798 | A1 | 3/2014 | Li |
| 2014/0114072 | A1 | 4/2014 | Li |
| 2014/0147996 | A1 | 5/2014 | Vogt |
| 2014/0148594 | A1 | 5/2014 | Li |
| 2014/0249310 | A1 | 9/2014 | Li |
| 2014/0330019 | A1 | 11/2014 | Li |
| 2014/0364605 | A1 | 12/2014 | Li |
| 2015/0008419 | A1 | 1/2015 | Li |
| 2015/0018558 | A1 | 1/2015 | Li |
| 2015/0060804 | A1 | 3/2015 | Kanitz |
| 2015/0105556 | A1 | 4/2015 | Li |
| 2015/0123047 | A1 | 5/2015 | Maltenberger |
| 2015/0162552 | A1 | 6/2015 | Li |
| 2015/0194616 | A1 | 7/2015 | Li |
| 2015/0207086 | A1 | 7/2015 | Li |
| 2015/0228914 | A1 | 8/2015 | Li |
| 2015/0274762 | A1 | 10/2015 | Li |
| 2015/0287938 | A1 | 10/2015 | Li |
| 2015/0311456 | A1 | 10/2015 | Li |
| 2015/0318500 | A1 | 11/2015 | Li |
| 2015/0349279 | A1 | 12/2015 | Li |
| 2016/0028028 | A1 | 1/2016 | Li |
| 2016/0028029 | A1 | 1/2016 | Li |
| 2016/0043331 | A1 | 2/2016 | Li |
| 2016/0133861 | A1 | 5/2016 | Li |
| 2016/0133862 | A1 | 5/2016 | Li |
| 2016/0190473 | A1 | 6/2016 | Kim |
| 2016/0190474 | A1 | 6/2016 | Kim |
| 2016/0194344 | A1 | 7/2016 | Li |
| 2016/0197291 | A1 | 7/2016 | Li |
| 2016/0285015 | A1 | 9/2016 | Li |
| 2016/0359120 | A1 | 12/2016 | Li |
| 2016/0359125 | A1 | 12/2016 | Li |
| 2017/0005278 | A1 | 1/2017 | Li |
| 2017/0012224 | A1 | 1/2017 | Li |
| 2017/0040555 | A1 | 2/2017 | Li |
| 2017/0047533 | A1 | 2/2017 | Li |
| 2017/0066792 | A1 | 3/2017 | Li |
| 2017/0069855 | A1 | 3/2017 | Li |
| 2017/0077420 | A1 | 3/2017 | Li |
| 2017/0125708 | A1 | 5/2017 | Li |
| 2017/0267923 | A1 | 9/2017 | Li |
| 2017/0271611 | A1 | 9/2017 | Li |
| 2017/0301871 | A1 | 10/2017 | Li |
| 2017/0305881 | A1 | 10/2017 | Li |
| 2017/0331056 | A1 | 11/2017 | Li |
| 2017/0342098 | A1 | 11/2017 | Li |
| 2017/0373260 | A1 | 12/2017 | Li |
| 2018/0006246 | A1 | 1/2018 | Li |
| 2018/0053904 | A1 | 2/2018 | Li |
| 2018/0130960 | A1 | 5/2018 | Li |
| 2018/0138428 | A1 | 5/2018 | Li |
| 2018/0148464 | A1 | 5/2018 | Li |
| 2018/0159051 | A1 | 6/2018 | Li |
| 2018/0166655 | A1 | 6/2018 | Li |
| 2018/0175329 | A1 | 6/2018 | Li |
| 2018/0194790 | A1 | 7/2018 | Li |
| 2018/0219161 | A1 | 8/2018 | Li |
| 2018/0226592 | A1 | 8/2018 | Li |
| 2018/0226593 | A1 | 8/2018 | Li |
| 2018/0277777 | A1 | 9/2018 | Li |
| 2018/0301641 | A1 | 10/2018 | Li |
| 2018/0312750 | A1 | 11/2018 | Li |
| 2018/0331307 | A1 | 11/2018 | Li |
| 2018/0334459 | A1 | 11/2018 | Li |
| 2018/0337345 | A1 | 11/2018 | Li |
| 2018/0337349 | A1 | 11/2018 | Li |
| 2018/0337350 | A1 | 11/2018 | Li |
| 2019/0013485 | A1 | 1/2019 | Li |
| 2019/0067602 | A1 | 2/2019 | Li |
| 2019/0109288 | A1 | 4/2019 | Li |
| 2019/0194536 | A1 | 6/2019 | Li |
| 2019/0259963 | A1 | 8/2019 | Li |
| 2019/0276485 | A1 | 9/2019 | Li |
| 2019/0312217 | A1 | 10/2019 | Li |
| 2019/0367546 | A1 | 12/2019 | Li |
| 2019/0389893 | A1 | 12/2019 | Li |
| 2020/0006678 | A1 | 1/2020 | Li |
| 2020/0071330 | A1 | 3/2020 | Li |

(56) References Cited

U.S. PATENT DOCUMENTS

| | | | |
|---|---|---|---|
| 2020/0075868 | A1 | 3/2020 | Li |
| 2020/0119288 | A1 | 4/2020 | Li |
| 2020/0152891 | A1 | 5/2020 | Li |
| 2020/0227656 | A1 | 7/2020 | Li |
| 2020/0227660 | A1 | 7/2020 | Li |
| 2020/0239505 | A1 | 7/2020 | Li |
| 2020/0243776 | A1 | 7/2020 | Li |
| 2020/0287153 | A1 | 9/2020 | Li |
| 2020/0332185 | A1 | 10/2020 | Li |
| 2020/0373505 | A1 | 11/2020 | Li |
| 2020/0403167 | A1 | 12/2020 | Li |
| 2021/0024526 | A1 | 1/2021 | Li |
| 2021/0024559 | A1 | 1/2021 | Li |
| 2021/0047296 | A1 | 2/2021 | Li |
| 2021/0091316 | A1 | 3/2021 | Li |
| 2021/0104687 | A1 | 4/2021 | Li |
| 2021/0111355 | A1 | 4/2021 | Li |
| 2021/0126208 | A1 | 4/2021 | Li |
| 2021/0193936 | A1 | 6/2021 | Li |
| 2021/0193947 | A1 | 6/2021 | Li |
| 2021/0217973 | A1 | 7/2021 | Li |
| 2021/0230198 | A1 | 7/2021 | Li |
| 2021/0261589 | A1 | 8/2021 | Li |
| 2021/0273182 | A1 | 9/2021 | Li |

FOREIGN PATENT DOCUMENTS

| | | | |
|---|---|---|---|
| CN | 108948044 | A | 12/2018 |
| CN | 110713482 | A | 1/2020 |
| EP | 1617493 | | 1/2006 |
| EP | 1968131 | | 9/2008 |
| EP | 2020694 | | 2/2009 |
| EP | 2684932 | | 1/2014 |
| KR | 20110066763 | | 6/2011 |
| KR | 20130043460 | A | 4/2013 |
| KR | 20140027030 | | 3/2014 |
| KR | 20140065357 | A | 5/2014 |
| KR | 20160067034 | A | 6/2016 |
| WO | 2000070655 | | 11/2000 |
| WO | 2006081780 | | 8/2006 |
| WO | 2009003455 | | 1/2009 |
| WO | 2009008277 | | 1/2009 |
| WO | 2009011327 | | 1/2009 |
| WO | 2009086209 | | 7/2009 |
| WO | 2009111299 | | 9/2009 |
| WO | 2010050778 | | 5/2010 |
| WO | 2010105141 | | 9/2010 |
| WO | 2010118026 | A2 | 10/2010 |
| WO | 2011137429 | A2 | 11/2011 |
| WO | 2011137431 | A2 | 11/2011 |
| WO | 2012074909 | | 6/2012 |
| WO | 2012112853 | A1 | 8/2012 |
| WO | 2012142387 | | 10/2012 |
| WO | 2012162488 | A1 | 11/2012 |
| WO | 2013130483 | A1 | 9/2013 |
| WO | 2014009310 | | 1/2014 |
| WO | 2014031977 | | 2/2014 |
| WO | 2014047616 | A1 | 3/2014 |
| WO | 2014109814 | | 7/2014 |
| WO | 2015027060 | A1 | 2/2015 |
| WO | 2015099507 | | 7/2015 |
| WO | 2015131158 | | 9/2015 |
| WO | 2016025921 | A1 | 2/2016 |
| WO | 2016029137 | | 2/2016 |
| WO | 2016029186 | | 2/2016 |
| WO | 2016197019 | | 12/2016 |
| WO | 2018071697 | | 4/2018 |
| WO | 2018140765 | | 8/2018 |
| WO | 2019079505 | | 4/2019 |
| WO | 2019079508 | | 4/2019 |
| WO | 2019079509 | | 4/2019 |
| WO | 2019236541 | | 12/2019 |
| WO | 2020018476 | | 1/2020 |

OTHER PUBLICATIONS

Su "Pyridine-Containing Bipolar Host Materials for Highly Efficient Blue Phosphorescent OLEDs" Chem. Mater. 2008, 20, 1691-1693 1691.

Bunz "Large N-Heteroacenes: New Tricks for Very Old Dogs?" Angew. Chem. Int. Ed. 2013, 52, 3810-3821.

Kader Azaindolo[3,2,1-jk]carbazoles New Building Blocks for Functional Organic Materials Chem. Eur. J. 2019, 25, 4412-4425.

Kotwica "Azaacenes Based Electroactive Materials: Preparation, Structure, Electrochemistry, Spectroscopy and Applications—A Critical Review" Materials 2021, 14, 5155.

Miao "Ten Years of N-Heteropentacenes as Semiconductors for Organic Thin-Film Transistors" Adv. Mater. 2014, 26, 5541-5549.

Richards "Putting the 'N' in ACENE: Pyrazinacenes and their structural relatives" Org. Biomol. Chem., 2011, 9, 5005.

Baldo et al., "Very High-Efficiency Green Organic Light-Emitting Devices Based on Electrophosphorescence", Appl Phys Lett, 75(3):4-6 (1999).

Baldo et al., "Highly Efficient Phosphorescent Emission from Organic Electroluminescent Devices," Nature, vol. 395, Sep. 10, 1998, pp. 151-154.

Machine Translation of KR20160067034A (Year: 2016).

STN Abstract of KR 2013043460 A (Year: 2013).

Uoyama et al., "Highly efficient organic light-emitting diodes from delayed fluorescence" Nature, 492:234-238, (2012).

Yan, et al., "Palladium-catalyzed tandem N—H/C—H arylation: regioselective synthesis of N-heterocycle-fused phenanthridines as versatile blue-emitting luminophores," Organic & Biomolecular Chemistry, 11(45), 2013, 7966-7977.

* cited by examiner

SUBSTITUTED HETEROARYLS AS THERMALLY ASSISTED DELAYED FLUORESCENT MATERIALS

CROSS-REFERENCE TO RELATED APPLICATION

The present application is a continuation of U.S. patent application Ser. No. 17/066,965, filed Oct. 9, 2020, now allowed, which is a continuation of U.S. patent application Ser. No. 16/552,585, filed Aug. 27, 2019, U.S. Pat. No. 10,851,106, which is a continuation of U.S. Patent application Ser. No. 15/984,102, filed May 18, 2018, now U.S. Pat. No. 10,392,387, which claims the benefit of U.S. Patent Application No. 62/508,555, filed May 19, 2017, all of which applications are incorporated herein by reference in their entireties.

STATEMENT OF GOVERNMENT INTEREST

This invention was made with government support under DE-EE0007090 awarded by the Department of Energy. The government has certain rights in the invention.

TECHNICAL FIELD

This invention relates to thermally assisted delayed fluorescent materials with triad-type materials for use in full color displays and lighting applications.

BACKGROUND

Most thermally assisted delayed fluorescent (TADF) material designs rely on the donor-acceptor concept, which requires a strong donor and a strong acceptor group with large molecular geometry distortion to lower the highest occupied molecular orbital (HOMO)-lowest unoccupied molecular orbital (LUMO) energy gap and minimize the energy splitting between the lowest singlet excited state (S1) and the lowest triplet excited state (T1). Such design tends to use an acceptor type group with less electrochemical stability, resulting in decreased device operational stability.

SUMMARY

Light emitting complexes represented by the following General Formulas are described.

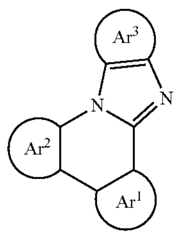
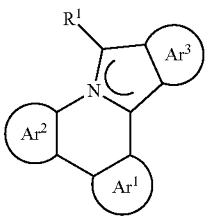
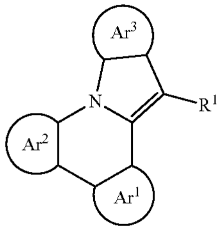
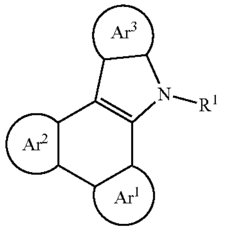

-continued

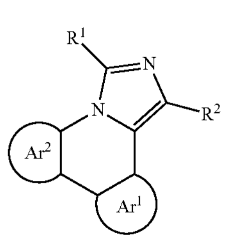
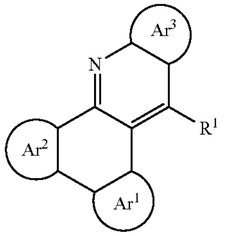
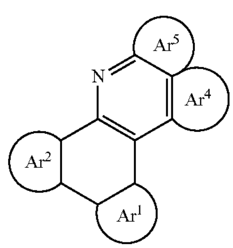
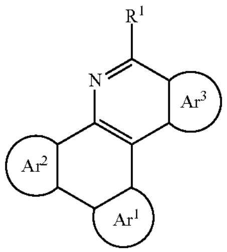
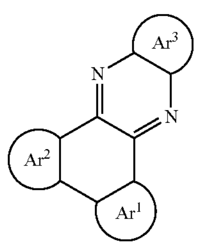
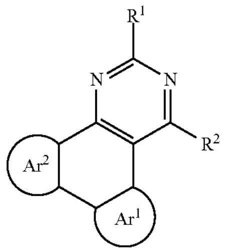
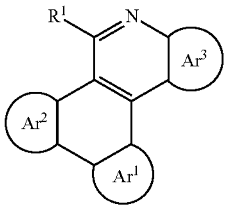
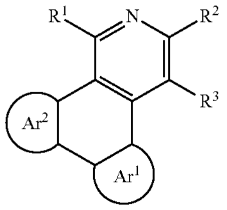
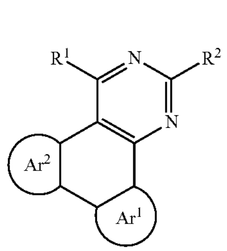
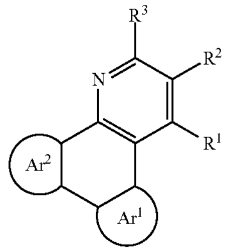
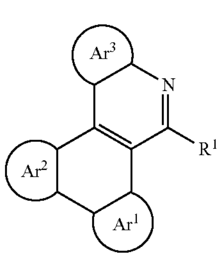
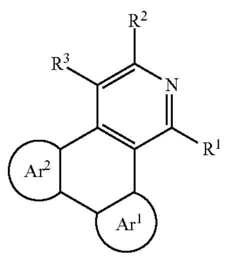
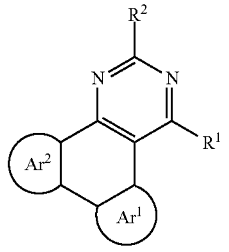
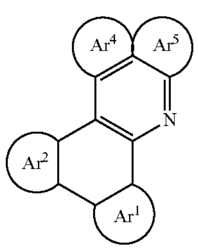

-continued

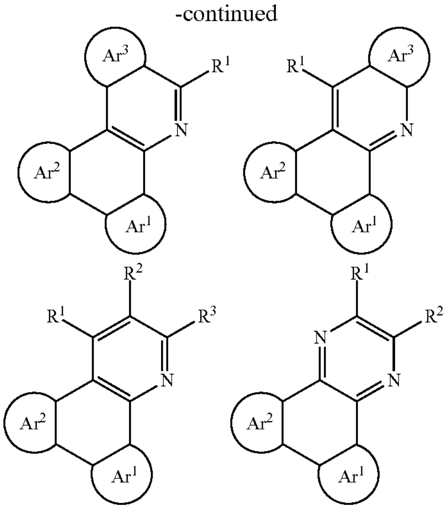

Implementations include a light emitting diode including a light emitting complex represented by one of the General Formulas above, as well as a light emitting device including the light emitting diode.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

DETAILED DESCRIPTION

Figure 1:
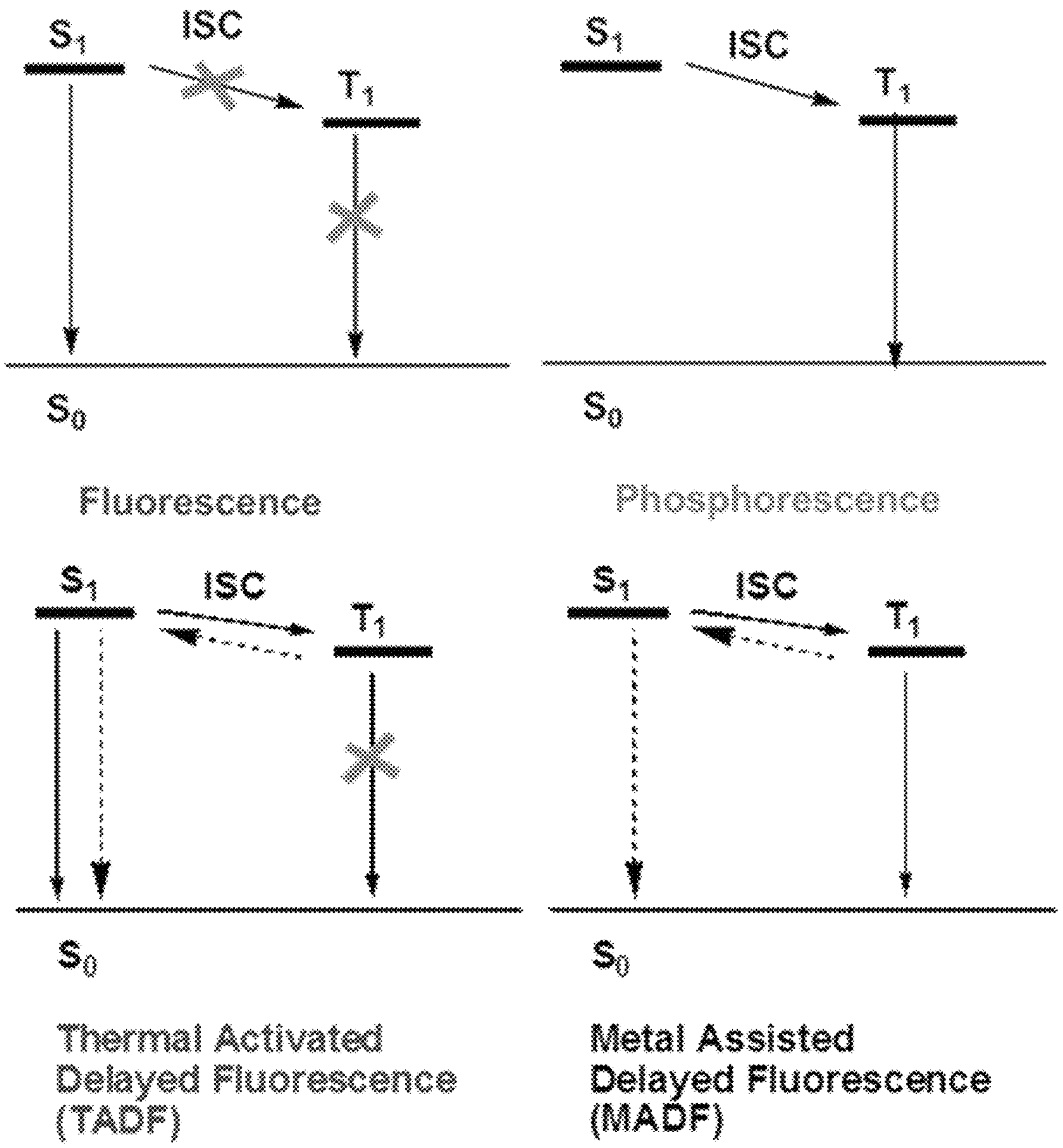
FIG. 1 depicts emission mechanisms of organic emitters.
Figure 2A:
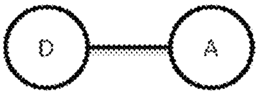
FIGS. 2A-2E depict donor-acceptor (D-A) type, non-cyclic donor-acceptor-donor' (D-A-D') type, non-cyclic acceptor-donor-acceptor' (A-D-A') type, cyclic donor-acceptor-donor' (D-A-D') type, and cyclic acceptor-donor-acceptor' (A-D-A') type TADF materials, respectively.
Figure 2B:
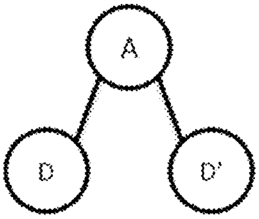
Figure 2C:
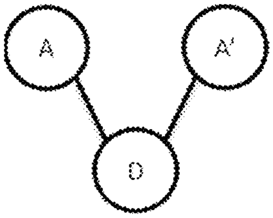
Figure 2D:
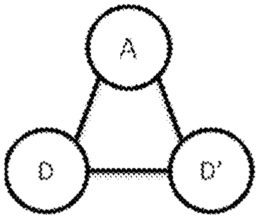
Figure 2E:
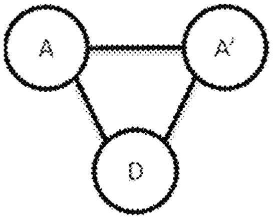

Emission mechanisms inside of device settings for organic emissive materials include fluorescence, phosphorescence, thermally assisted delayed fluorescence (TADF) and metal-assisted delayed fluorescence (MADF), as illustrated in FIG. 1. The latter three have the potential to harvest 100% electro-generated excitons. TADF designs described herein include triad-type materials, such as cyclic donor-donor'-acceptor (D-D'-A) or cyclic donor-acceptor-acceptor' (D-A-A') materials depicted in FIG. 1, with a possible pair of conjugated donor-type (or acceptor-type) functional groups that are also individually conjugated with the corresponding acceptor-type (or donor-type) functional group through covalent bonding. Thus, the singlet excited state energy will be significantly reduced due to the conjugation of D-D'-A (or D-A-A') while the triplet will still prefer to localize on one of D-A pairs and maintain the similar triplet state energy, leading to a small singlet-triplet energy splitting. Such a design allows the incorporation of weak donors or acceptors, making TADF material more feasible as stable emitters or host materials for organic light emitting diode (OLED) applications.

Figure 3A:
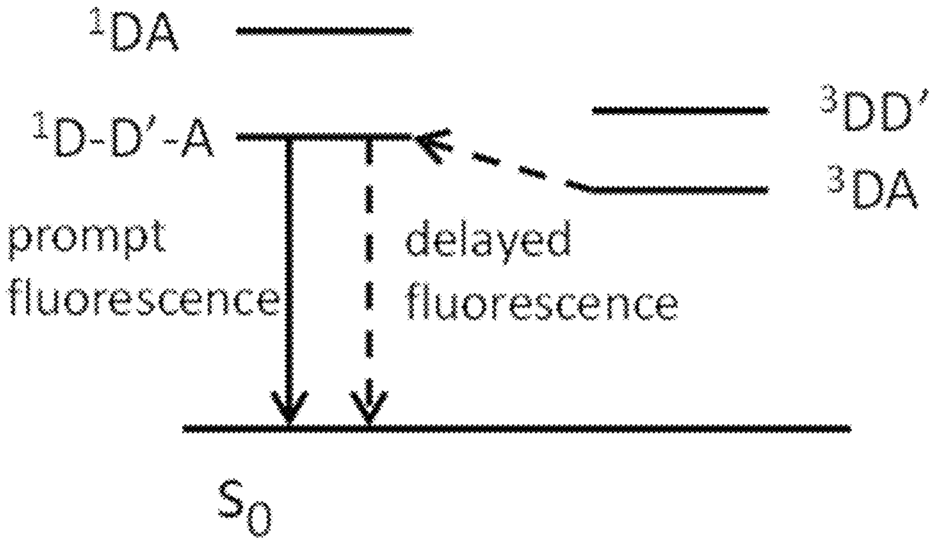
FIGS. 3A and 3B depict proposed emission mechanisms for cyclic D-A-D' type and cyclic A-D-A' type TADF materials, respectively.
Figure 3B:
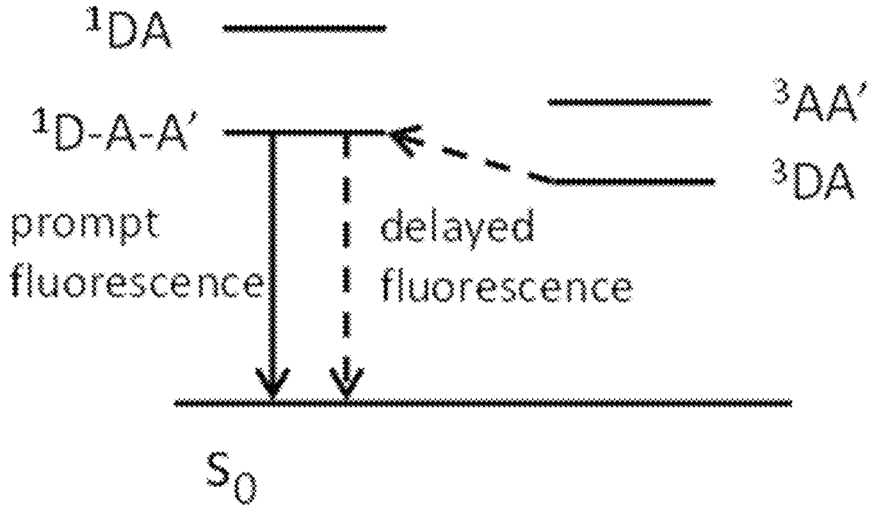

FIGS. 2A-2E depict D-A type, non-cyclic D-A-D' type, non-cyclic A-D-A' type, cyclic D-A-D' type, and cyclic A-D-A' type TADF materials, respectively. FIGS. 3A and 3B depict proposed emission mechanisms for cyclic D-A-D' type and cyclic A-D-A' type TADF materials, respectively.

Examples of donor groups are shown below.

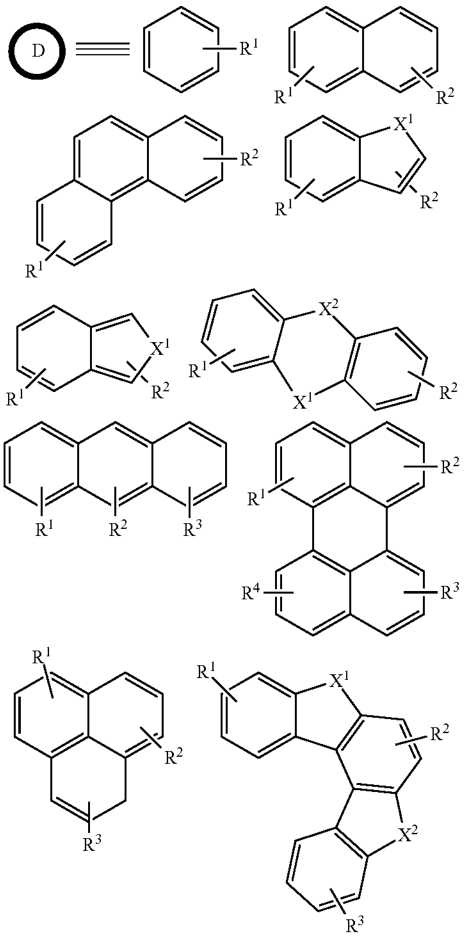

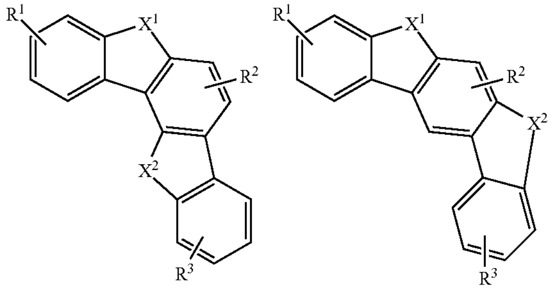

-continued

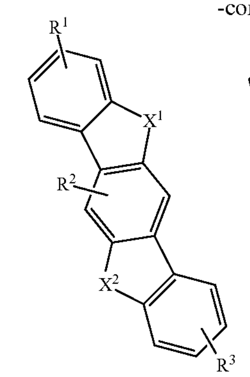

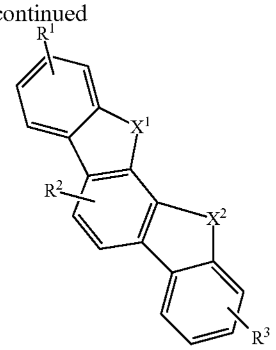

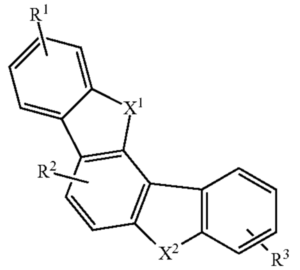

in which:

$X^1$ represents O, $NR^1$, S, or $PR^1$, $X^2$ represents O, $NR^1$, S, $CR^1R^2$, $SiR^1R^2$, C═O, $GeR^1R^2$, $PR^1$, $R^1P$═O, As $R^1$, $R^1As$═O, S═O, $SO_2$, Se═O, $SeO_2$, $BR^1$, $AlR^1$, $R^1Bi$═O, or $BiR^1$, or

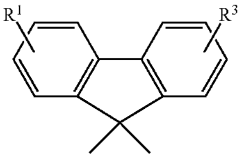

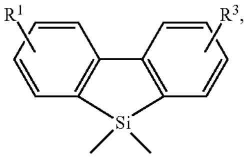

each of $R^1$, $R^2$, $R^3$, and $R^4$ is independently absent or present as a single substituent or multiple substituents, valency permitting, and each $R^1$, $R^2$, $R^3$, and $R^4$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In some implementations, each —$R^1$, —$R^2$, —$R^3$, and —$R^4$ independently represents one of the following moieties.

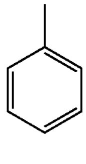

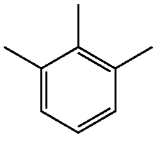

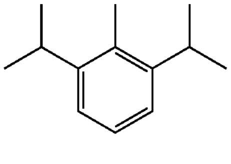

-continued

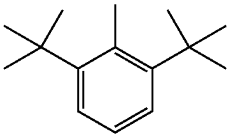

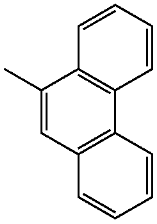

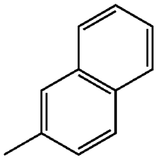

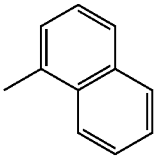

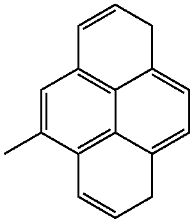

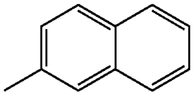

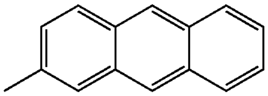

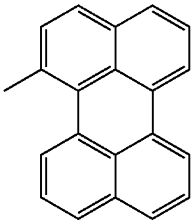

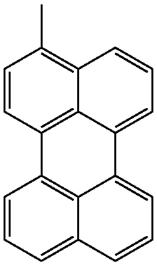

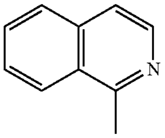

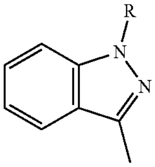

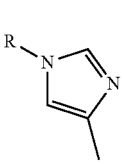

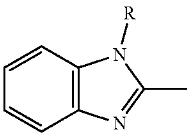

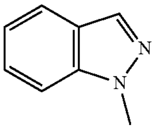

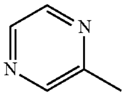

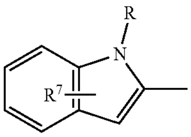

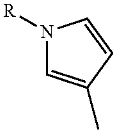

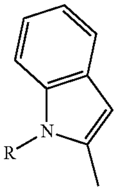

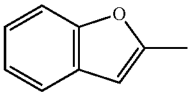

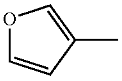

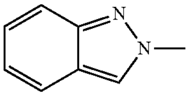

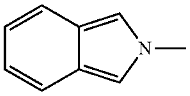

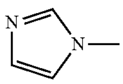

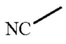

where R and each $R^7$ present, valency permitting, independently represents deuterium, halogen, hydroxyl, thiol, nitro, cyano, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.
Examples of acceptor groups are shown below.
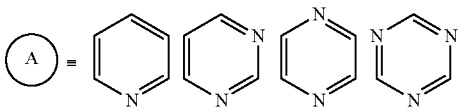
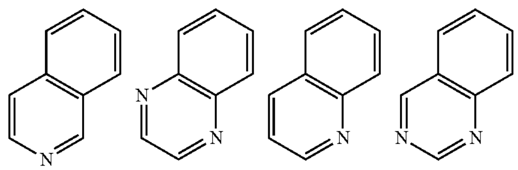
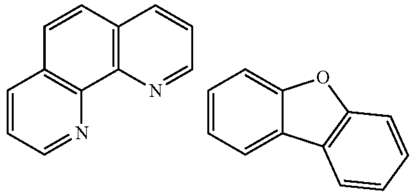
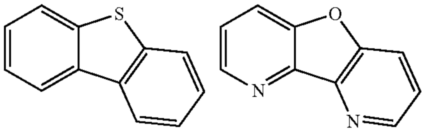
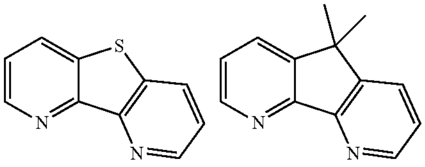
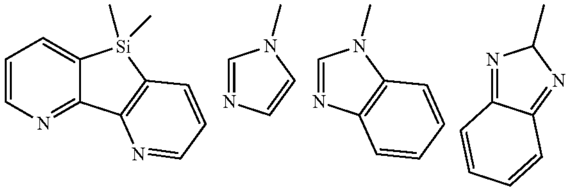
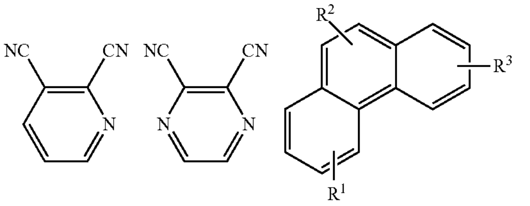
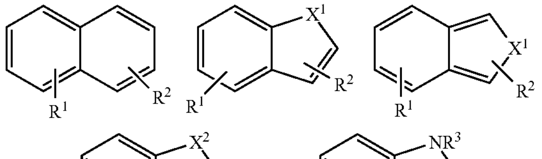
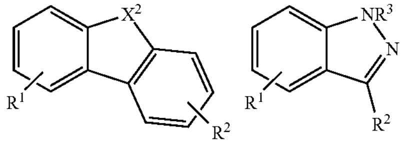
-continued
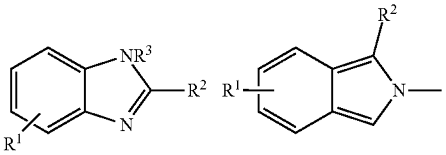
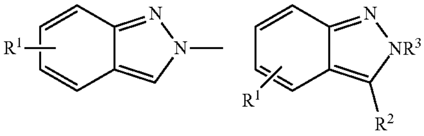
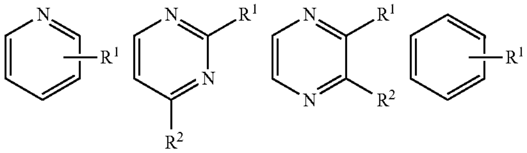
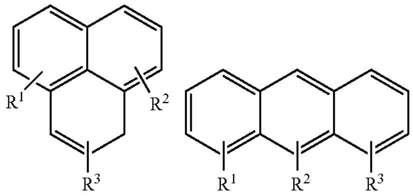
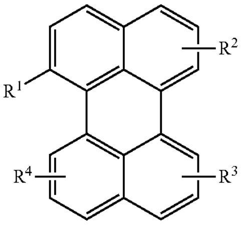
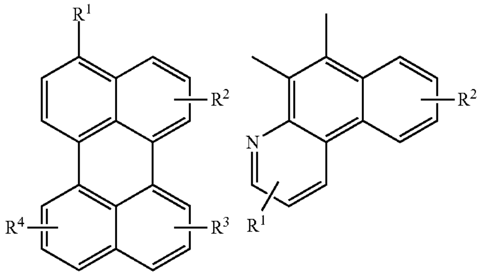
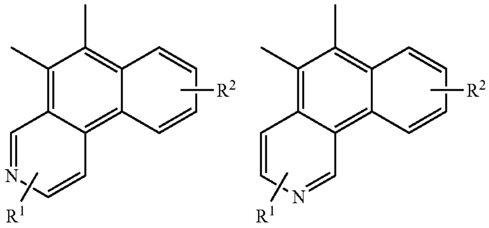
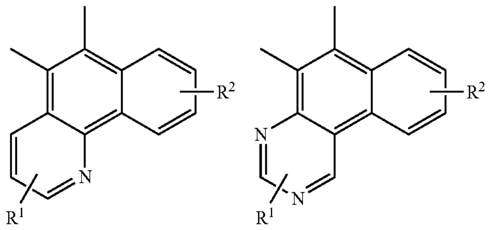

-continued
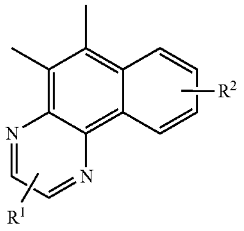
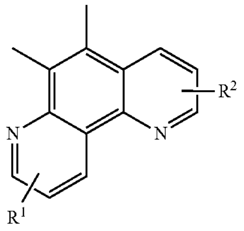
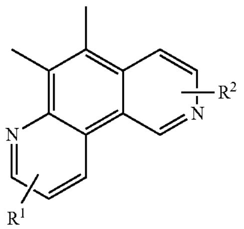
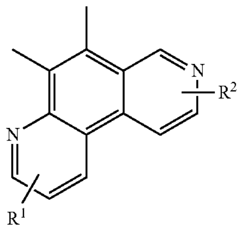
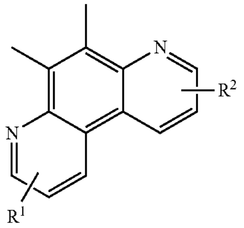
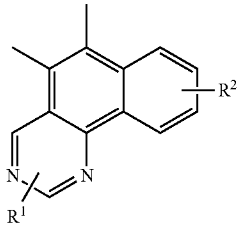
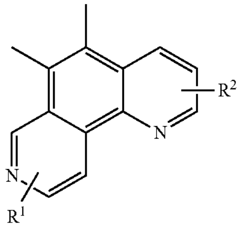
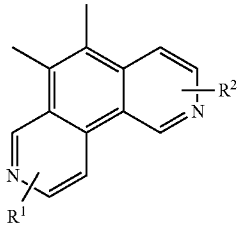
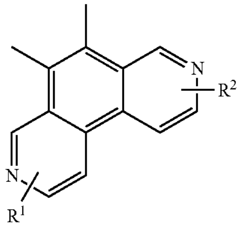
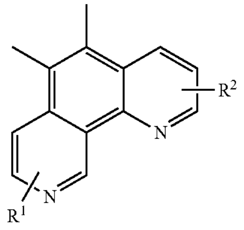
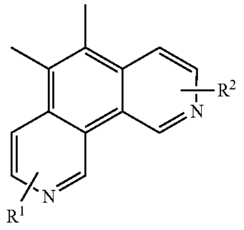
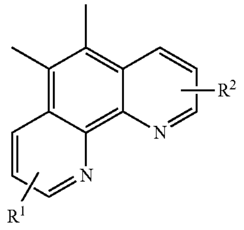
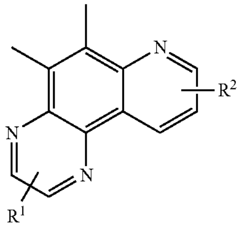
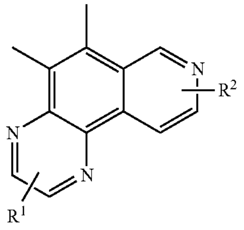
-continued
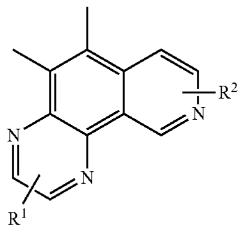
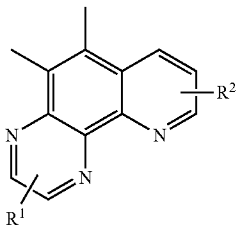
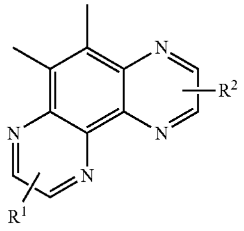
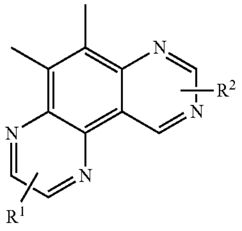
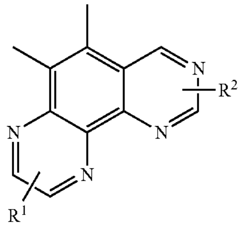
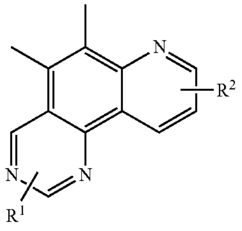
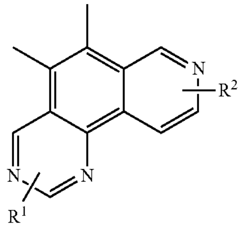
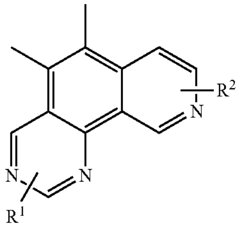
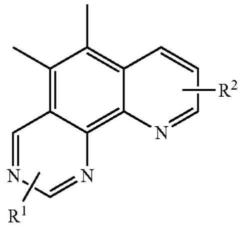
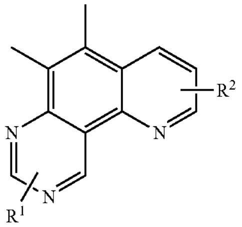
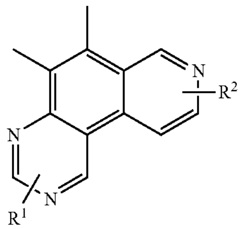
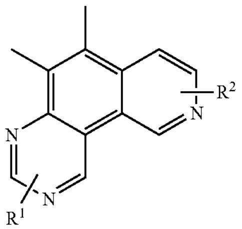
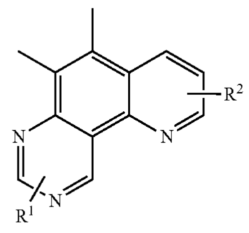
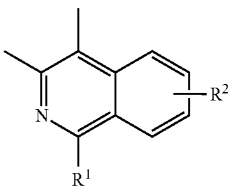

-continued
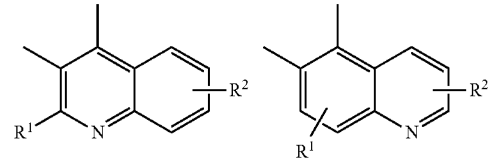
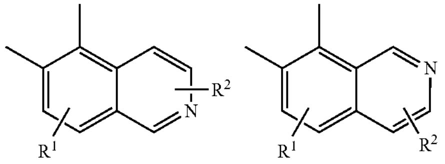
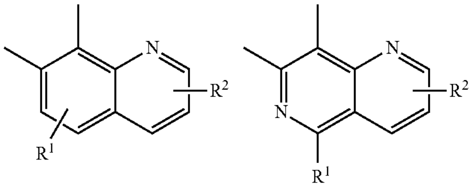
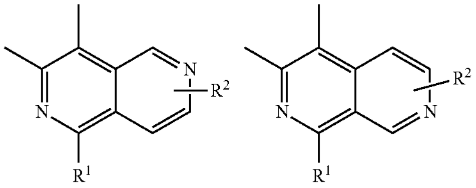
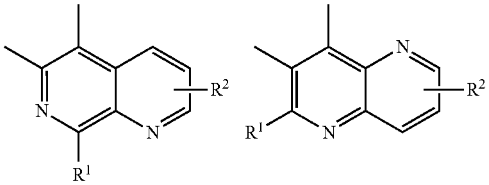
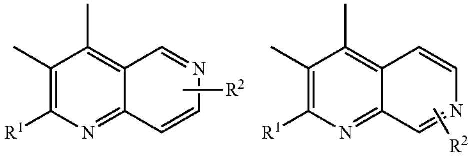
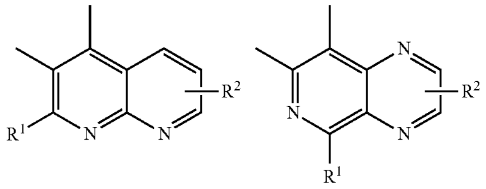
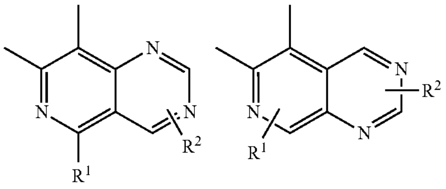
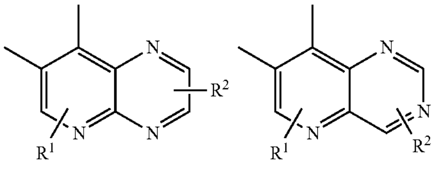
-continued
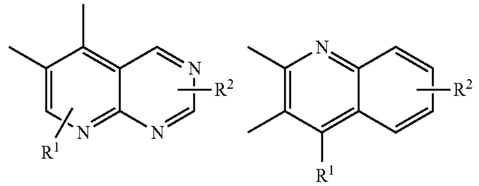
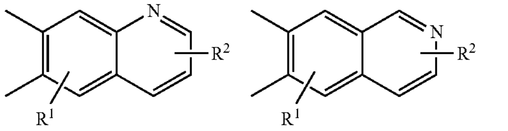
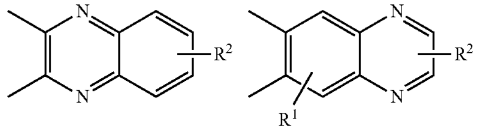
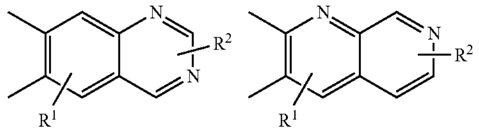
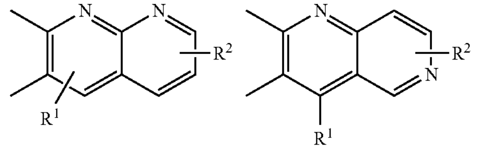
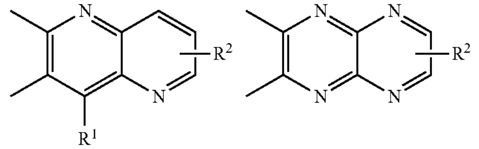
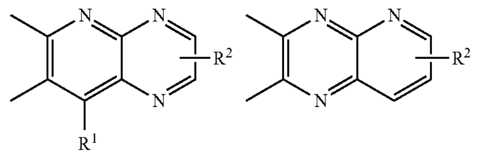
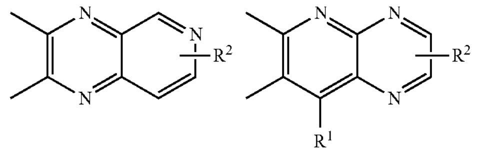
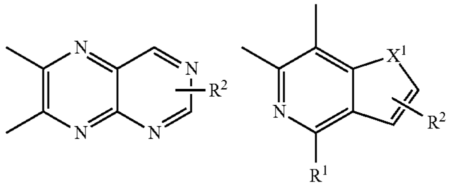
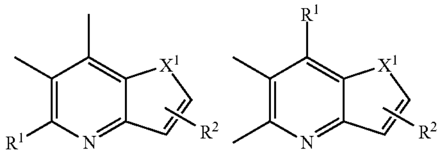
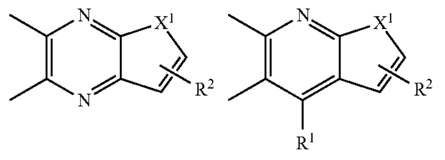

-continued

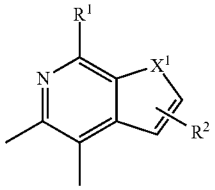
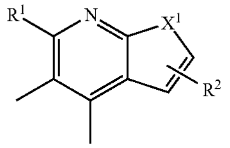
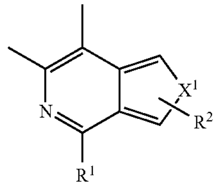
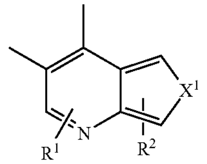
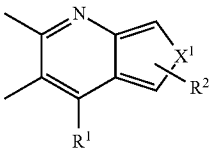
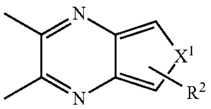
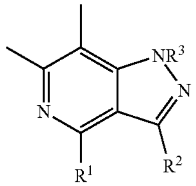
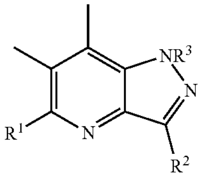
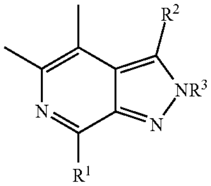
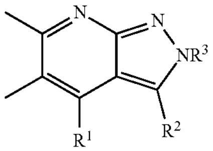
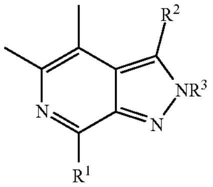
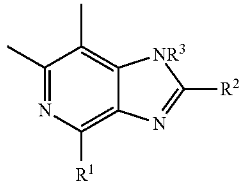
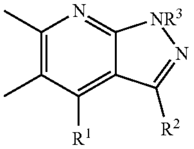
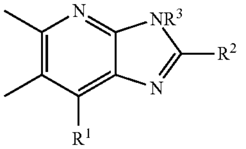
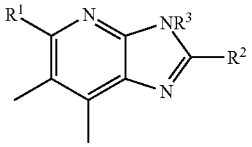
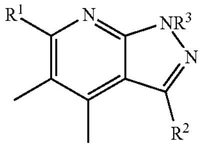
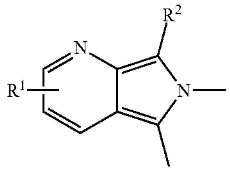
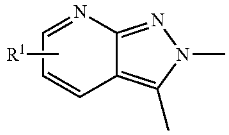
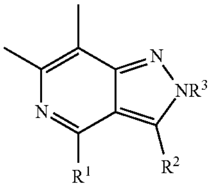
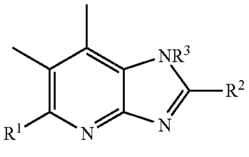

-continued

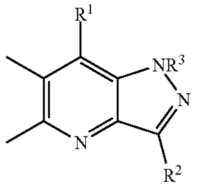
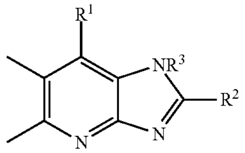
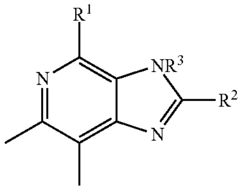
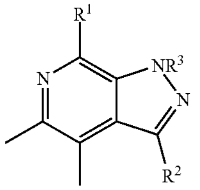
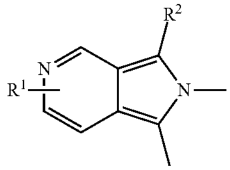
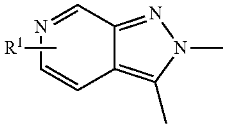
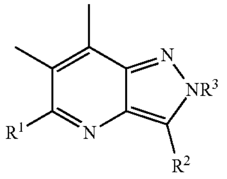

in which:

$X^1$ represents O, $NR^1$, S, or $PR^1$, $X^2$ represents O, $NR^1$, S, $CR^1R^2$, $SiR^1R^2$, C=O, $GeR^1R^2$, $PR^1$, $R^1P$=O, As $R^1$, $R^1As$=O, S=O, $SO_2$, Se=O, $SeO_2$, $BR^1$, $AlR^1$, $R^1Bi$=O, $BiR^1$,

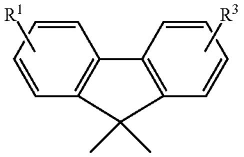
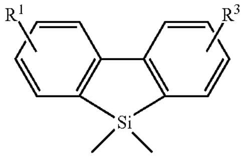

each of $R^1$, $R^2$, $R^3$, and $R^4$ is independently absent or present as a single substituent or multiple substituents, valency permitting, and each $R^1$, $R^2$, $R^3$, and $R^4$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In some implementations, $-R^1$, $-R^2$, $-R^3$, and $-R^4$ may independently represent one of the following moieties, where R and $R^7$ are defined herein.

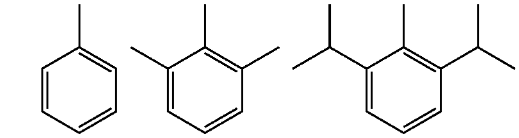
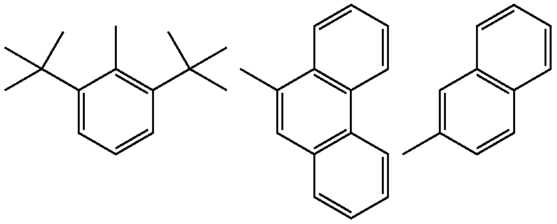
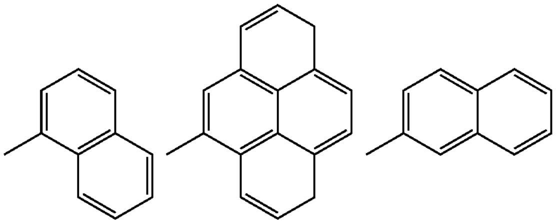
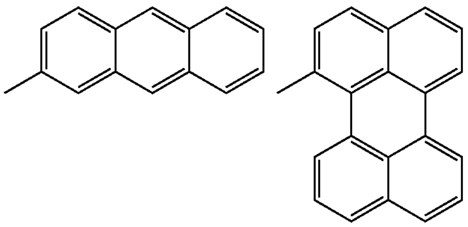
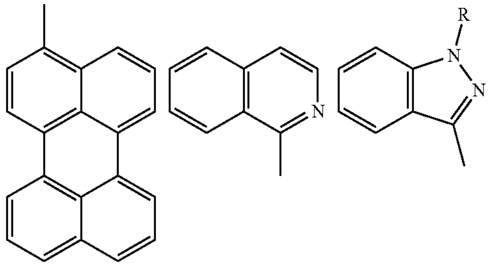
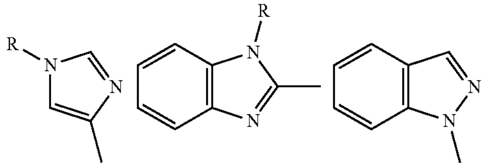
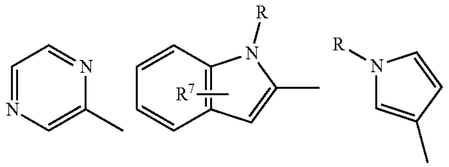
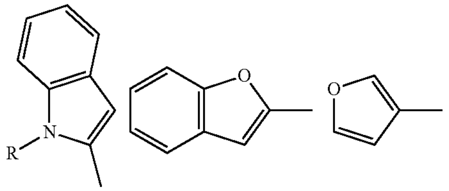
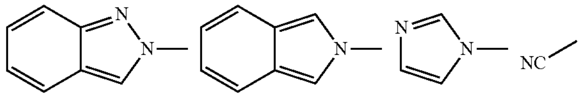
The following General Formulas represent cyclic D-A-D' and A-D-A' TADF materials.
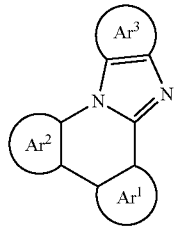
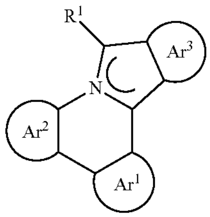
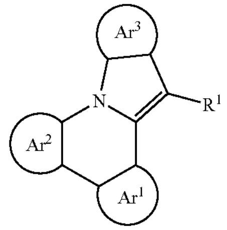
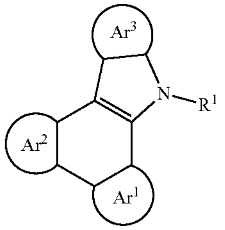
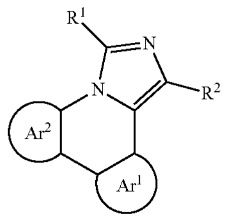
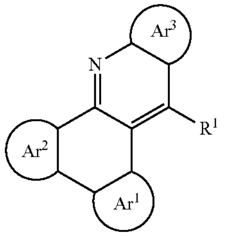
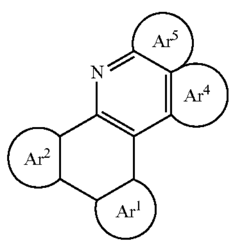
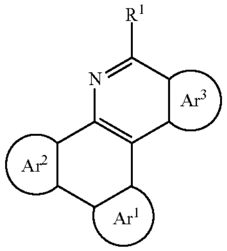
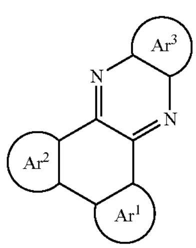
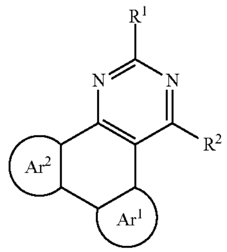
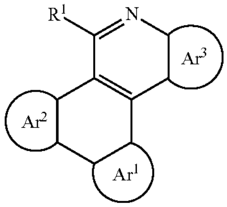
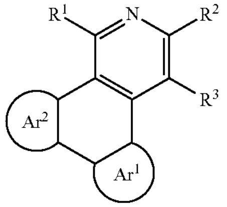
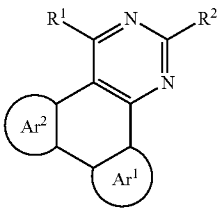
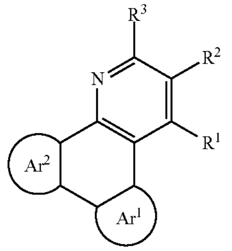

-continued
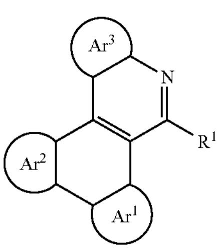
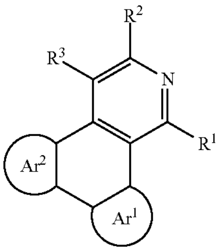
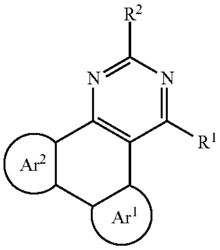
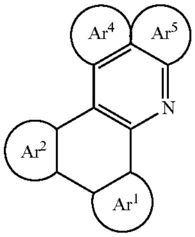
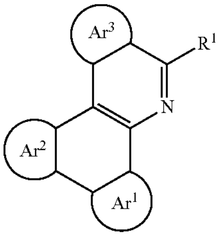
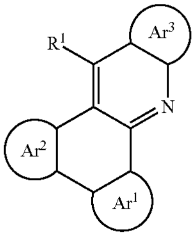
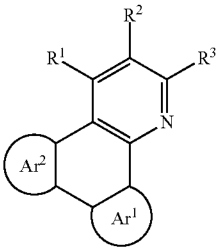
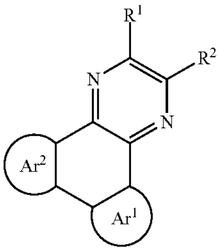
Examples of
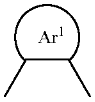
are shown below.
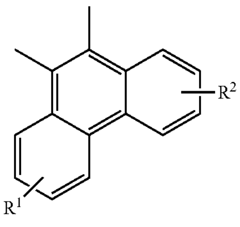
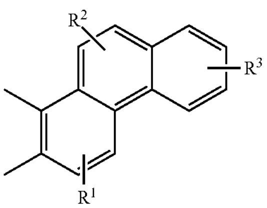
-continued
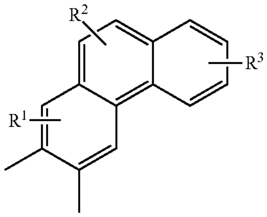
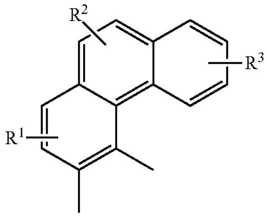
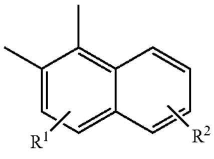
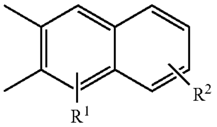
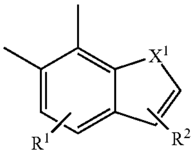
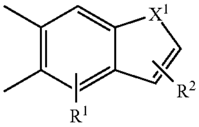
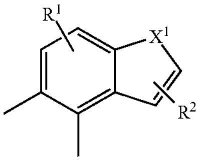
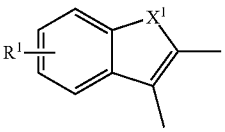
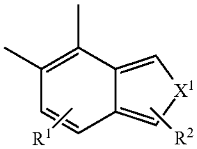
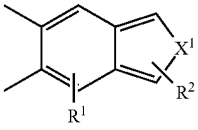
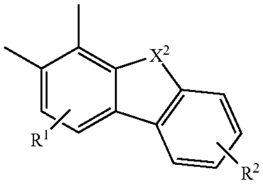
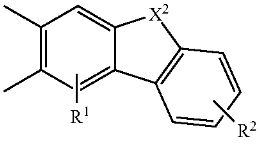
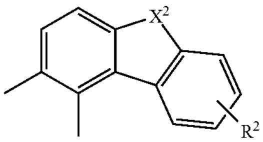
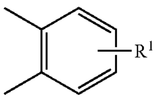
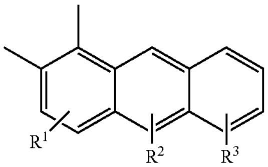
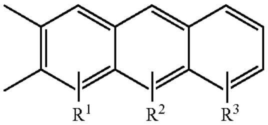
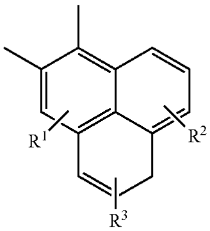
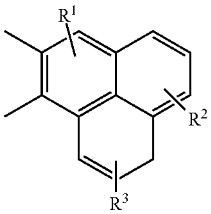

-continued
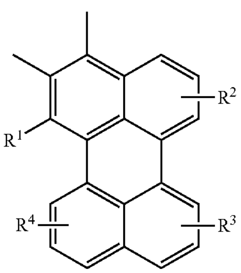
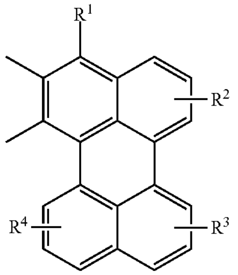
Examples of
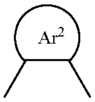
are shown below.
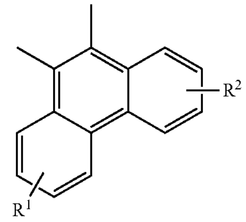
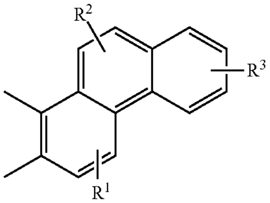
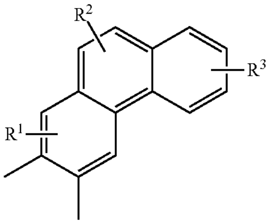
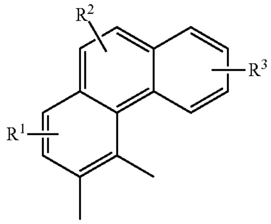
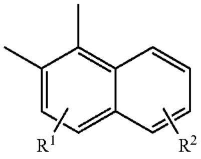
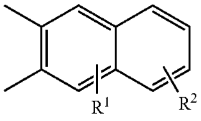
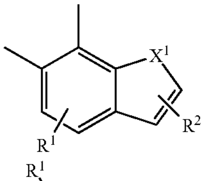
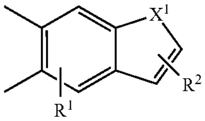
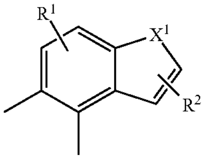
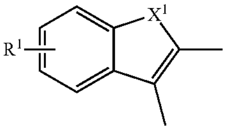
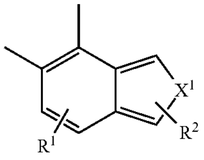
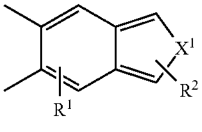
-continued
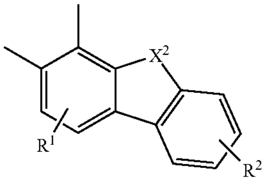
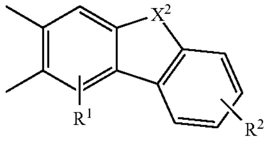
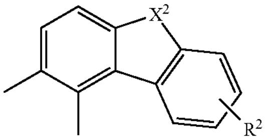
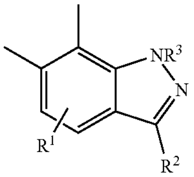
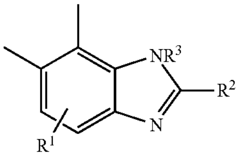
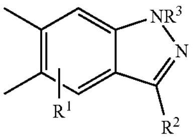
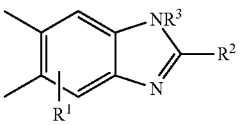
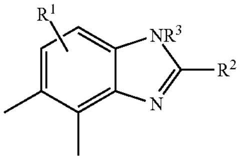
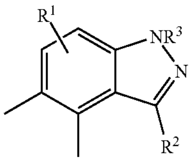
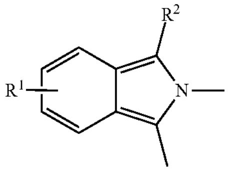
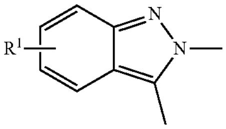
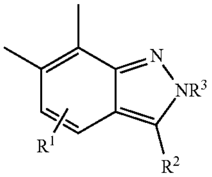
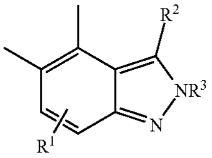
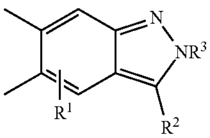
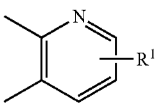
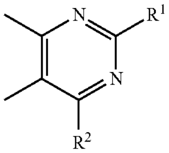
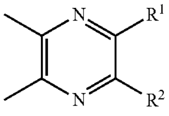
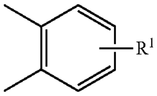
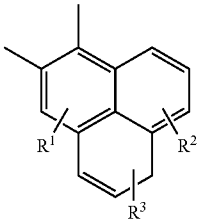

-continued
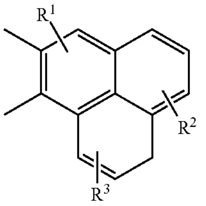
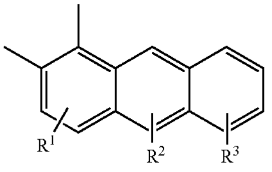
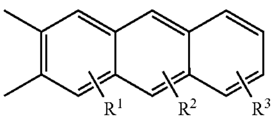
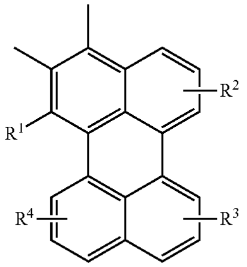
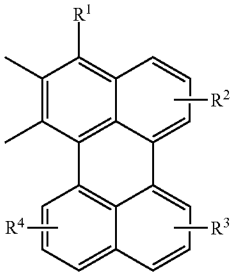
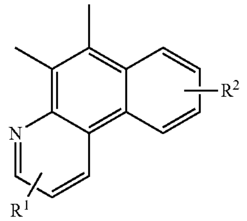
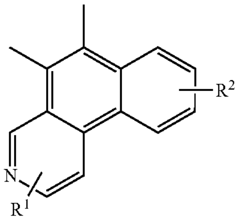
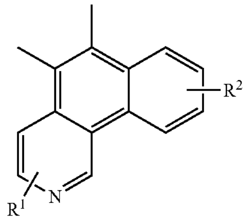
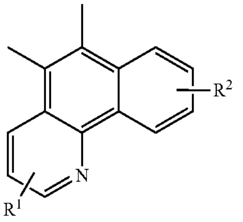
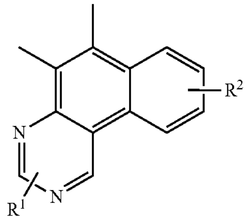
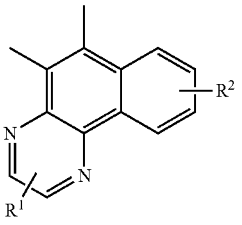
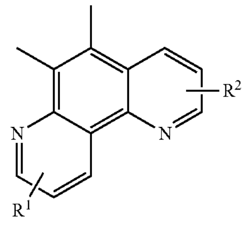
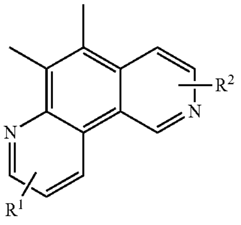
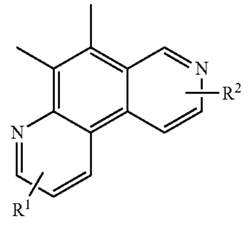
-continued
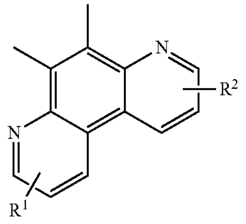
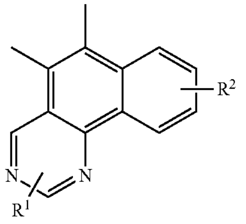
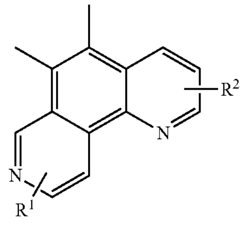
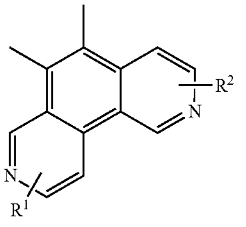
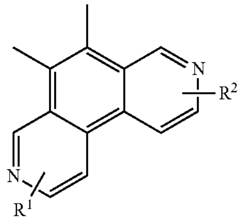
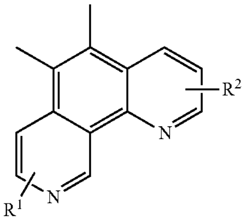
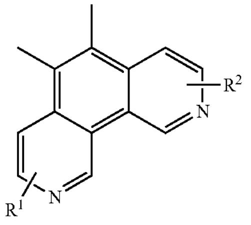
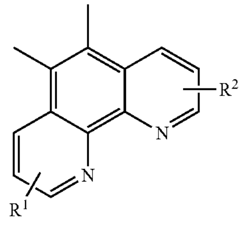
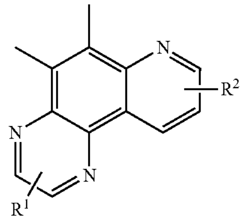
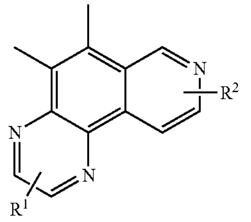
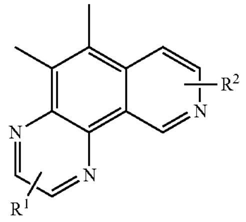
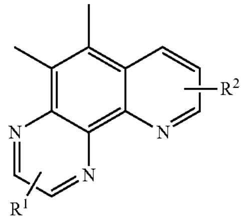
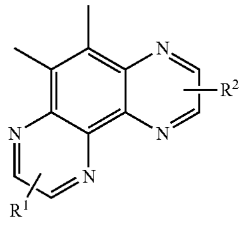
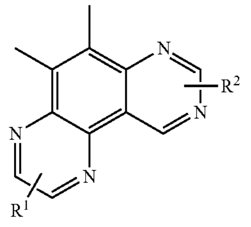

-continued
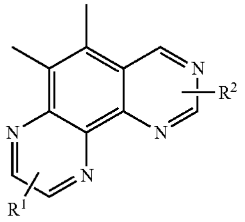
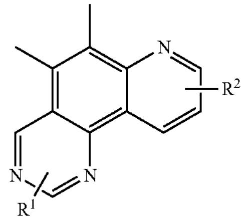
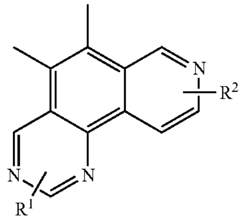
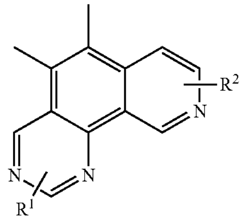
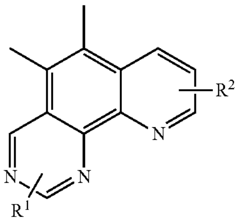
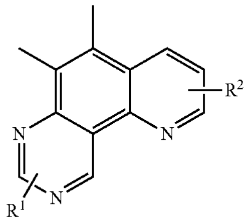
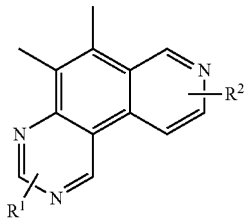
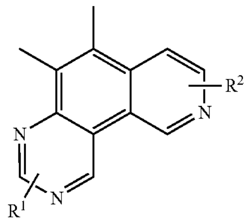
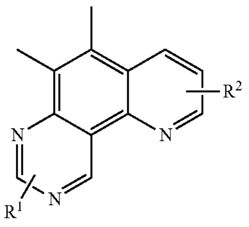
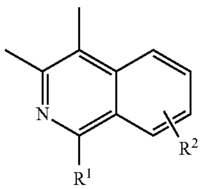
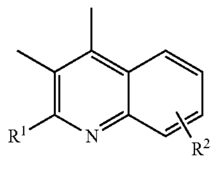
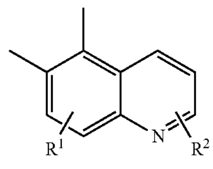
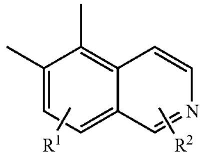
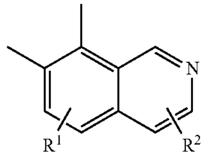
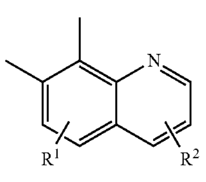
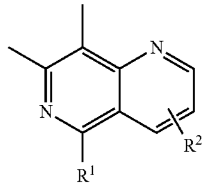
-continued
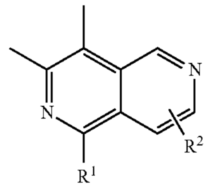
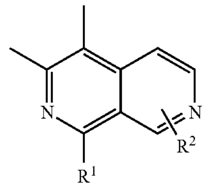
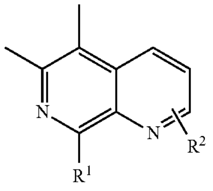
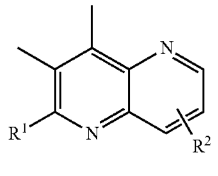
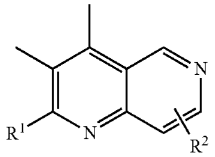
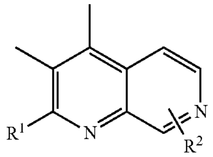
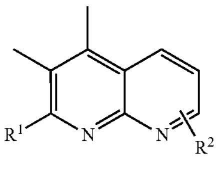
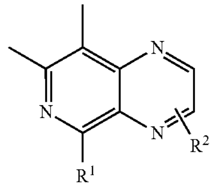
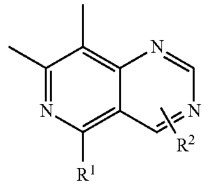
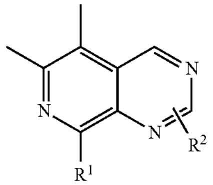
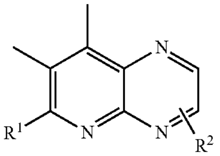
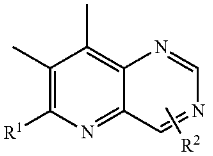
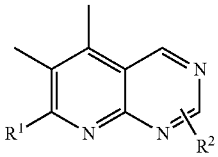
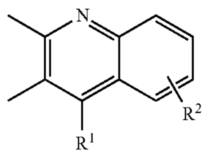
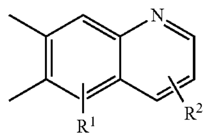
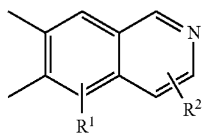
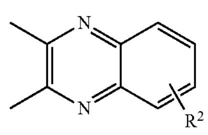
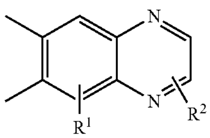
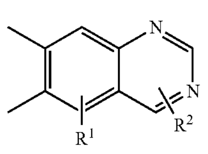
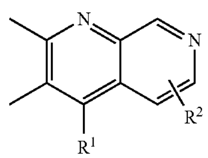

-continued
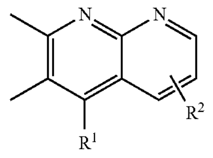
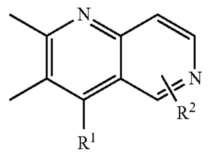
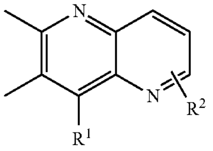
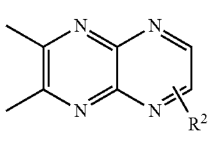
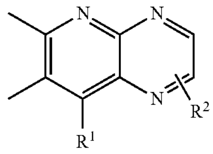
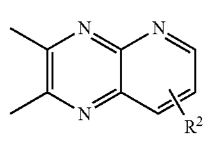
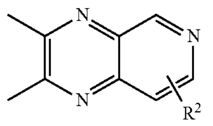
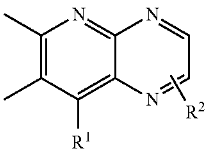
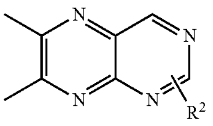
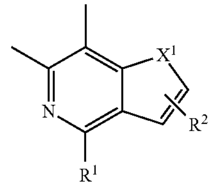
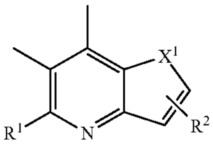
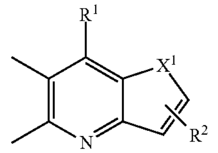
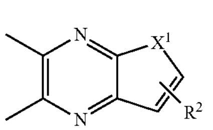
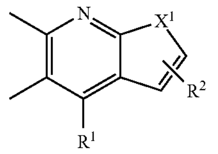
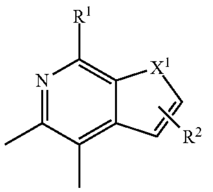
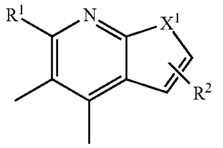
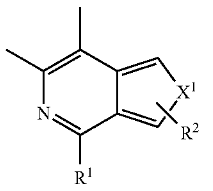
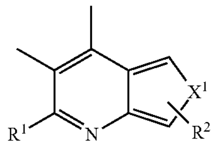
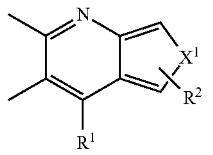
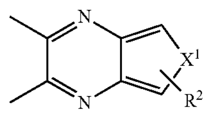
-continued
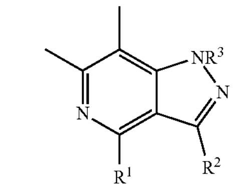
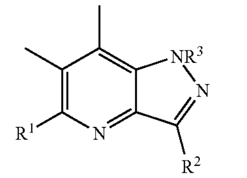
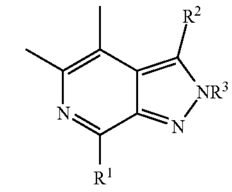
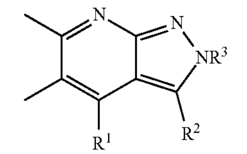
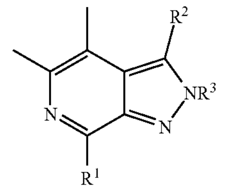
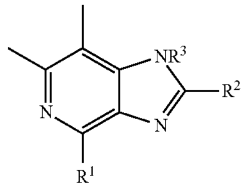
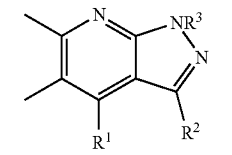
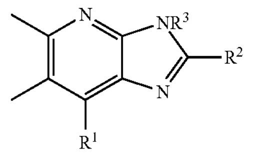
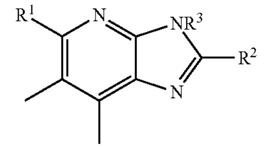
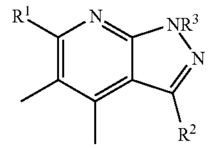
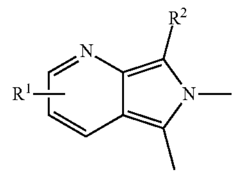
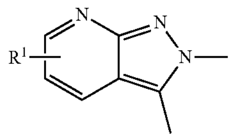
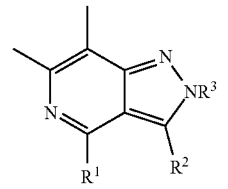
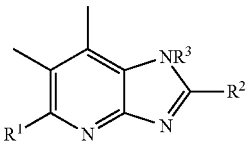
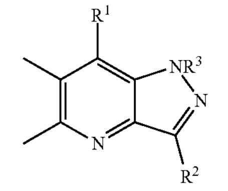
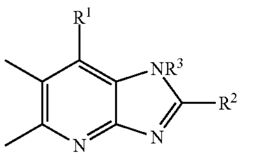
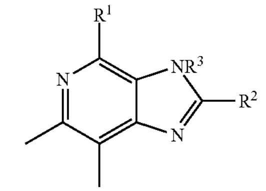
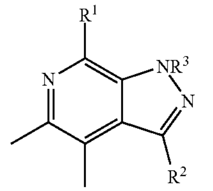

-continued
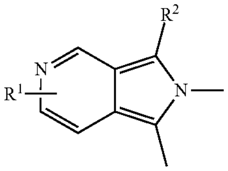
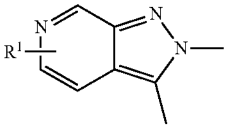
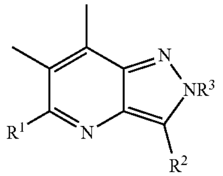
Examples of
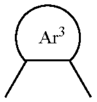
are shown below.
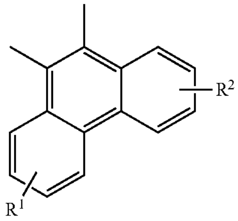
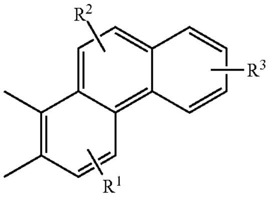
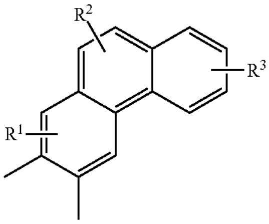
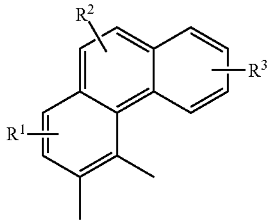
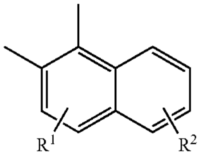
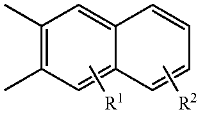
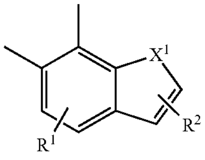
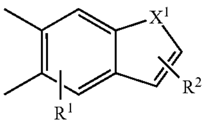
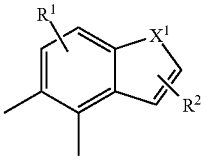
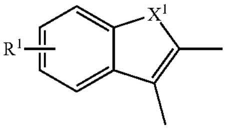
-continued
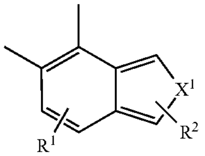
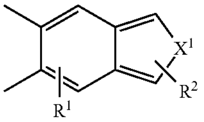
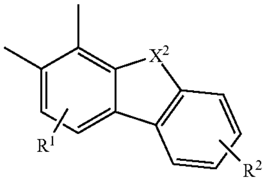
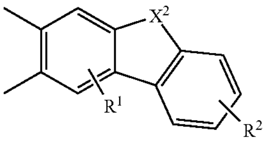
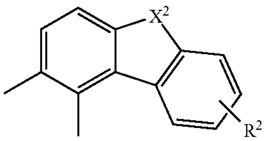
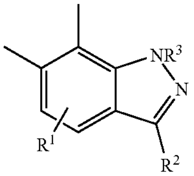
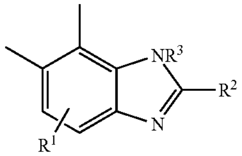
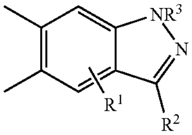
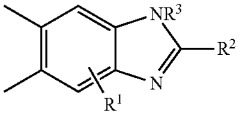
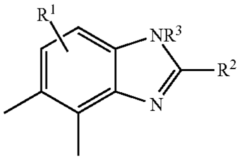
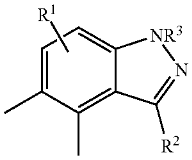
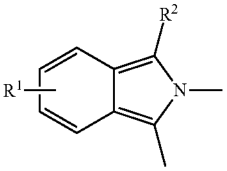
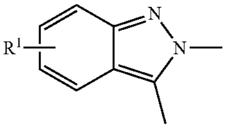
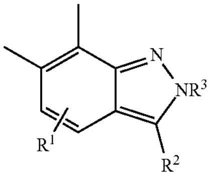
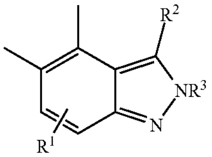
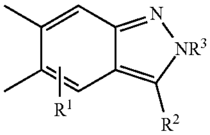
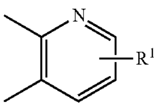
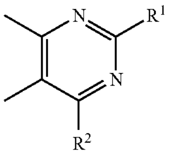
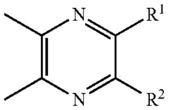
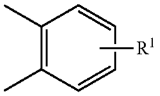
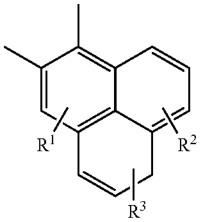

-continued
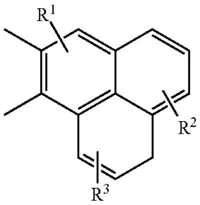
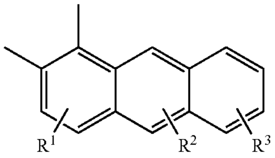
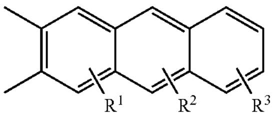
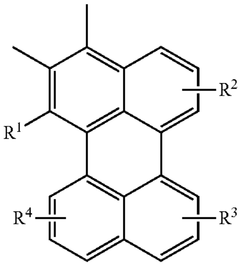
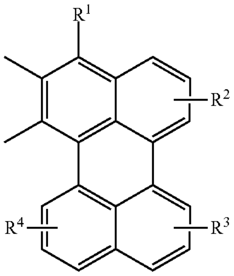
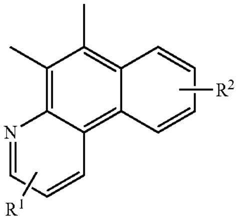
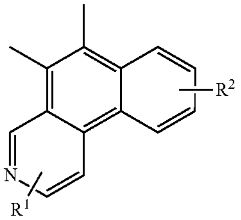
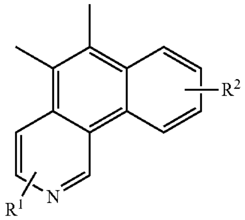
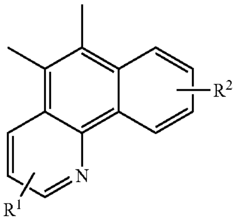
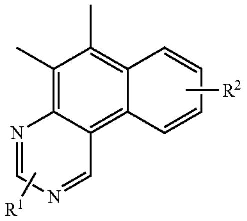
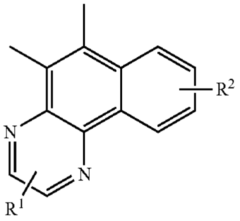
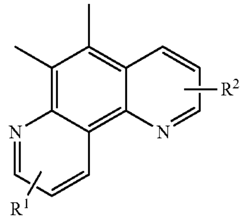
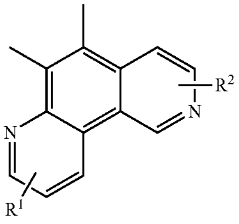
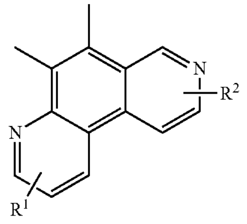
-continued
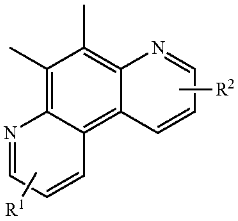
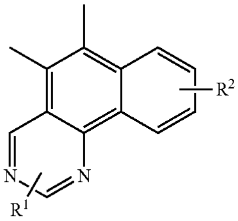
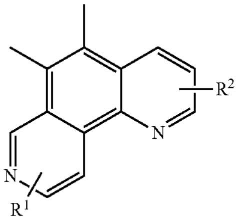
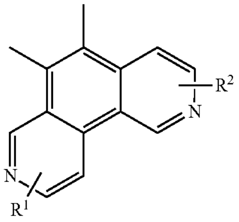
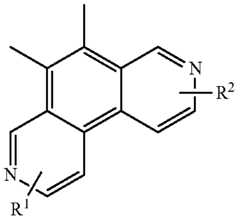
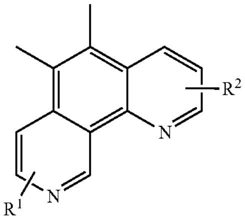
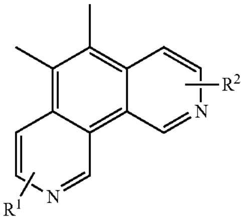
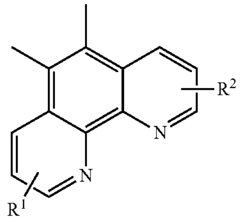
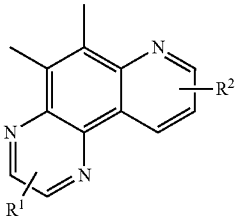
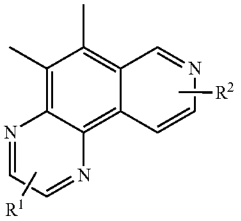
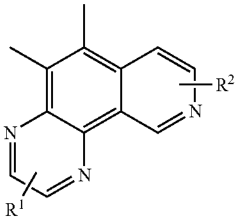
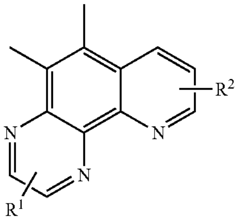
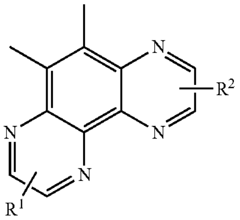
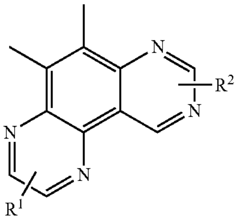

-continued
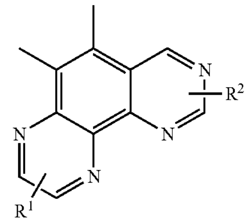 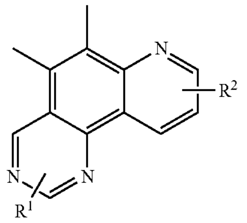
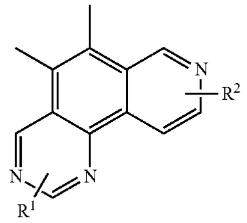 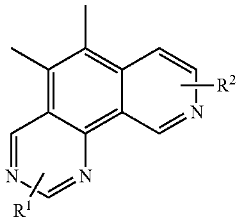
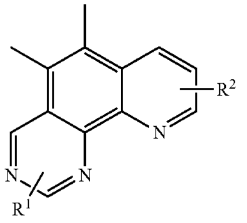 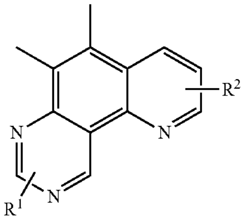
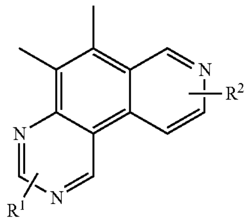 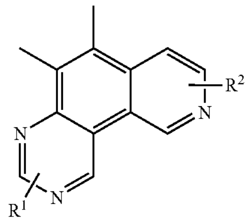
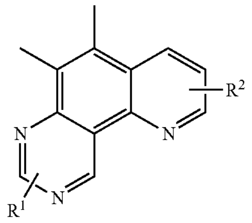 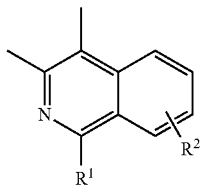
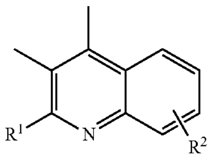 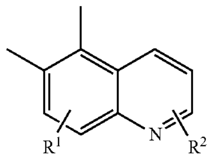
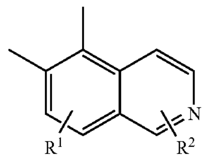 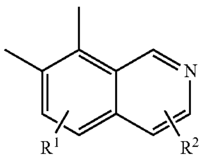
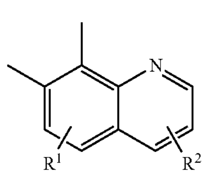 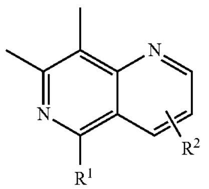
-continued
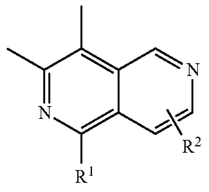 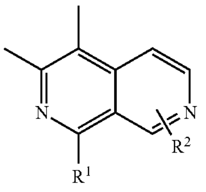
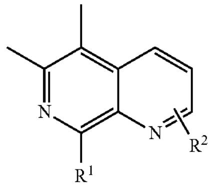 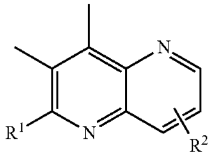
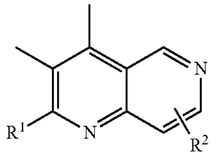 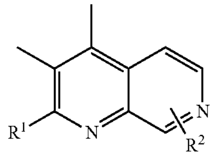
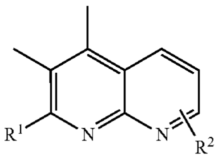 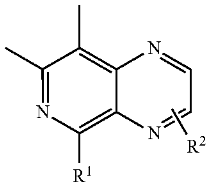
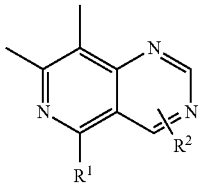 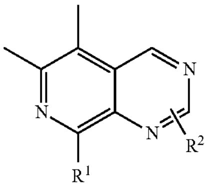
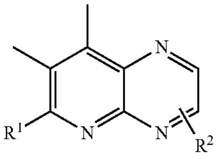 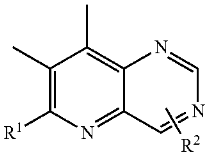
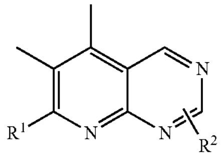 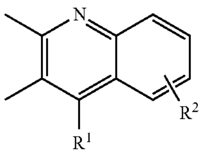
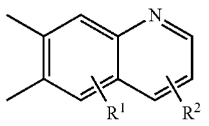 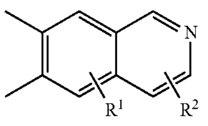
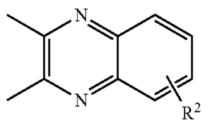 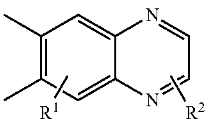
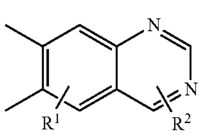 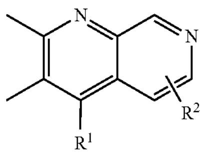

-continued
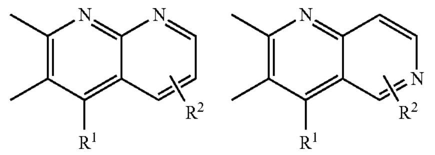
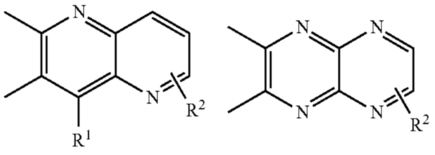
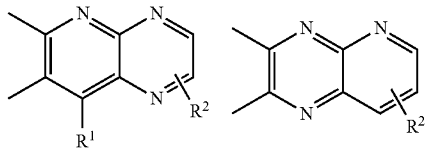
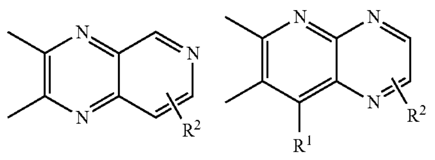
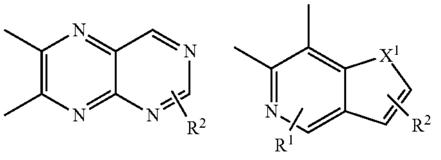
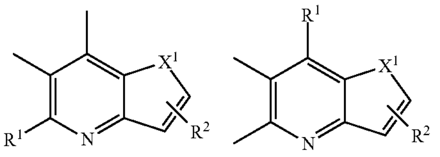
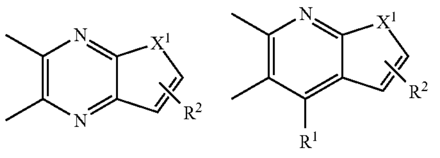
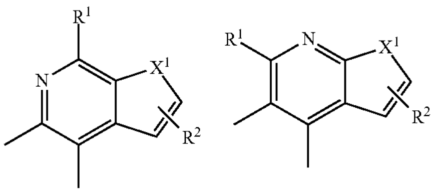
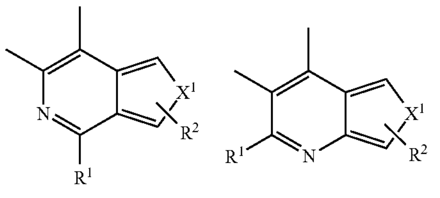
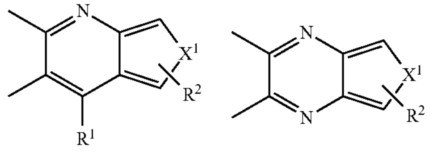
-continued
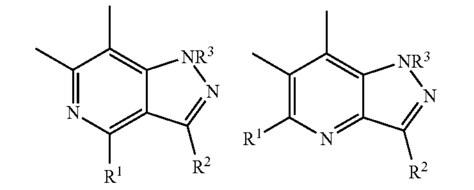
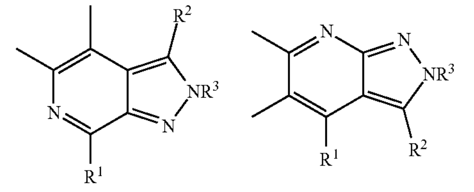
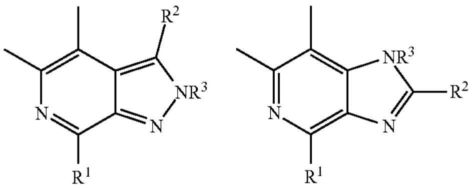
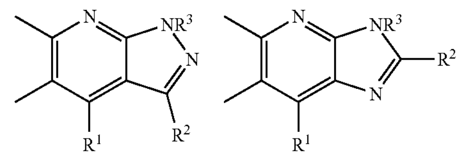
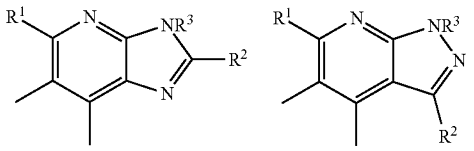
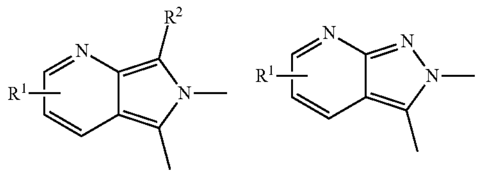
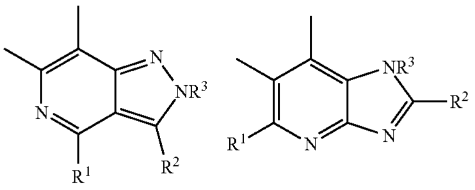
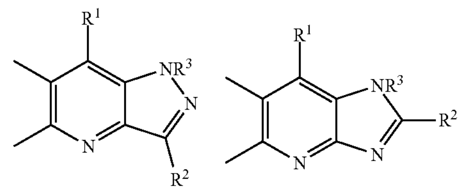
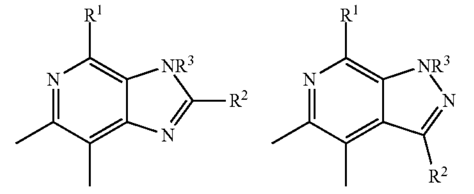

-continued
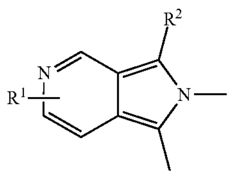
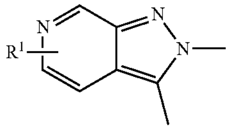
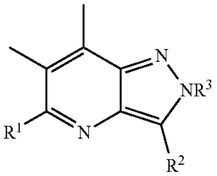
Examples of
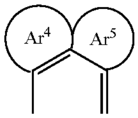
are shown below.
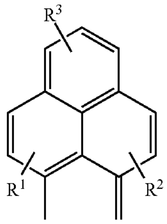
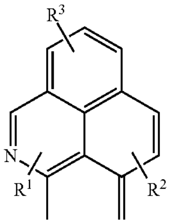
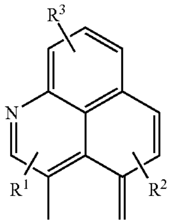
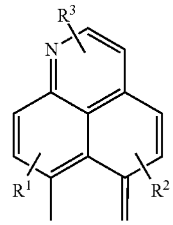
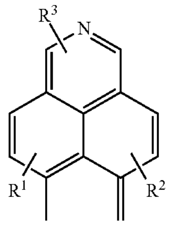
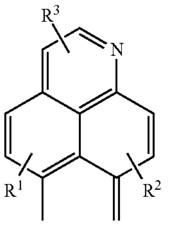
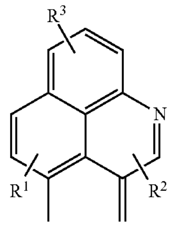
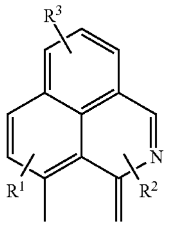
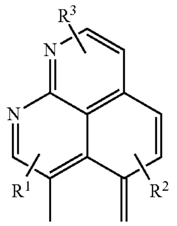
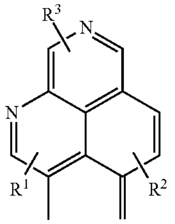
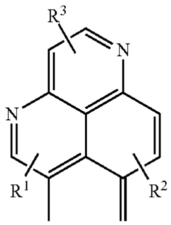
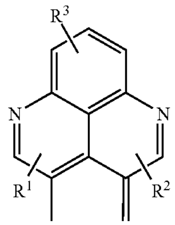
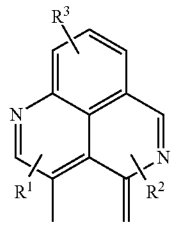
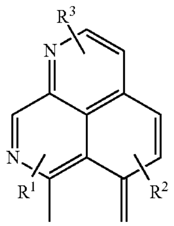
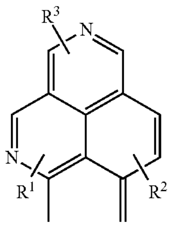
-continued
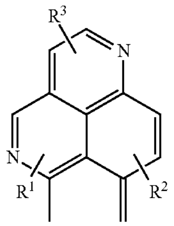
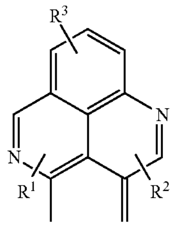
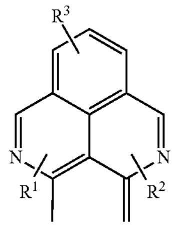
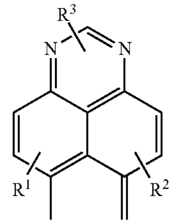
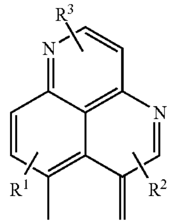
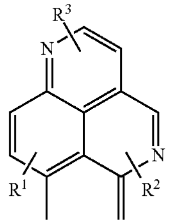
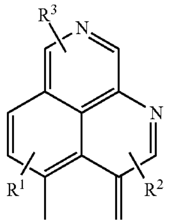
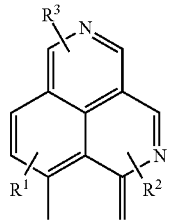
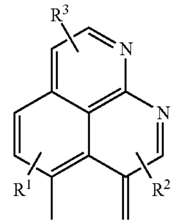
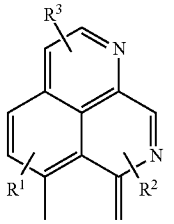
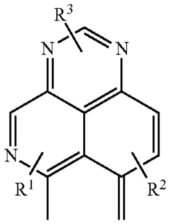
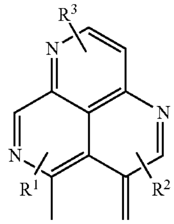
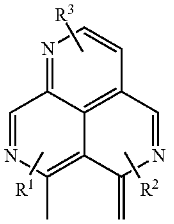
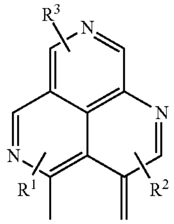
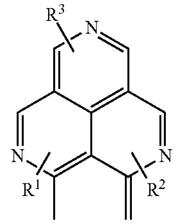
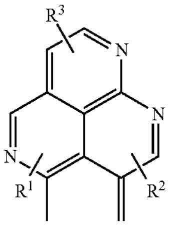
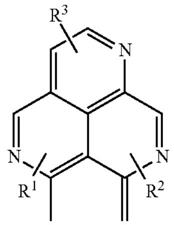
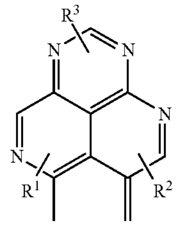

-continued
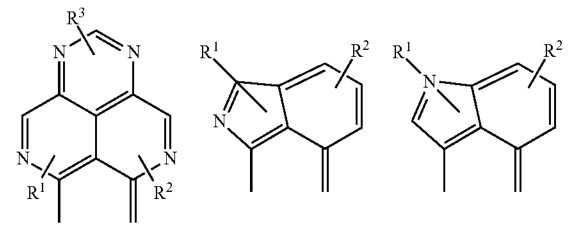
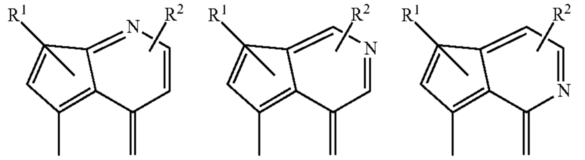
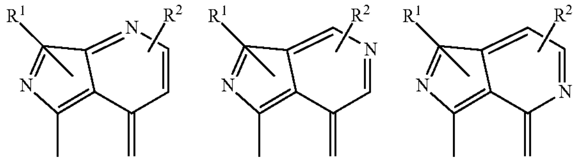
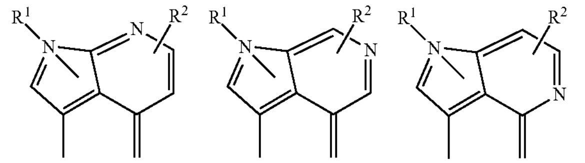
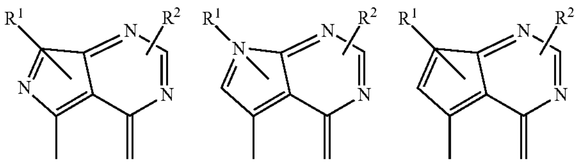
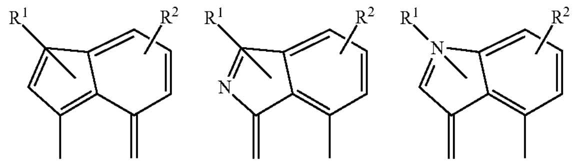
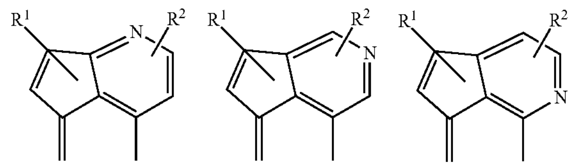
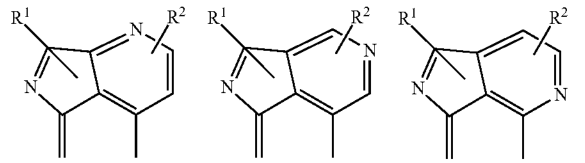
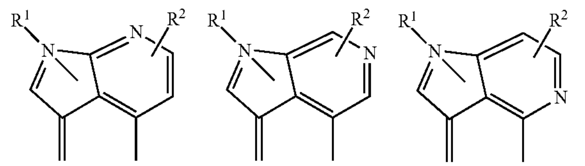
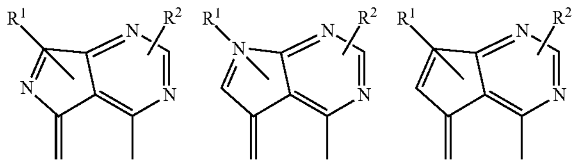
-continued
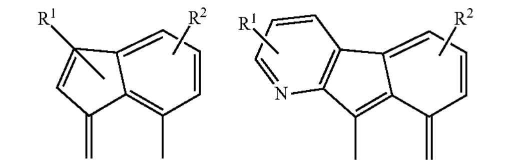
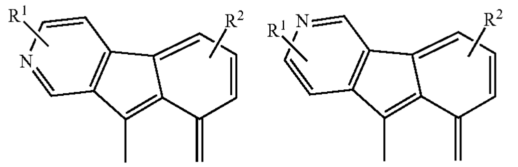
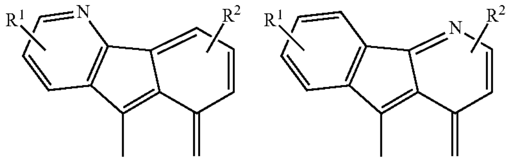
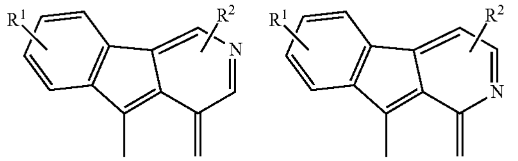
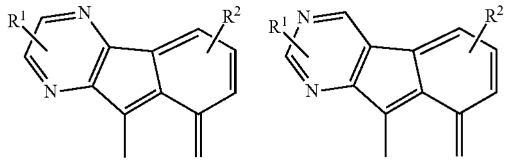
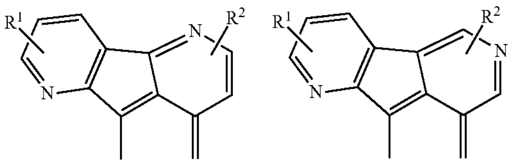
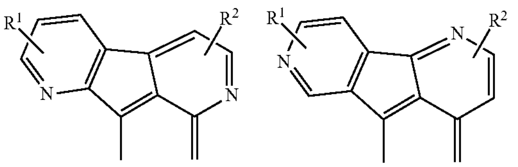
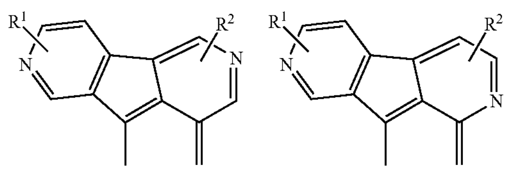
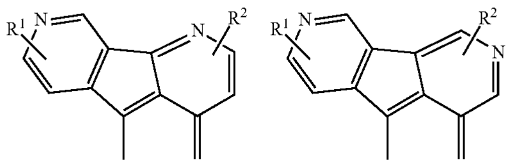
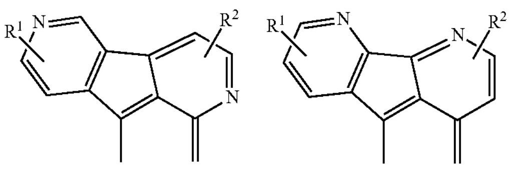

-continued
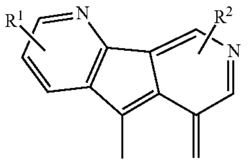 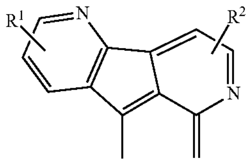
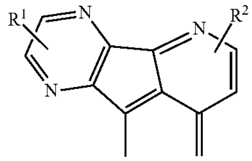 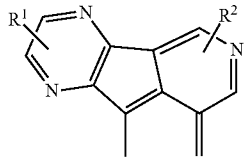
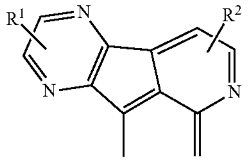 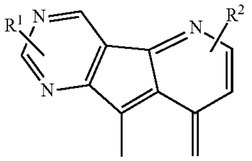
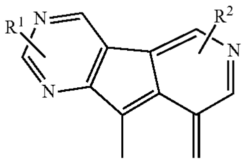 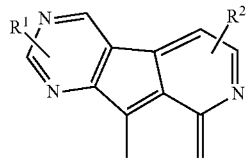
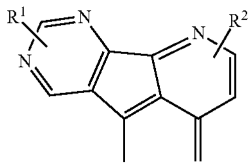 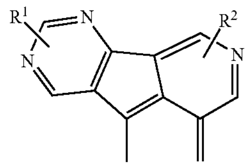
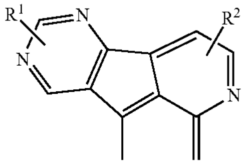 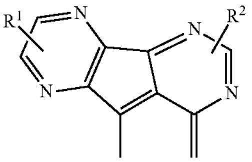
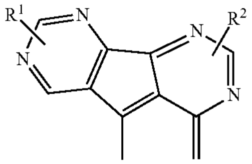 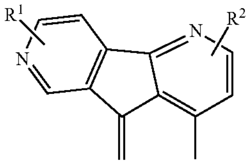
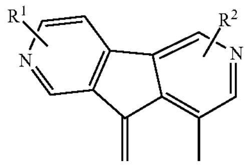 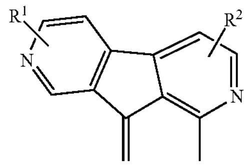
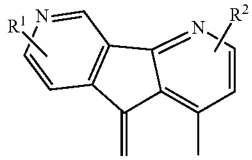 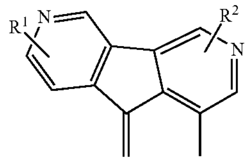
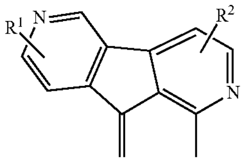 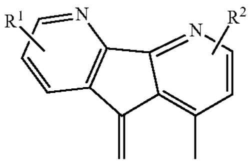
-continued
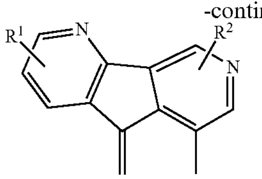 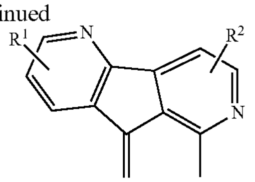
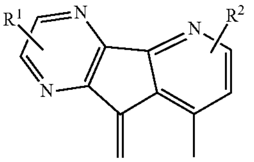 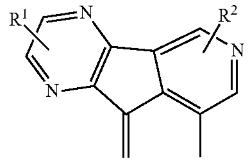
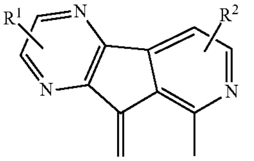 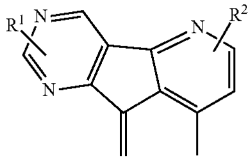
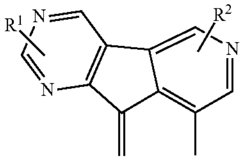 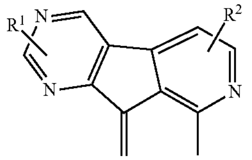
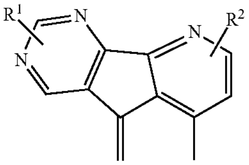 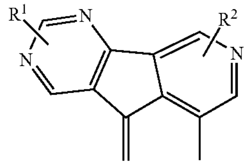
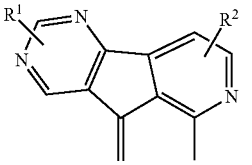 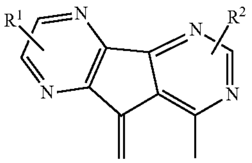
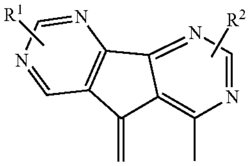
In the examples:
N is nitrogen;
$X^1$ represents O, $NR^1$, S, or $PR^1$,
$X^2$ represents O, $NR^1$, S, $CR^1R^2$, $SiR^1R^2$, C═O, $GeR^1R^2$, $PR^1$, $R^1P$═O, As $R^1$, $R^1As$═O, S═O, $SO_2$, Se═O, $SeO_2$, $BR^1$, $AlR^1$, $R^1Bi$═O, or $BiR^1$,
or

represents one of

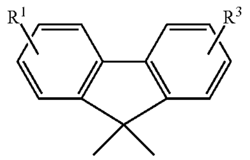

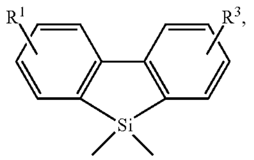

each of $R^1$, $R^2$, $R^3$, and $R^4$ is independently absent or present as a single substituent or multiple substituents, valency permitting, and each $R^1$, $R^2$, $R^3$, and $R^4$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In some implementations, one or more of —$R^1$, —$R^2$, —$R^3$, and —$R^4$ each independently represents one of the following moieties, where R and $R^7$ are defined herein.

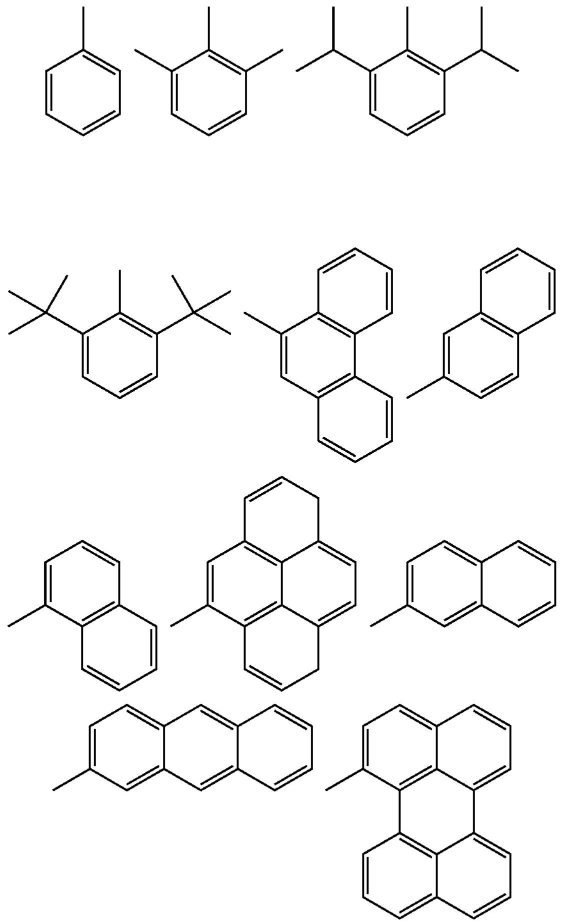

-continued

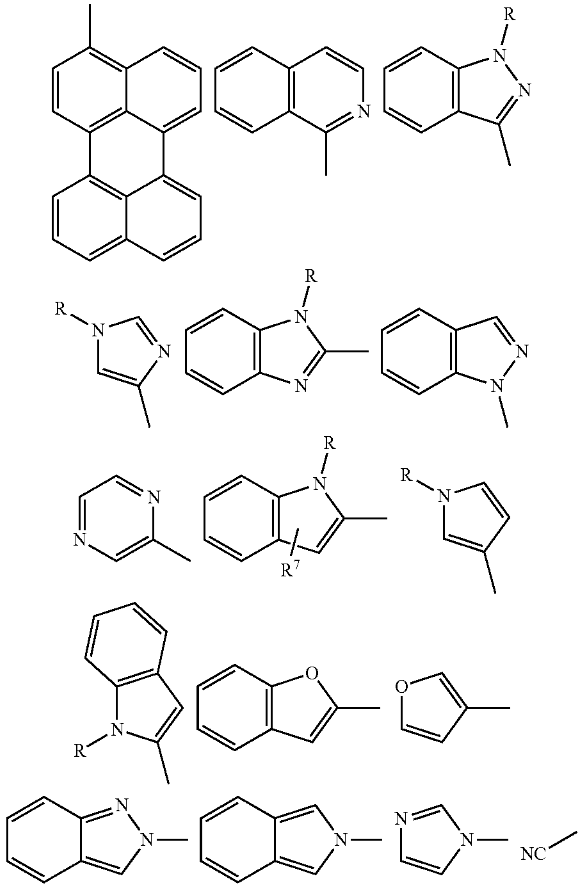

Examples of cyclic D-A-D' and A-D-A' TADF materials are shown below.

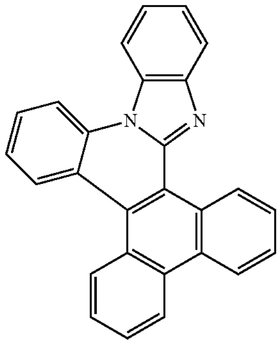

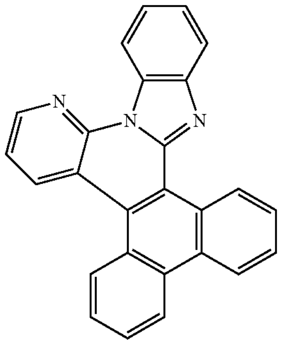

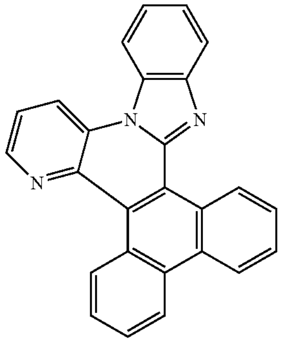

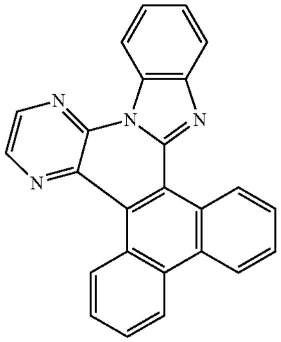

-continued
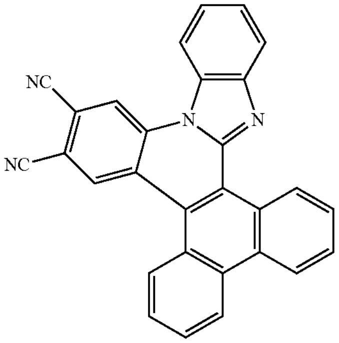
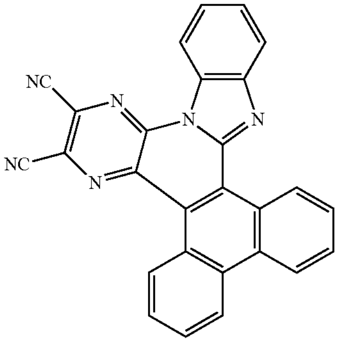
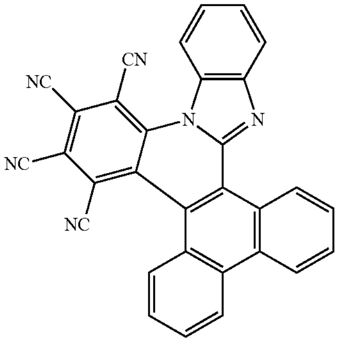
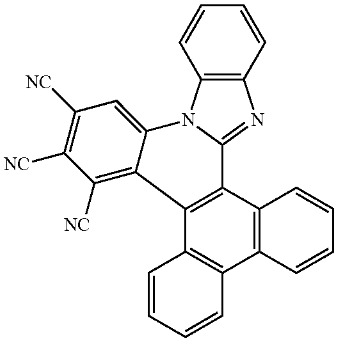
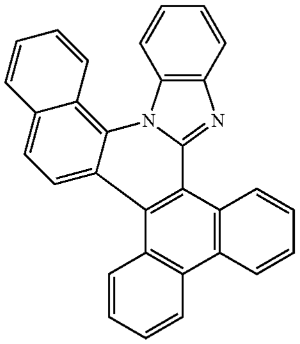
-continued
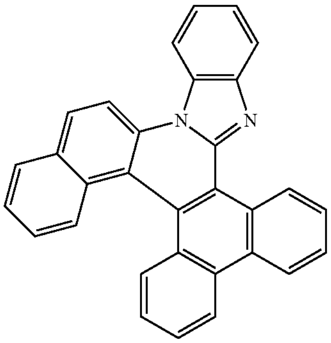
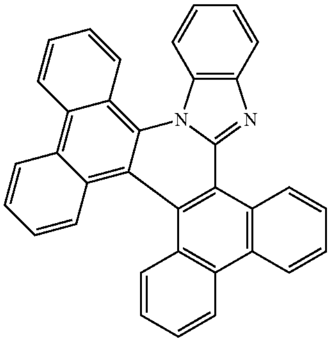
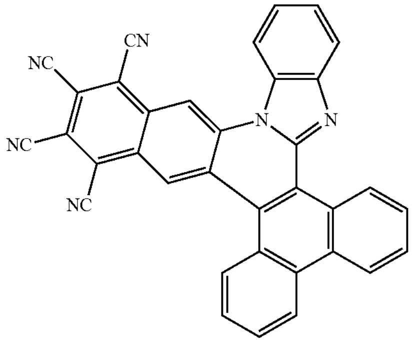
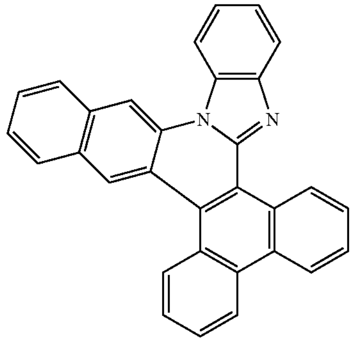
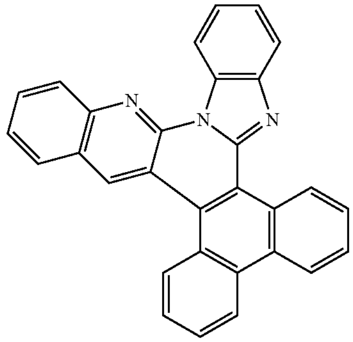

-continued
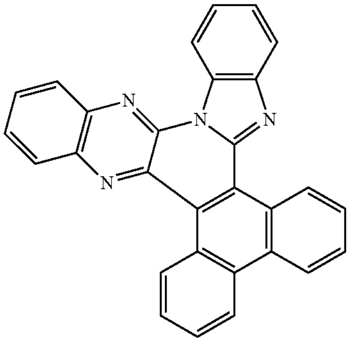
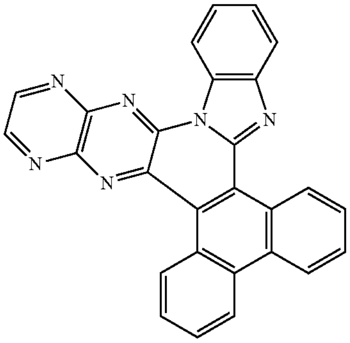
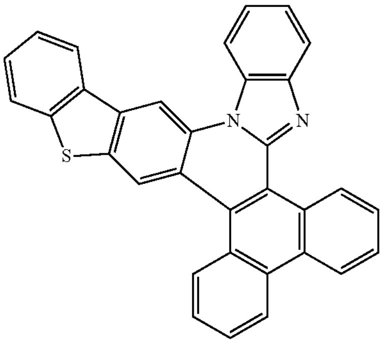
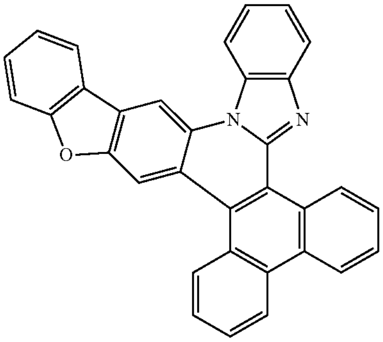
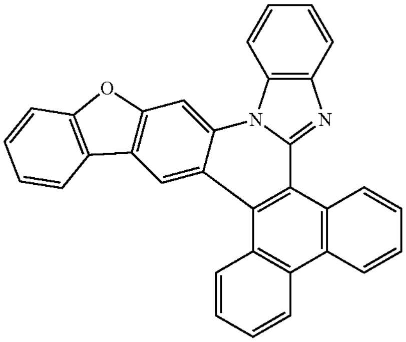
-continued
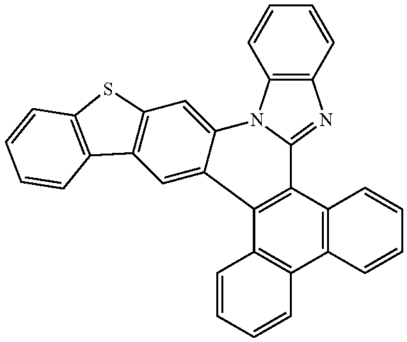
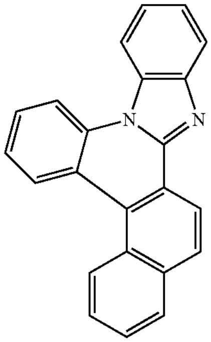
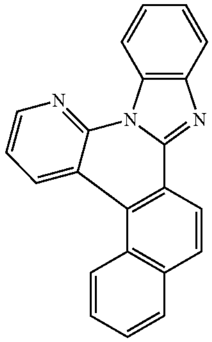
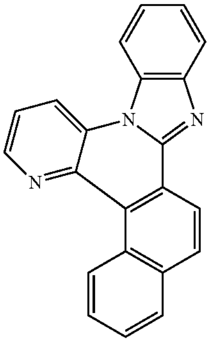
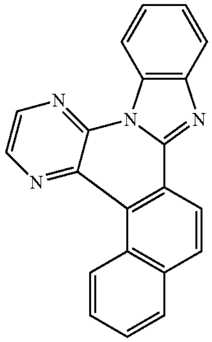
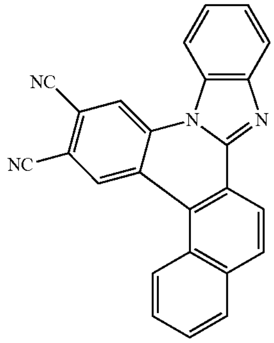
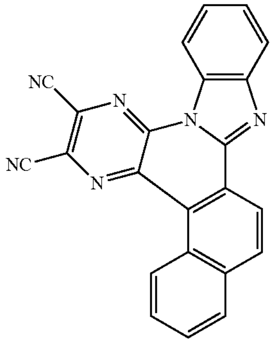
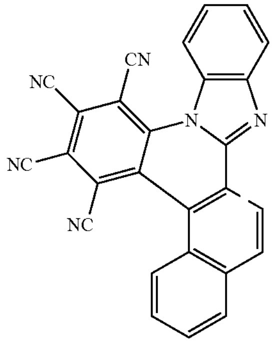
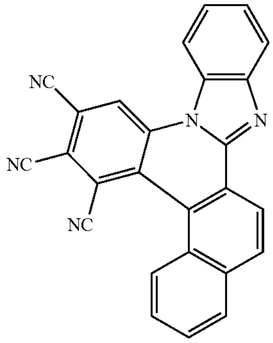

-continued
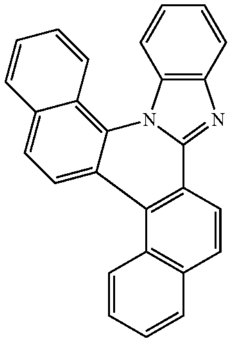
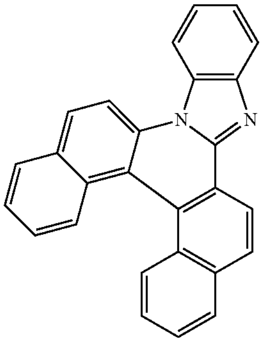
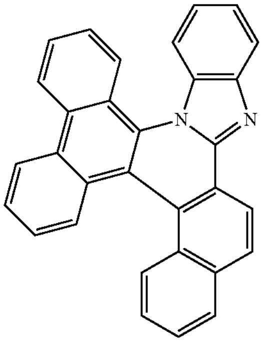
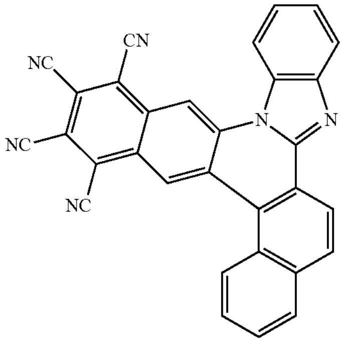
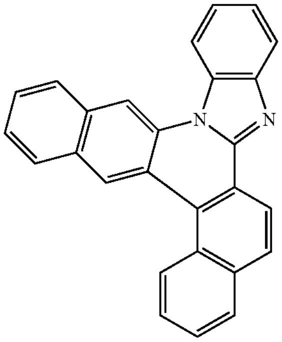
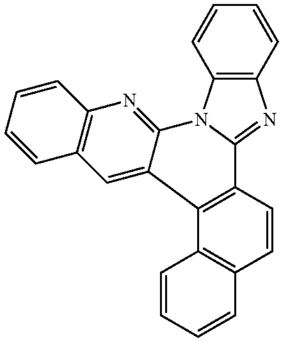
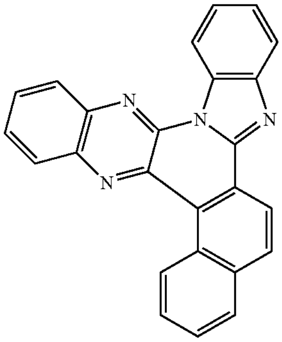
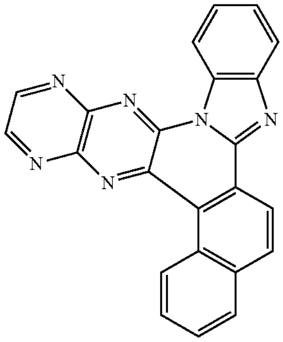
-continued
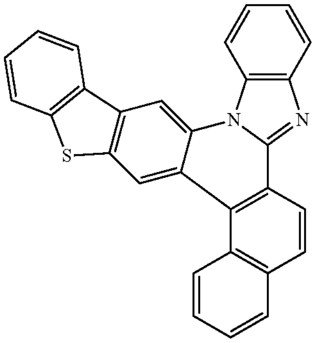
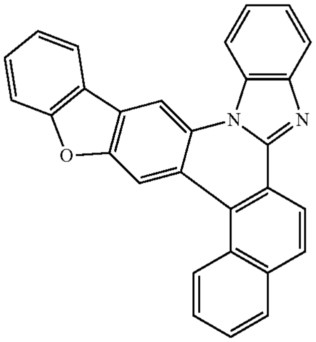
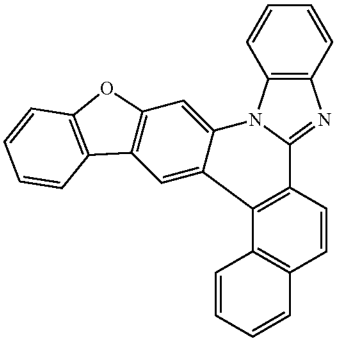
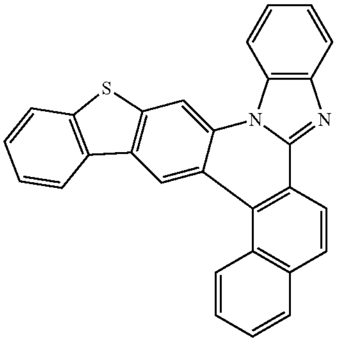
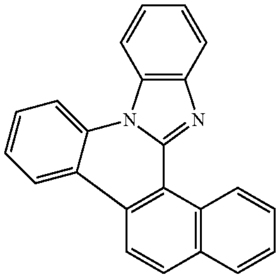
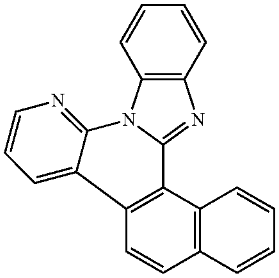

-continued
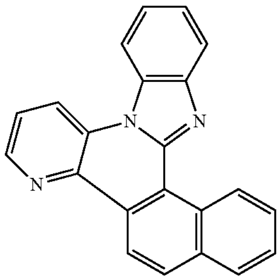
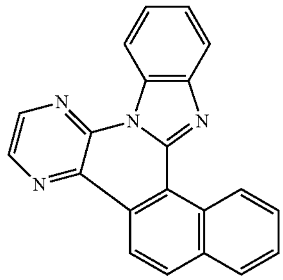
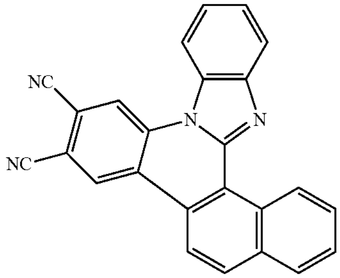
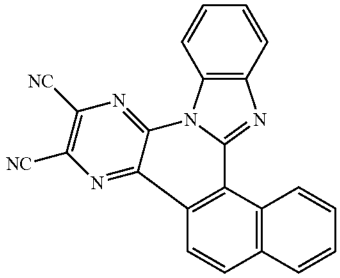
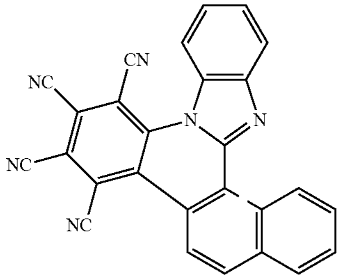
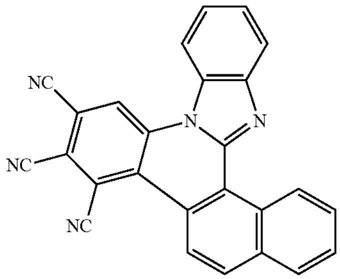
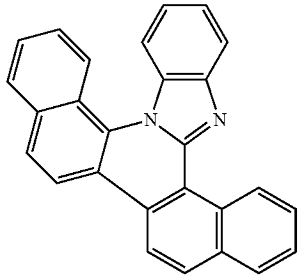
-continued
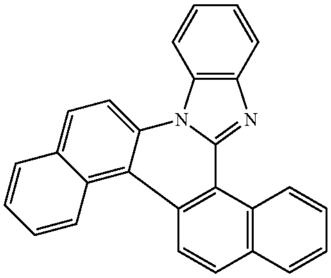
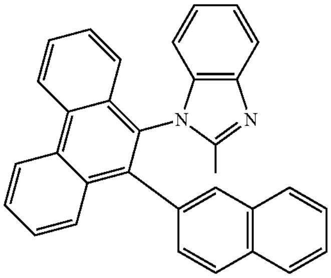
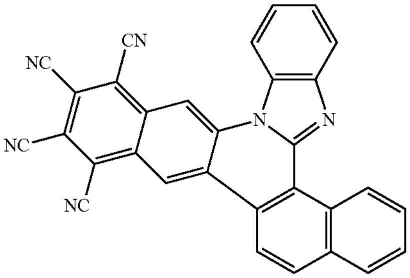
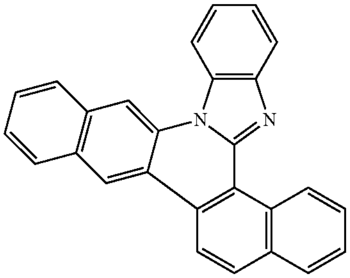
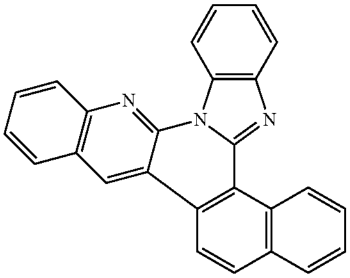
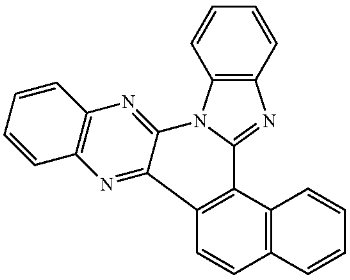

-continued
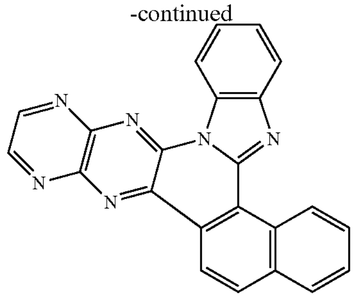
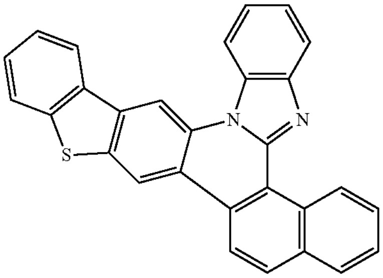
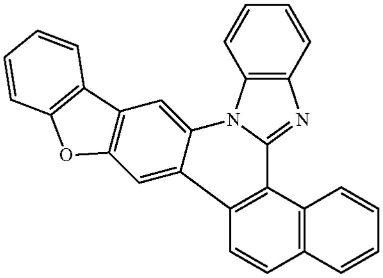
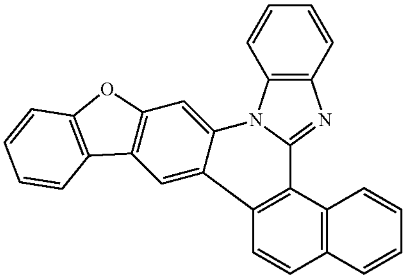
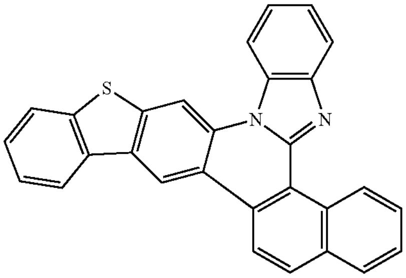
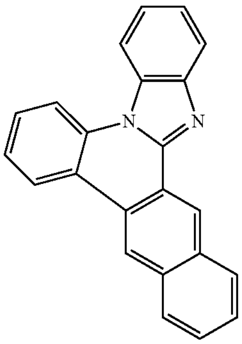
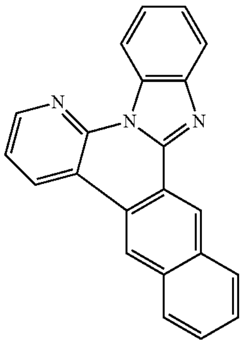
-continued
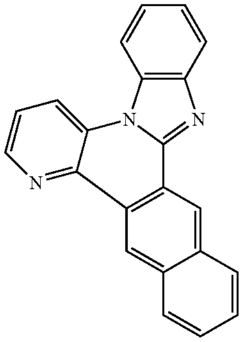
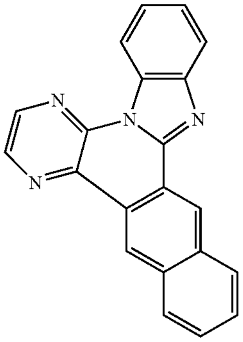
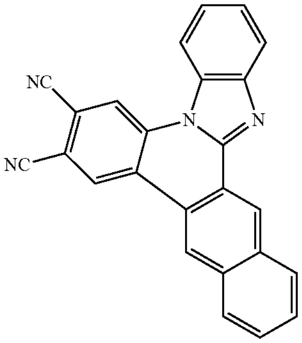
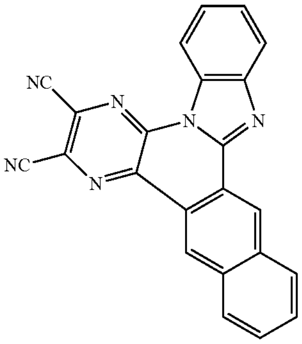
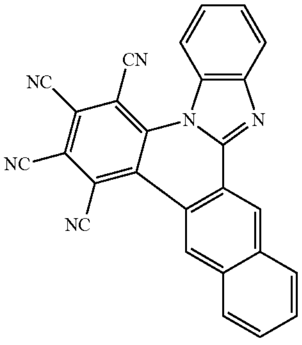
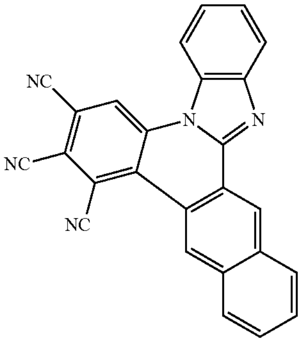

-continued
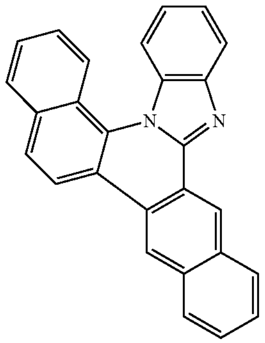
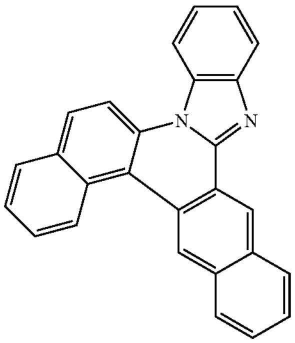
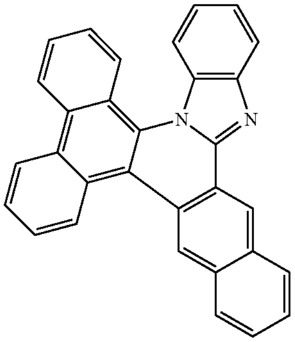
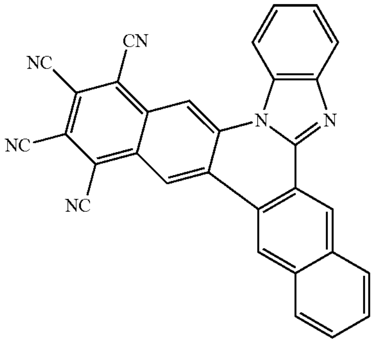
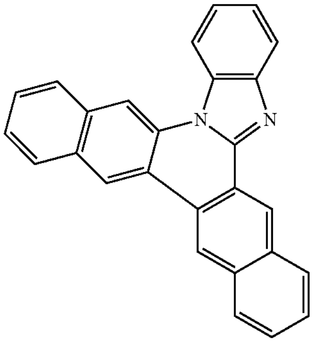
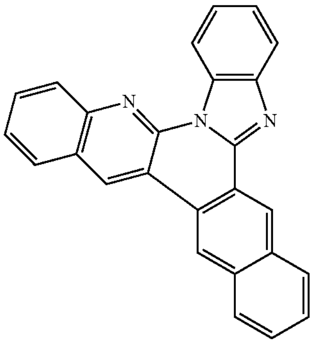
-continued
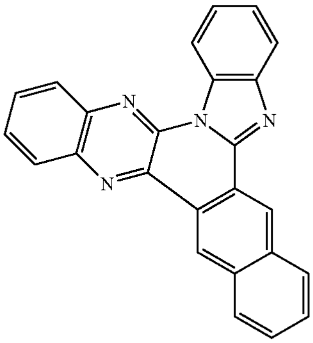
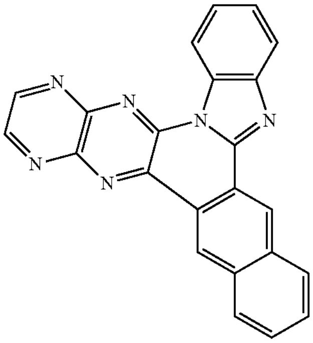
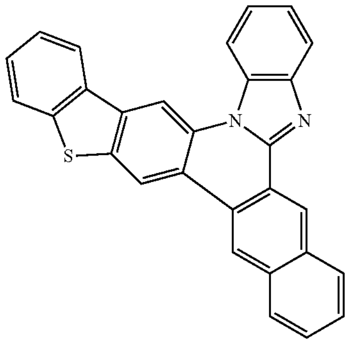
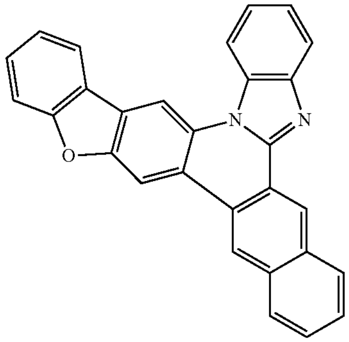
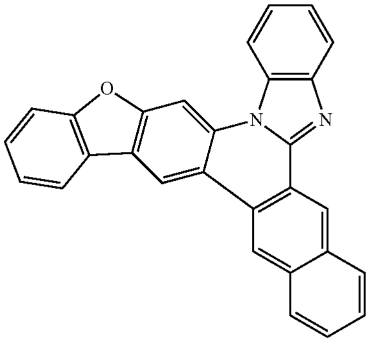

-continued
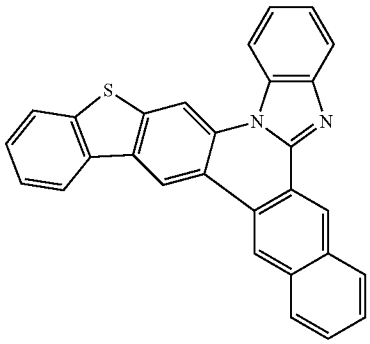
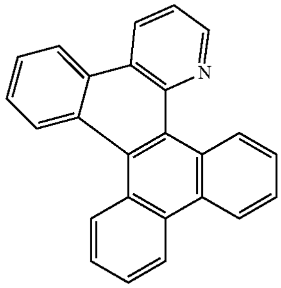
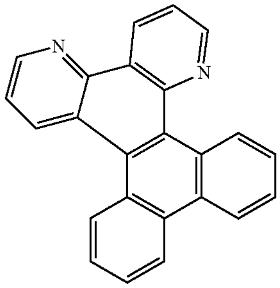
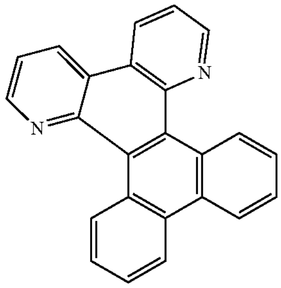
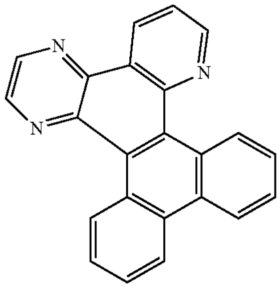
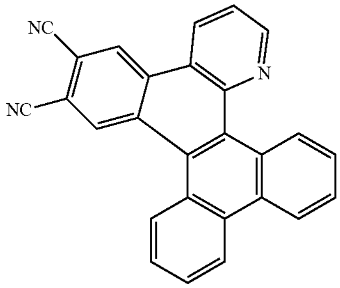
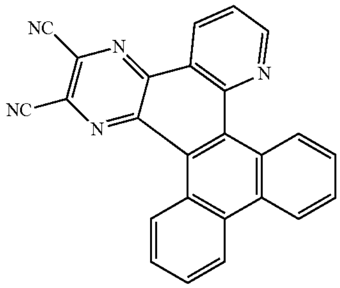
-continued
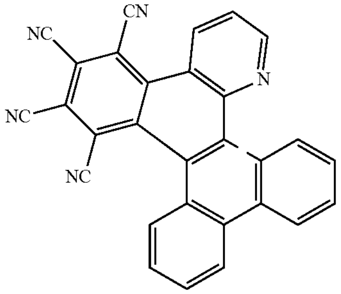
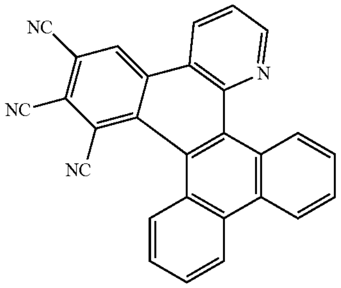
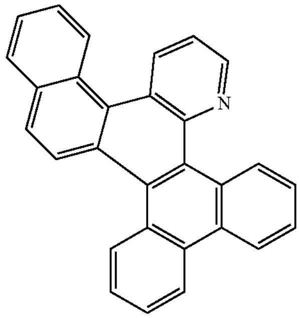
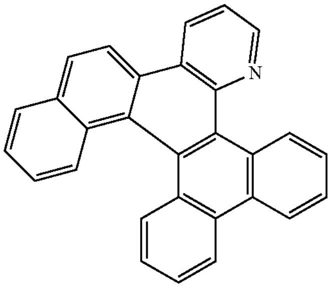
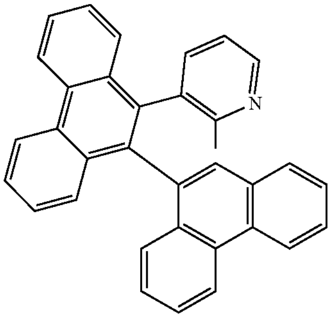

-continued
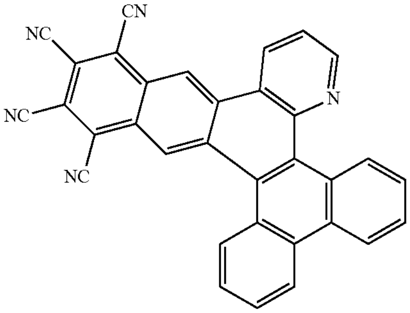
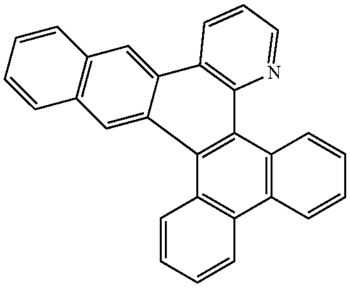
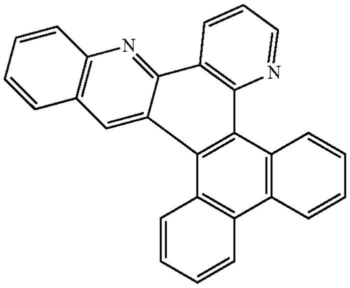
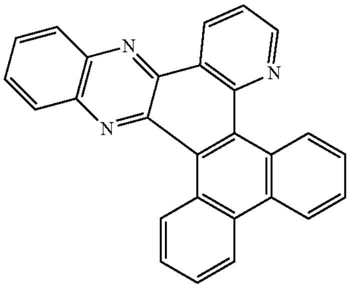
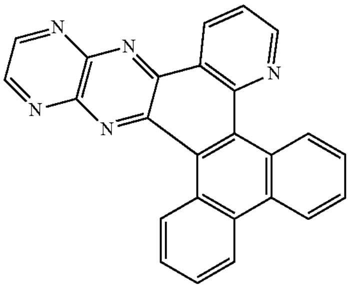
-continued
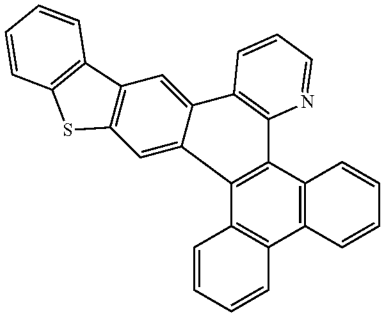
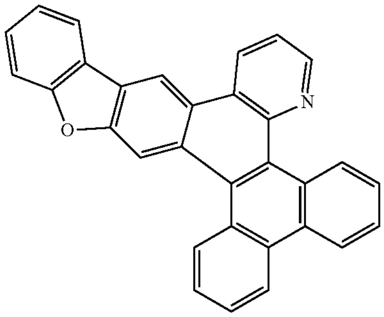
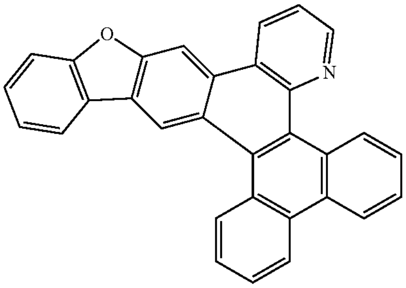
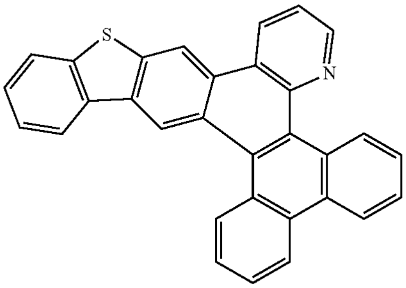
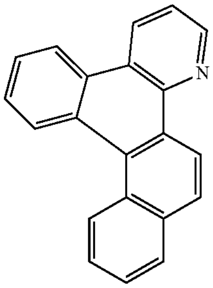
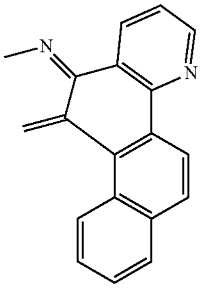

-continued
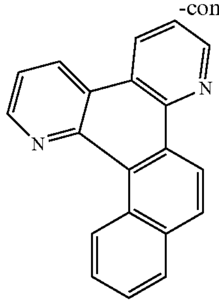
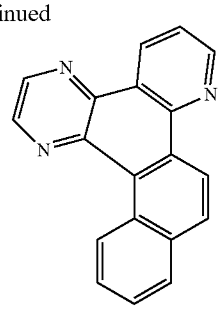
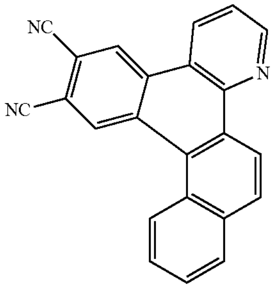
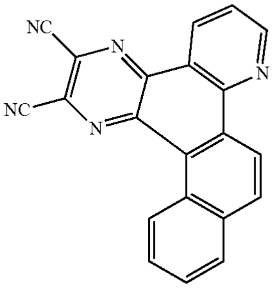
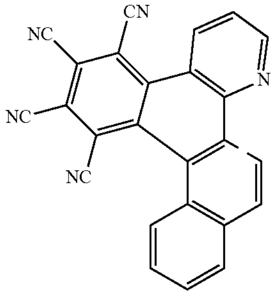
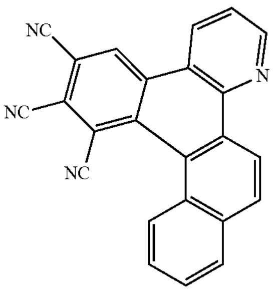
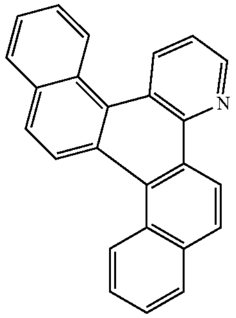
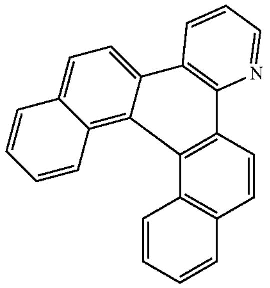
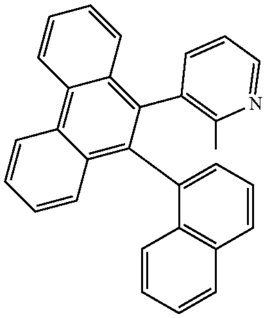
-continued
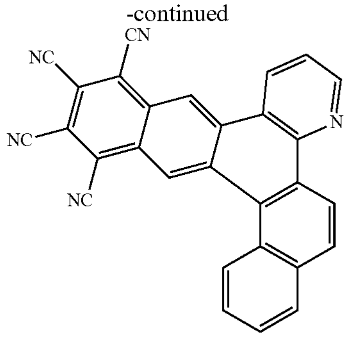
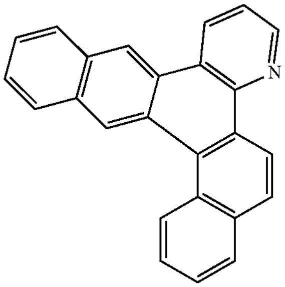
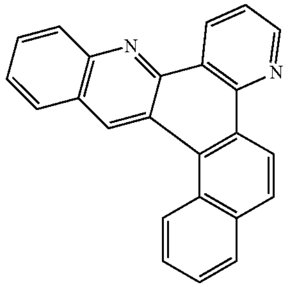
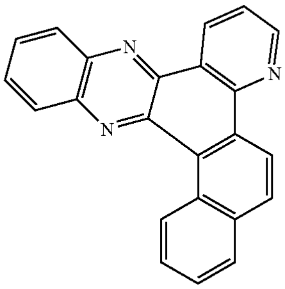
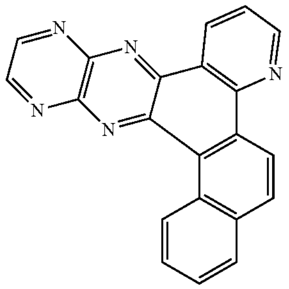
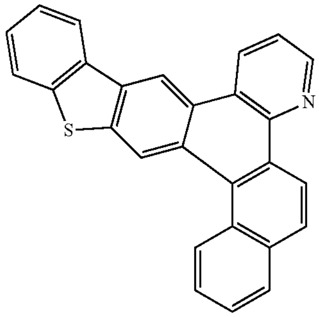
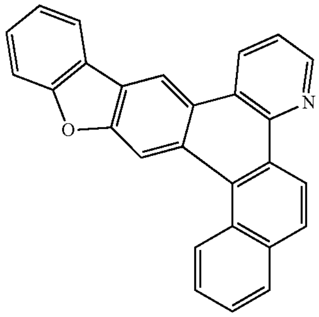

-continued
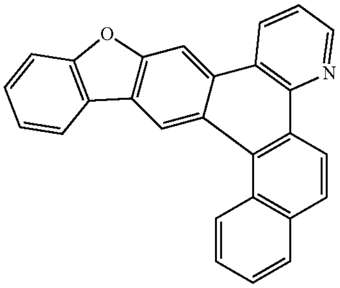
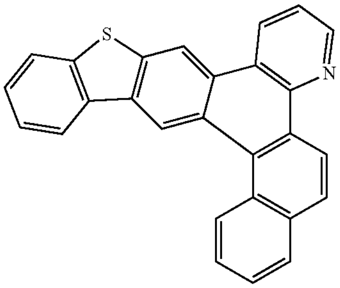
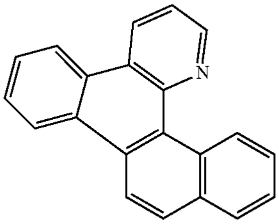
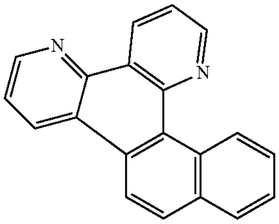
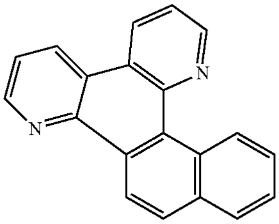
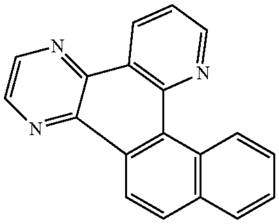
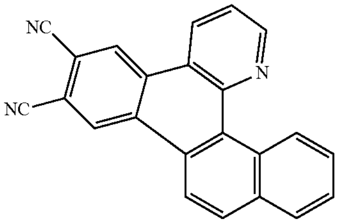
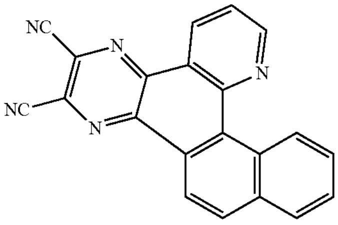
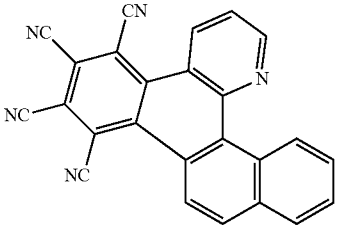
-continued
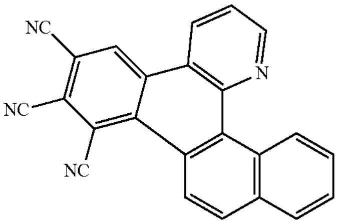
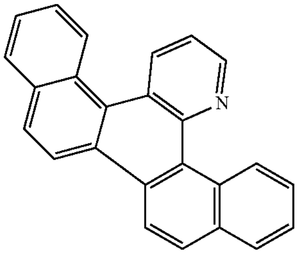
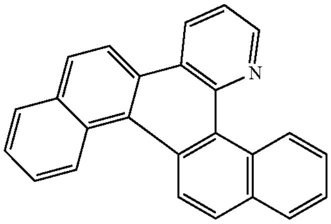
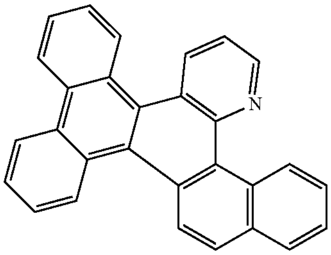
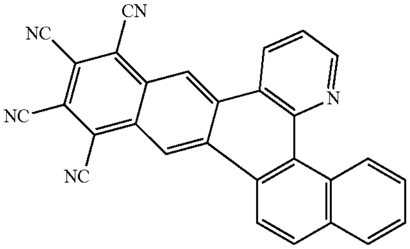
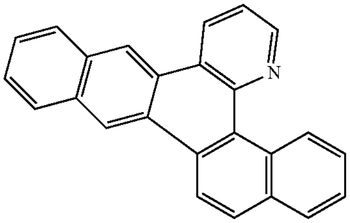
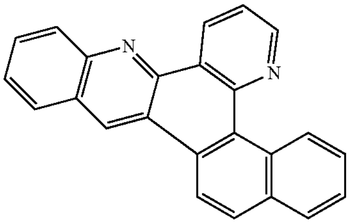

-continued
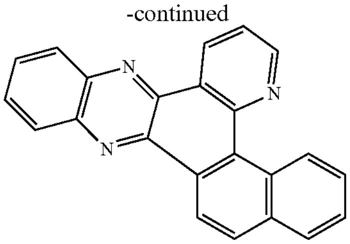
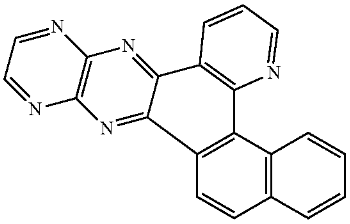
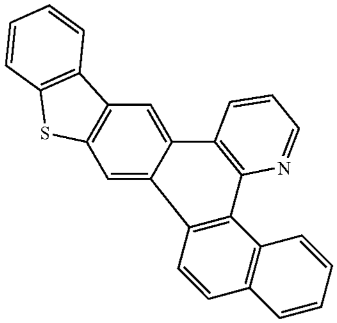
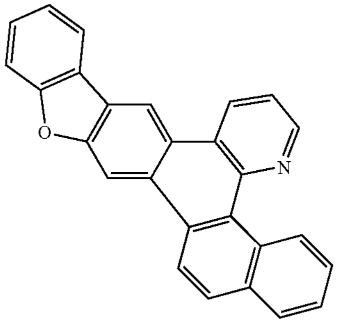
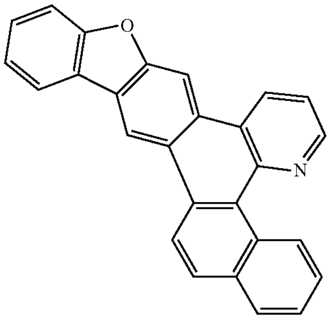
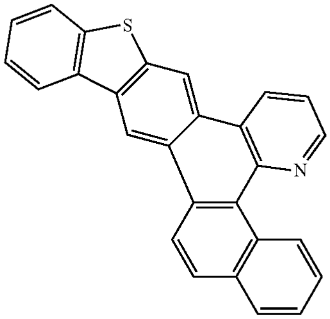
-continued
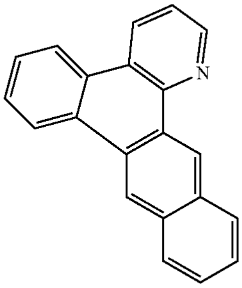
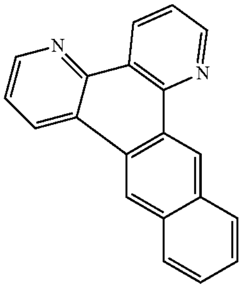
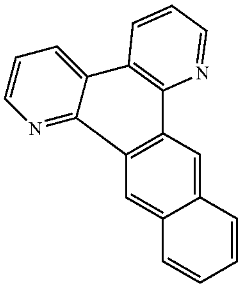
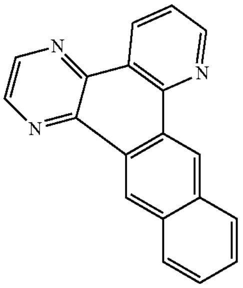
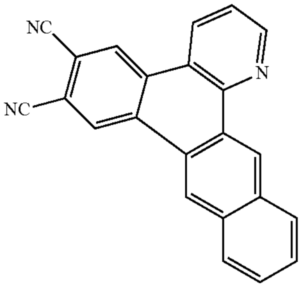
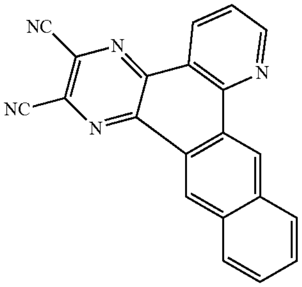
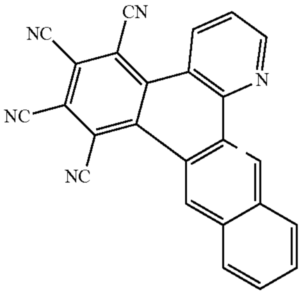
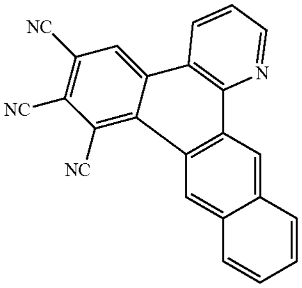

-continued
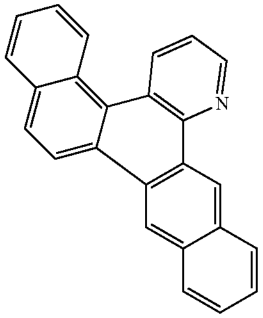
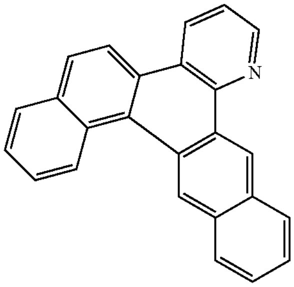
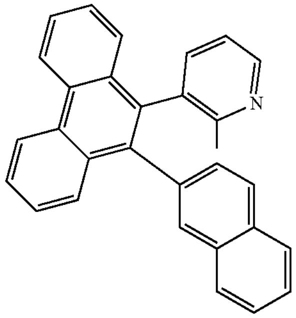
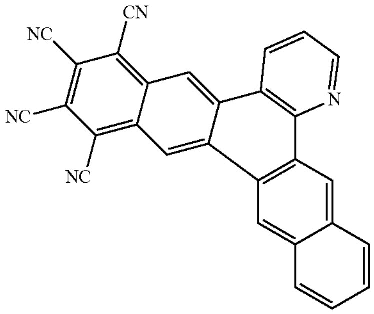
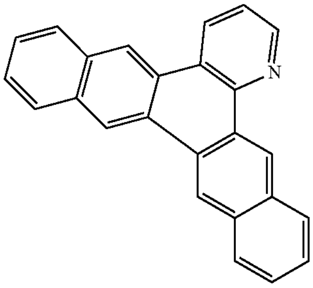
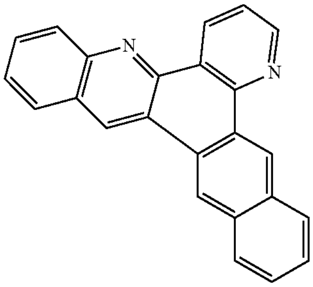
-continued
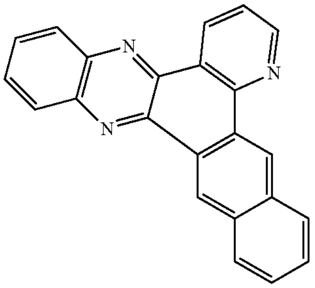
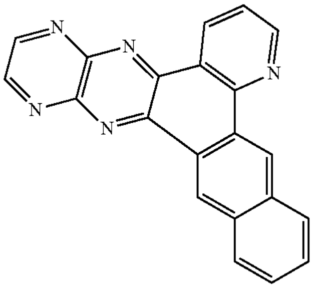
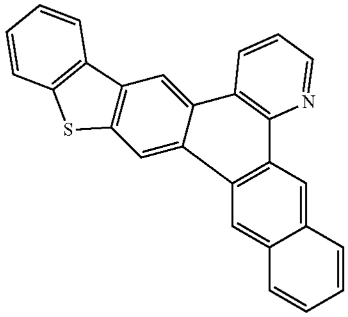
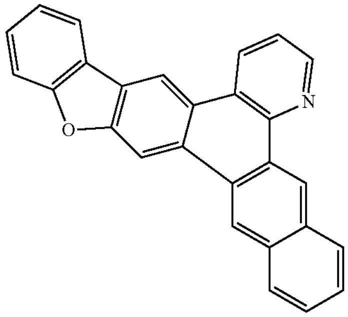
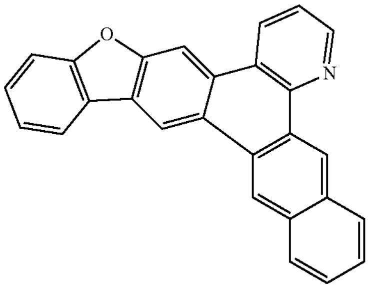

-continued
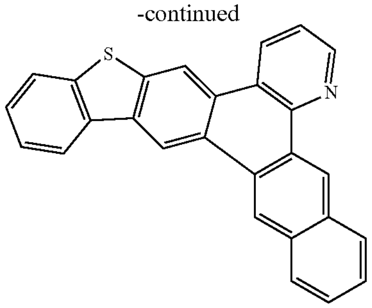
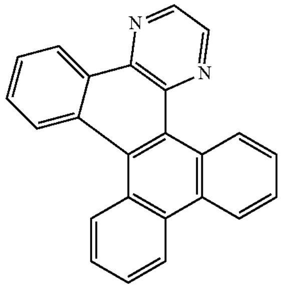
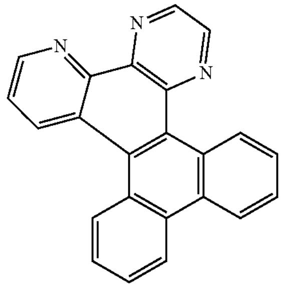
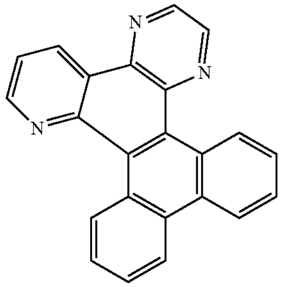
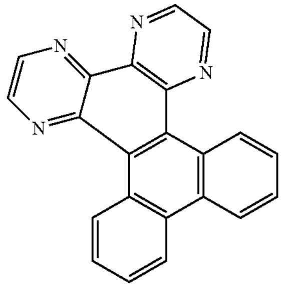
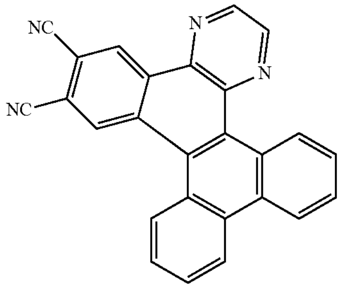
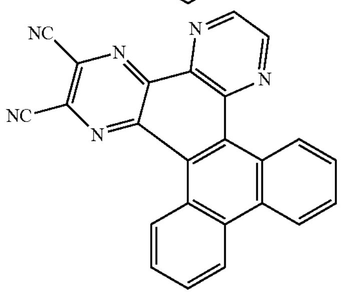
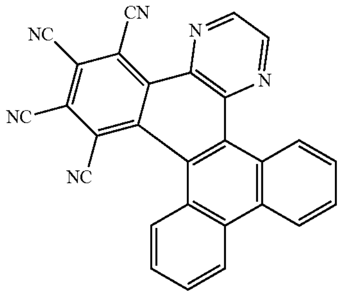
-continued
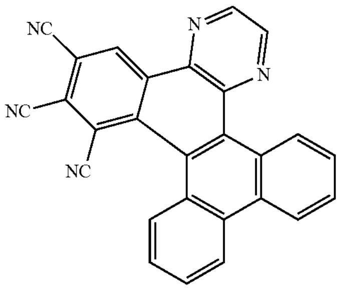
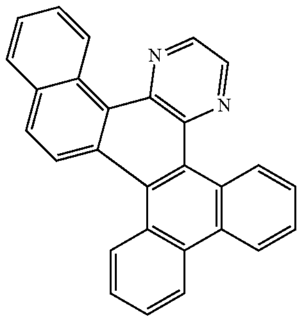
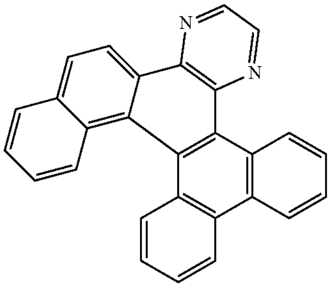
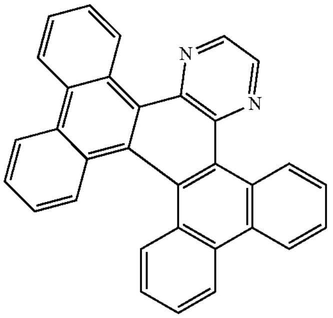
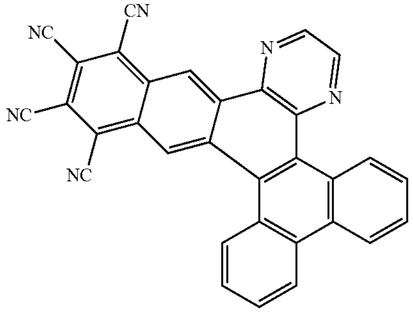

-continued
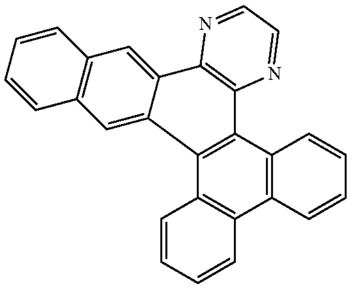
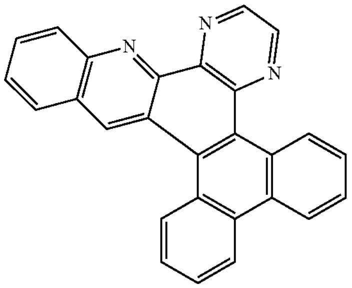
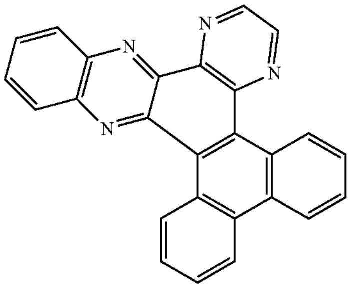
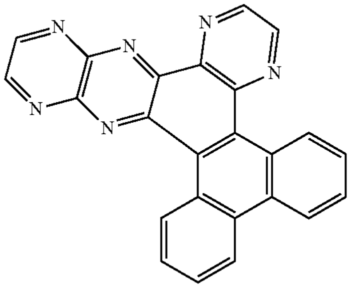
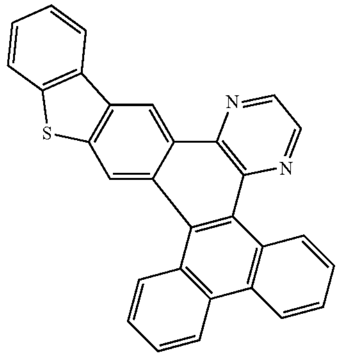
-continued
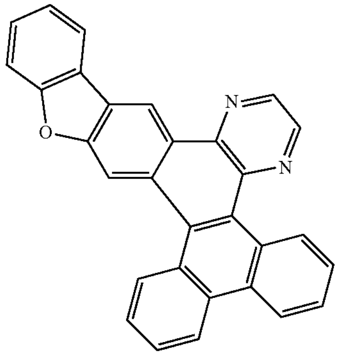
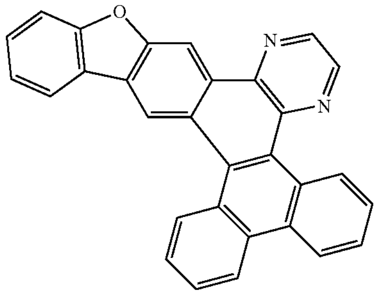
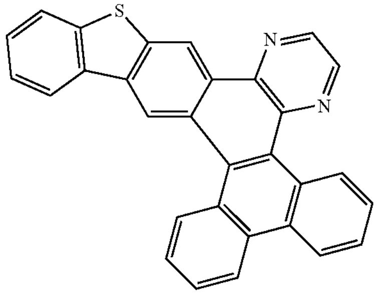
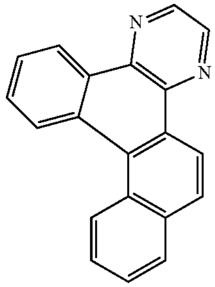
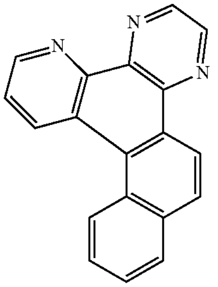
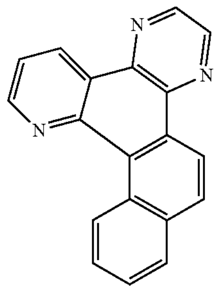
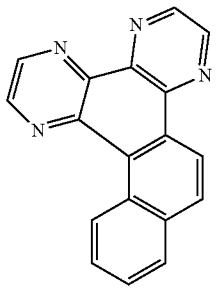

-continued
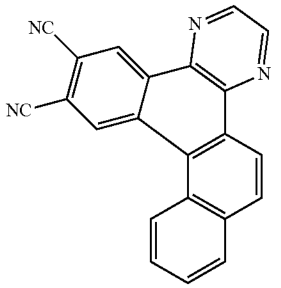
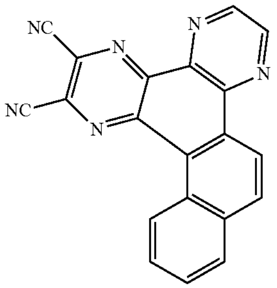
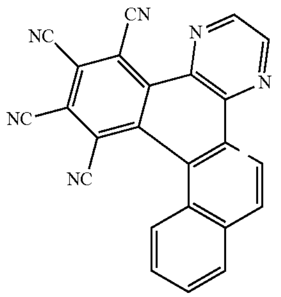
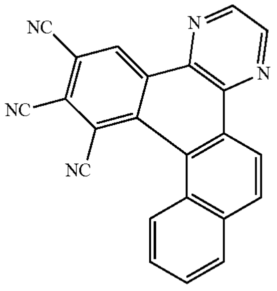
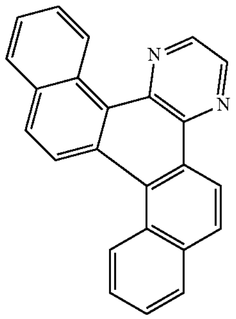
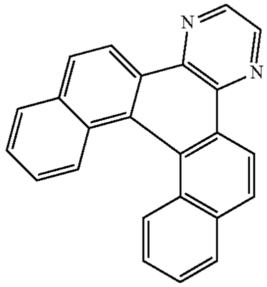
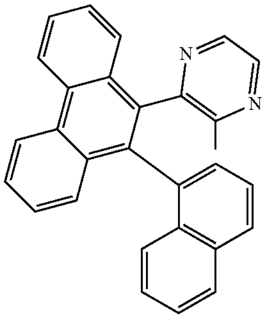
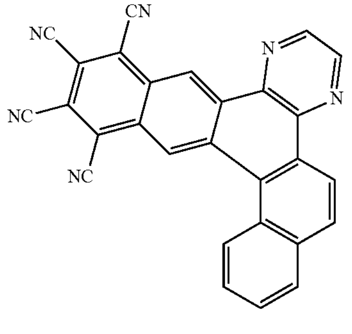
-continued
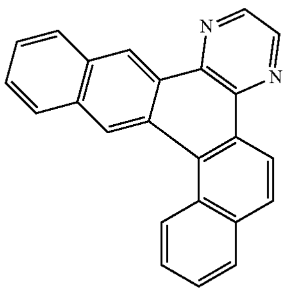
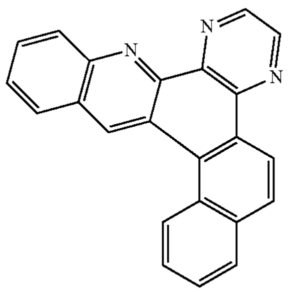
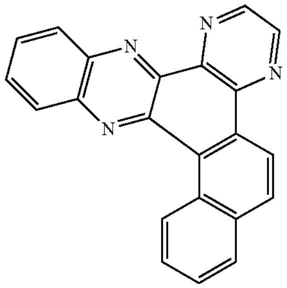
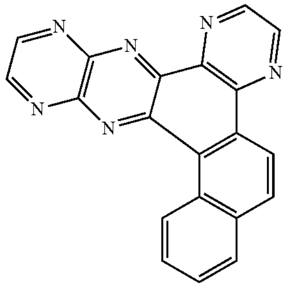
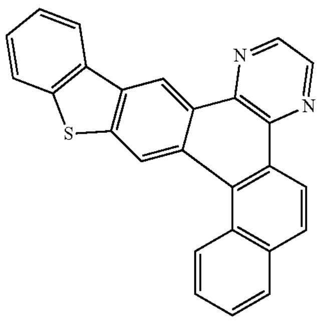
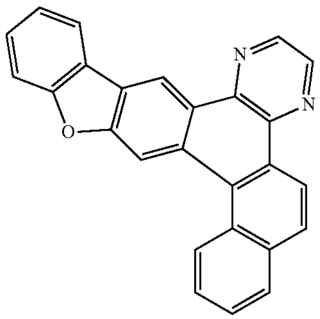
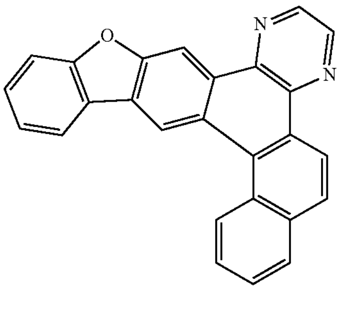

-continued
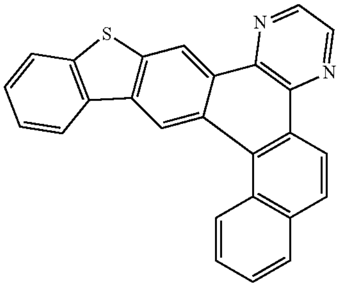
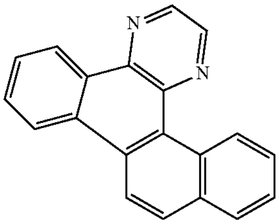
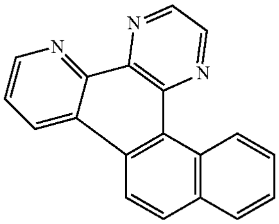
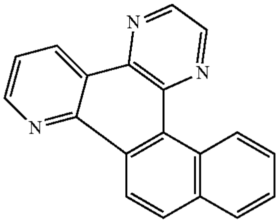
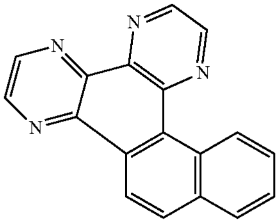
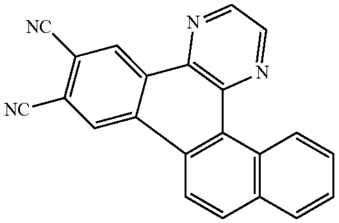
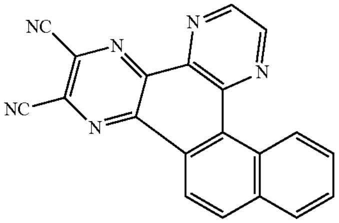
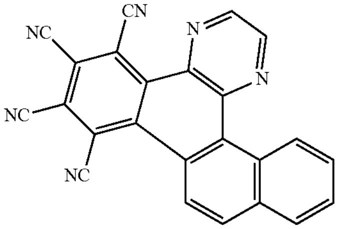
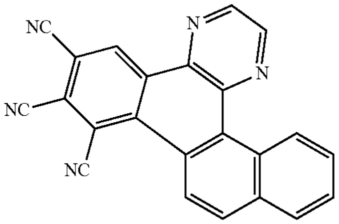
-continued
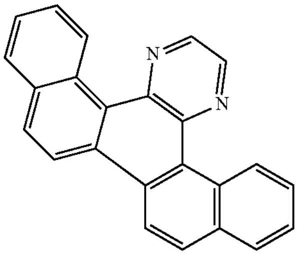
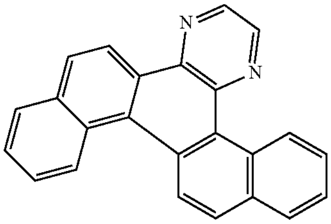
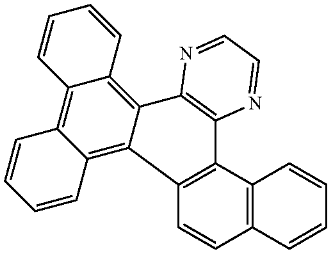
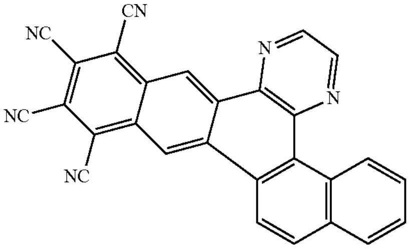
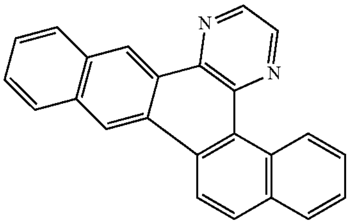
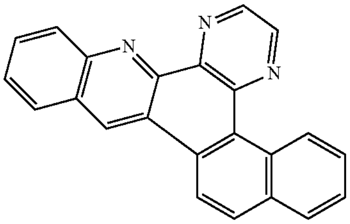
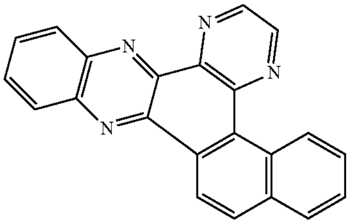

-continued
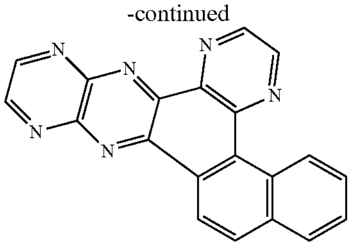
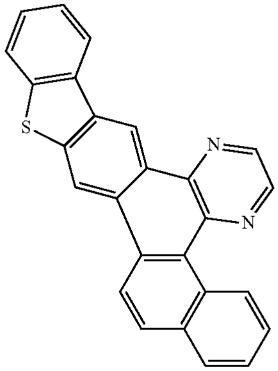
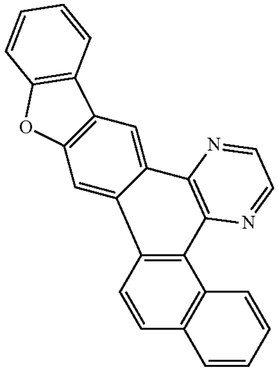
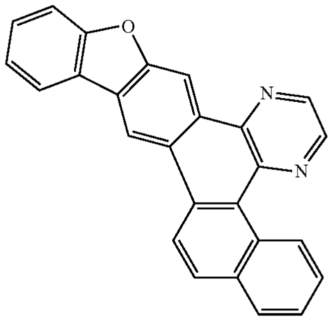
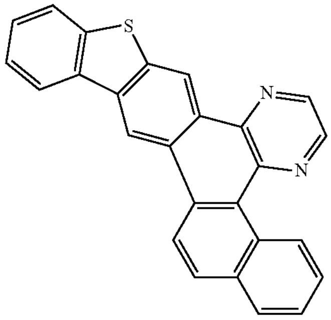
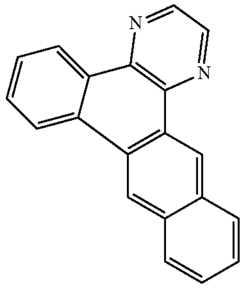
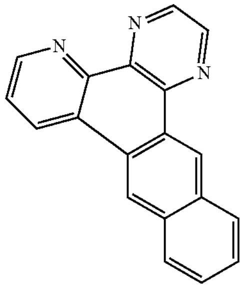
-continued
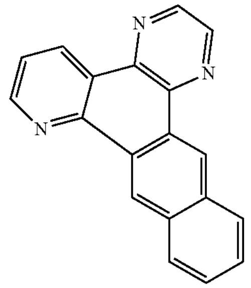
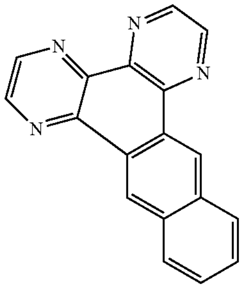
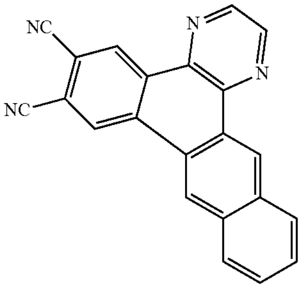
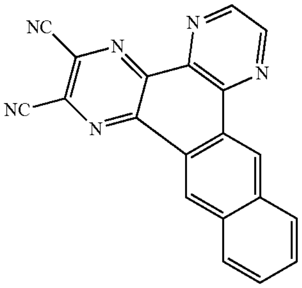
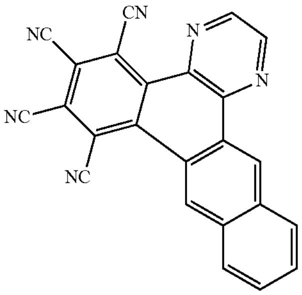
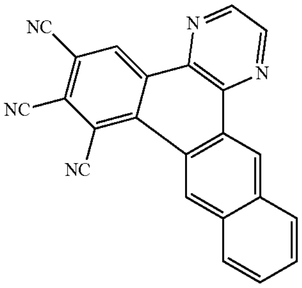

-continued
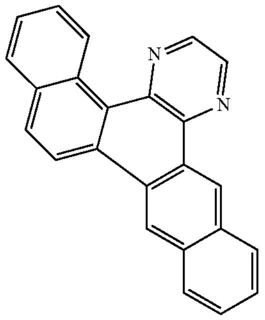
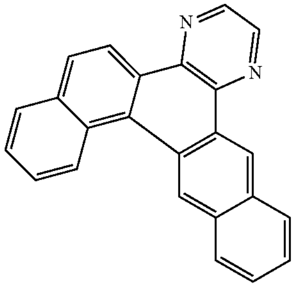
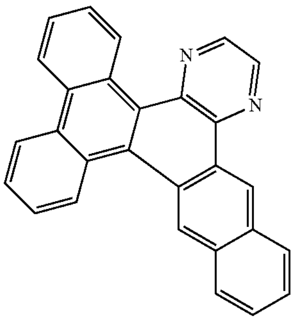
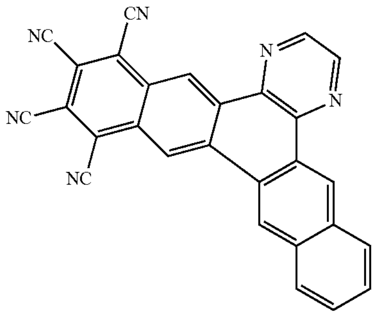
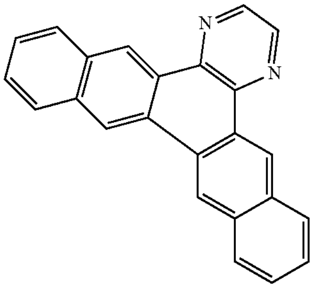
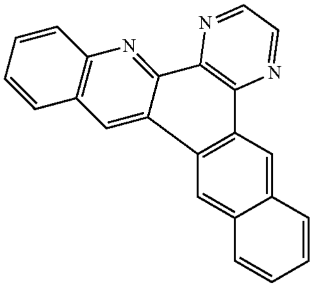
-continued
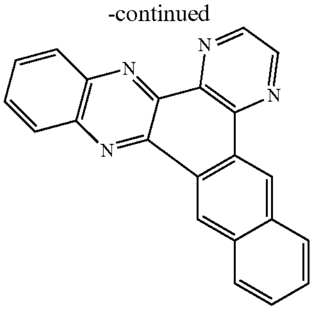
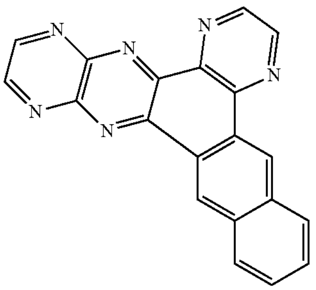
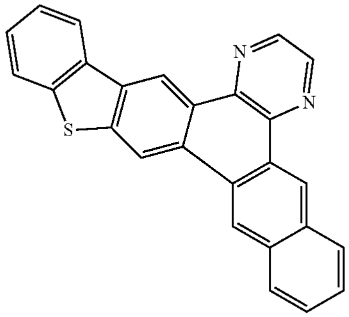
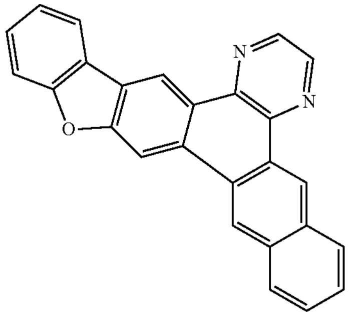
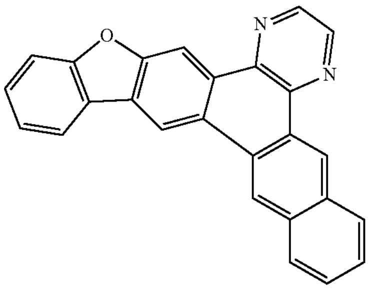

-continued
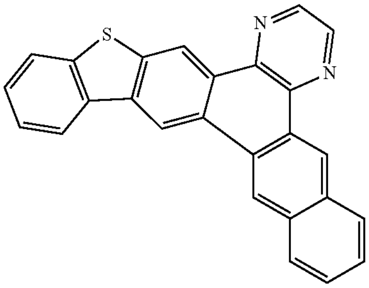
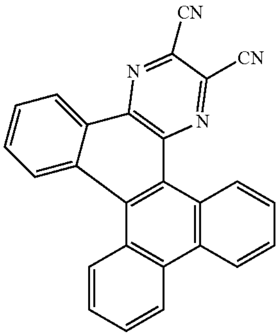
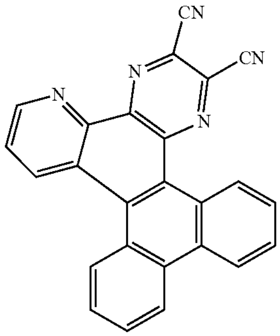
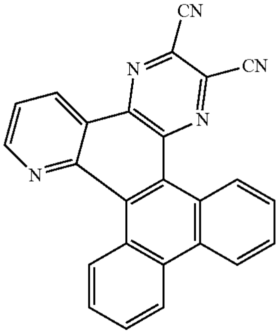
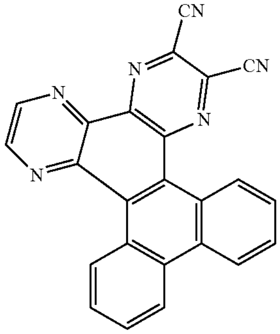
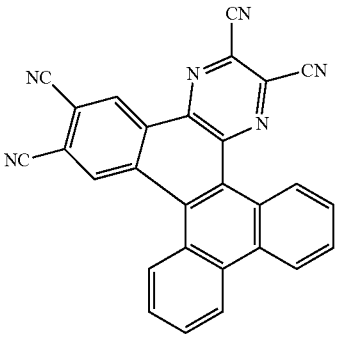
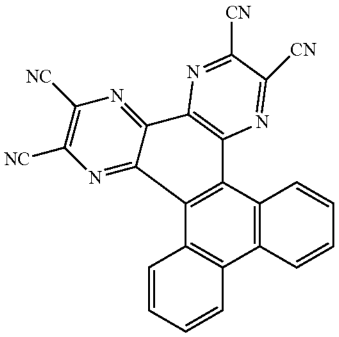
-continued
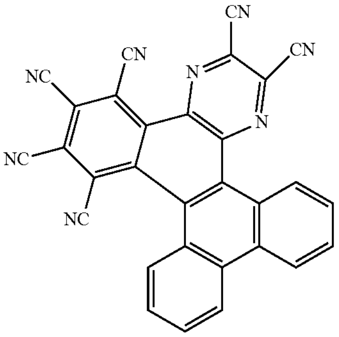
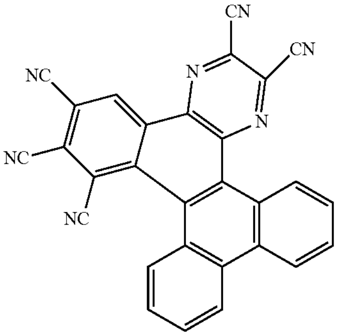
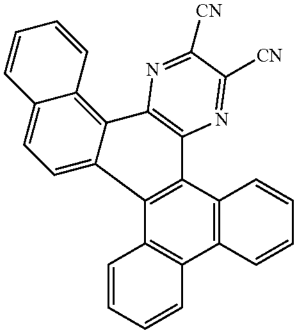
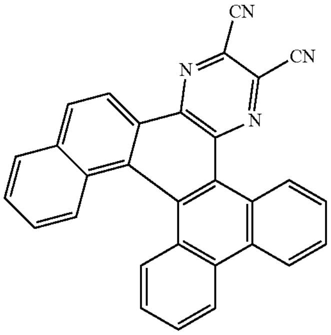
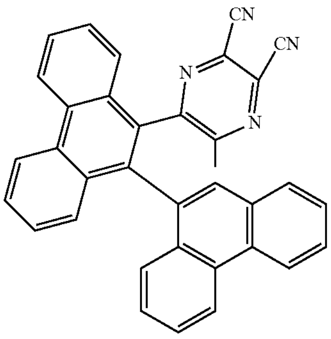

-continued
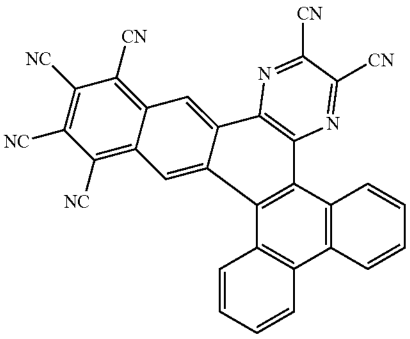
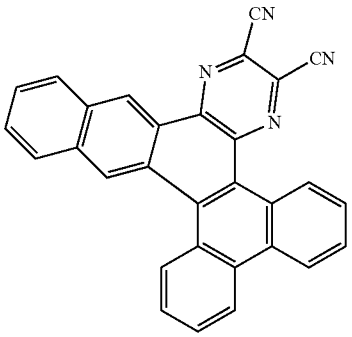
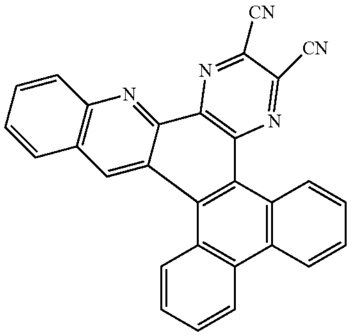
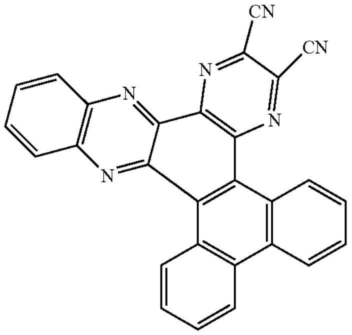
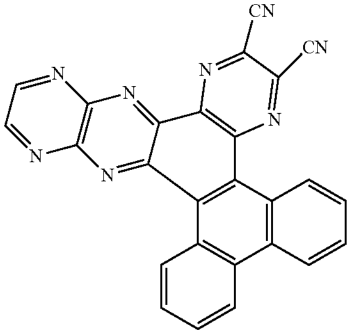
-continued
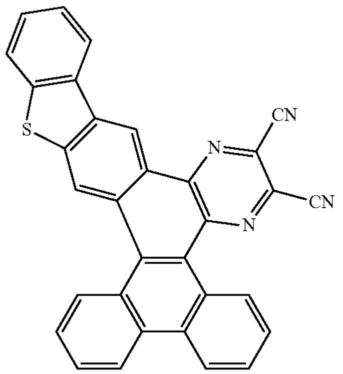
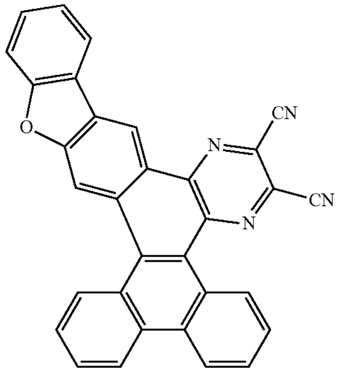
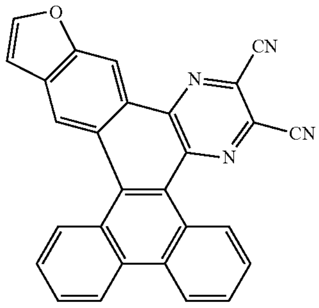
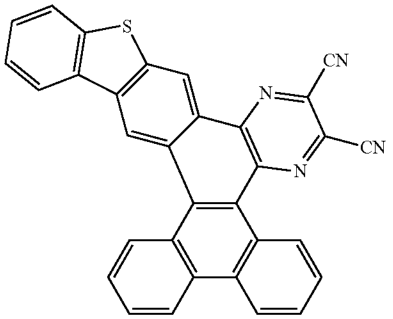
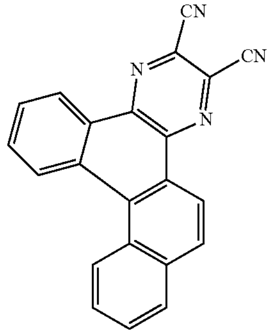
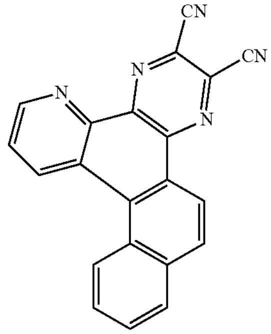

-continued
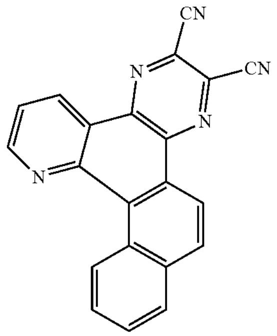
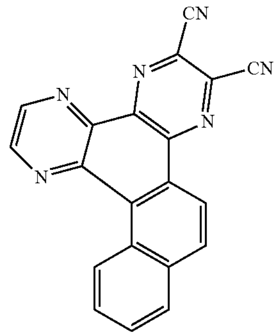
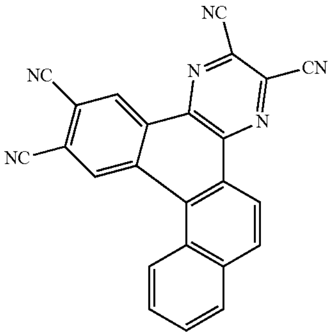
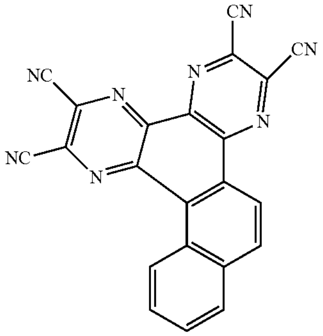
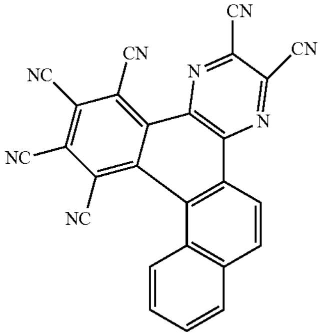
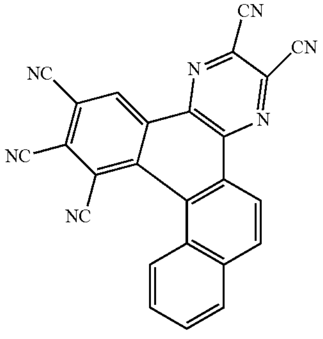
-continued
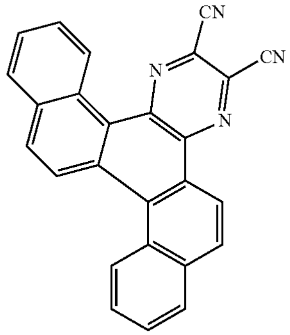
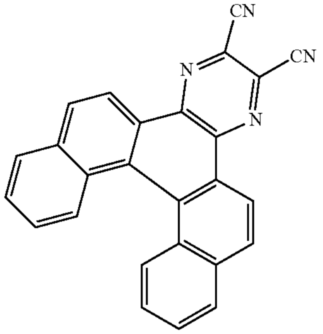
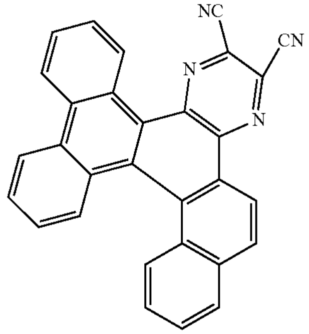
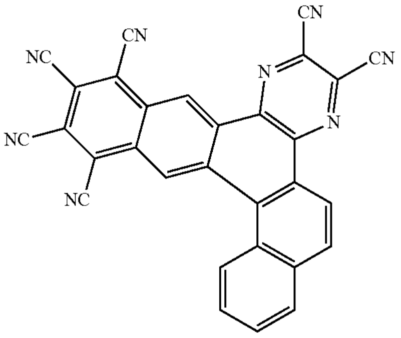
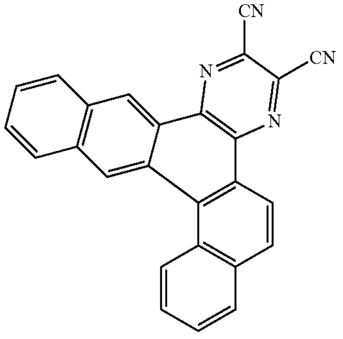

-continued
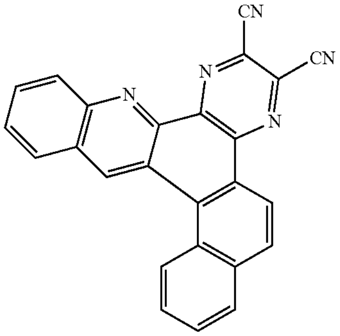
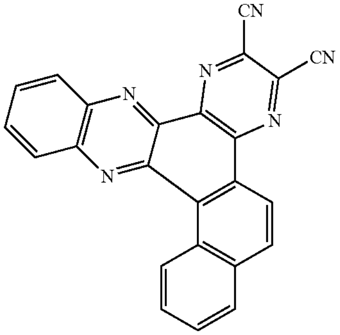
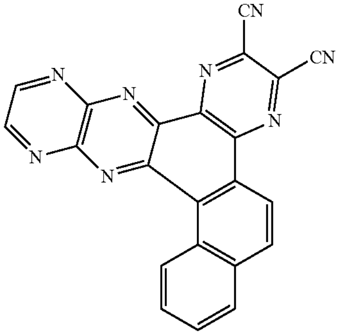
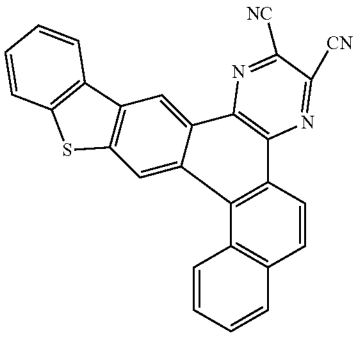
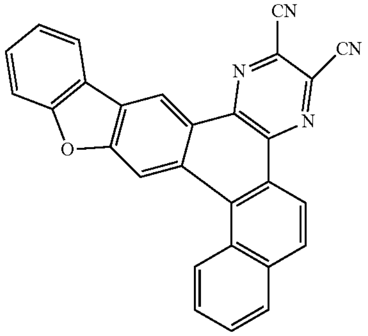
-continued
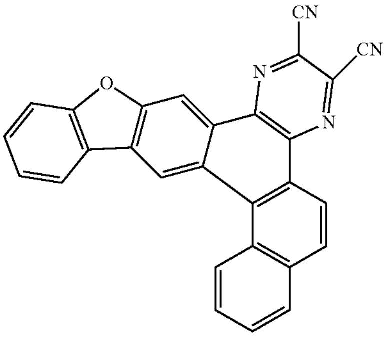
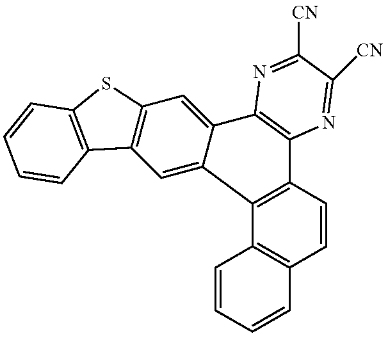
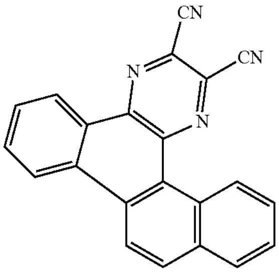
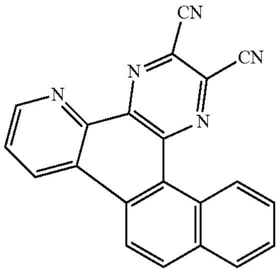
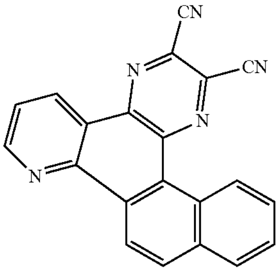
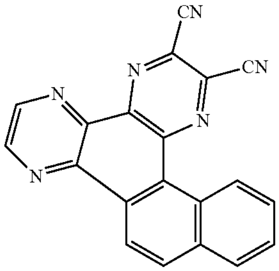
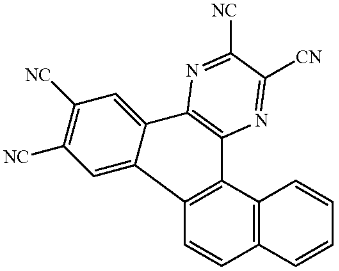

-continued
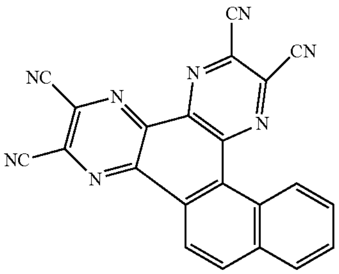
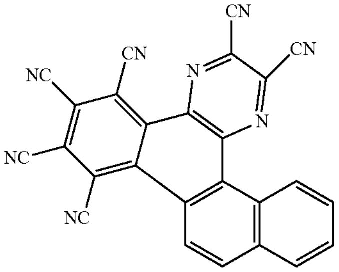
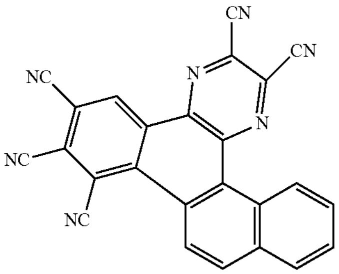
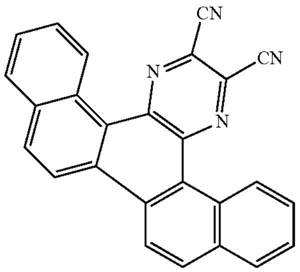
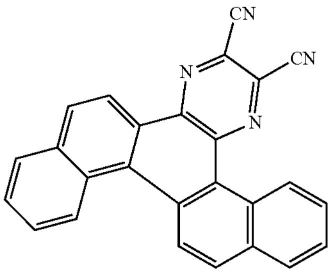
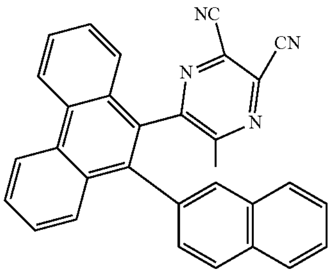
-continued
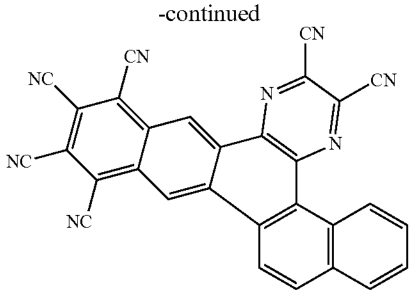
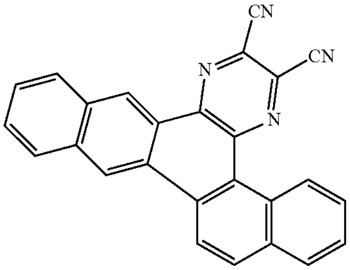
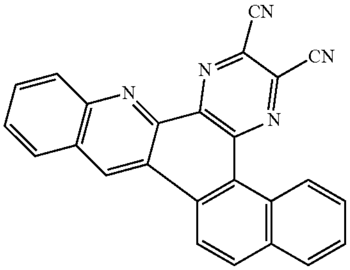
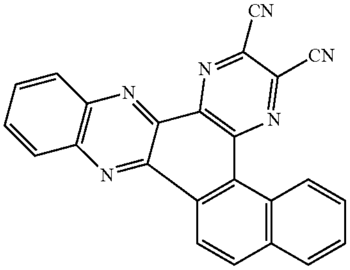
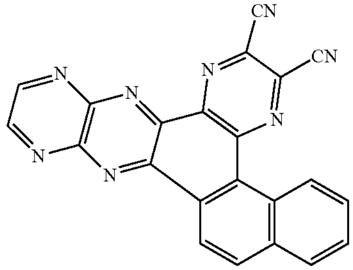
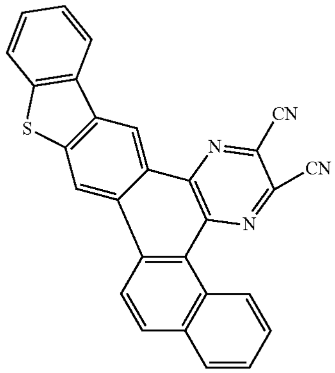

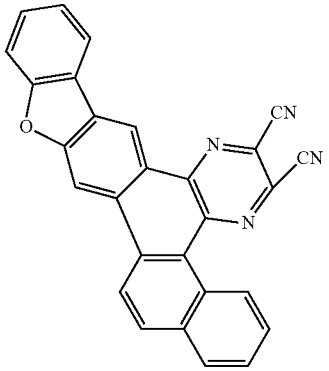
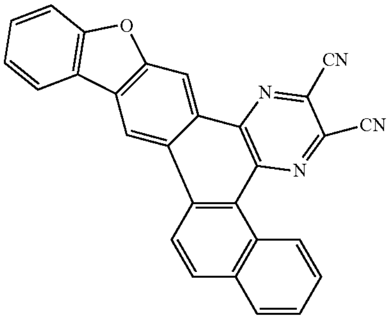
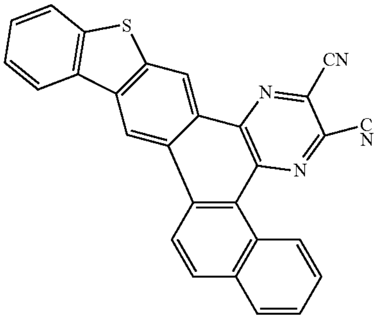
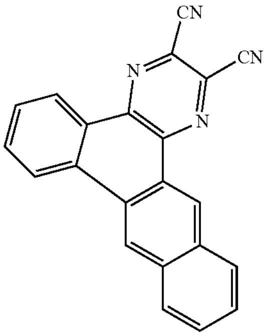
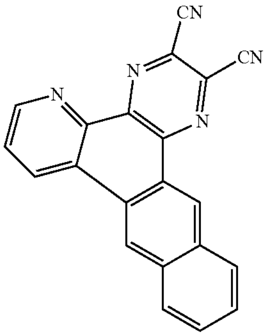
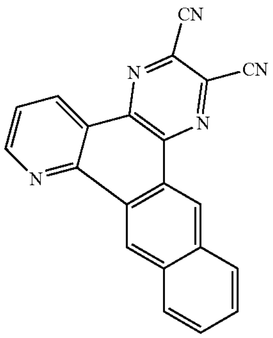
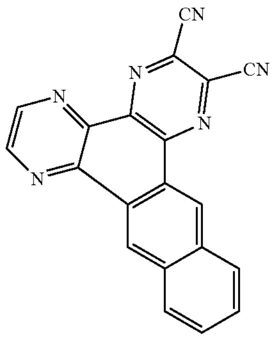
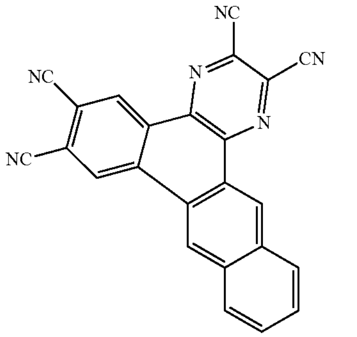
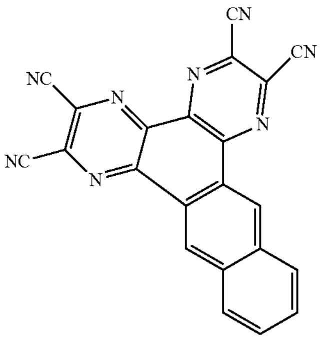
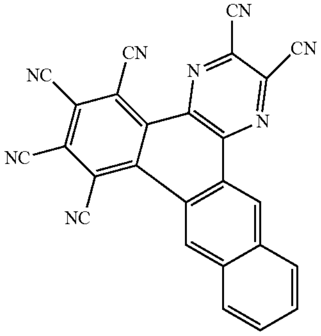
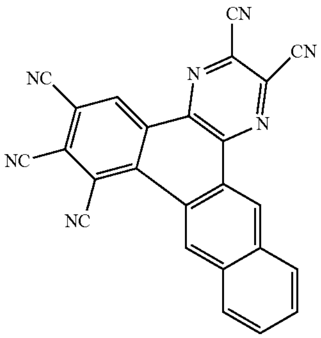
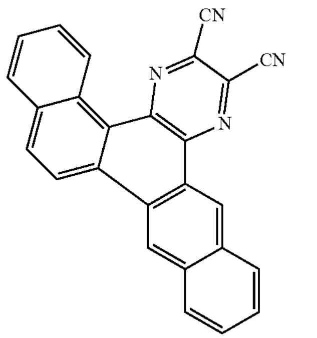

-continued
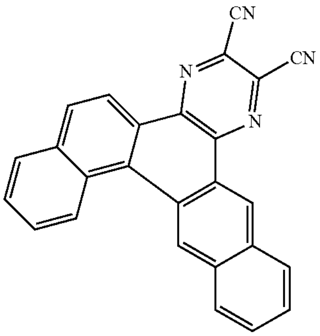
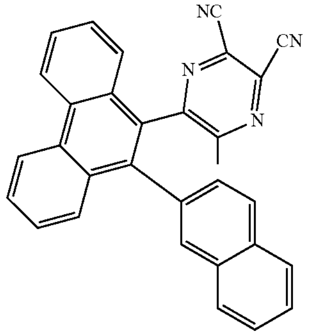
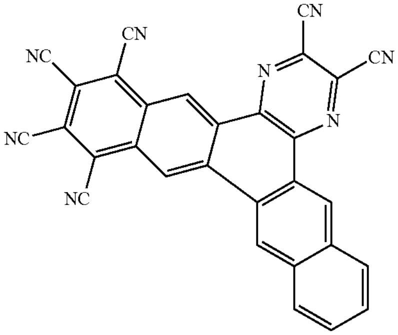
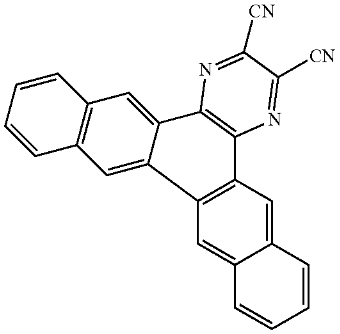
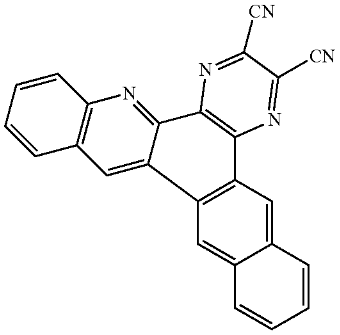
-continued
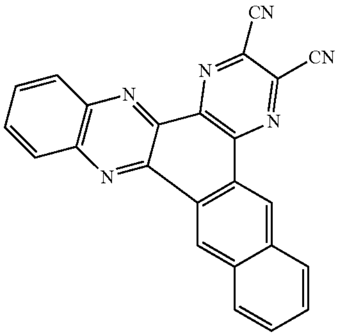
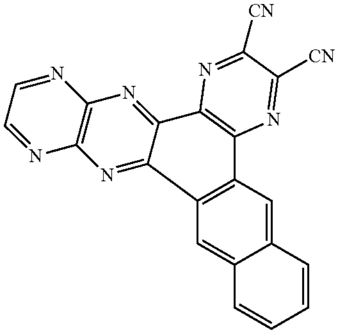
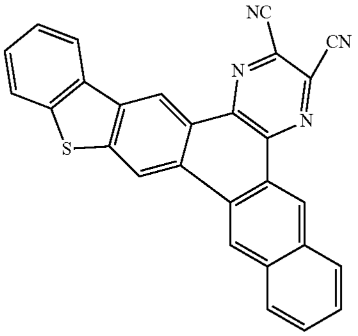
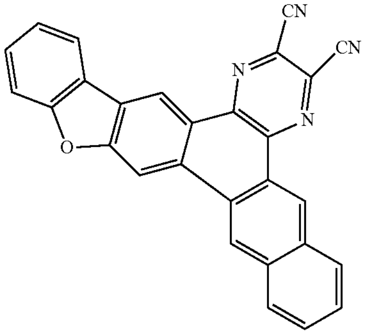
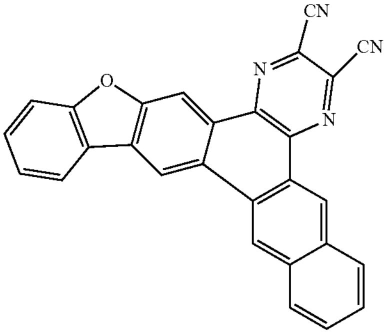

-continued
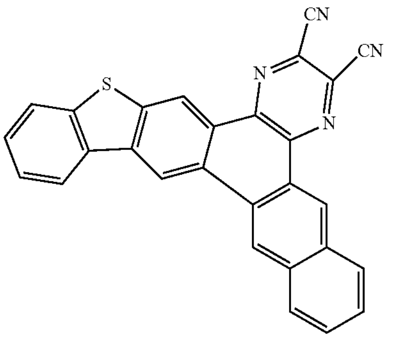
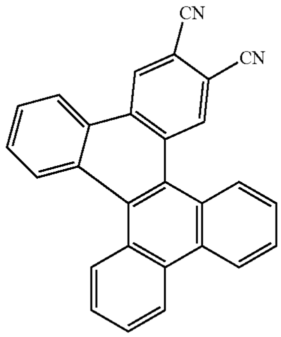
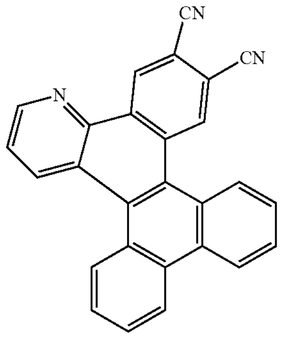
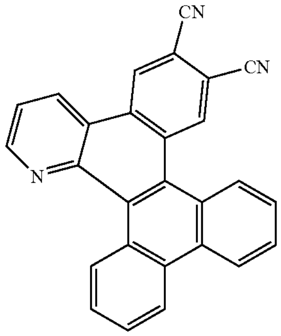
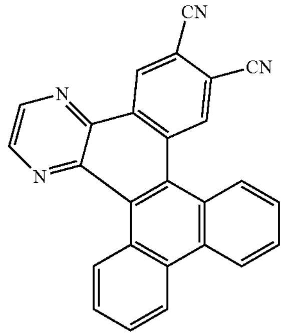
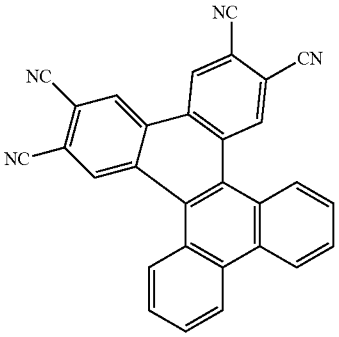
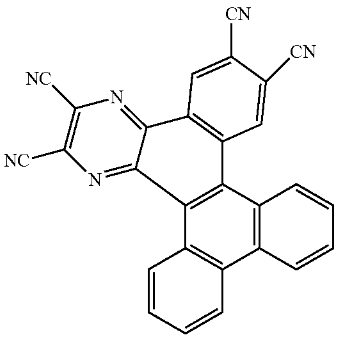
-continued
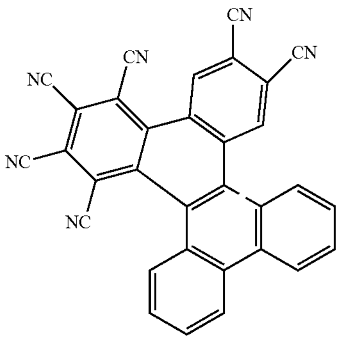
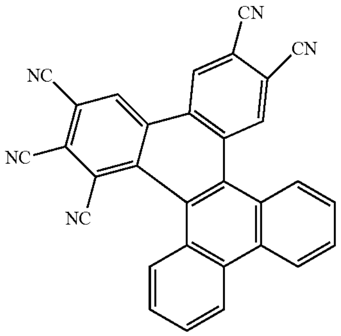
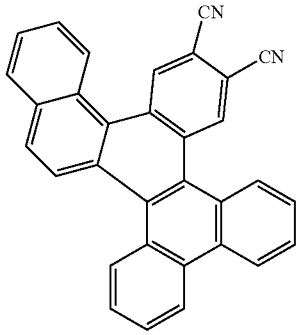
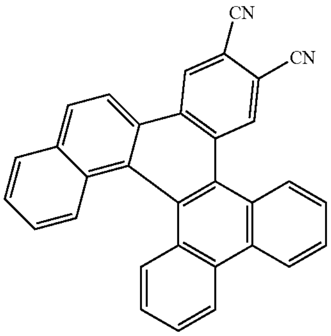
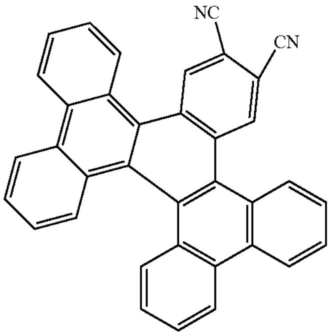

-continued
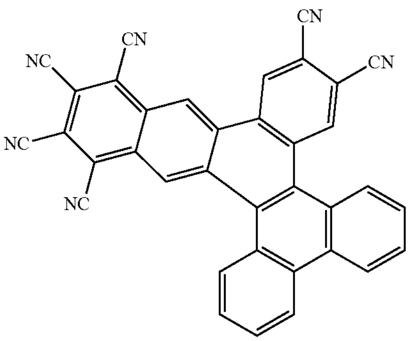
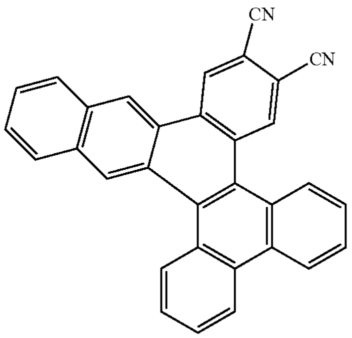
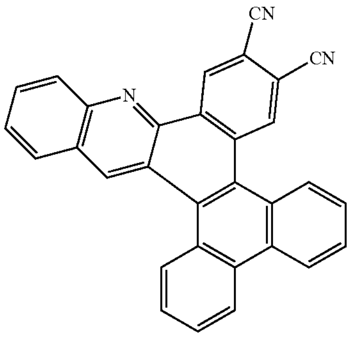
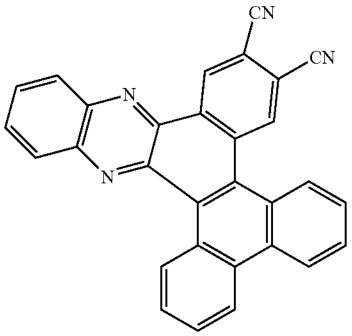
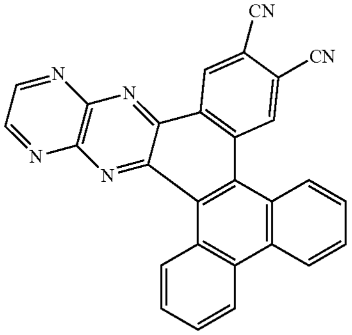
-continued
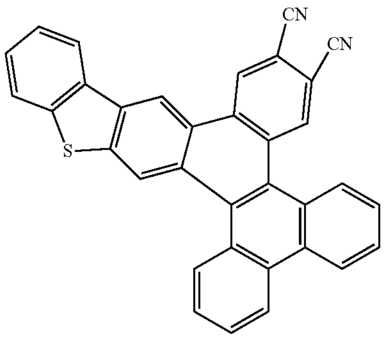
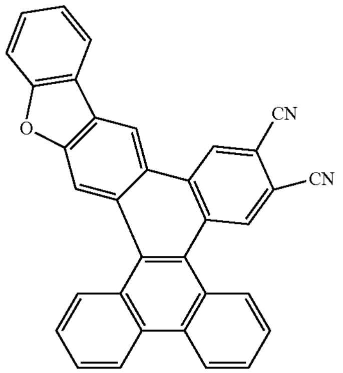
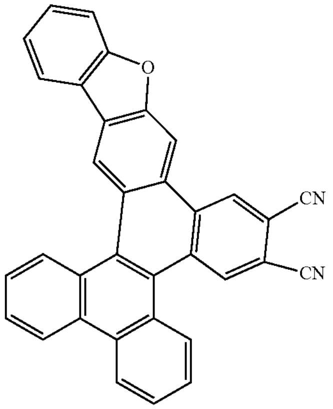
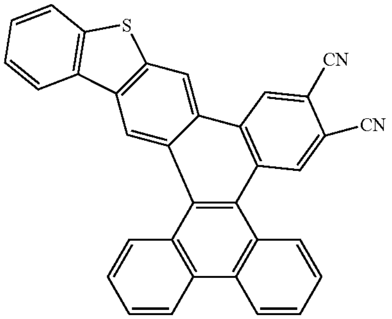

-continued
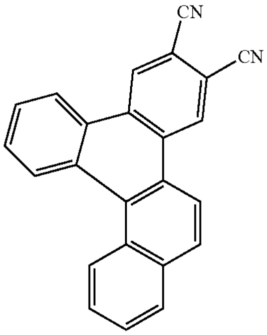
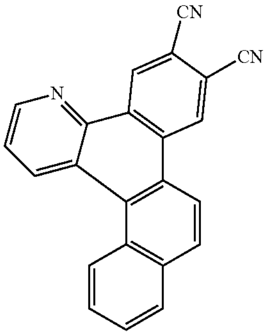
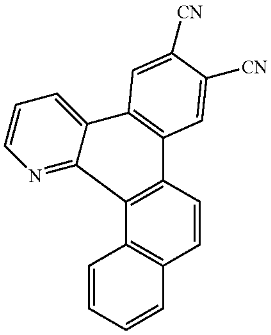
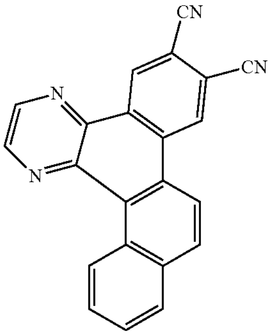
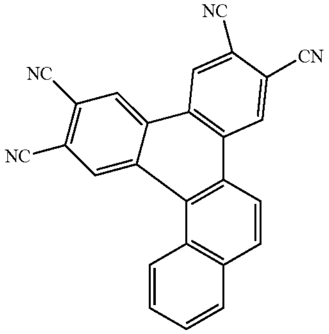
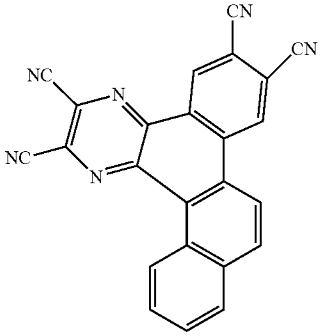
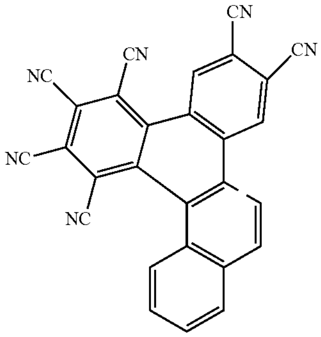
-continued
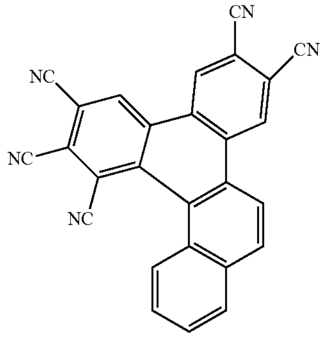
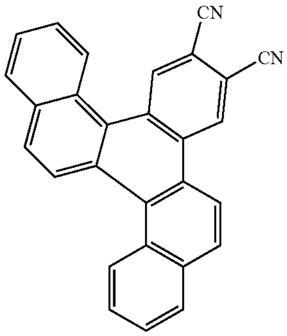
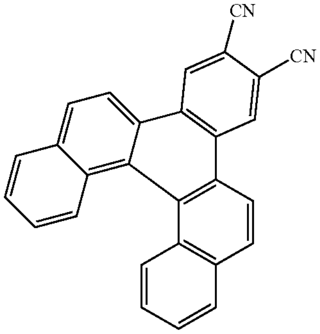
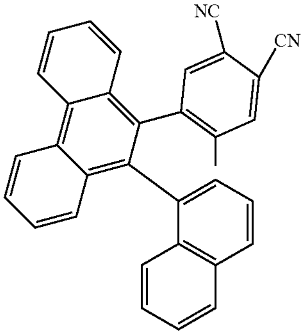
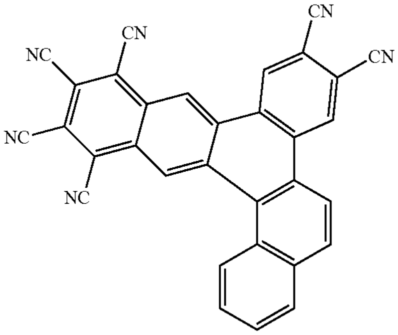

-continued
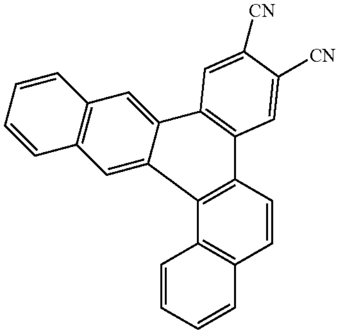
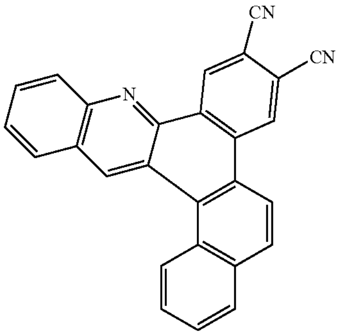
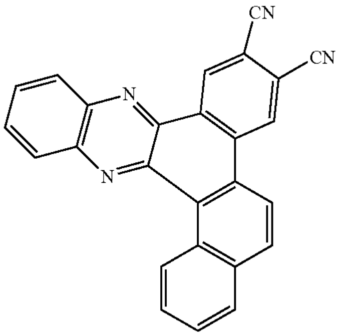
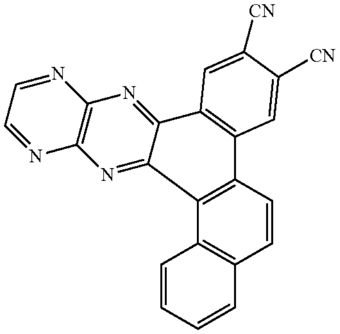
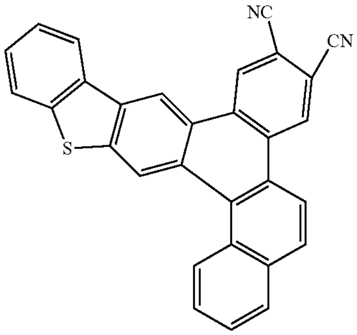
-continued
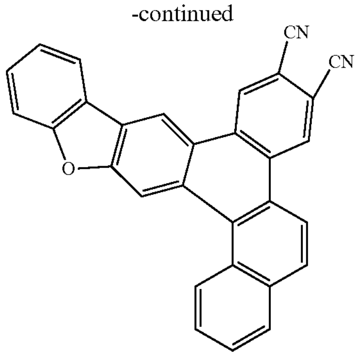
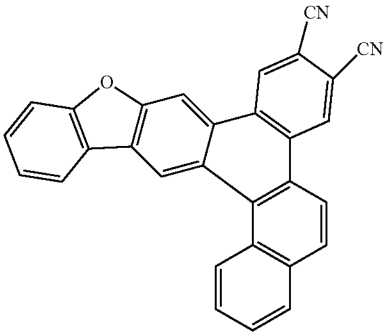
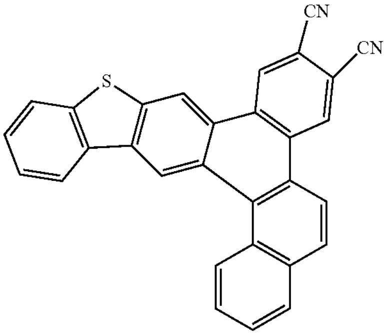
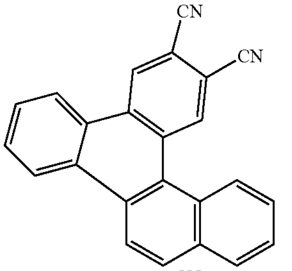
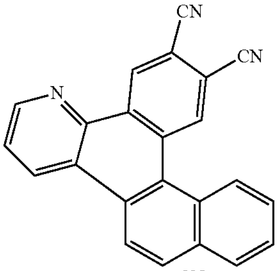
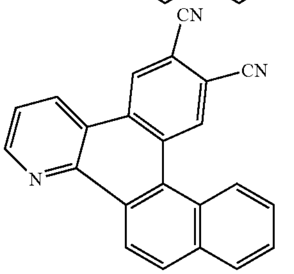
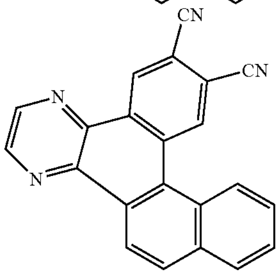

-continued
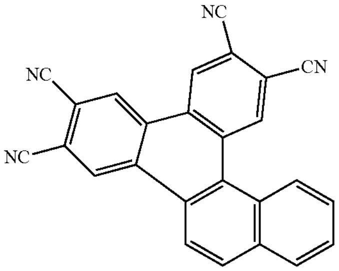
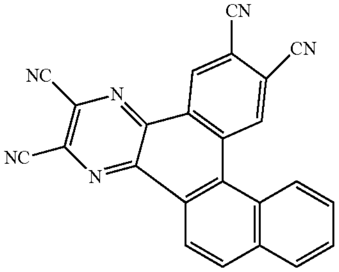
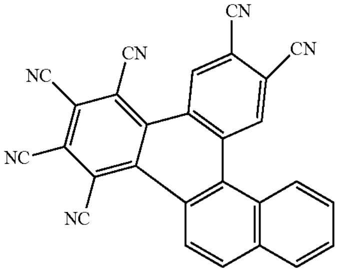
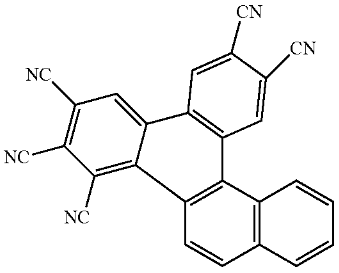
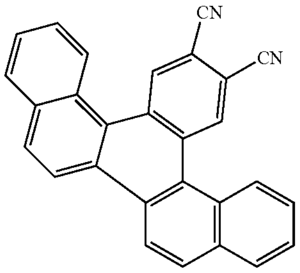
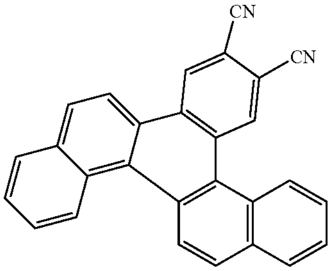
-continued
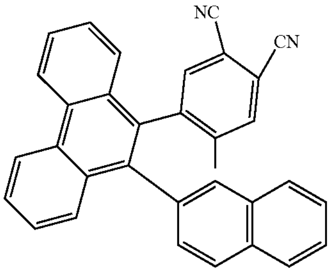
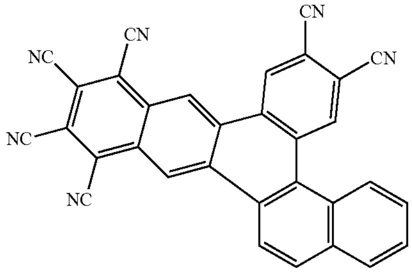
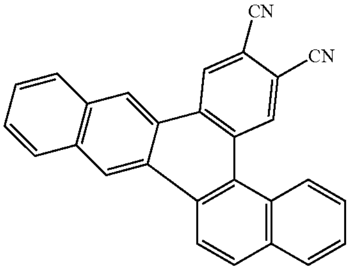
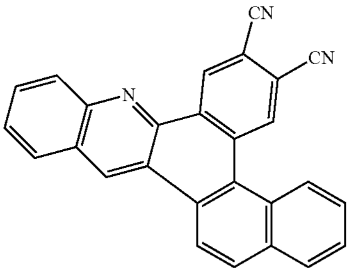
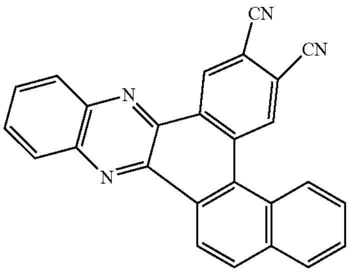
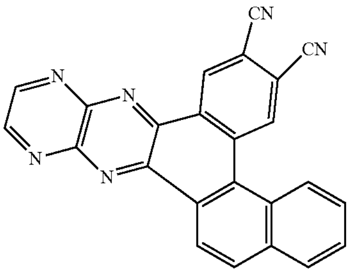

-continued
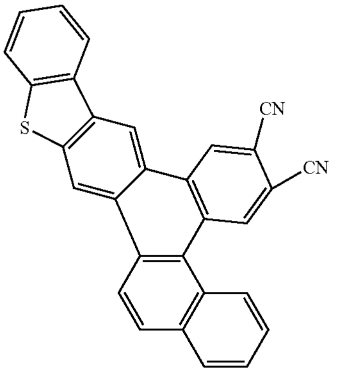
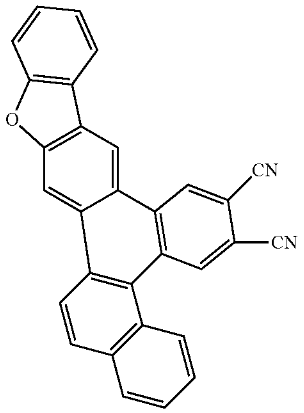
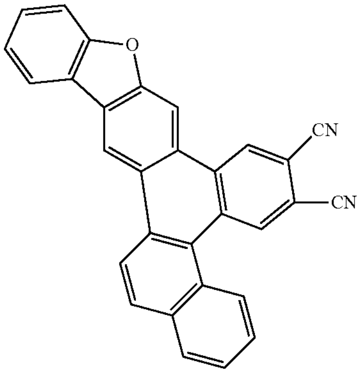
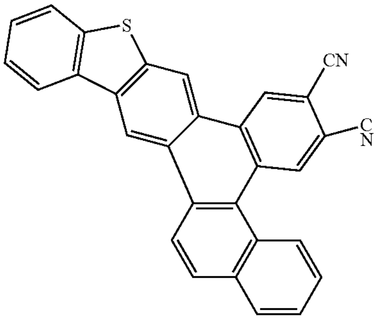
-continued
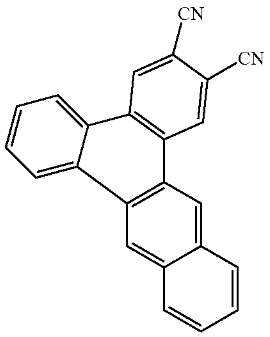
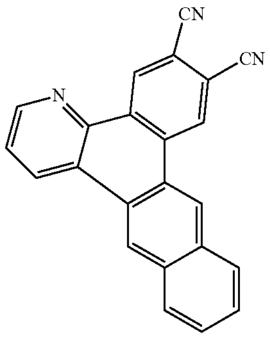
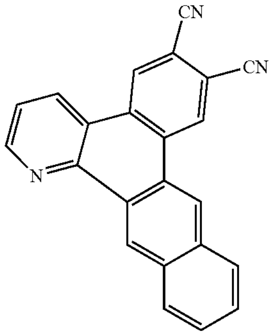
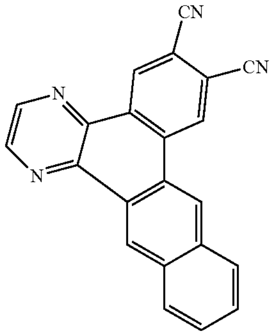
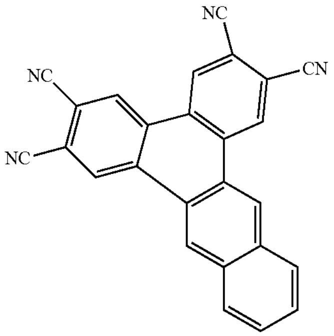
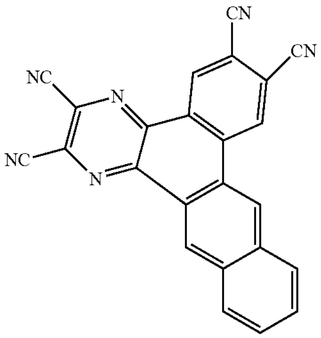
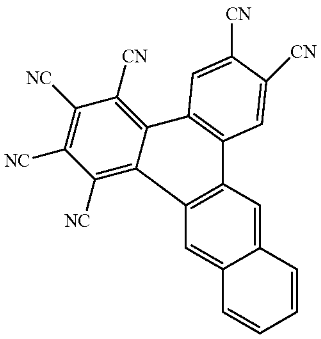

-continued
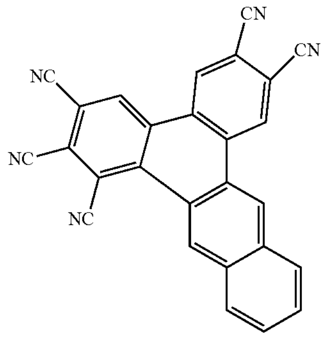
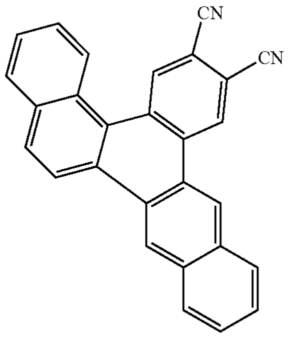
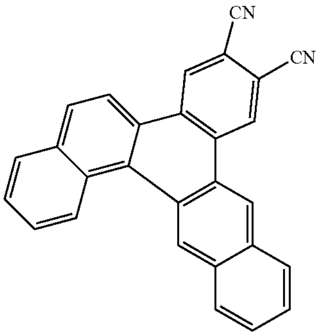
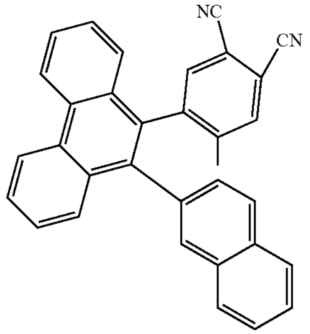
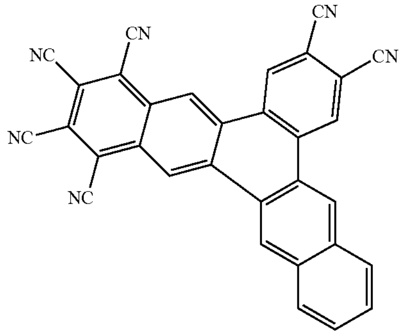
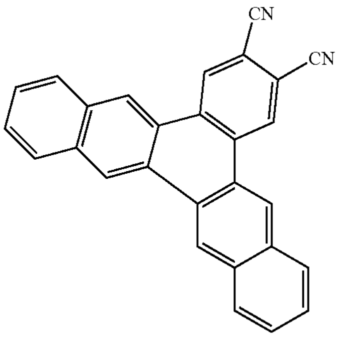
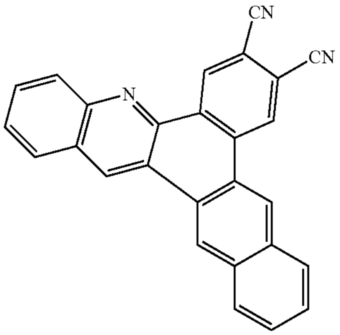
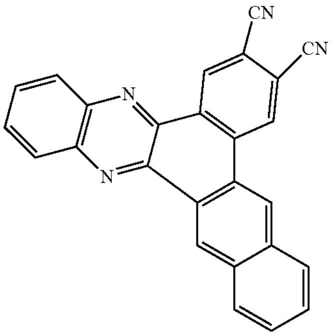
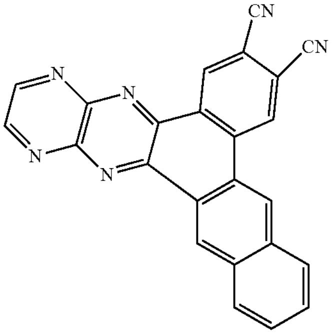
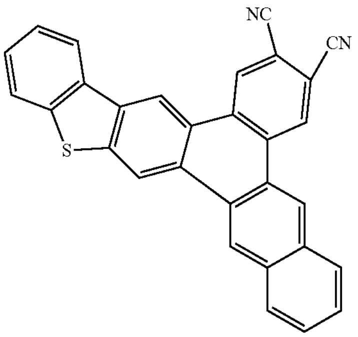
-continued -continued
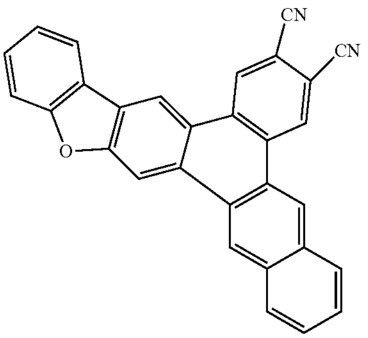
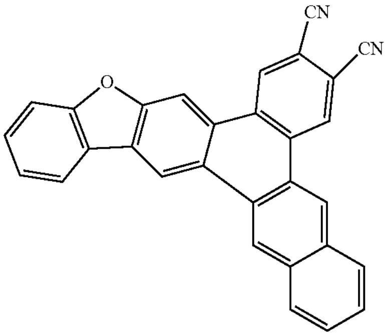
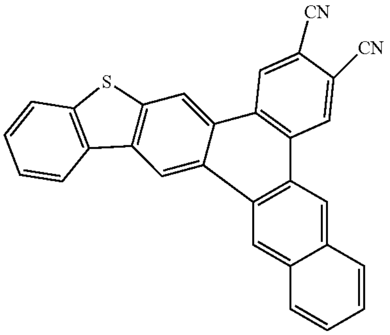
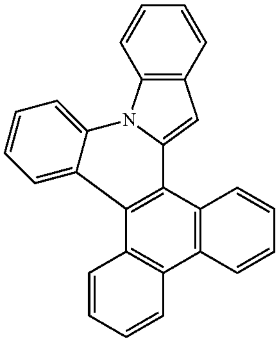
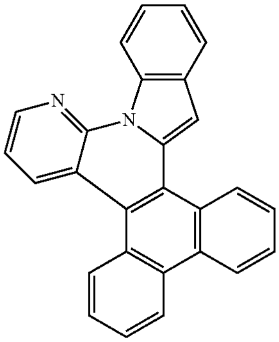
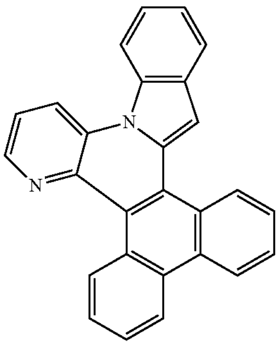
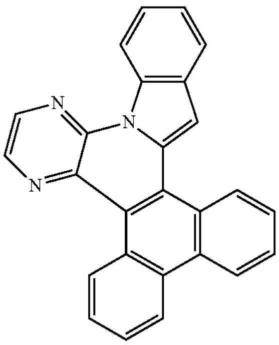
-continued
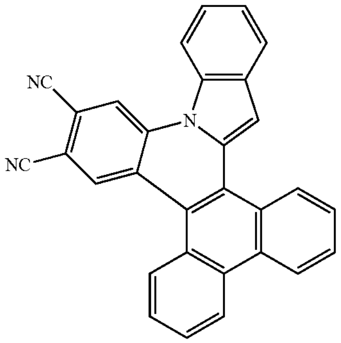
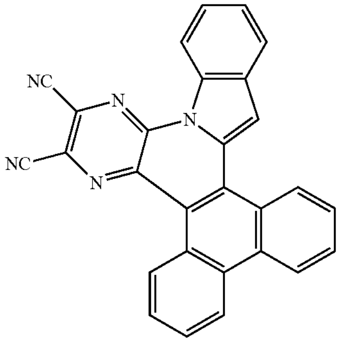
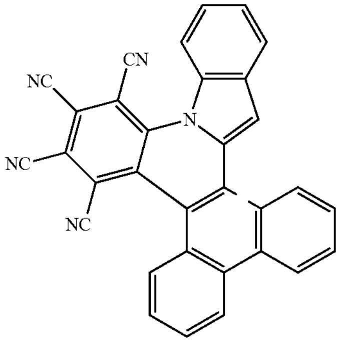
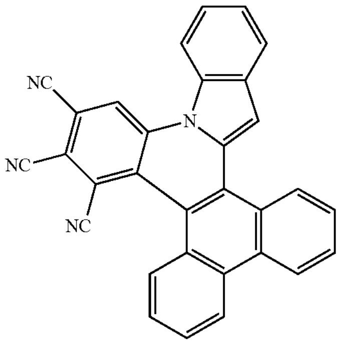
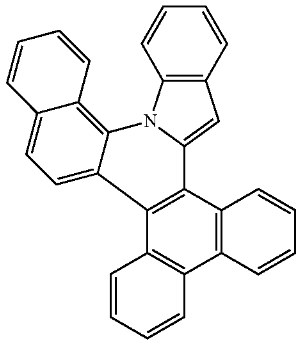

-continued
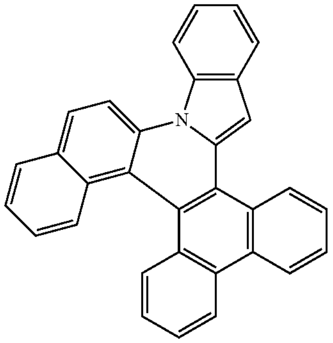
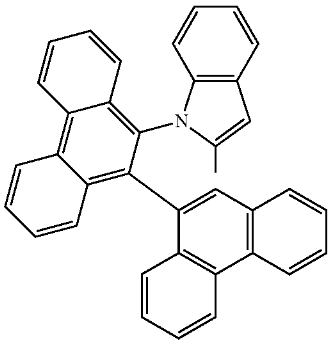
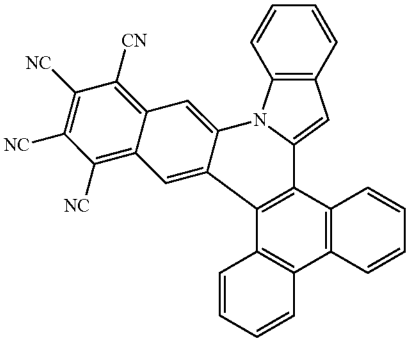
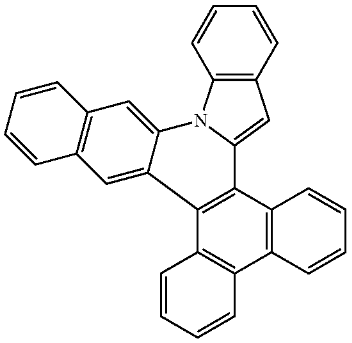
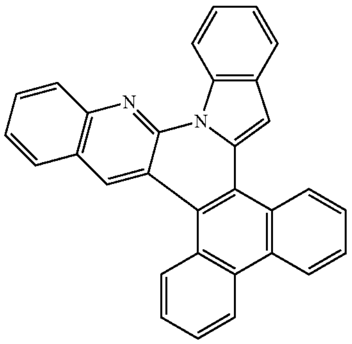
-continued
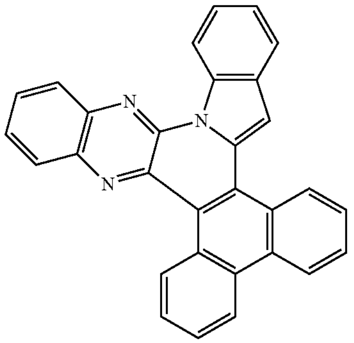
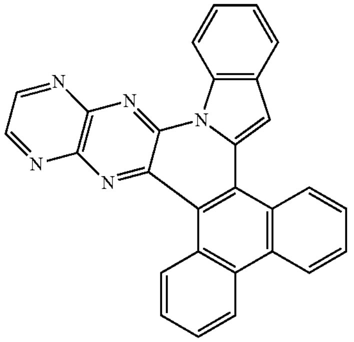
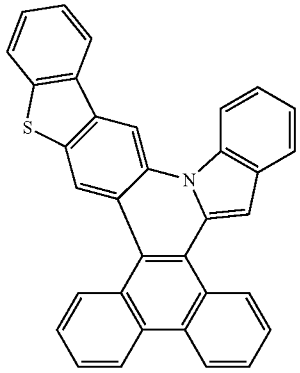
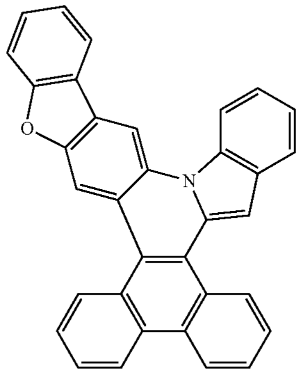

-continued
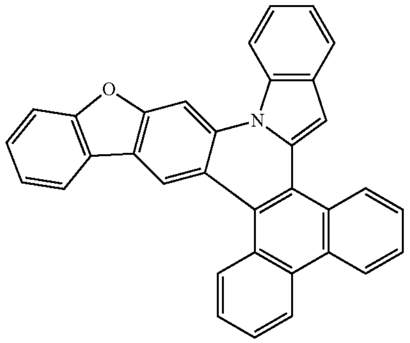
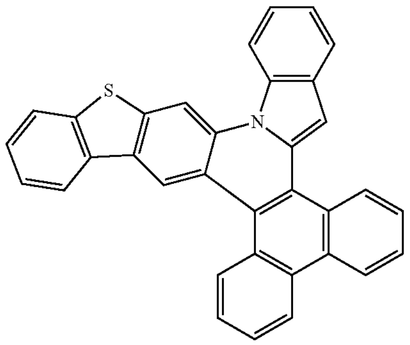
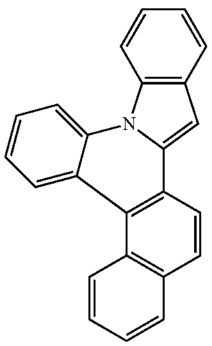
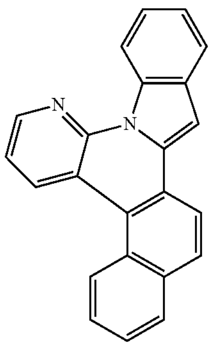
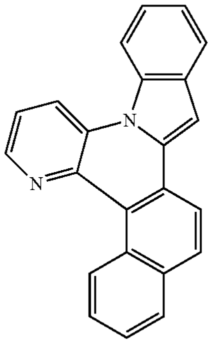
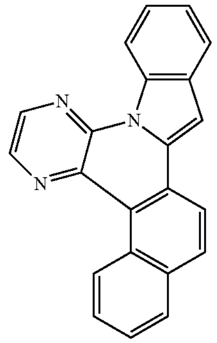
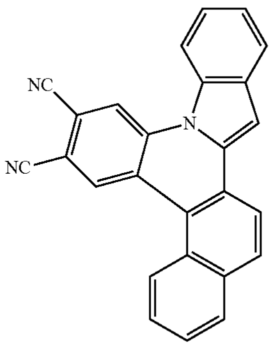
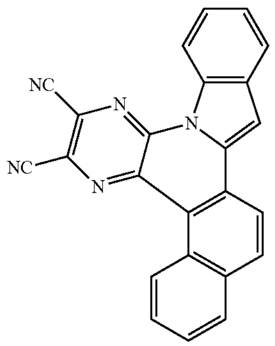
-continued
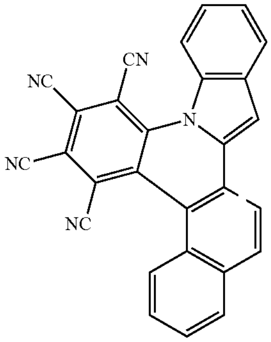
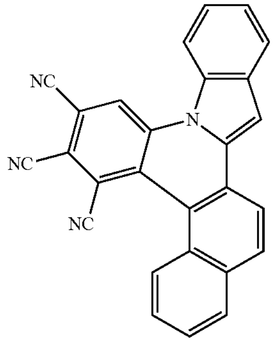
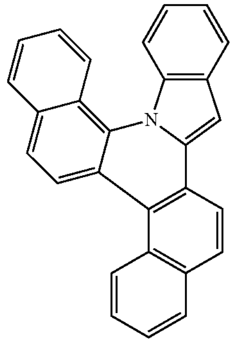
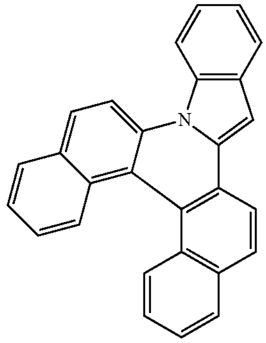
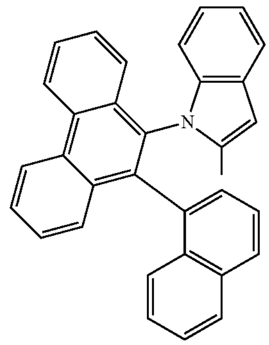
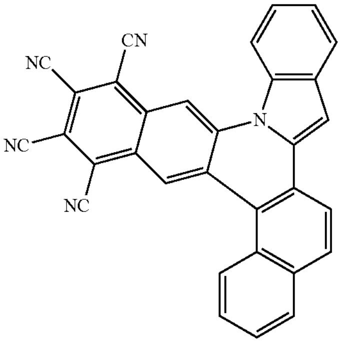
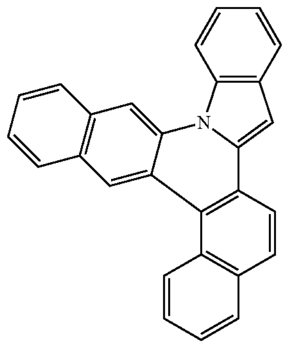
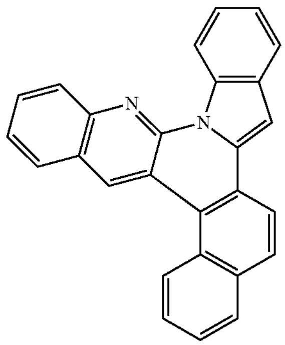

-continued
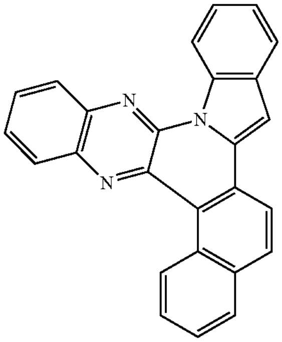
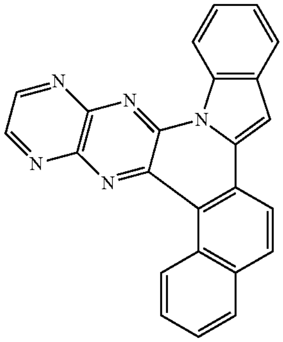
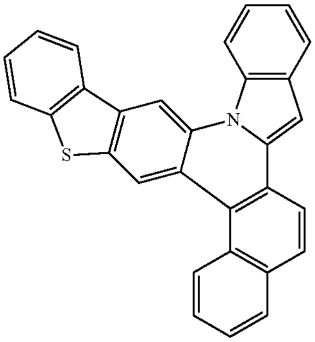
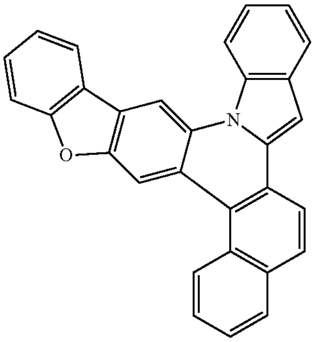
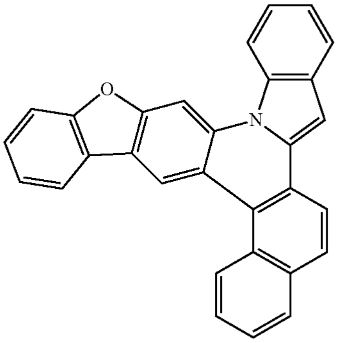
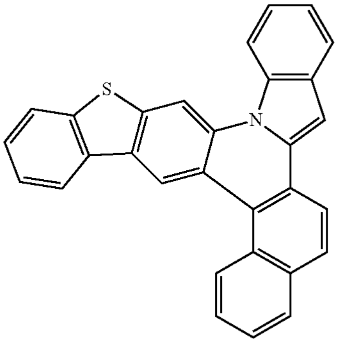
-continued
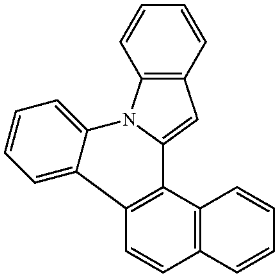
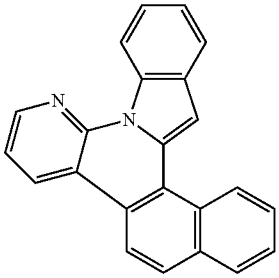
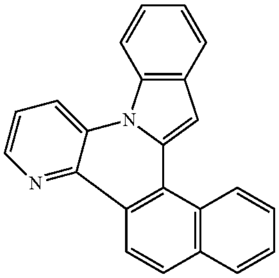
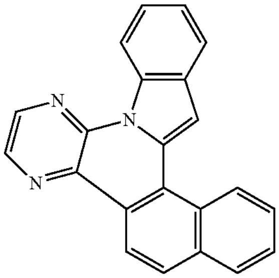
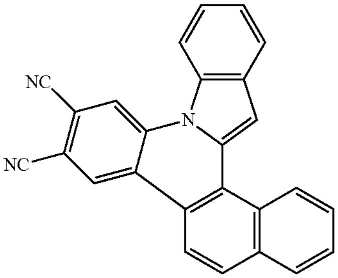
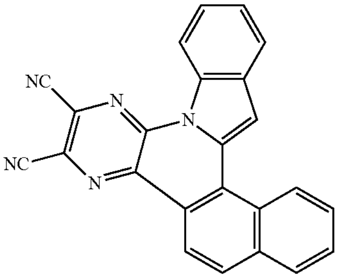
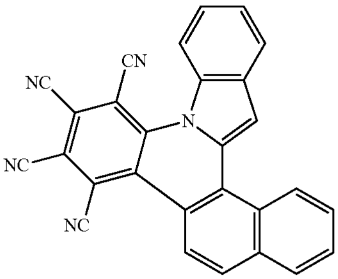
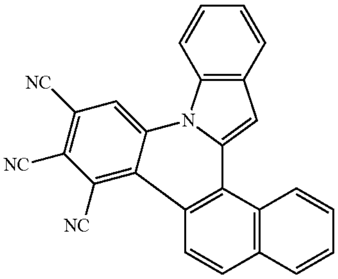

-continued
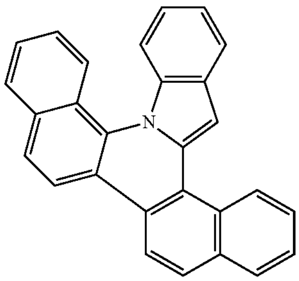
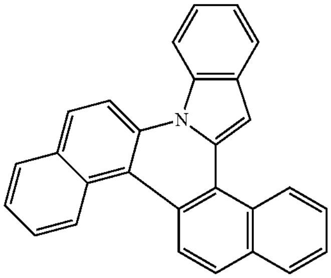
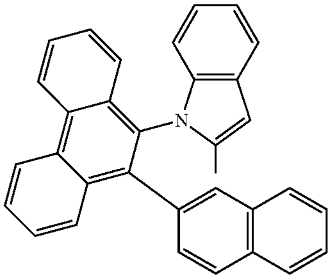
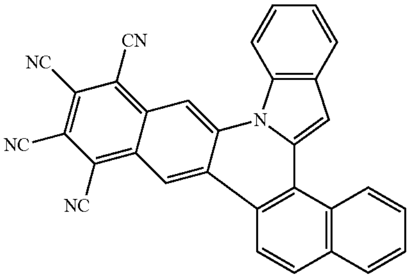
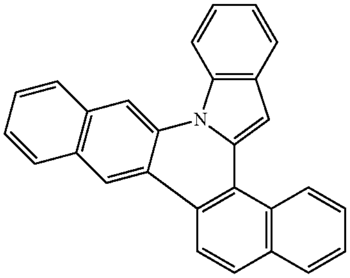
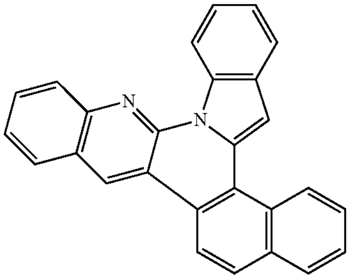
-continued
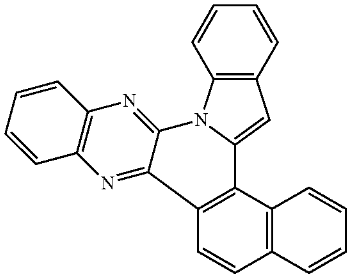
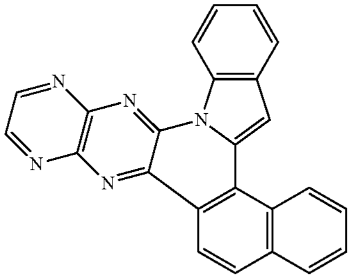
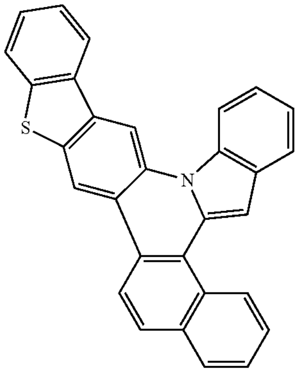
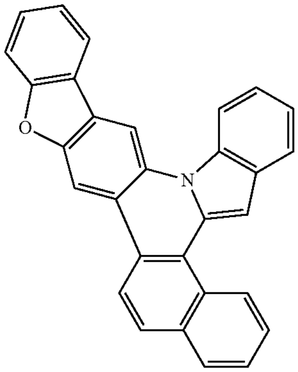
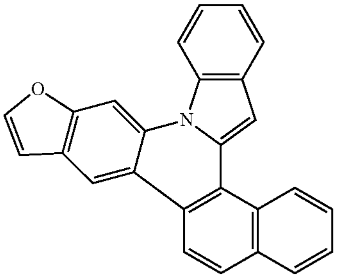

-continued
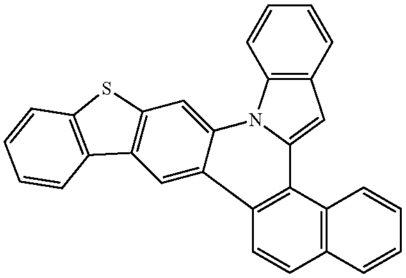
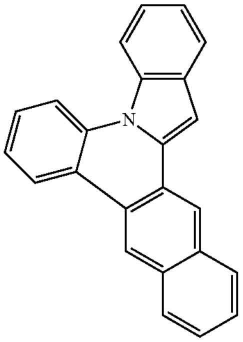
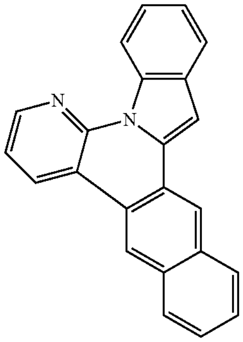
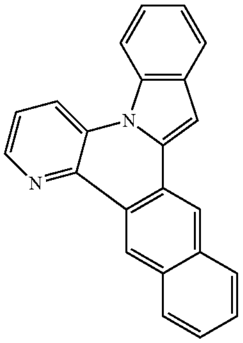
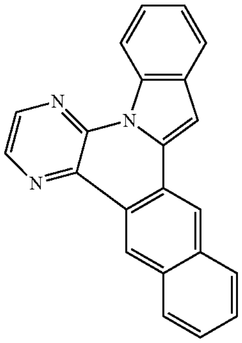
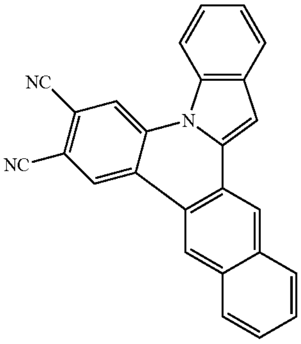
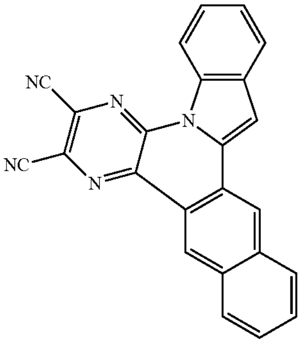
-continued
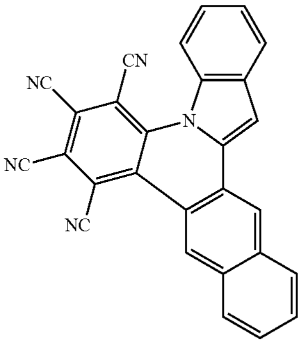
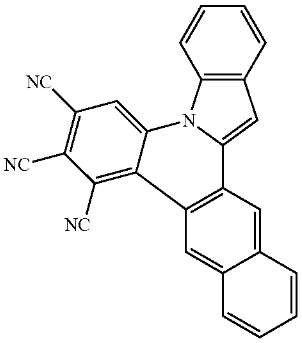
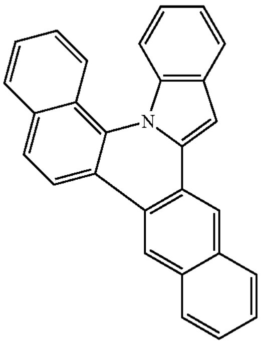
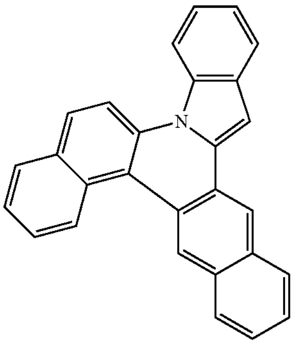
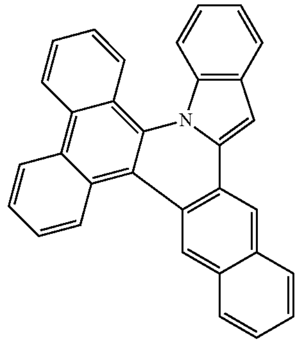
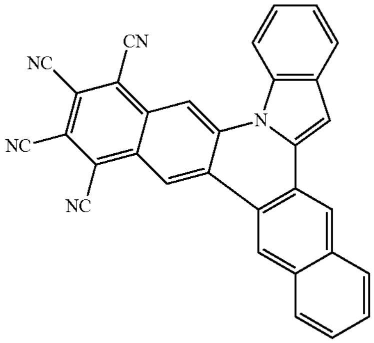

-continued
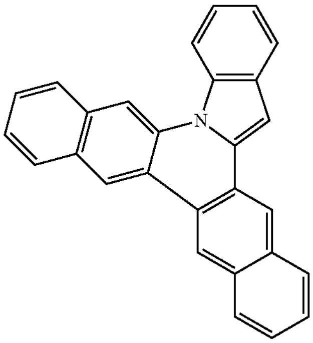
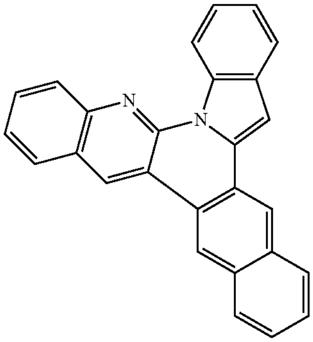
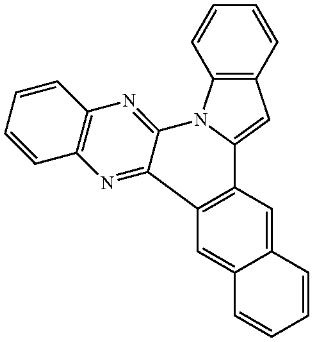
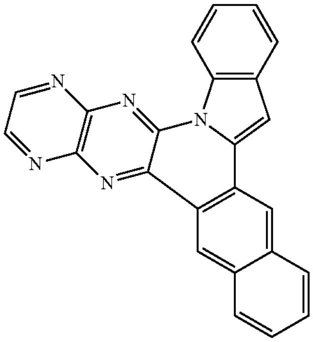
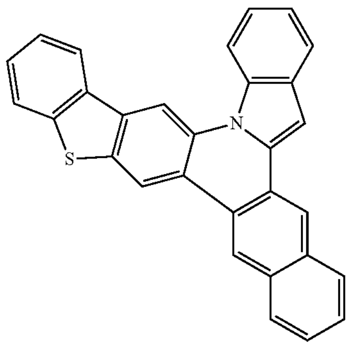
-continued
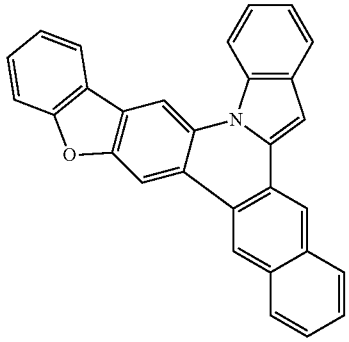
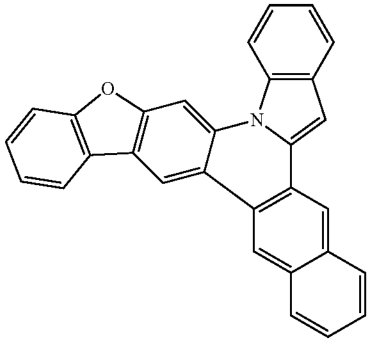
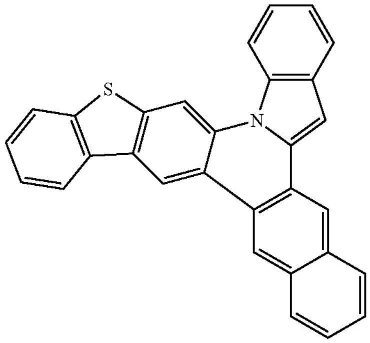
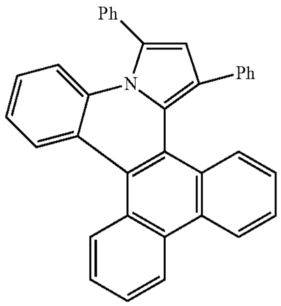
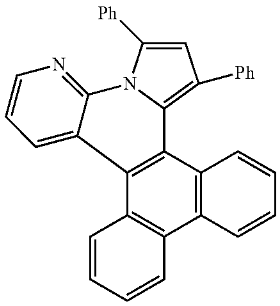
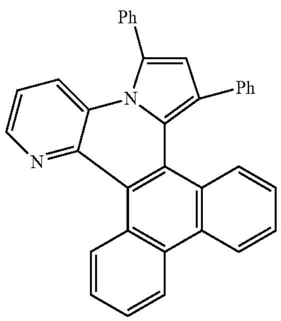
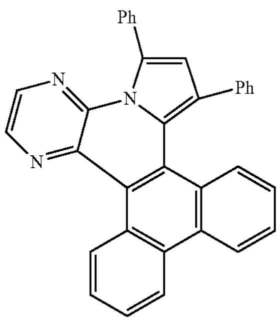

-continued
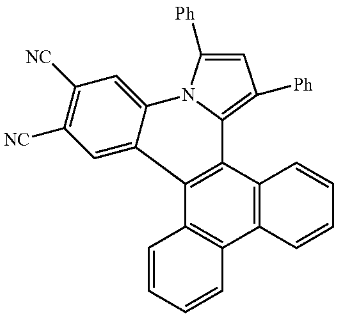
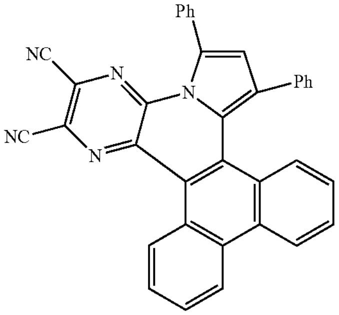
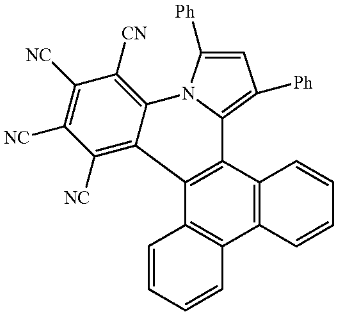
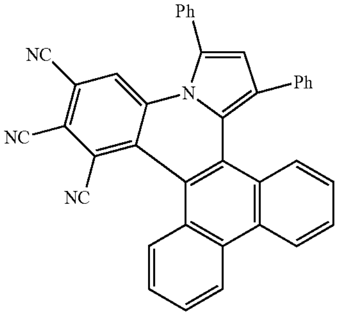
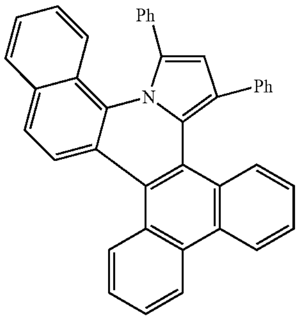
-continued
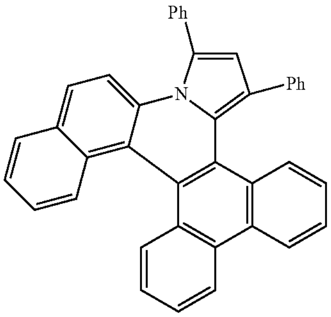
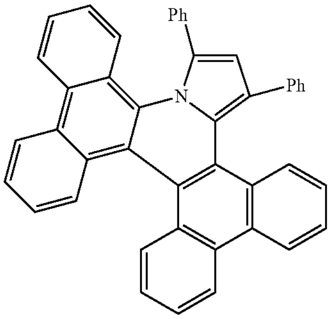
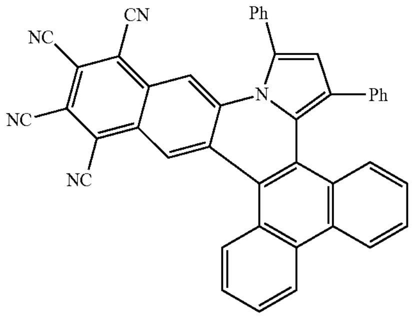
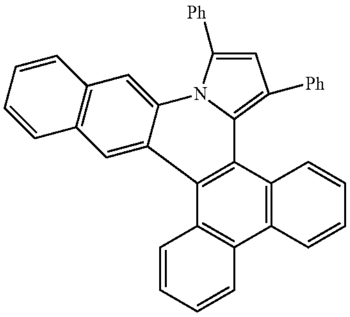
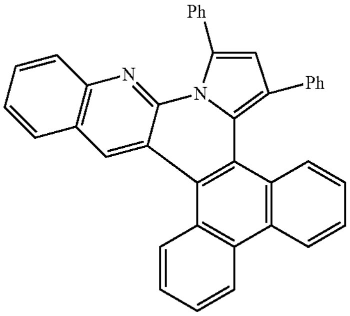

-continued
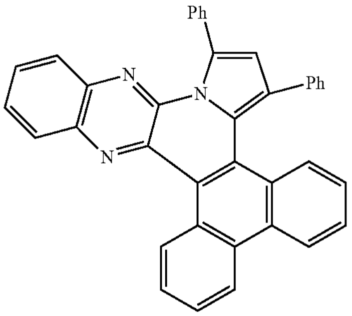
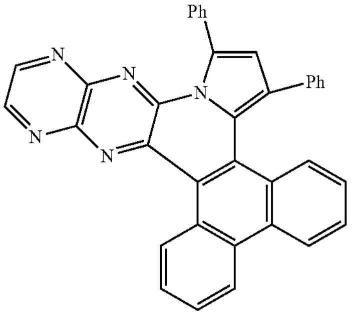
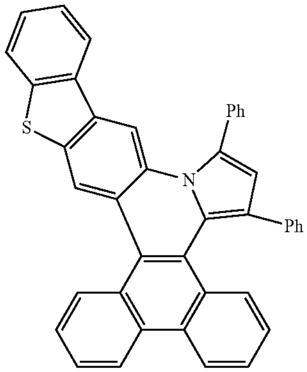
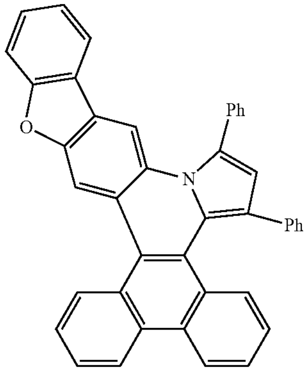
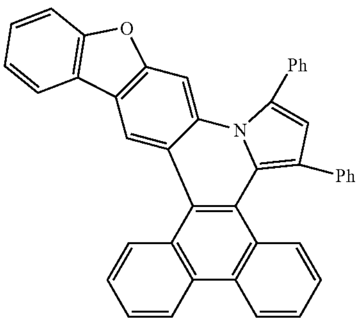
-continued
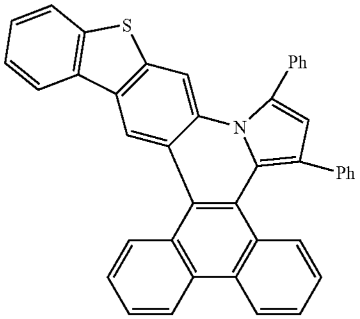
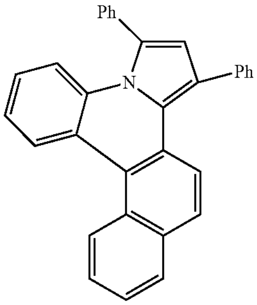
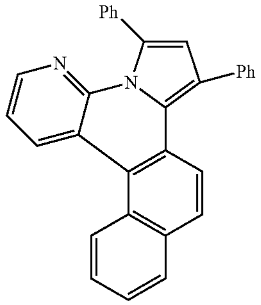
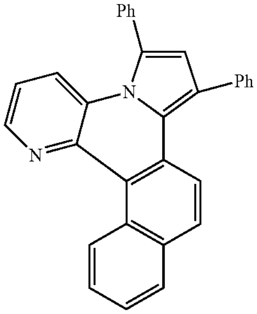
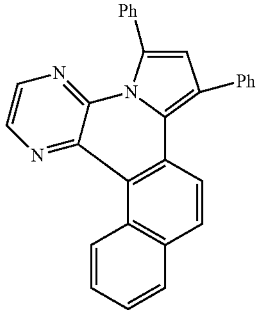
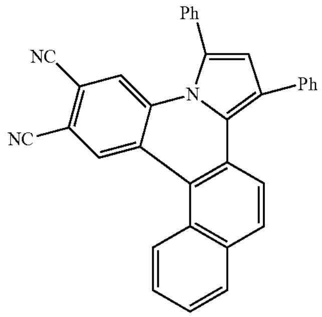
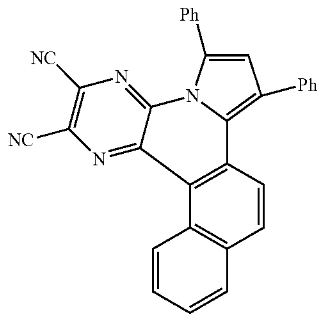

-continued
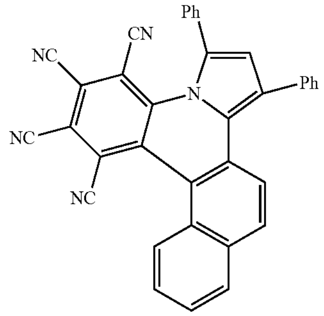
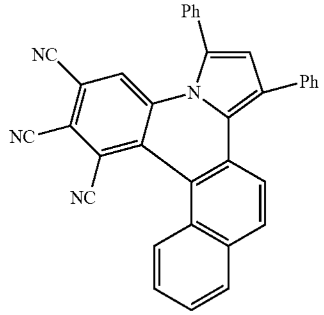
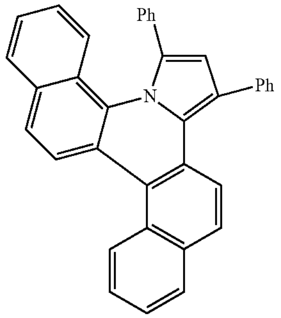
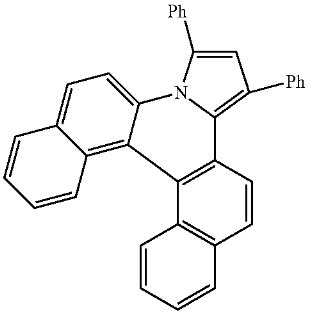
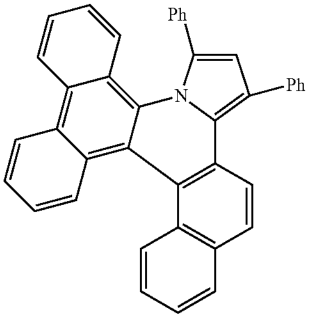
-continued
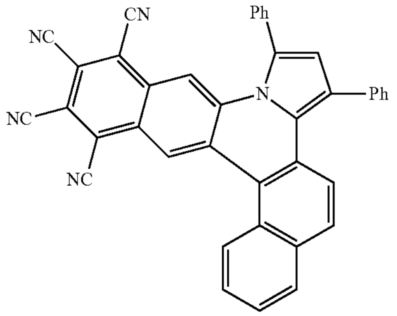
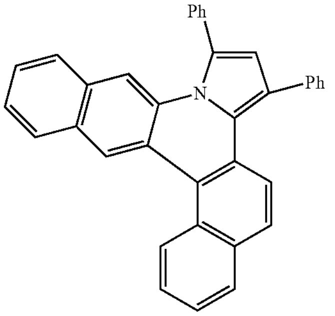
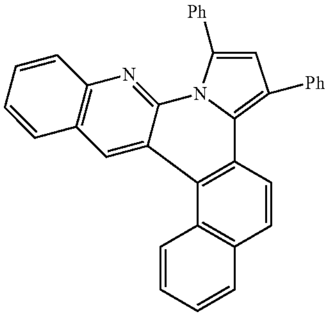
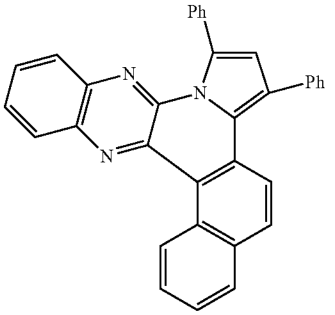
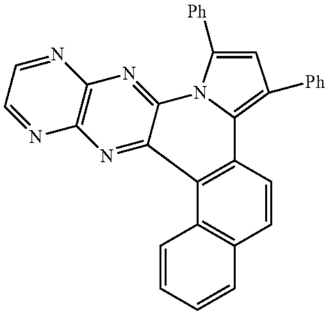

-continued
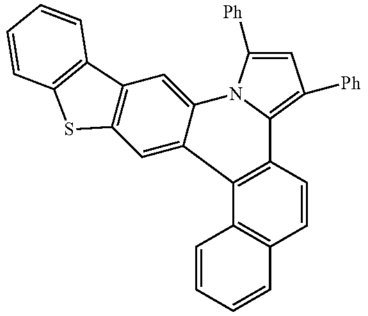
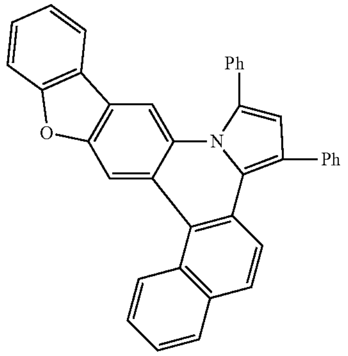
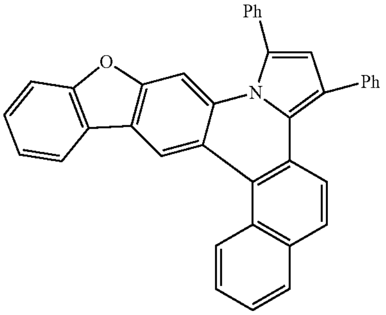
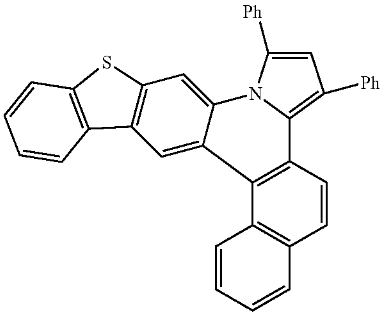
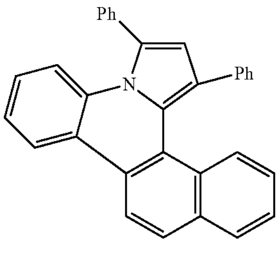
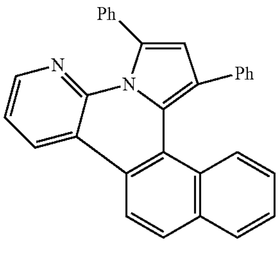
-continued
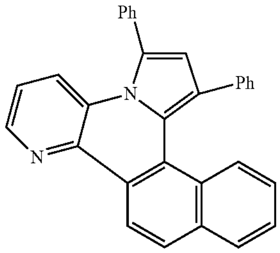
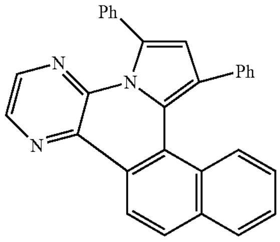
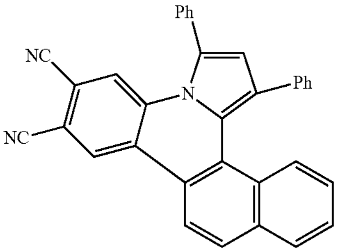
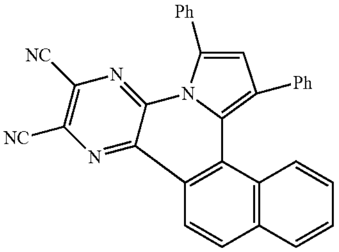
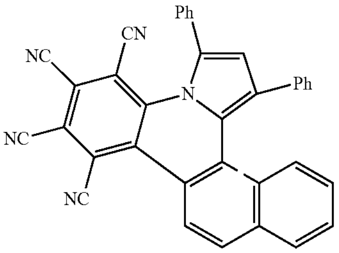
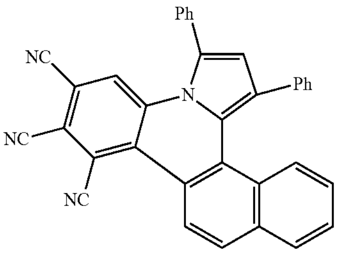
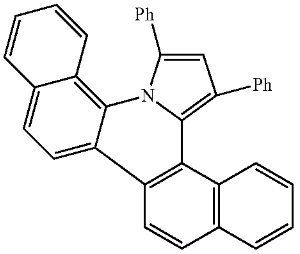

-continued
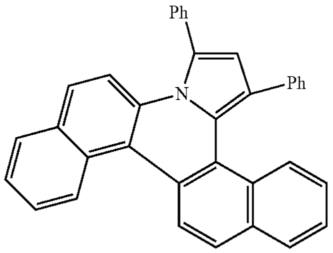
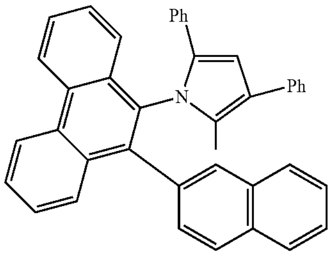
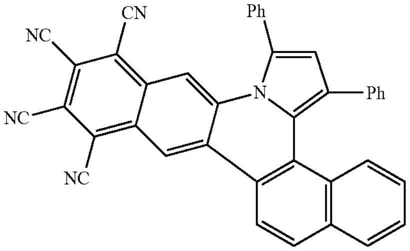
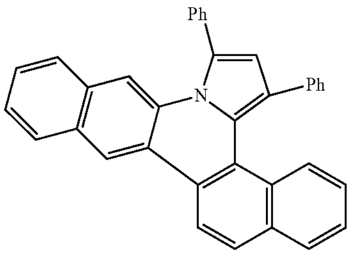
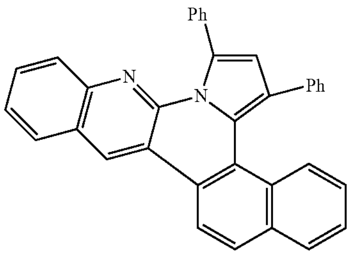
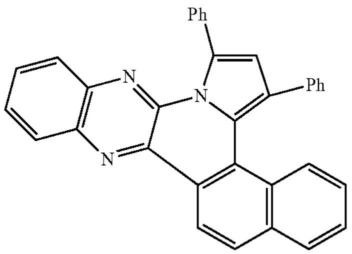
-continued
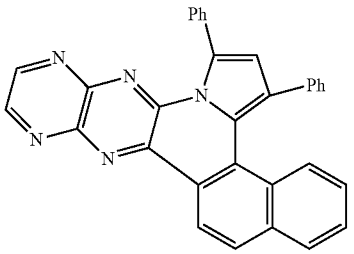
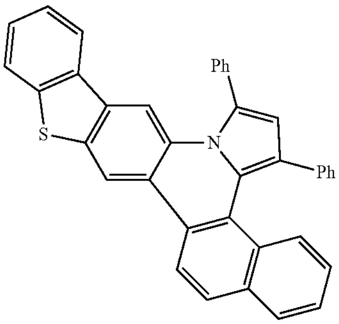
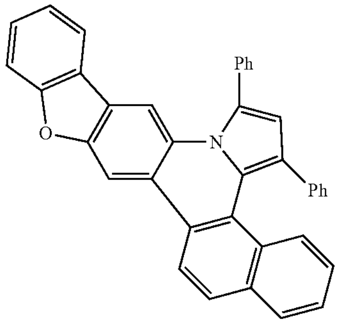
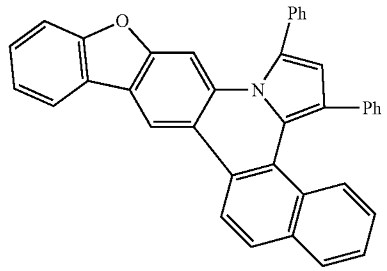
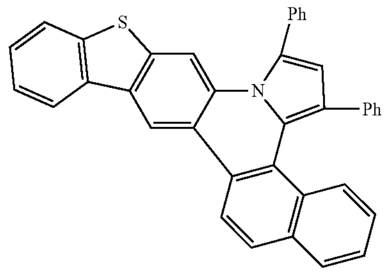

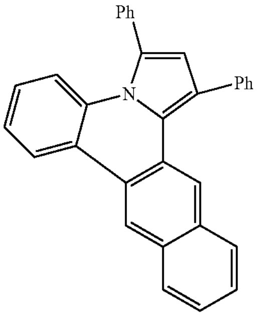
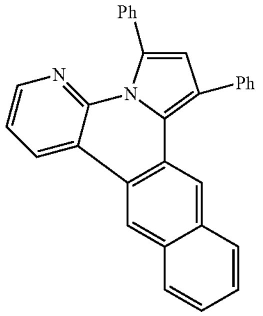
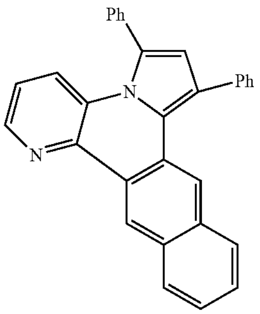
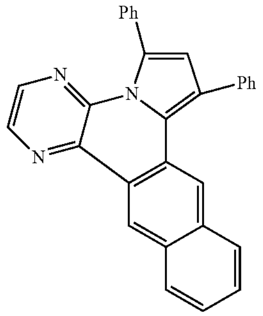
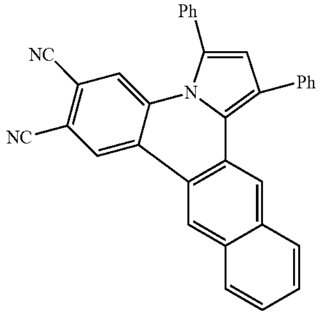
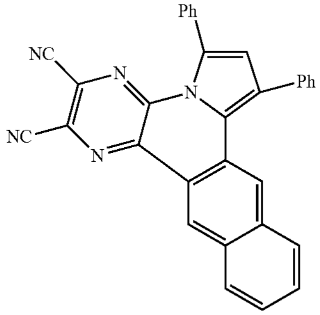
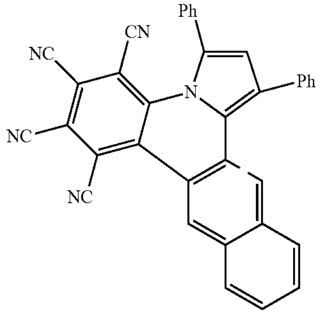
-continued
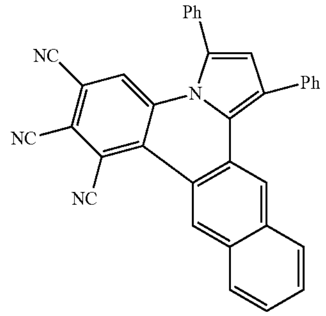
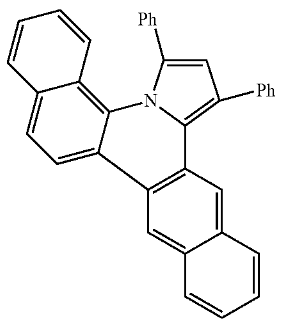
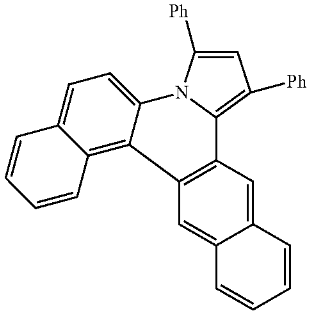
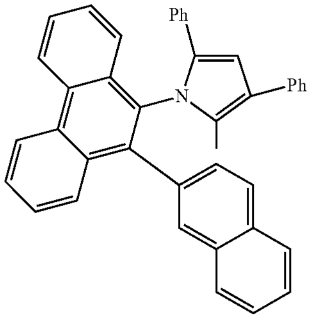
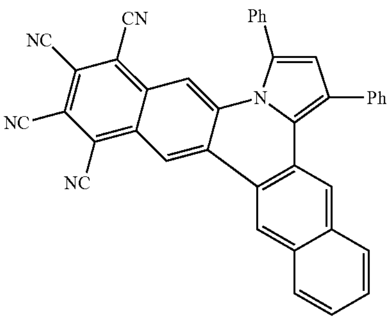

-continued
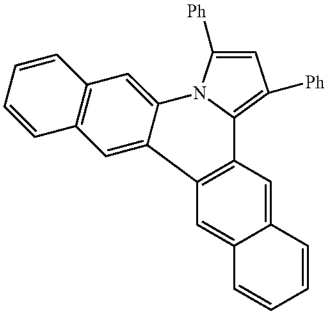
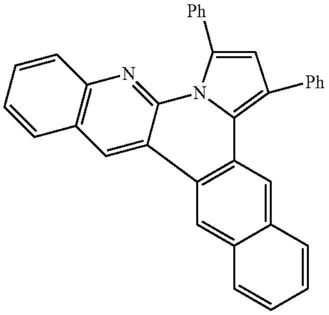
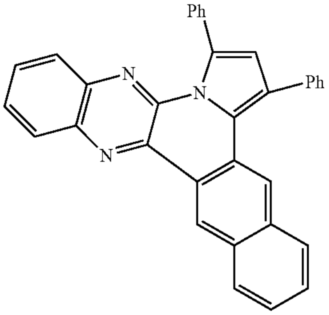
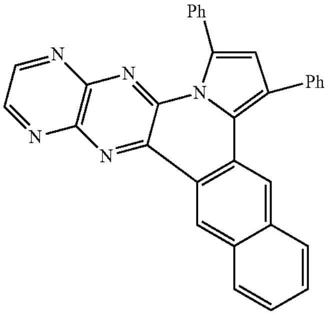
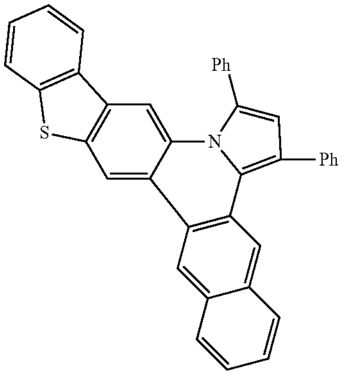
-continued
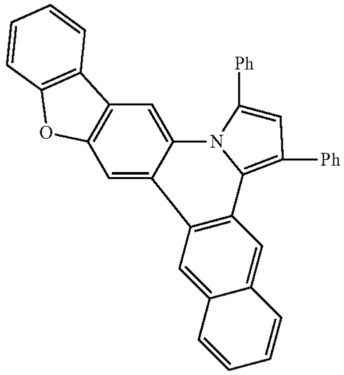
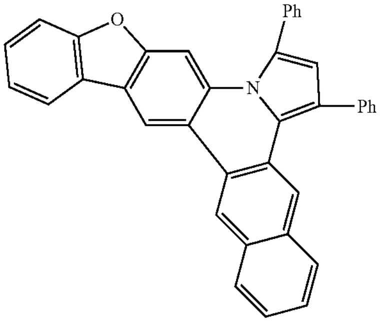
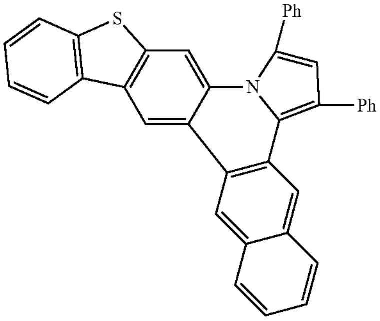
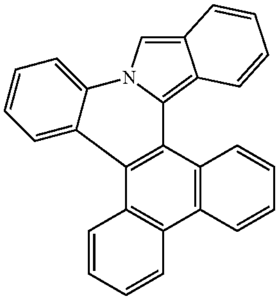
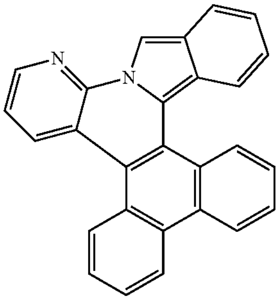
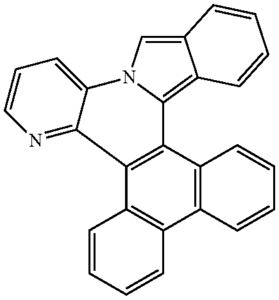
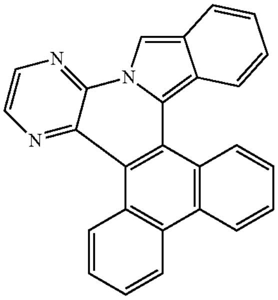

-continued
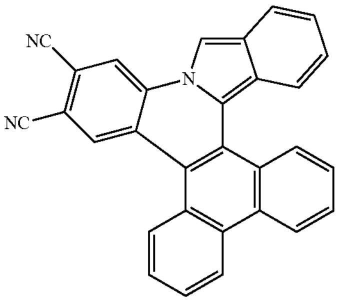
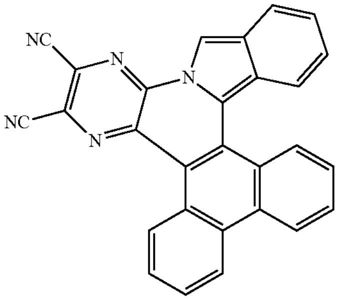
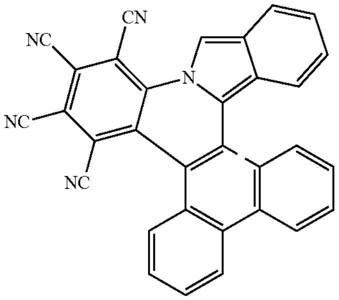
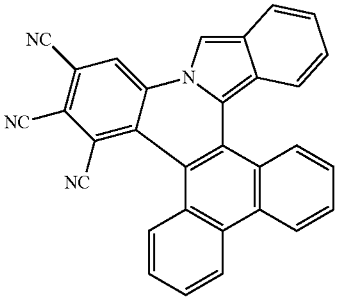
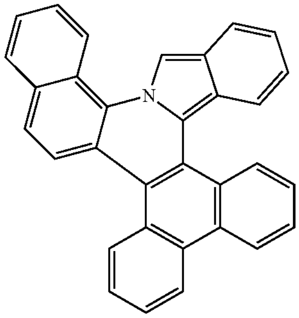
-continued
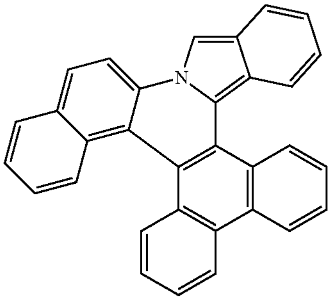
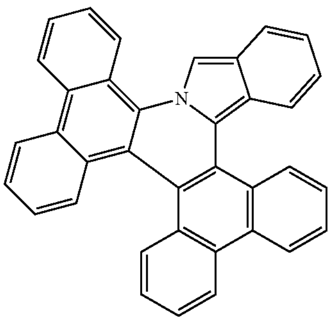
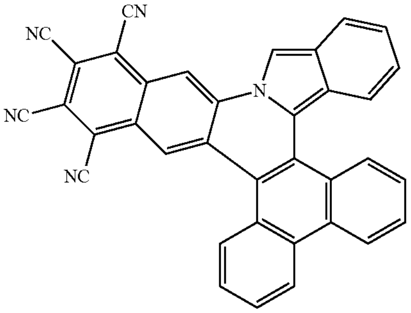
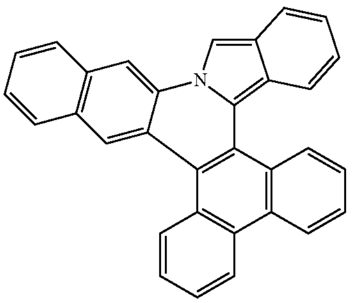
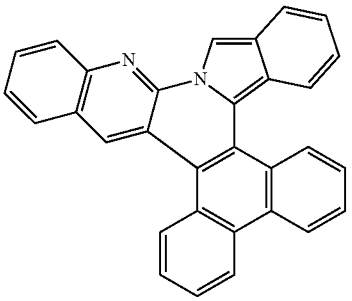

-continued
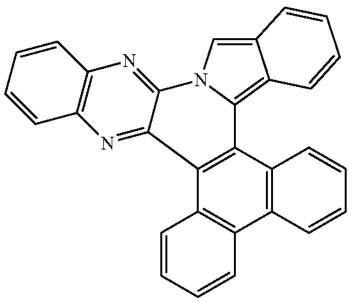
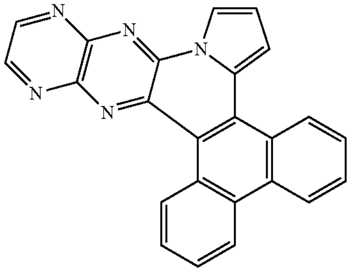
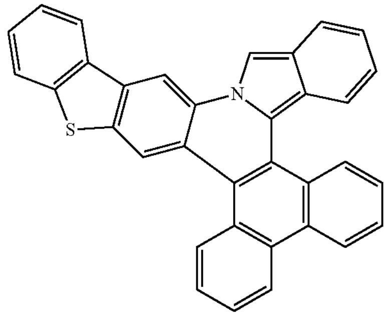
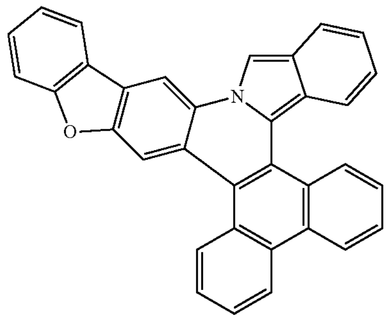
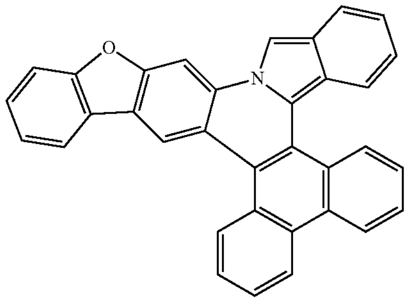
-continued
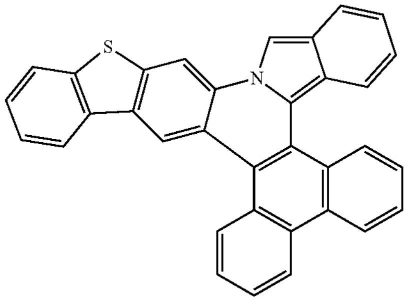
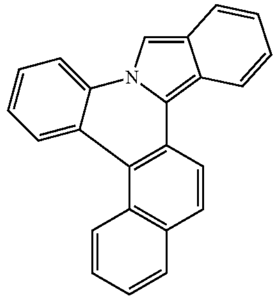
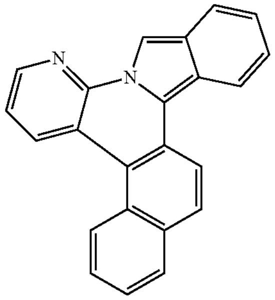
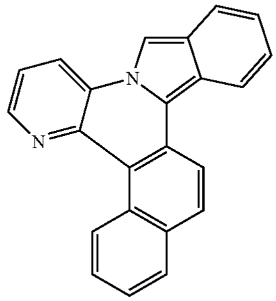
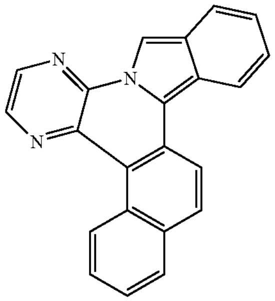
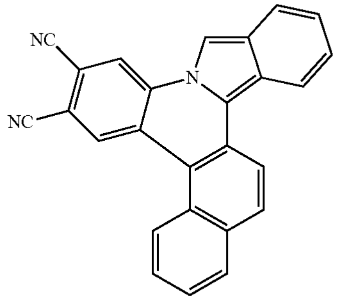
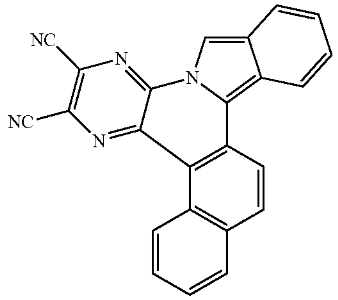

-continued
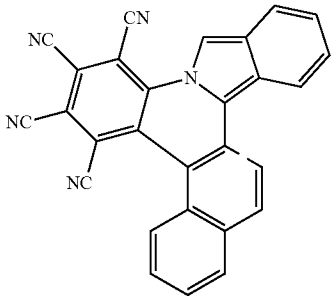
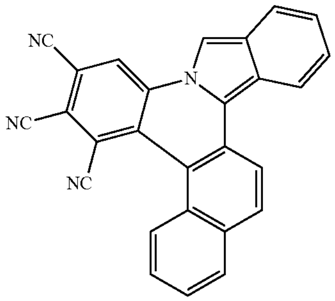
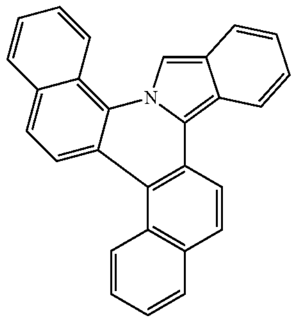
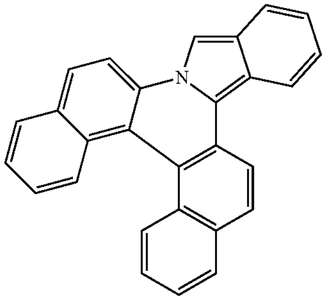
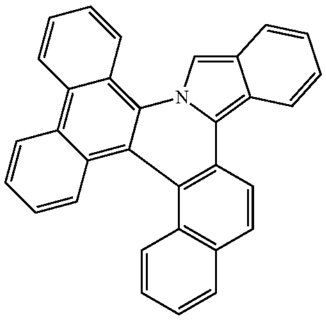
-continued
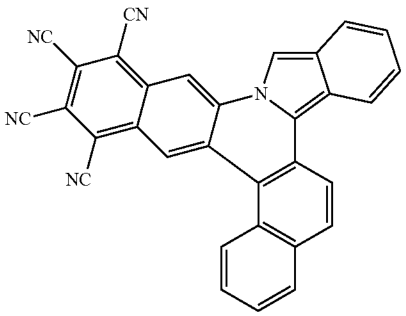
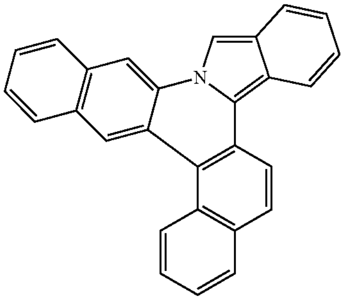
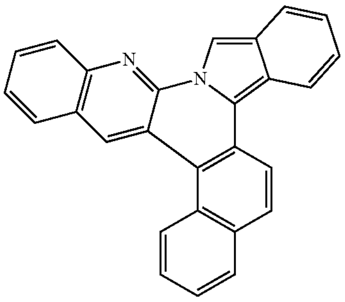
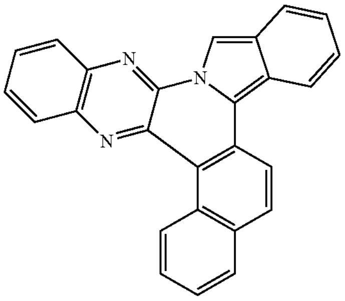
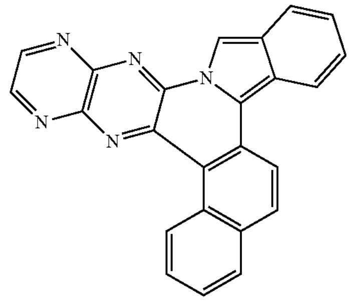

-continued
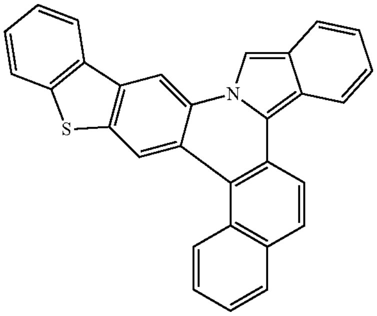
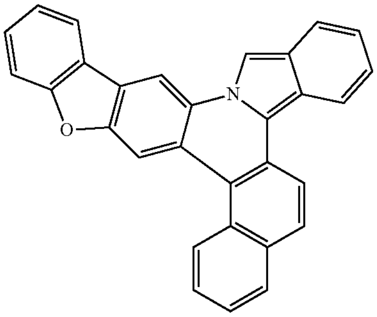
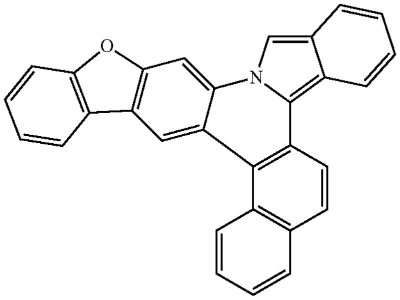
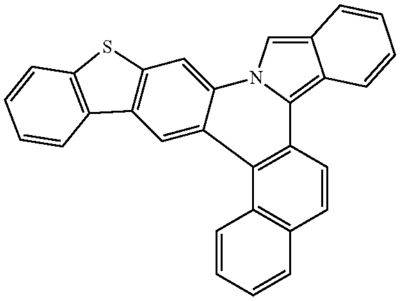
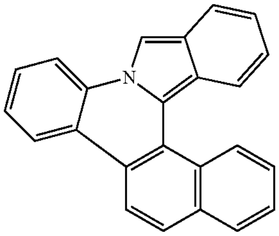
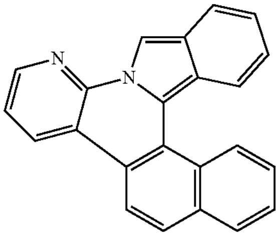
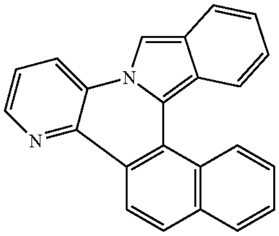
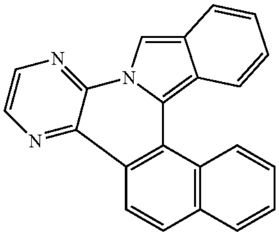
-continued
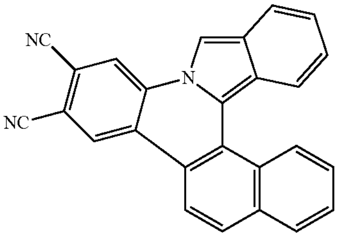
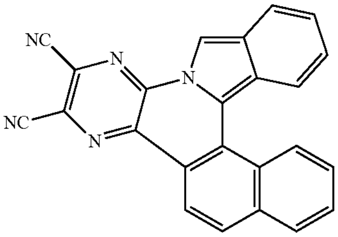
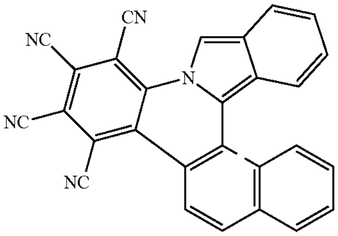
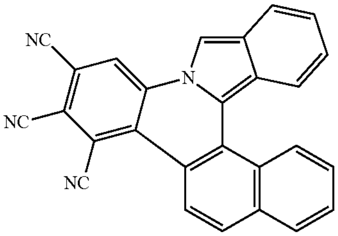
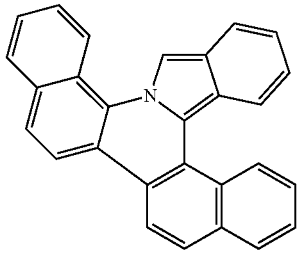
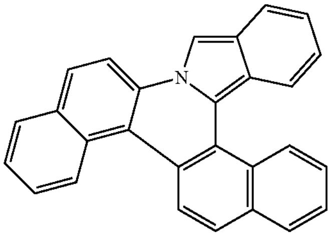
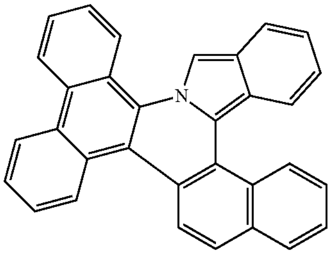

-continued
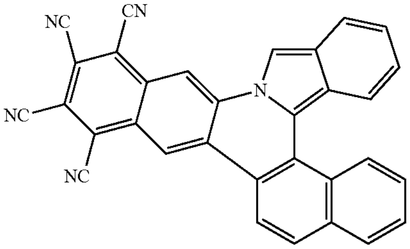
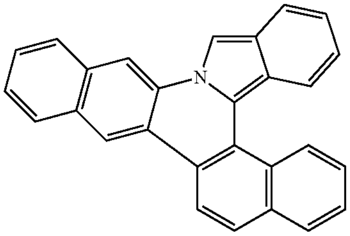
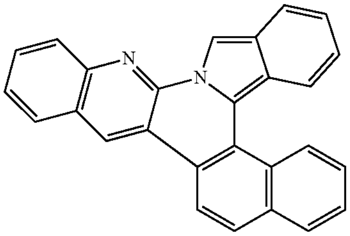
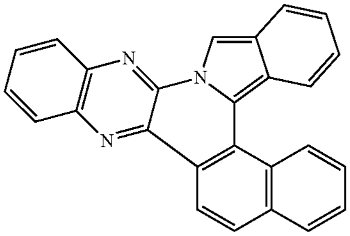
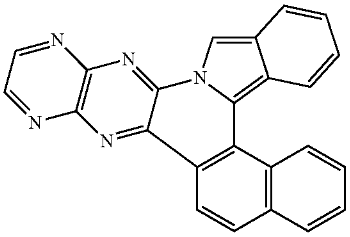
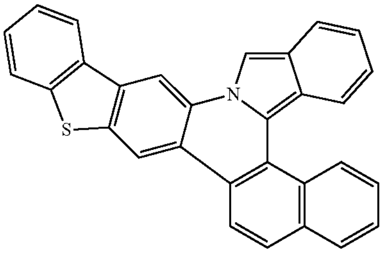
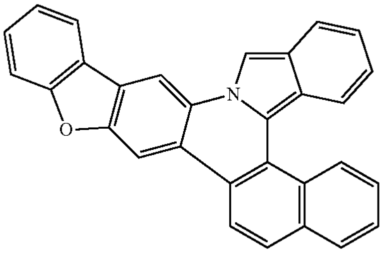
-continued
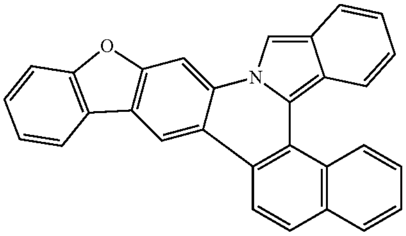
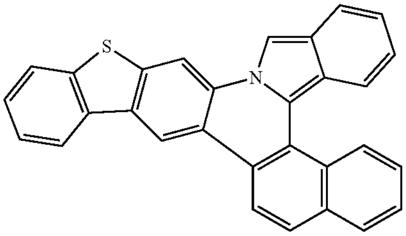
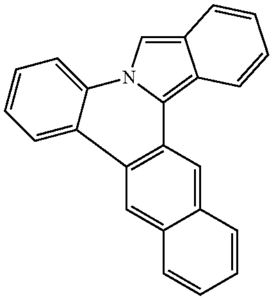
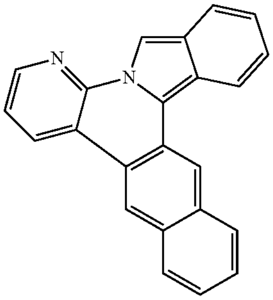
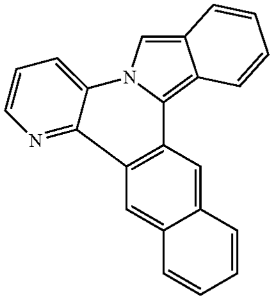
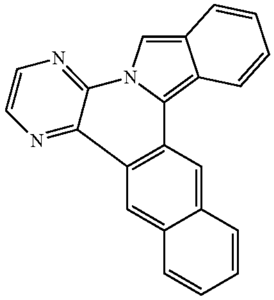
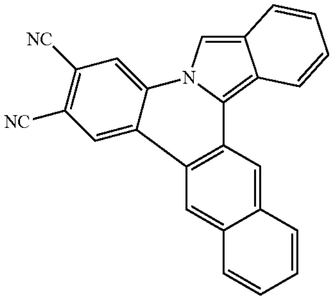
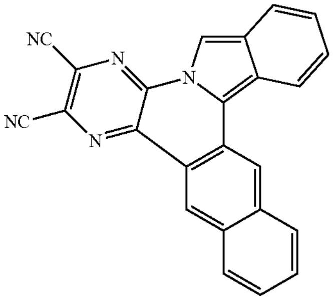

-continued
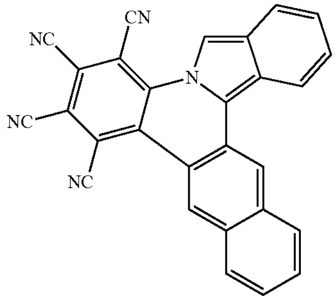
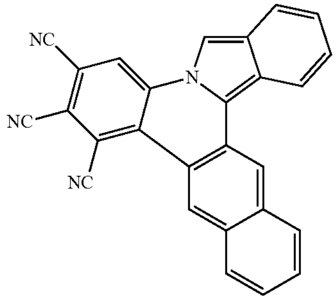
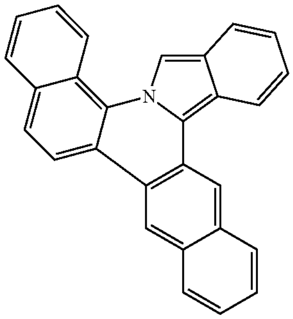
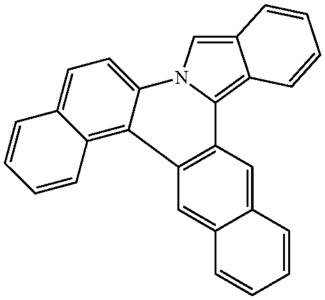
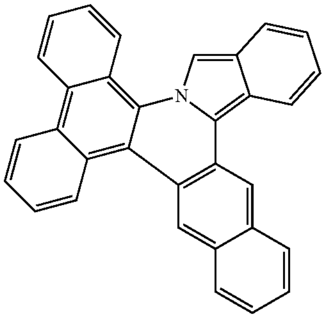
-continued
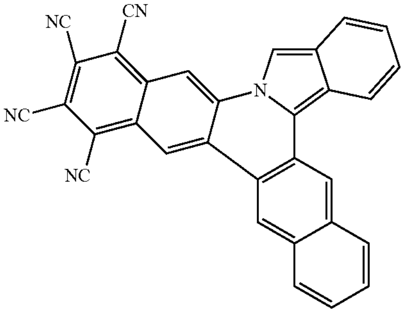
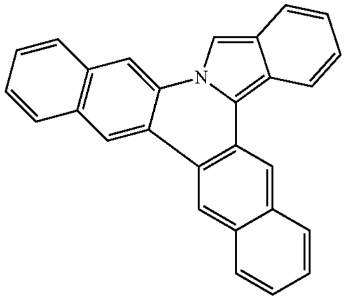
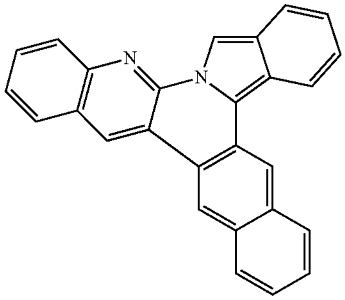
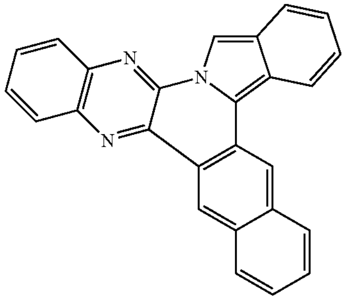
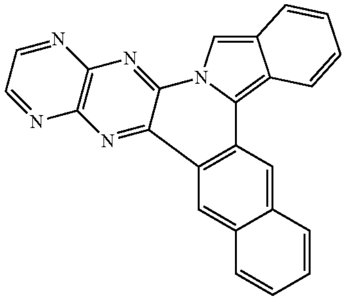

-continued

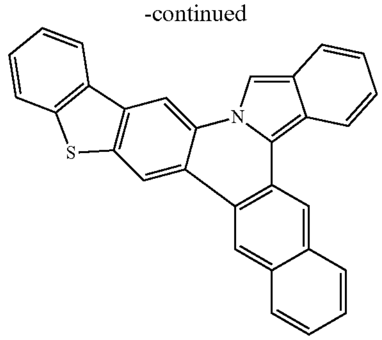

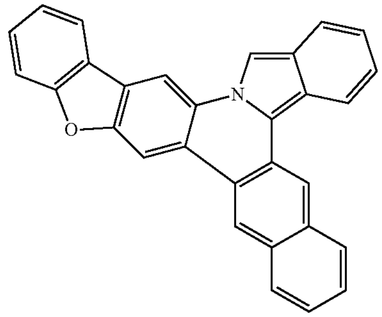

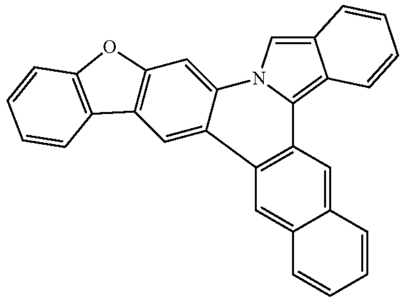

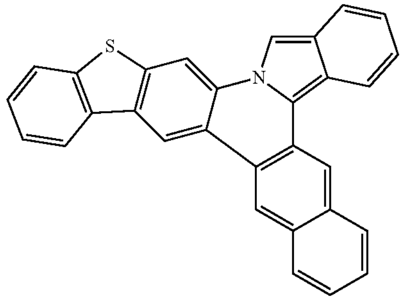

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1\text{-}OA^2$ or $—OA^1\text{-}(OA^2)_a\text{-}OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula $—N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "cyanide" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A'S(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

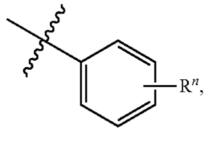

which is understood to be equivalent to a formula:

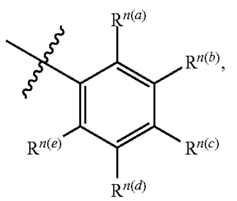

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. In a case where there is a single $R^n$ (e.g., only $R^{n(a)}$), $R^n$ is referred to as a "single substituent." In a case where there are two or more $R^n$ (e.g., at least $R^{n(a)}$ and $R^{n(b)}$) $R^n$ is referred to as a "multiple substituents."

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

The compounds disclosed herein are suited for use in a wide variety of devices, including, for example, organic light emitting diodes (OLEDs) for full color displays and lighting applications.

Also disclosed herein are compositions including one or more compounds disclosed herein. The present disclosure provides light emitting devices that include one or more compositions described herein. The present disclosure also provides a photovoltaic device comprising one or more complexes or compositions described herein. Further, the present disclosure also provides a luminescent display device comprising one or more compounds described herein.

Figure 4:
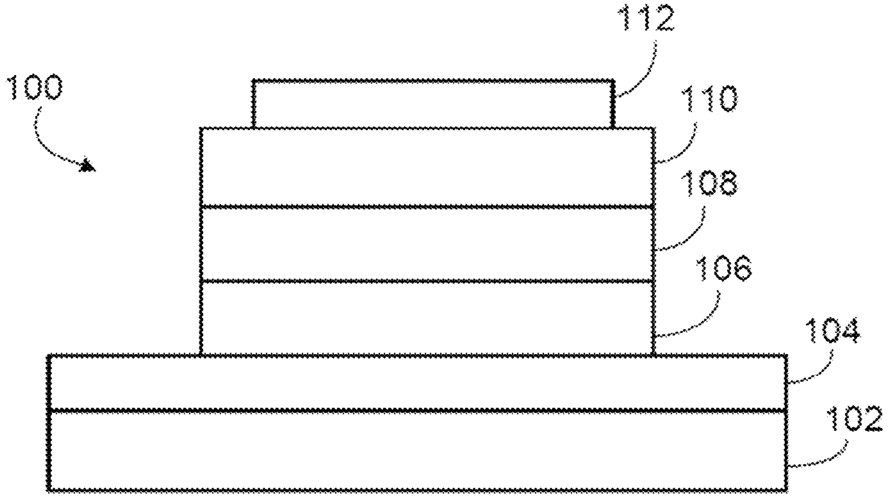
FIG. 4 depicts an organic light emitting diode (OLED).

Compounds described herein can be used in a light emitting device such as an OLED. FIG. 4 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Some of these synthetic examples have been performed. Others are based on an understanding of related synthetic procedures and are predictive in nature. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

An ortho-phenylenediamine (1.0 mmol; 1.0 equiv) and an aldehyde (1.0 mmol; 1.0 equiv) were dissolved in wet DMF (DMF 9.0 mL, $H_2O$ 1.0 mL). The resulting reaction mixture was stirred at 80° C. in an open flask, and the reaction progress was monitored by TLC. On the complete consumption of aldehyde, the reaction mixture was cooled to room temperature and concentrated under reduced pressure. The crude product obtained was purified by column chromatography on silica gel to afford the corresponding product.

A flame-dried Schlenk tube with a magnetic stir bar was charged with $Pd(PPh_3)_4$ (28.8 mg, 25.0 μmol, 10 mol %), Xantphos (14.6 mg, 25.0 μmol, 10 mol %), $Cs_2CO_3$ (243 mg, 0.75 mmol) and 2-aryl-N-heteroarenes (0.30 mmol, 1.2 equiv.). Then, 1,2-dihaloarenes (0.25 mmol) and DMF (2.0 mL) were added to the reaction mixture under an $N_2$ atmosphere. The reaction mixture was stirred for 10 min at room temperature, and then heated at 140° C. in a pre-heated oil bath for 24 h. After that, the reaction mixture was cooled to room temperature, diluted with $CH_2Cl_2$ (10 mL), filtered through a Celite pad, and washed with $CH_2Cl_2$ (10-20 mL). The combined organic extracts were concentrated and the resulting residue was purified by column chromatography on silica gel to provide the desired product.

Example 1

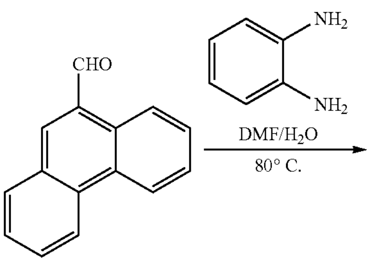

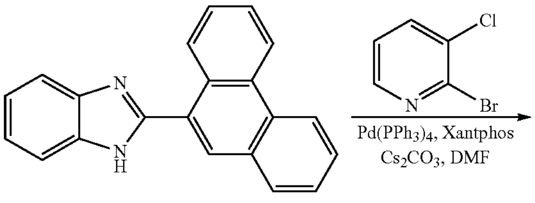

BImPhen

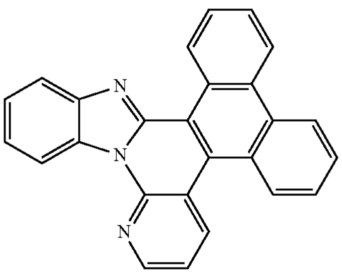

DFE-1

Synthesis of DFE-1

To a flame-dried flask were added $Pd(PPh_3)_4$ (10 mol %), Xantphos (10 mol %), $Cs_2CO_3$ (3 eq) and 2-bromo-3-chloropyridine (1.2 eq). Then, BImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-1 in 23% yield.

Example 2

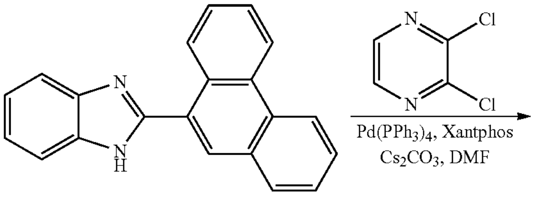

BImPhen

-continued

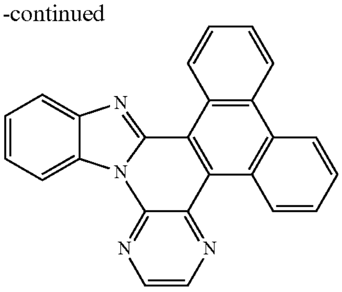

DFE-2

Synthesis of DFE-2

To a flame-dried flask were added $Pd(PPh_3)_4$ (10 mol %), Xantphos (10 mol %), $Cs_2CO_3$ (3 eq) and 2,3-dichloropyrazine (1.2 eq). Then, BImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-2 in 34% yield.

Example 3

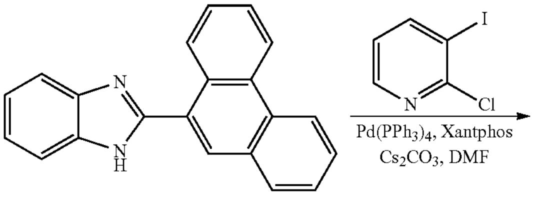

BImPhen

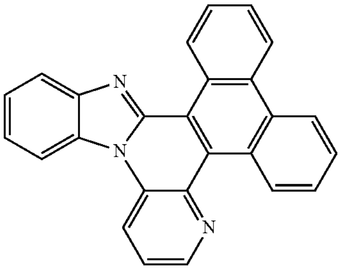

DFE-3

Synthesis of DFE-3

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-3 in 29% yield.

Figure 5A:
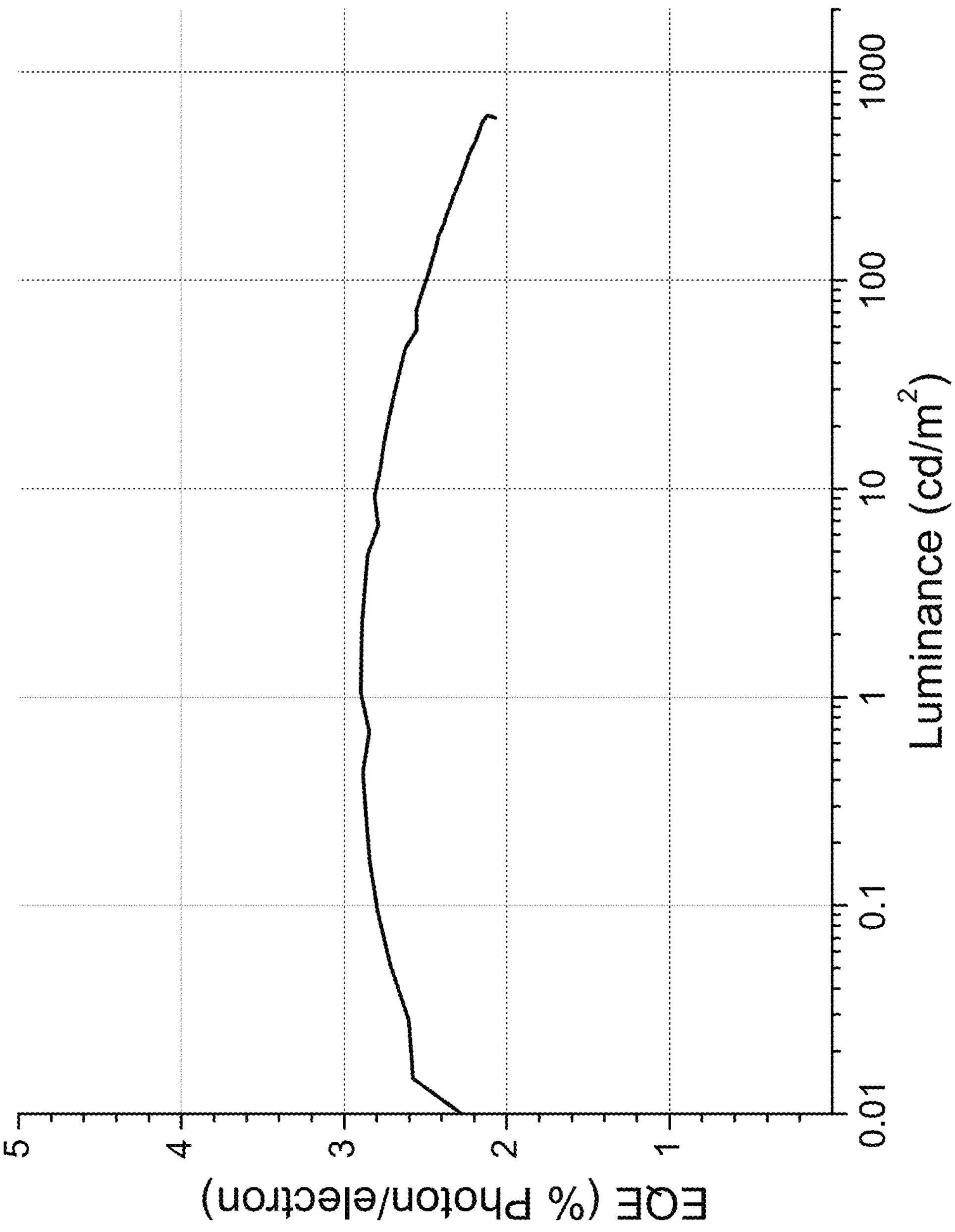
FIGS. 5A-5C show external quantum efficiency (EQE) vs. luminance, EQE vs. current density, and an electroluminescence (EL) spectrum, respectively, of DFE-3 with the device structure described in Example 3.
Figure 5B:
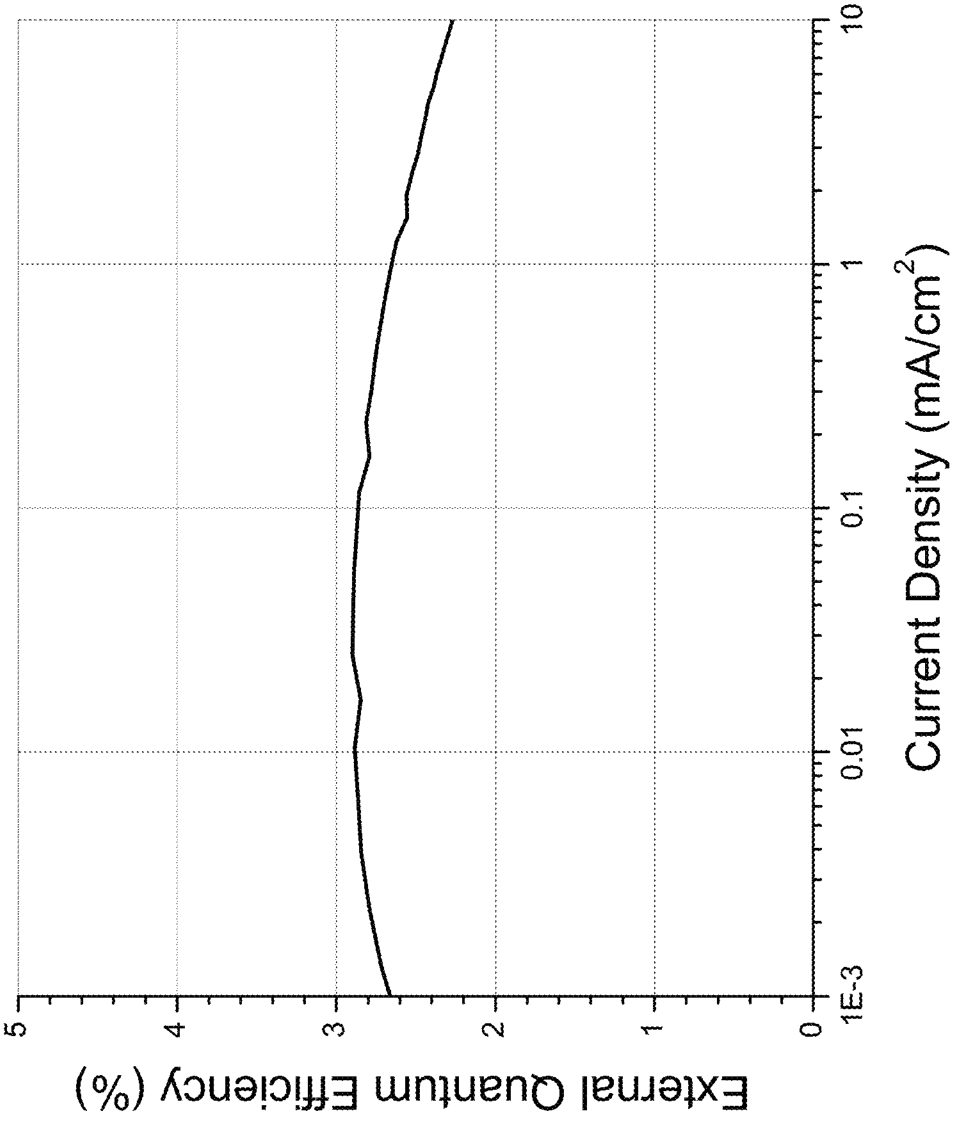
Figure 5C:
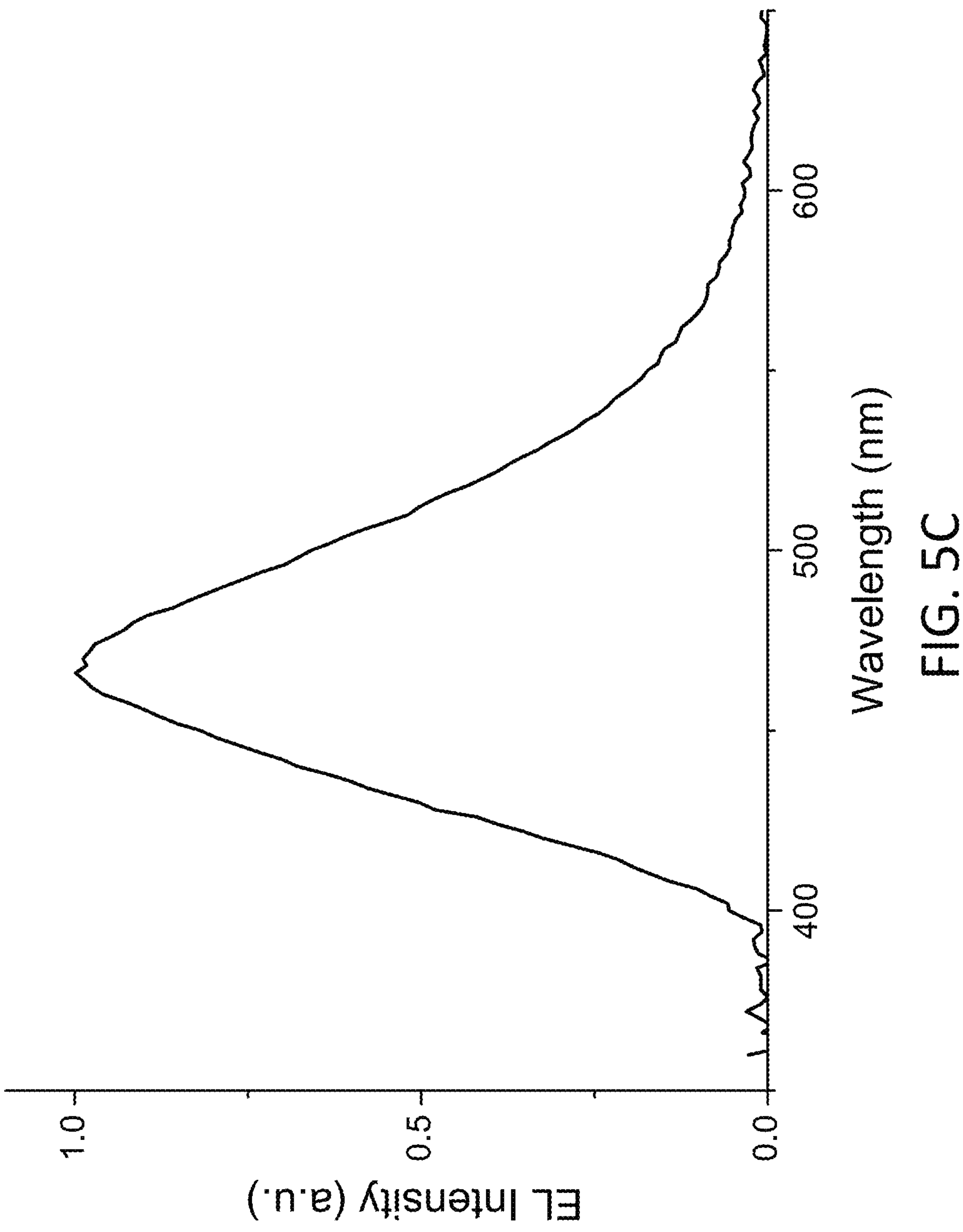
Figure 5D:
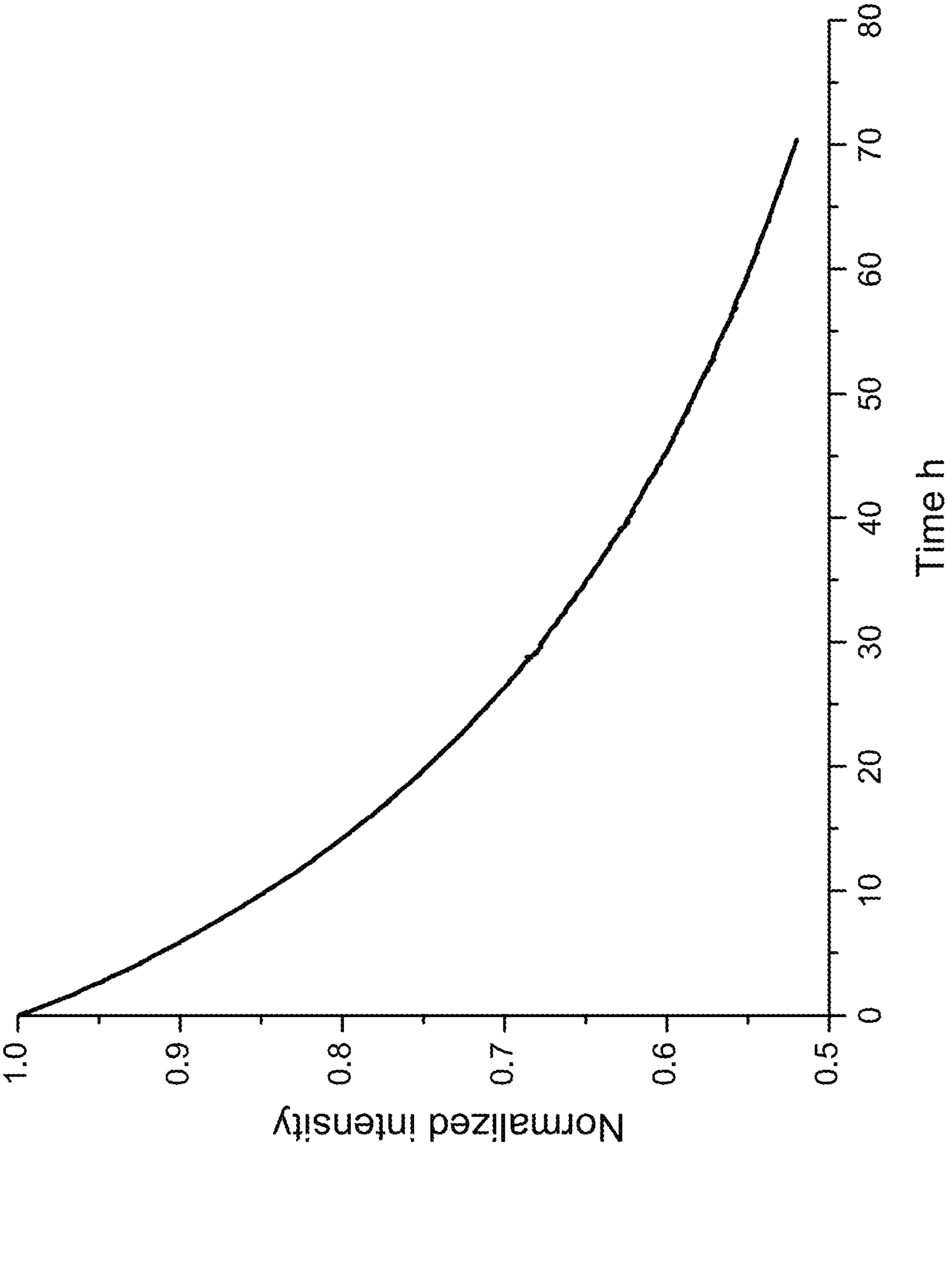
FIG. 5D shows device operational lifetime for the device.

FIGS. 5A-5C show a plot of external quantum efficiency (EQE) vs. luminance, a plot of EQE vs. current density, and an EL spectrum of DFE-3 with device structure: ITO (40 nm)/HATCN (10 nm)/NPD (40 nm)/BisPCz (10 nm)/6% PyPID:mCBP (25 nm)/mCBT (10 nm)/BPyTP (40 nm)/Liq (2 nm)/Al (100 nm), where HATCN is 1,4,5,8,9,12-hexaaza-triphenylene-hexacarbonitrile, NPD is N,N'-diphenyl-N,N'-bis(1-naphthyl)-1,1'-biphenyl-4,4'-diamine, BisPCz is 9,9'-diphenyl-9H,9'H-3,3'-bicarbazole, mCBT is 3,3'-di(9H-carbazol-9-yl)-1,1'-biphenyl, BPyTP is 2,7-di(2,2'-bipyridin-5-yl)triphenylene and Liq is 8-hydroxyquinoline lithium. FIG. 5D shows device operational lifetime.

Example 4

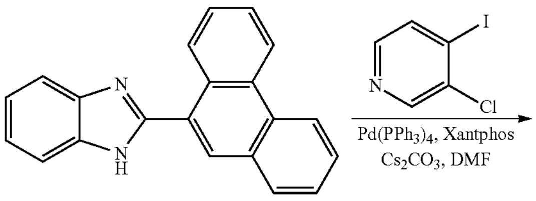

BImPhen

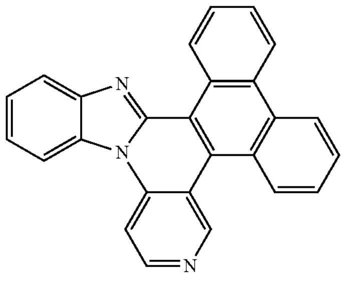

DFE-4

Synthesis of DFE-4

To a flame-dried flask were added $Pd(PPh_3)_4$ (10 mol %), Xantphos (10 mol %), $Cs_2CO_3$ (3 eq) and 3-chloro-4-iodopyridine (1.2 eq). Then, BImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-4 in 31% yield.

Example 5

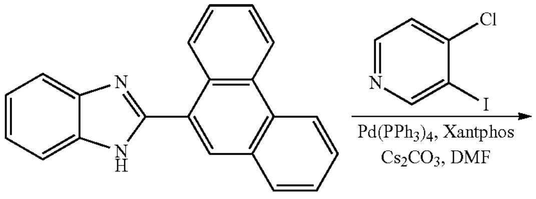

BImPhen

-continued

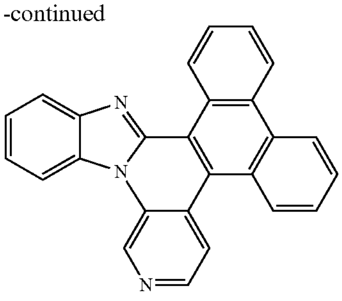

DFE-5

Synthesis of DFE-5

To a flame-dried flask were added $Pd(PPh_3)_4$ (10 mol %), Xantphos (10 mol %), $Cs_2CO_3$ (3 eq) and 4-chloro-3-iodopyridine (1.2 eq). Then, BImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-5 in 29% yield.

Example 6

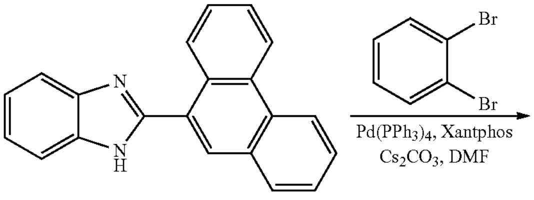

BImPhen

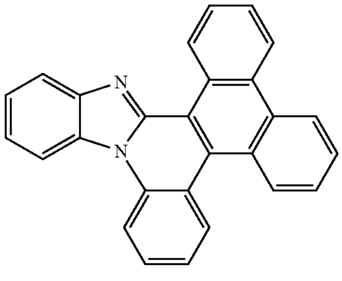

DFE-6

Synthesis of DFE-6

To a flame-dried flask were added $Pd(PPh_3)_4$ (10 mol %), Xantphos (10 mol %), $Cs_2CO_3$ (3 eq) and 1,2-dibromobenzene (1.2 eq). Then, BImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-6 in 55% yield.

Example 7

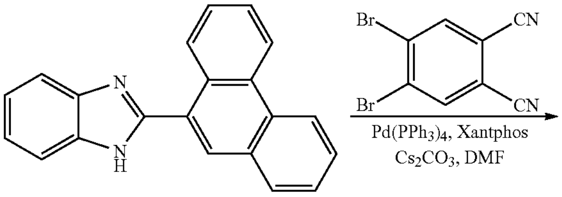

BImPhen

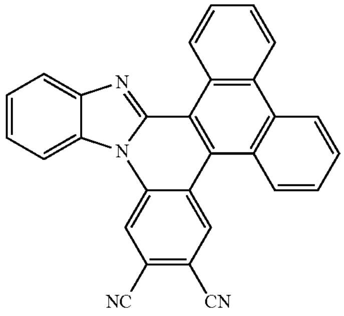

DFE-7

Synthesis of DFE-6

To a flame-dried flask were added $Pd(PPh_3)_4$ (10 mol %), Xantphos (10 mol %), $Cs_2CO_3$ (3 eq) and 4,5-dibromophthalonitrile (1.2 eq). Then, BImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-7 in 46% yield.

Example 8

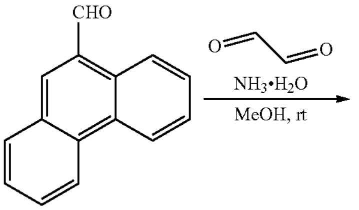

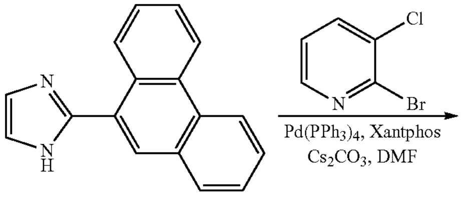

ImPhen

-continued

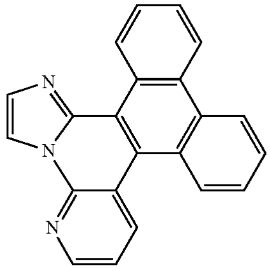

DFE-8

Synthesis of DFE-8

To a flame-dried flask were added $Pd(PPh_3)_4$ (10 mol %), Xantphos (10 mol %), $Cs_2CO_3$ (3 eq) and 2-bromo-3-chloropyridine (1.2 eq). Then, ImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-8 in 24% yield.

Example 9

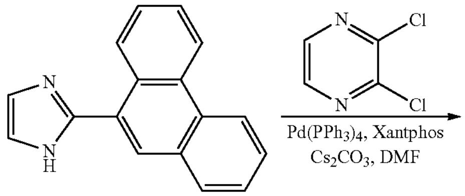

ImPhen

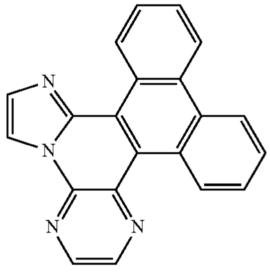

DFE-9

Synthesis of DFE-9

To a flame-dried flask were added $Pd(PPh_3)_4$ (10 mol %), Xantphos (10 mol %), $Cs_2CO_3$ (3 eq) and 2,3-dichloropyrazine (1.2 eq). Then, ImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-9 in 30% yield.

Example 10

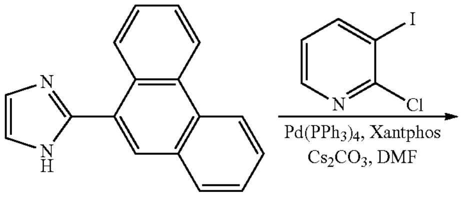

ImPhen

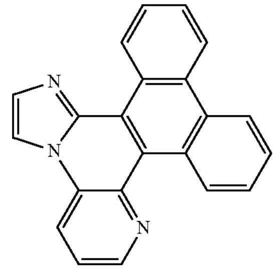

DFE-10

Synthesis of DFE-10

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, ImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-10 in 34% yield.

Example 11

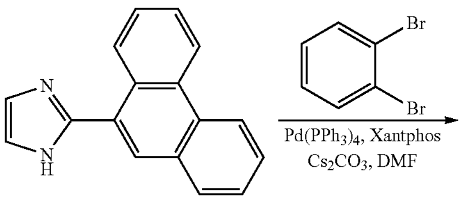

ImPhen

-continued

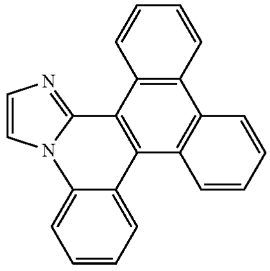

DFE-11

Synthesis of DFE-11

$Cs_2CO_3$ (3 eq) and 1,2-dibromobenzene (1.2 eq). Then, ImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-11 in 39% yield.

Example 12

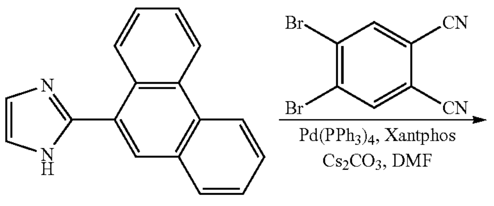

ImPhen

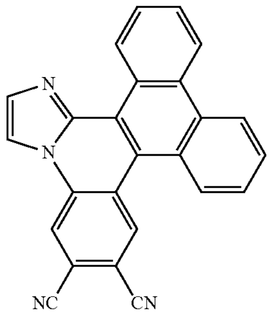

DFE-12

Synthesis of DFE-6

To a flame-dried flask were added $Pd(PPh_3)_4$ (10 mol %), Xantphos (10 mol %), $Cs_2CO_3$ (3 eq) and 4,5-dibromophthalonitrile (1.2 eq). Then, ImPhen (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-12 in 37% yield.

Example 13

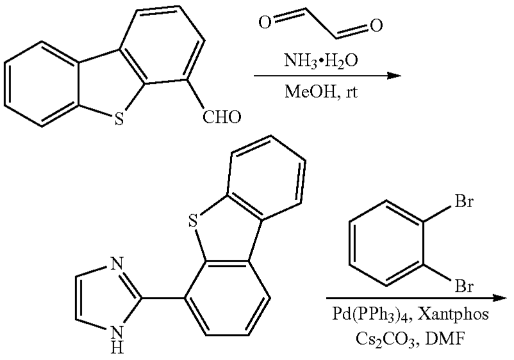

ImBT-1

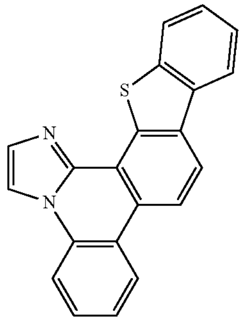

DFE-13

Synthesis of DFE-14

To a flame-dried flask were added $Pd(PPh_3)_4$ (10 mol %), Xantphos (10 mol %), $Cs_2CO_3$ (3 eq) and 1,2-dibromobenzene (1.2 eq). Then, ImBT-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-13 in 39% yield.

Example 14

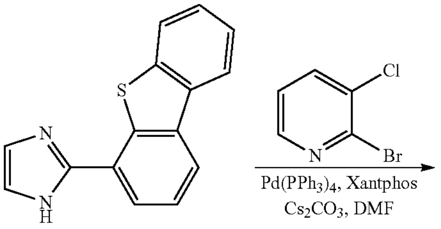

ImBT-1

-continued

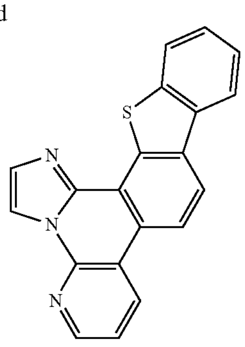

DFE-14

Synthesis of DFE-8

To a flame-dried flask were added $Pd(PPh_3)_4$ (10 mol %), Xantphos (10 mol %), $Cs_2CO_3$ (3 eq) and 2-bromo-3-chloropyridine (1.2 eq). Then, ImBT-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-14 in 21% yield.

Example 15

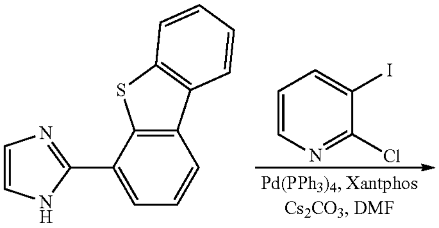

ImBT-1

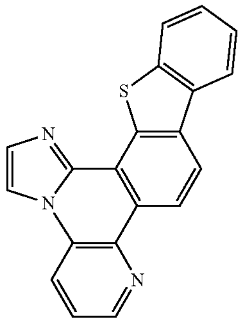

DFE-15

Synthesis of DFE-15

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, ImBT-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-15 in 34% yield.

Example 16

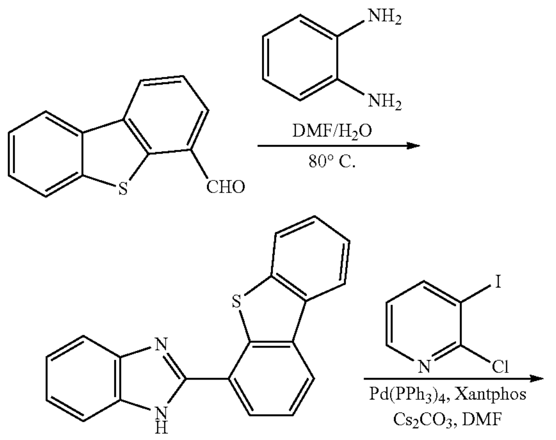

BImBT-1

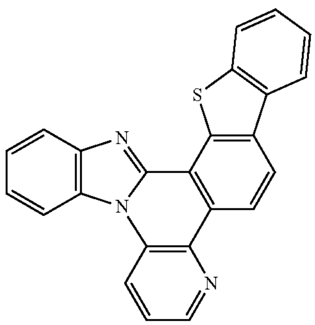

DFE-16

Synthesis of DFE-16

$Cs_2CO_3$ (3 eq) and 2-chloro-3-iodopyridine (1.2 eq). Then, BImBT-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-16 in 28% yield.

Example 17

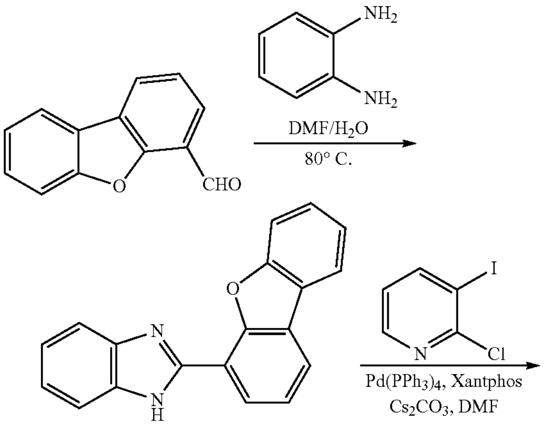

BImBF-1

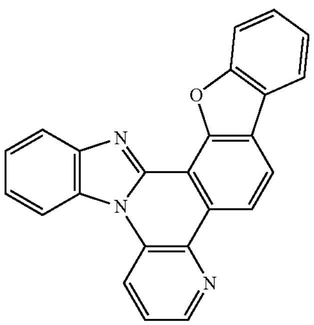

DFE-17

Synthesis of DFE-17

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImBF-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-17 in 28% yield.

Example 18

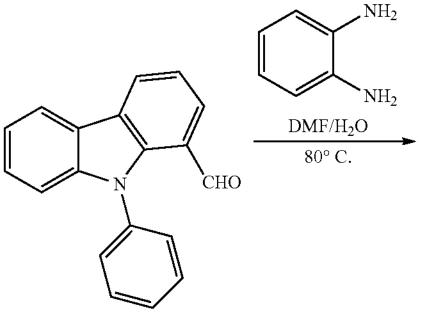

-continued

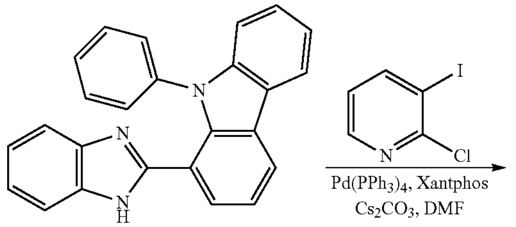

BImPCz-1

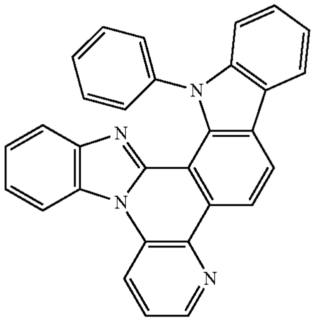

DFE-18

Synthesis of DFE-18

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImPCz-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-18 in 23% yield.

Example 19

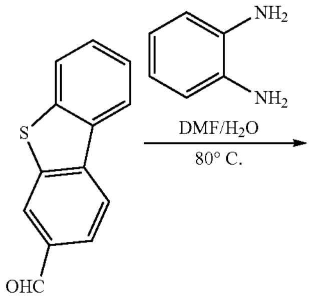

-continued

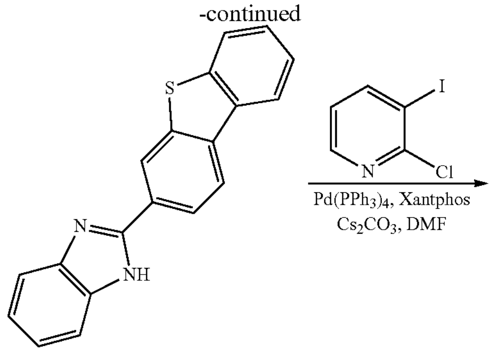

BImBT-2

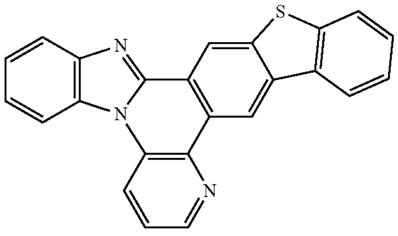

DFE-19

Synthesis of DFE-19

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImBT-2 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-19 in 21% yield.

Example 20

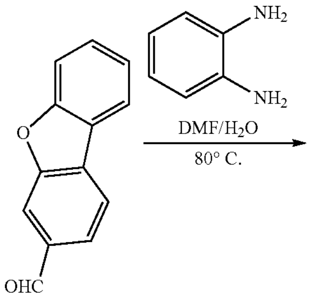

-continued

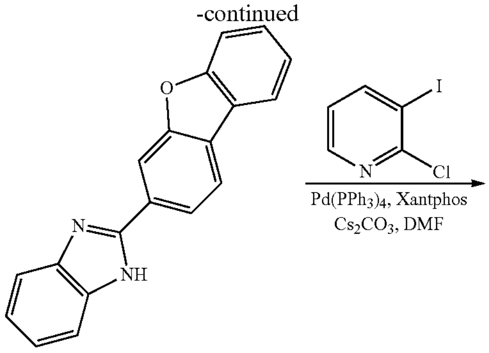

BImBF-2

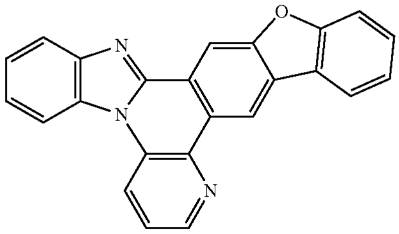

DFE-20

Synthesis of DFE-20

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImBF-2 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-20 in 26% yield.

Example 21

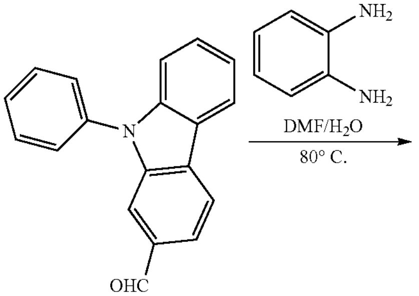

-continued

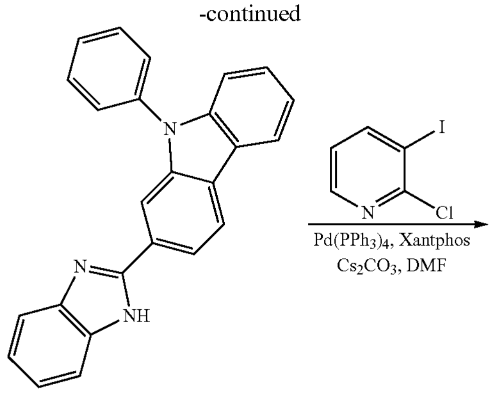

BImPCz-2

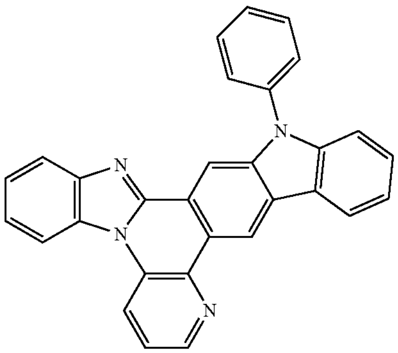

DFE-21

Synthesis of DFE-21

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImPCz-2 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-21 in 23% yield.

Example 22

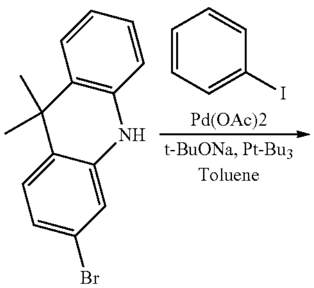

-continued

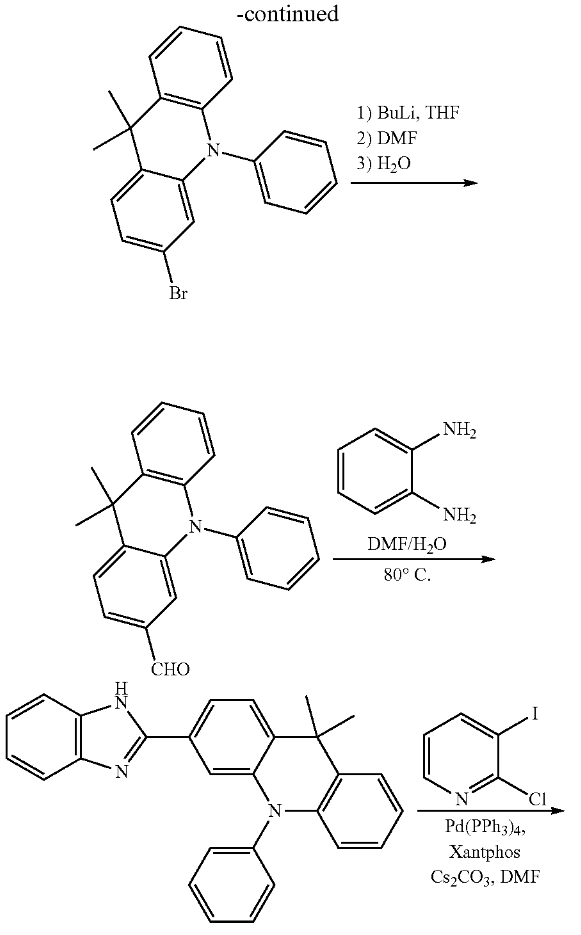

BImPAd-1

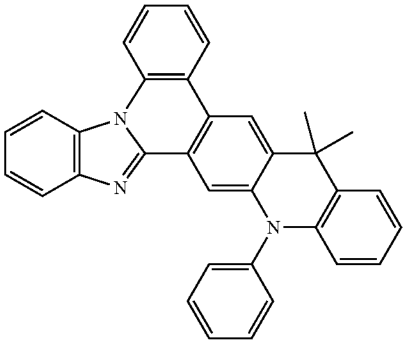

DFE-22

Example 23

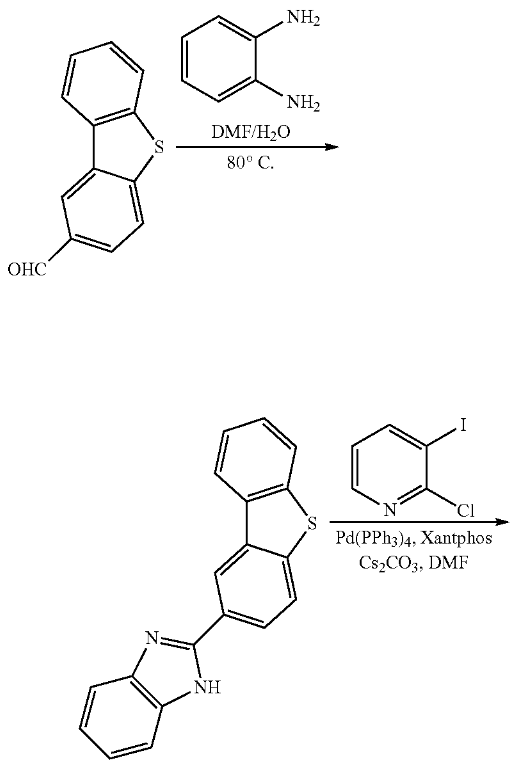

BImBT-3

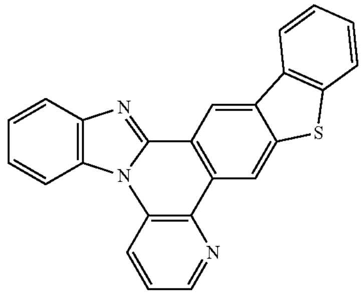

DFE-23

Synthesis of DFE-22

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImPAd-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-22 in 19% yield.

Synthesis of DFE-23

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImBT-3 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-23 in 25% yield.

Example 24

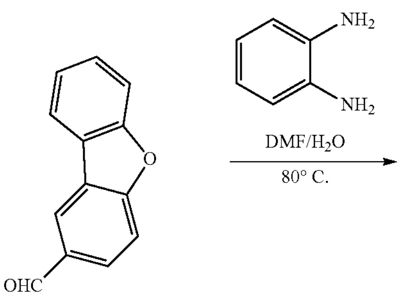

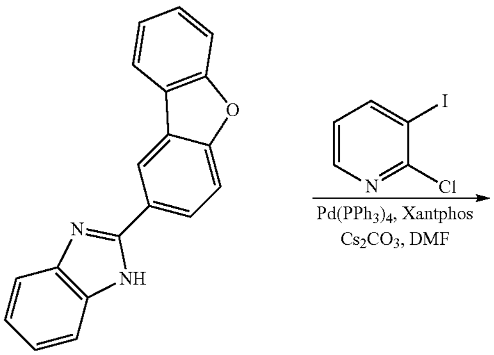

BlmBF-3

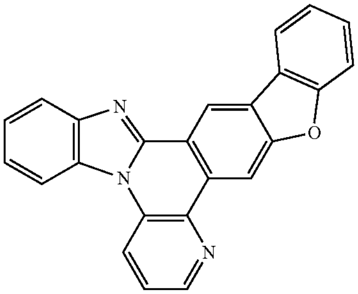

DFE-24

Synthesis of DFE-24

To a flame-dried flask were added Pd($PPh_3$)$_4$ (10 mol %), Xantphos (10 mol %), $Cs_2CO_3$ (3 eq) and 2-chloro-3-iodopyridine (1.2 eq). Then, BImBF-3 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-24 in 20% yield.

Example 25

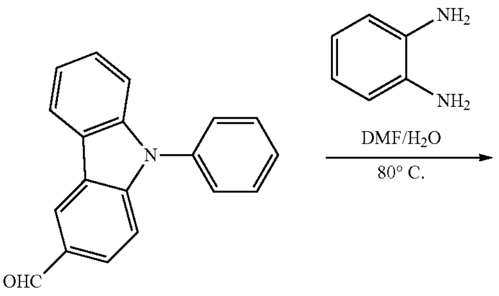

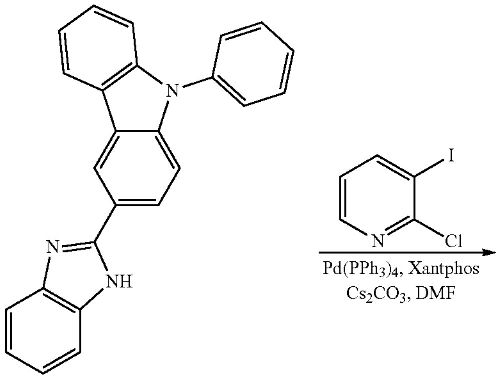

BlmPCz-3

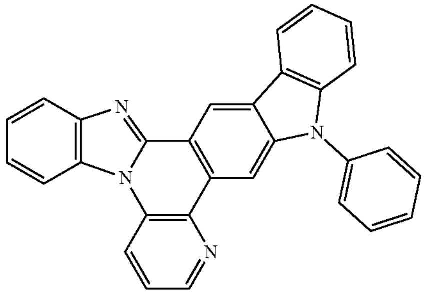

DFE-25

Synthesis of DFE-25

To a flame-dried flask were added Pd($PPh_3$)$_4$ (10 mol %), Xantphos (10 mol %), $Cs_2CO_3$ (3 eq) and 2-chloro-3-iodopyridine (1.2 eq). Then, BImBF-3 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-25 in 20% yield.

Example 26

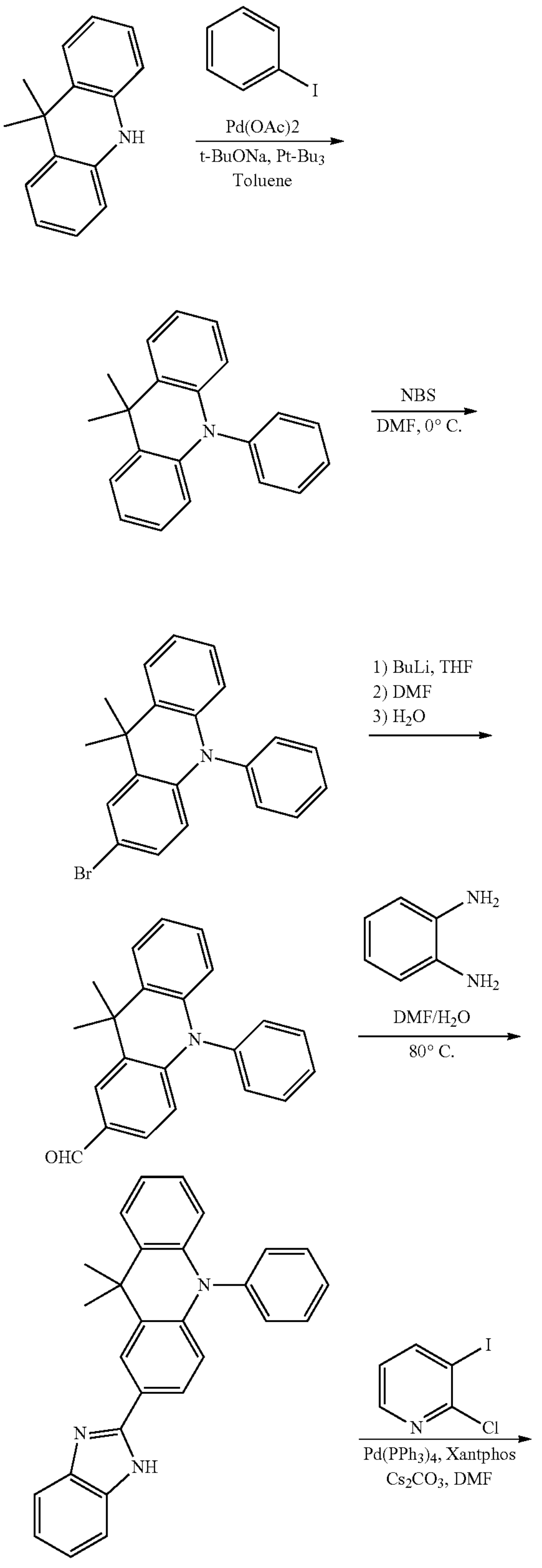

BlmPAd-2

-continued

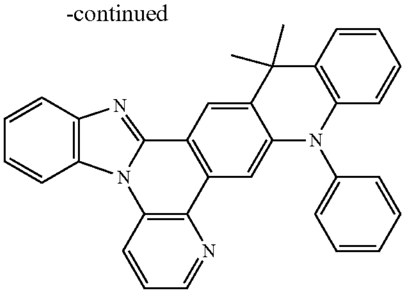

DFE-26

Synthesis of DFE-26

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImPAd-2 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-26 in 18% yield.

Example 27

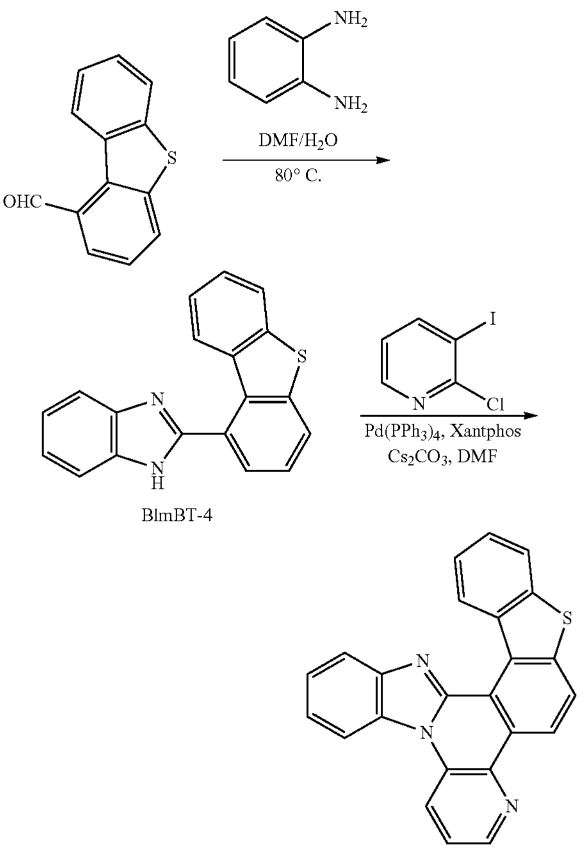

DFE-27

Synthesis of DFE-27

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImBT-4 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-27 in 24% yield.

Example 28

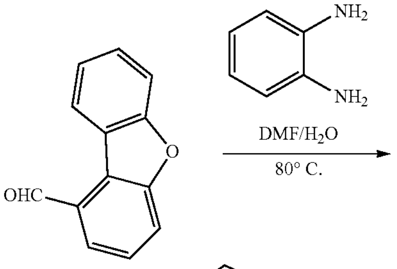

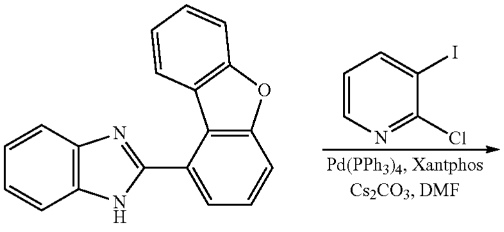

BImBF-4

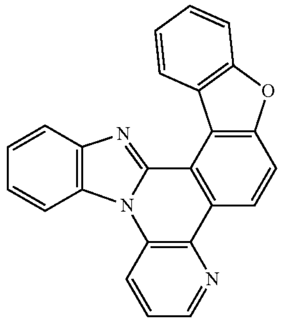

DFE-28

Synthesis of DFE-28

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImBF-4 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-28 in 21% yield.

Example 29

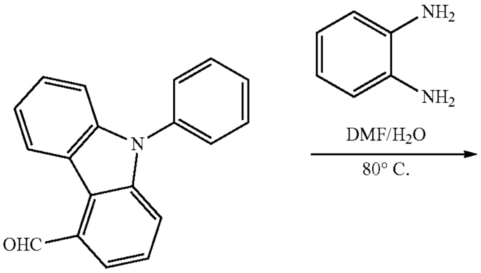

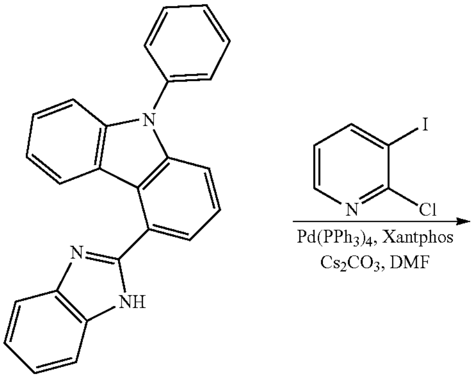

BImPCz-4

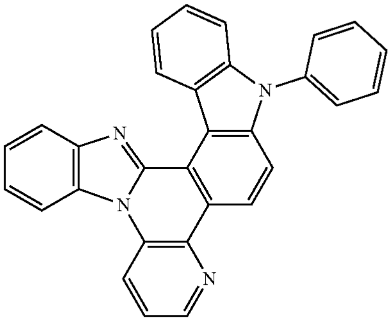

DFE-29

Synthesis of DFE-29

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, BImPCz-4 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-29 in 27% yield.

Example 30

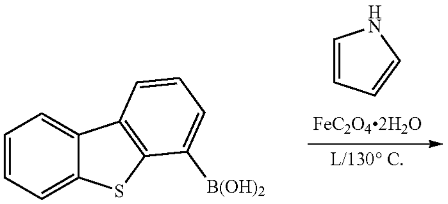

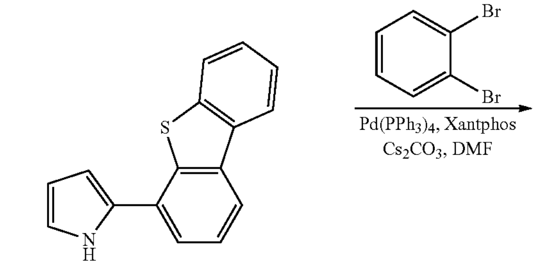

PBT-1

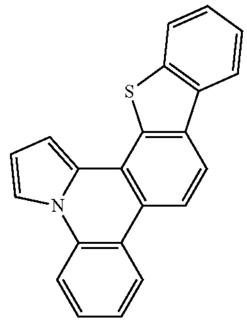

DFE-30

Synthesis of DFE-30

To a flame-dried flask were added $Pd(PPh_3)_4$ (10 mol %), Xantphos (10 mol %), $Cs_2CO_3$ (3 eq) and 1,2-dibromobenzene (1.2 eq). Then, PBT-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-30 in 43% yield.

Example 31

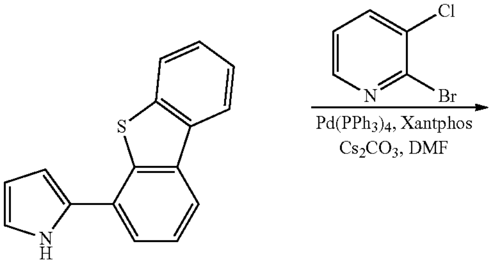

PBT-1

-continued

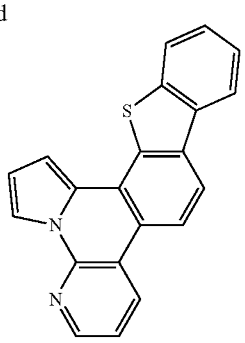

DFE-31

Synthesis of DFE-31

To a flame-dried flask were added $Pd(PPh_3)_4$ (10 mol %), Xantphos (10 mol %), $Cs_2CO_3$ (3 eq) and 2-bromo-3-chloropyridine (1.2 eq). Then, PBT-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-31 in 17% yield.

Example 32

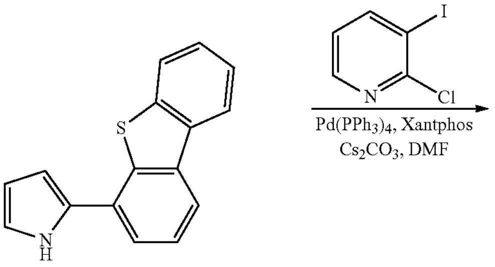

PBT-1

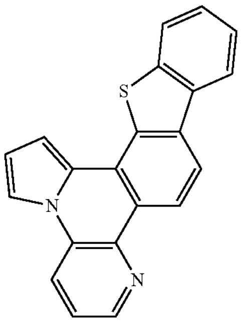

DFE-32

Synthesis of DFE-32

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, PBT-1 (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-32 in 21% yield.

Example 33

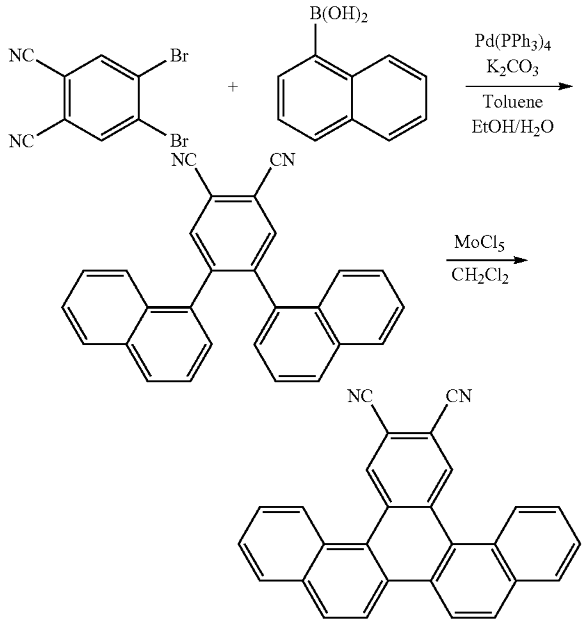

DFE-33

Synthesis of DFE-33

$MoCl_5$ (1.0 equiv) was added quickly to a solution of 4,5-di(naphthalen-1-yl)phthalonitrile (1.00 equiv) in $CH_2Cl_2$ (0.05 M) under nitrogen. The mixture was stirred at room temperature for 24 h; then the other one equiv of $MoCl_5$ was added quickly to the mixture again. After being stirred for 24 h, the mixture was quenched by methanol and stirred for another 1 h, filtered, and washed with $CH_2Cl_2$. The filtrate was concentrated, and the residue was purified through column chromatography on silica gel to afford the product DFE-33 in 41% yield.

Example 34

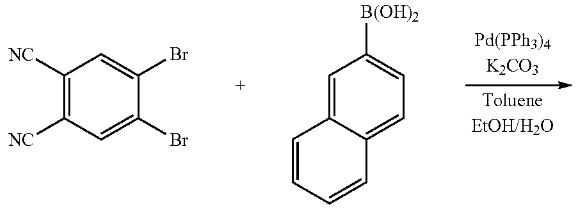

-continued

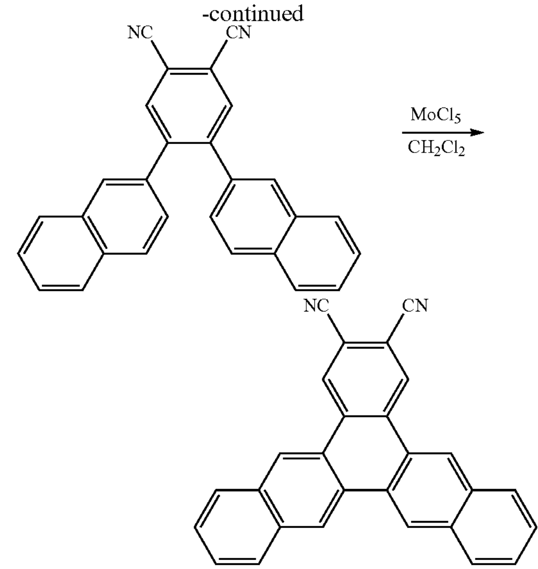

DFE-34

Synthesis of DFE-34

$MoCl_5$ (1.0 equiv) was added quickly to a solution of 4,5-di(naphthalen-2-yl)phthalonitrile (1.00 equiv) in $CH_2Cl_2$ (0.05 M) under nitrogen. The mixture was stirred at room temperature for 24 h; then the other one equiv of $MoCl_5$ was added quickly to the mixture again. After being stirred for 24 h, the mixture was quenched by methanol and stirred for another 1 h, filtered, and washed with $CH_2Cl_2$. The filtrate was concentrated, and the residue was purified through column chromatography on silica gel to afford the product DFE-33 in 37% yield.

Example 35

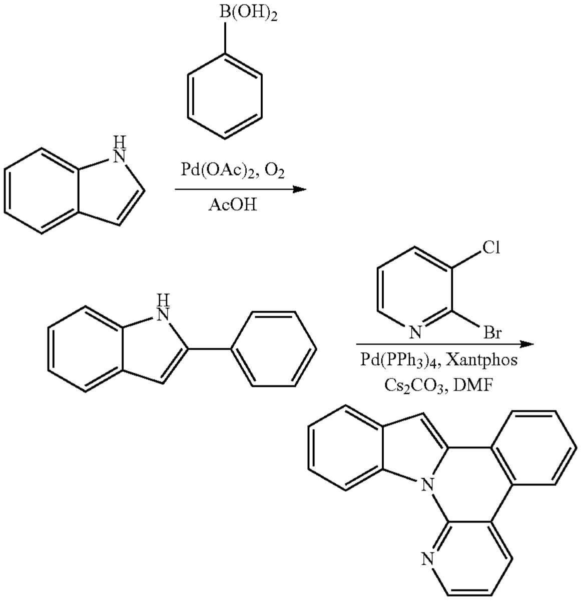

DFE-35

Synthesis of DFE-35

To a flame-dried flask were added $Pd(PPh_3)_4$ (10 mol %), Xantphos (10 mol %), $Cs_2CO_3$ (3 eq) and 2-bromo-3-chloropyridine (1.2 eq). Then, 2-phenyl-1H-indole (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-35 in 29% yield.

Example 36

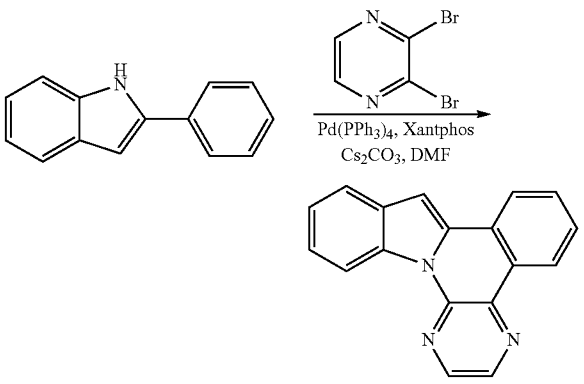

DFE-36

Synthesis of DFE-36

To a flame-dried flask were added $Pd(PPh_3)_4$ (10 mol %), Xantphos (10 mol %), $Cs_2CO_3$ (3 eq) and 2,3-dibromopyrazine (1.2 eq). Then, 2-phenyl-1H-indole (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-36 in 25% yield.

Example 37

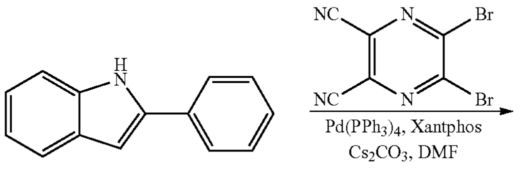

-continued

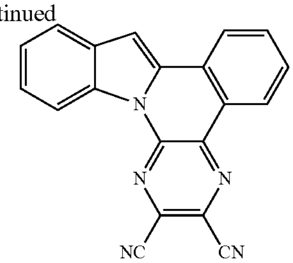

DFE-37

Synthesis of DFE-37

To a flame-dried flask were added $Pd(PPh_3)_4$ (10 mol %), Xantphos (10 mol %), $Cs_2CO_3$ (3 eq) and 5,6-dibromopyrazine-2,3-dicarbonitrile (1.2 eq). Then, 2-phenyl-1H-indole (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-37 in 22% yield.

Example 38

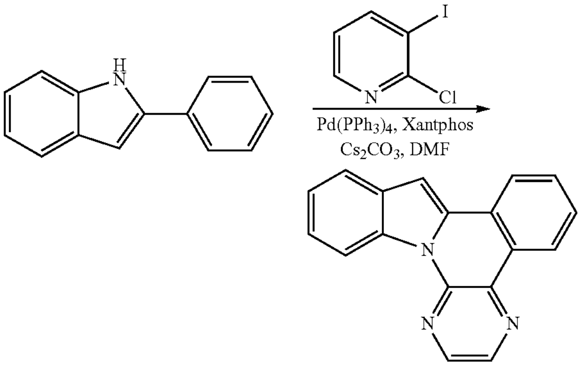

DFE-38

Synthesis of DFE-38

To a flame-dried flask were added $Pd(PPh_3)_4$ (10 mol %), Xantphos (10 mol %), $Cs_2CO_3$ (3 eq) and 2-chloro-3-iodopyridine (1.2 eq). Then, 2-phenyl-1H-indole (1 eq) and DMF (0.15 M) were added to the reaction mixture under the protection of $N_2$. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-38 in 25% yield.

Only a few implementations are described and illustrated. Variations, enhancements and improvements of the described implementations and other implementations can be made based on what is described and illustrated in this document.

What is claimed is:
1. A compound represented by any one of the following formulas:
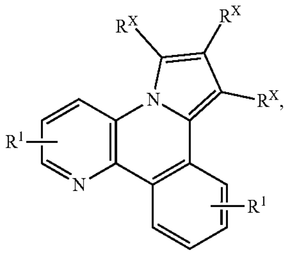
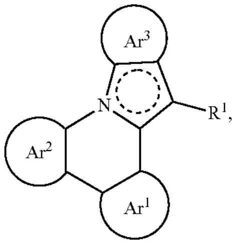
or
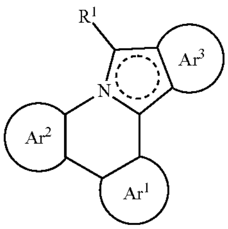
,
wherein:
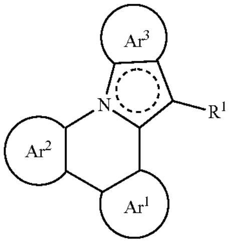
or
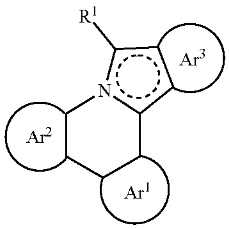
represents:
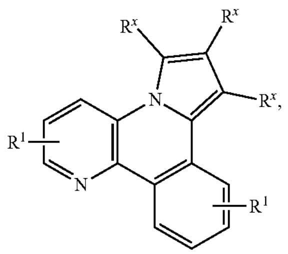
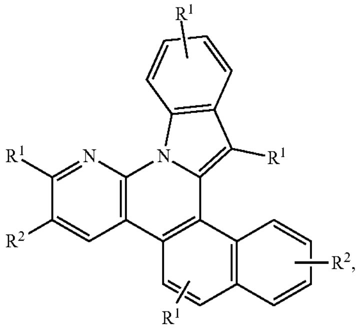
-continued
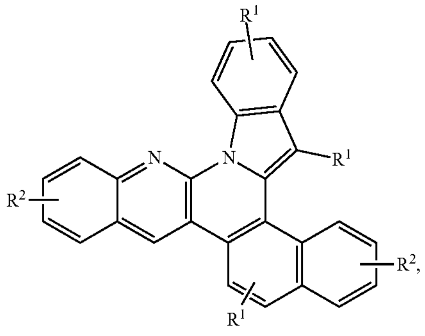
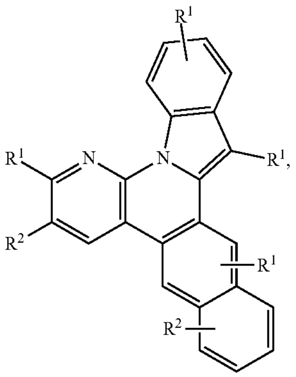
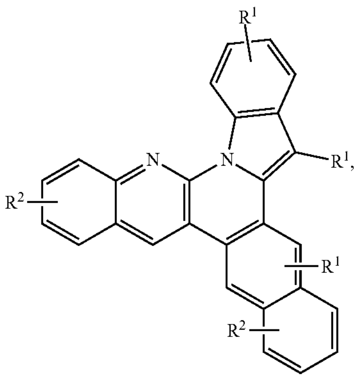
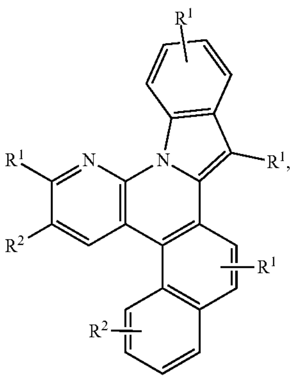

-continued
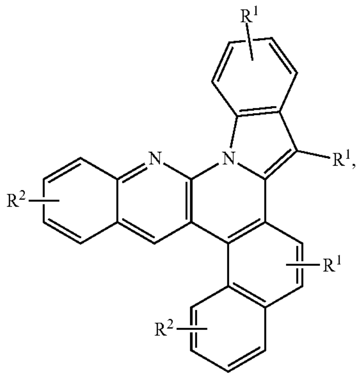
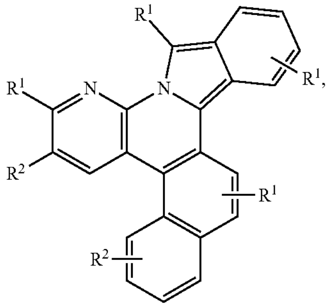
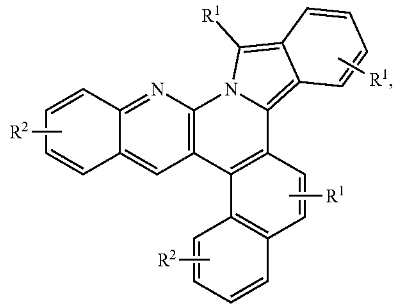
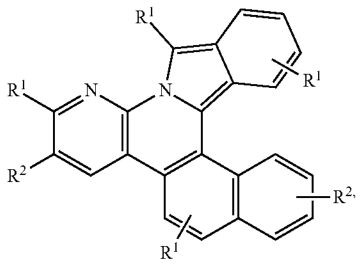
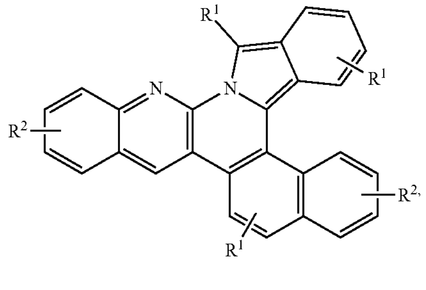
-continued
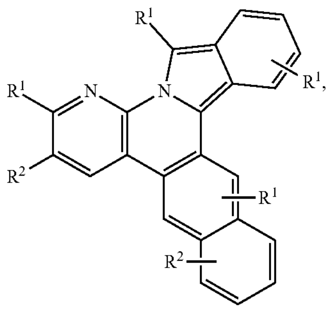
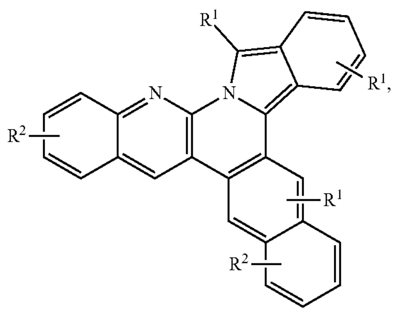
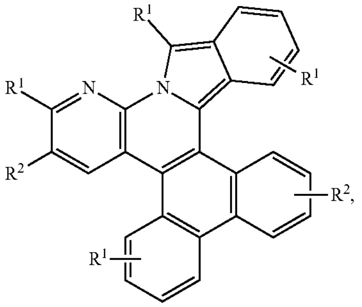
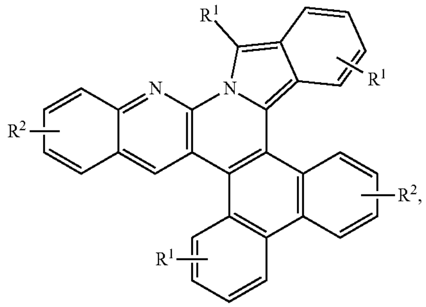
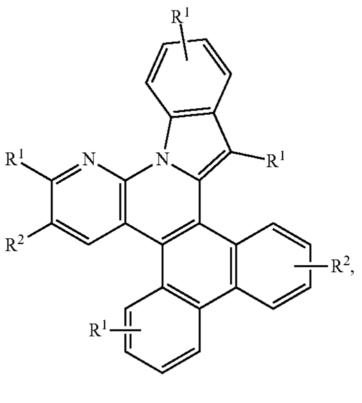

-continued
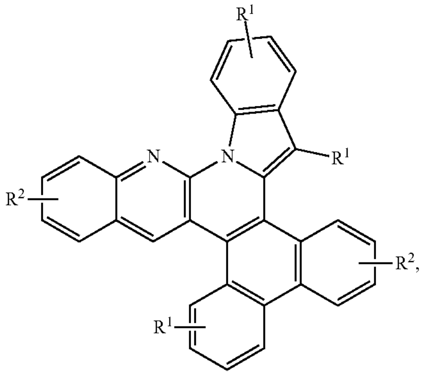
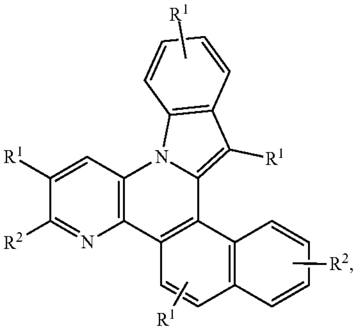
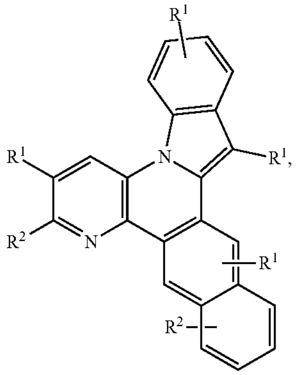
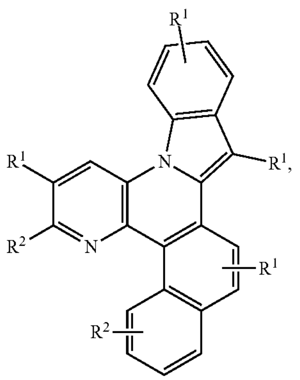
-continued
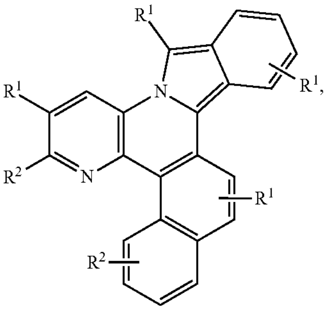
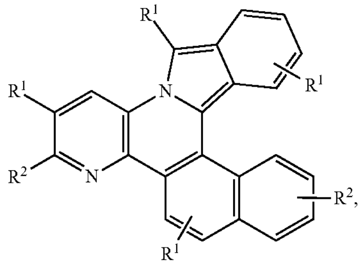
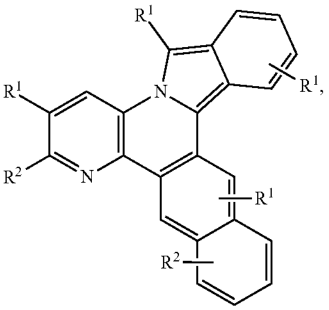
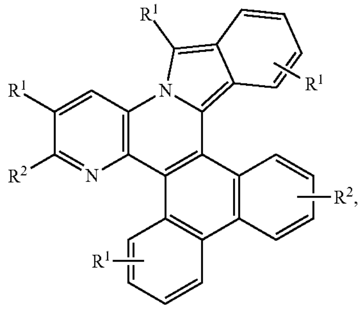
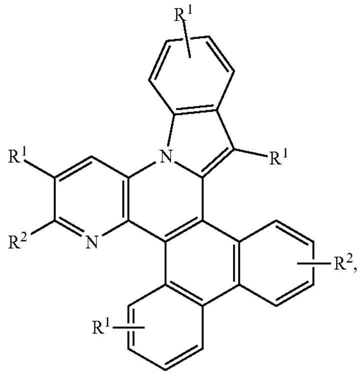

-continued
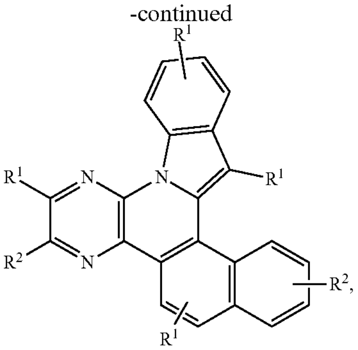
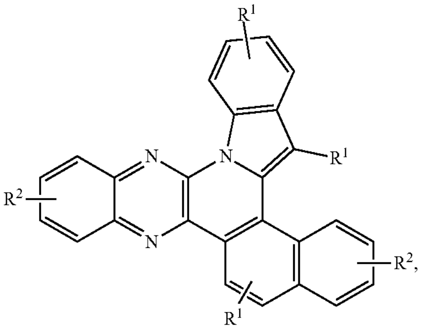
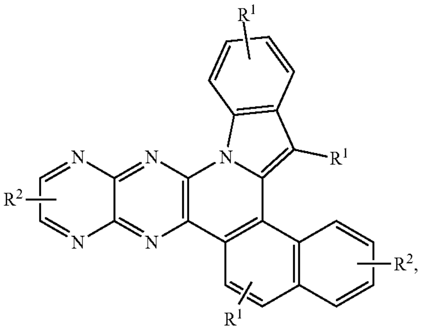
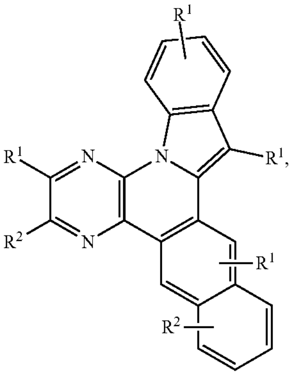
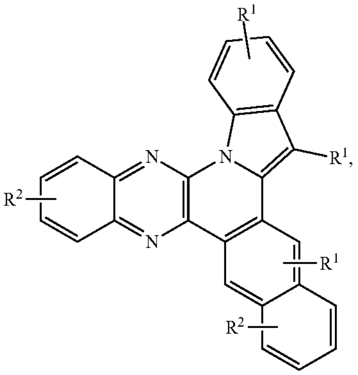
-continued
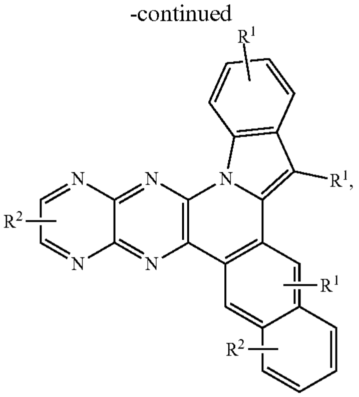
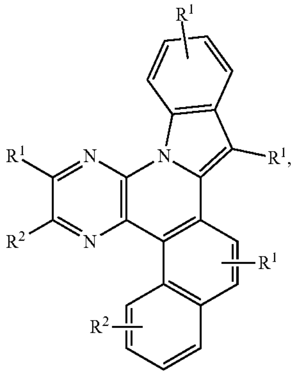
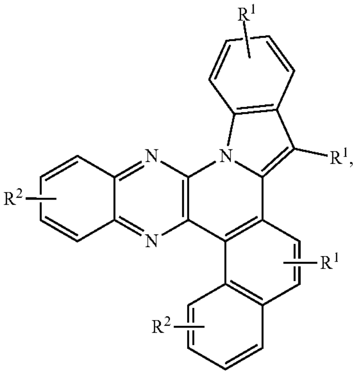
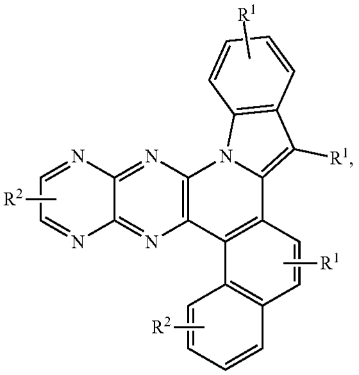

-continued
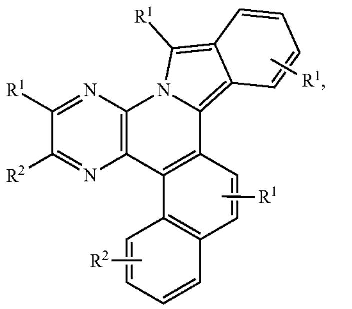
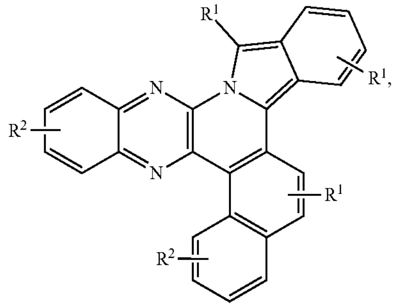
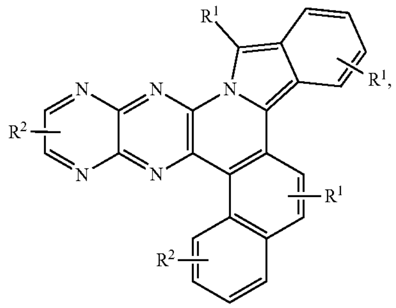
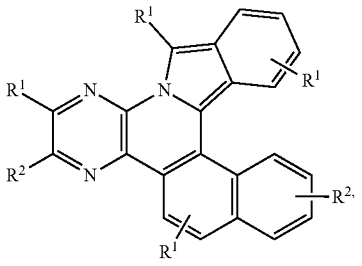
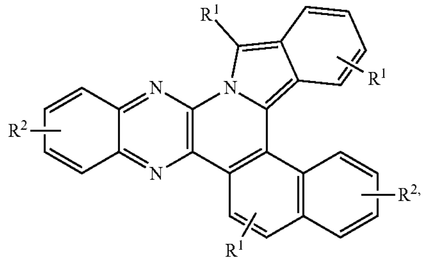
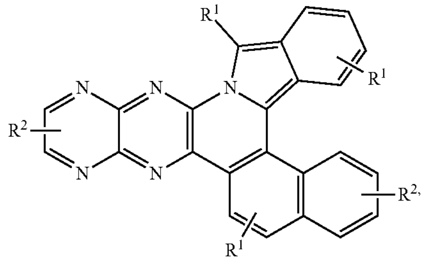
-continued
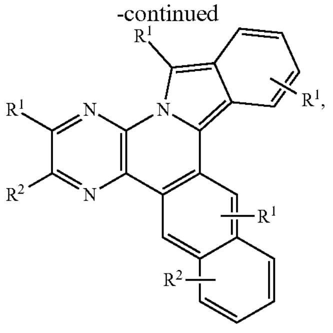
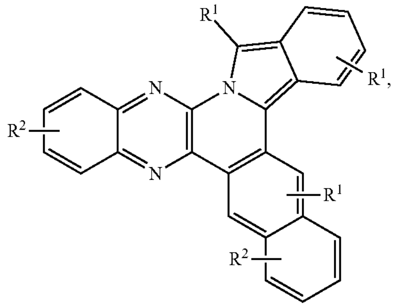
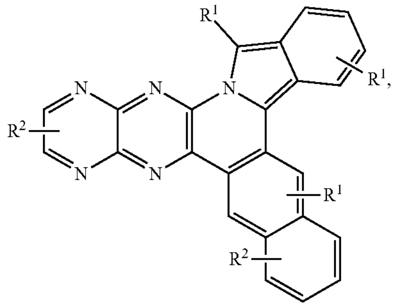
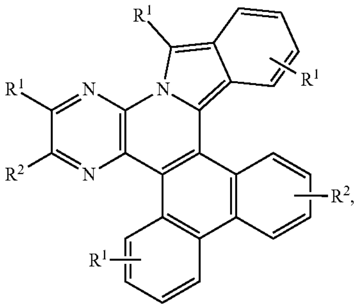
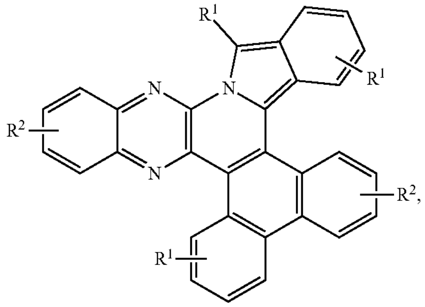

-continued

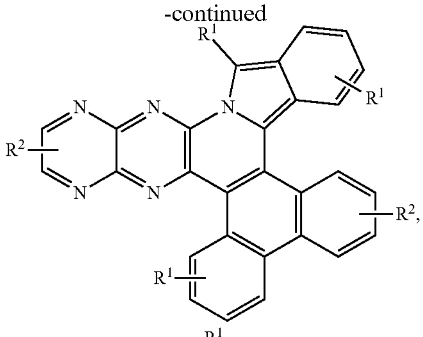

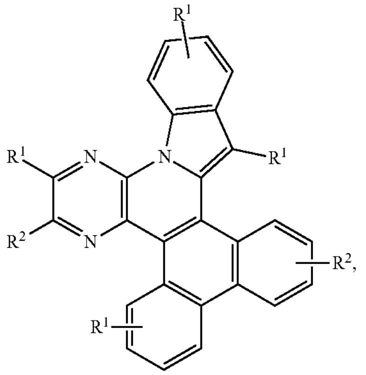

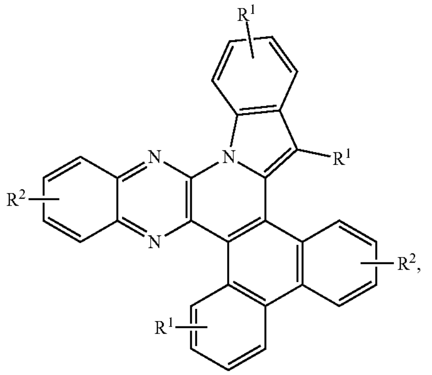

or

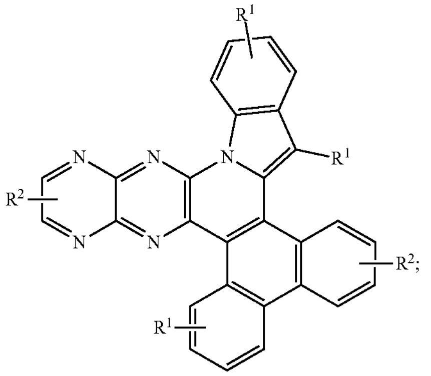

each $R^X$ independently represents hydrogen, deuterium, fluoro, bromo, iodo, cyano, isonitrile, nitro, alkyl, haloalkyl, aralkyl, alkenyl, alkynyl, carbamoyl, carboxy, alkoxycarbonyl, amino, monoalkylamino, monoarylamino, dialkylamino, diarylamino, acylamino, ureido, alkoxycarbonylamino, aryloxycarbonylamino, hydrazino, alkylsulfonylamino, arylsulfonylamino, hydroxy, alkoxy, aryloxy, trialkylsilyl, trialkoxysilyl, triarylsilyl, phosphoramide, thiol, alkylthio, alkylsulfinyl, sulfamoyl, sulfonic acid, cycloalkyl, cycloalkenyl, heterocyclyl, aryl, or heteroaryl;

each $R^1$ independently represents hydrogen, deuterium, halogen, cyano, isonitrile, nitro, alkyl, haloalkyl, aralkyl, alkenyl, alkynyl, carbamoyl, carboxy, alkoxycarbonyl, amino, monoalkylamino, monoarylamino, dialkylamino, diarylamino, acylamino, ureido, alkoxycarbonylamino, aryloxycarbonylamino, hydrazino, alkylsulfonylamino, arylsulfonylamino, hydroxy, alkoxy, aryloxy, trialkylsilyl, trialkoxysilyl, triarylsilyl, phosphoramide, thiol, alkylthio, alkylsulfinyl, sulfamoyl, sulfonic acid, cycloalkyl, cycloalkenyl, heterocyclyl, aryl, or heteroaryl; and each $R^2$ independently represents hydrogen, deuterium, halogen, cyano, isonitrile, nitro, alkyl, haloalkyl, aralkyl, alkenyl, alkynyl, carbamoyl, carboxy, alkoxycarbonyl, amino, monoalkylamino, monoarylamino, dialkylamino, diarylamino, acylamino, ureido, alkoxycarbonylamino, aryloxycarbonylamino, hydrazino, alkylsulfonylamino, arylsulfonylamino, hydroxy, alkoxy, aryloxy, trialkylsilyl, trialkoxysilyl, triarylsilyl, phosphoramide, thiol, alkylthio, alkylsulfinyl, sulfamoyl, sulfonic acid, cycloalkyl, cycloalkenyl, heterocyclyl, aryl, or heteroaryl;

wherein the alkyl, haloalkyl, and aralkyl of each $R^X$, $R^1$, and $R^2$ is optionally and independently substituted with one or more substituents independently selected from the group consisting of deuterium, halogen, cyano, isonitrile, nitro, carbamoyl, carboxy, alkoxycarbonyl, amino, monoalkylamino, monoarylamino, dialkylamino, diarylamino, acylamino, ureido, alkoxycarbonylamino, aryloxycarbonylamino, hydrazino, alkylsulfonylamino, arylsulfonylamino, hydroxy, alkoxy, aryloxy, trialkylsilyl, trialkoxysilyl, triarylsilyl, phosphoramide, thiol, alkylthio, alkylsulfinyl, sulfamoyl, sulfonic acid, cycloalkyl, cycloalkenyl, heterocyclyl, aryl, and heteroaryl;

wherein the alkenyl and alkynyl of each $R^X$, $R^1$, and $R^2$ is optionally and independently substituted with one or more substituents independently selected from the group consisting of deuterium, halogen, cyano, isonitrile, nitro, haloalkyl, aralkyl, carbamoyl, carboxy, alkoxycarbonyl, amino, monoalkylamino, monoarylamino, dialkylamino, diarylamino, acylamino, ureido, alkoxycarbonylamino, aryloxycarbonylamino, hydrazino, alkylsulfonylamino, arylsulfonylamino, hydroxy, alkoxy, aryloxy, trialkylsilyl, trialkoxysilyl, triarylsilyl, phosphoramide, thiol, alkylthio, alkylsulfinyl, sulfamoyl, sulfonic acid, cycloalkyl, cycloalkenyl, heterocyclyl, aryl, and heteroaryl; and wherein the carbamoyl, alkoxycarbonyl, amino, monoalkylamino, monoarylamino, dialkylamino, diarylamino, acylamino, ureido, alkoxycarbonylamino, aryloxycarbonylamino, alkylsulfonylamino, arylsulfonylamino, alkoxy, aryloxy, trialkylsilyl, trialkoxysilyl, triarylsilyl, phosphoramide, alkylthio, sulfamoyl, cycloalkyl, cycloalkenyl, heterocyclyl, aryl, and heteroaryl of each $R^X$, $R^1$, and $R^2$ is optionally and independently substituted with one or more substituents independently selected from the group consisting of deuterium, halogen, cyano, isonitrile, nitro, alkyl, haloalkyl, aralkyl, alkenyl, alkynyl, carbamoyl, carboxy, alkoxycarbonyl, amino, monoalkylamino, monoarylamino, dialkylamino, diarylamino, acylamino, ureido, alkoxycarbonylamino, aryloxycarbonylamino, hydrazino, alkylsulfonylamino, arylsulfonylamino, hydroxy, alkoxy, aryloxy, trialkylsilyl, trialkoxysilyl, triarylsilyl, phosphoramide, thiol, alkylthio, alkylsulfinyl, sulfamoyl, sulfonic acid, cycloalkyl, cycloalkenyl, heterocyclyl, aryl, and heteroaryl.
2. The compound of claim 1, wherein
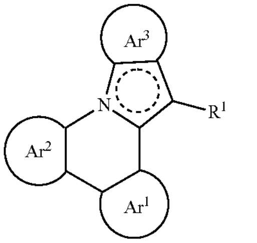
or
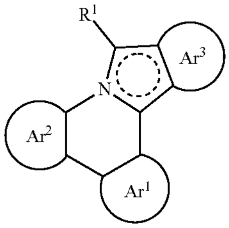
represents:
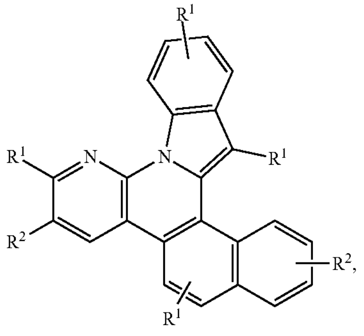
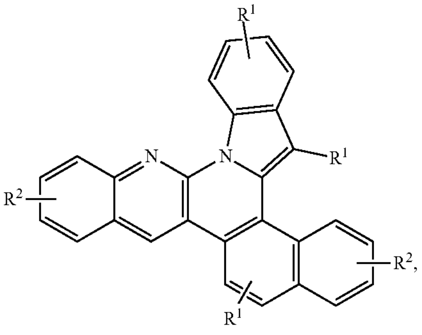
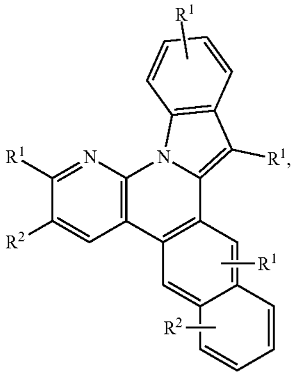
-continued
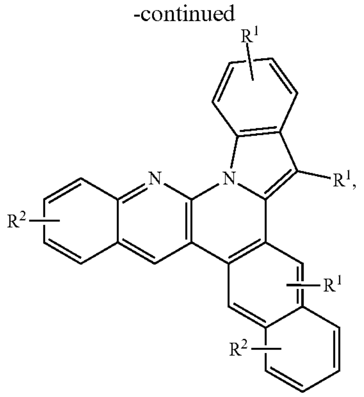
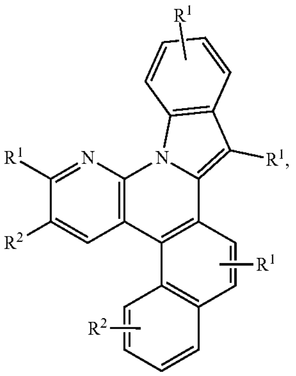
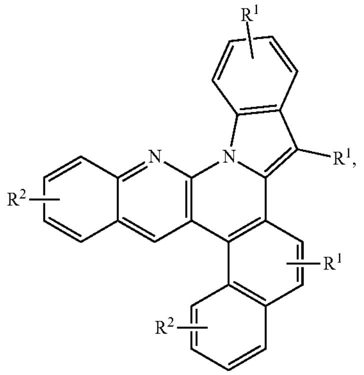
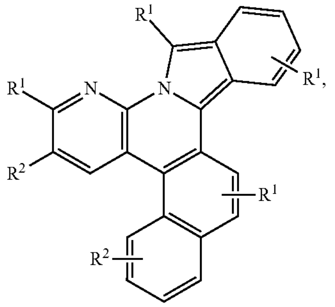

-continued
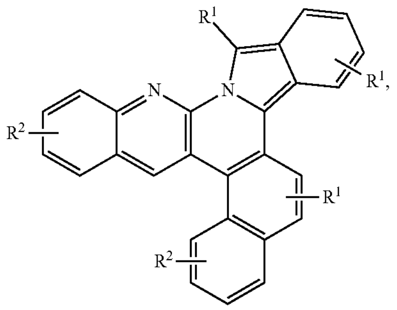
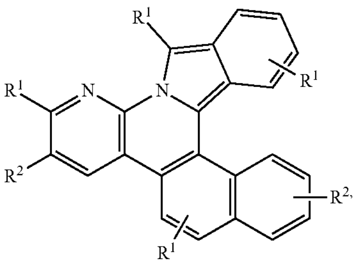
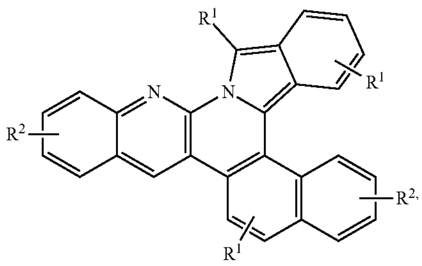
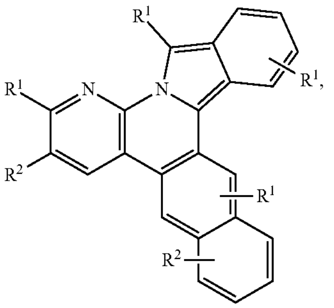
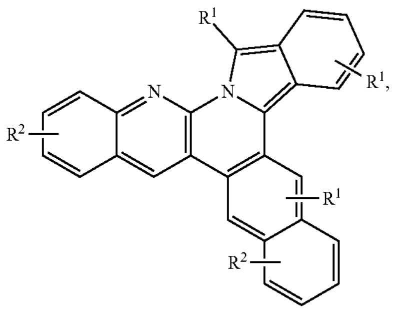
-continued
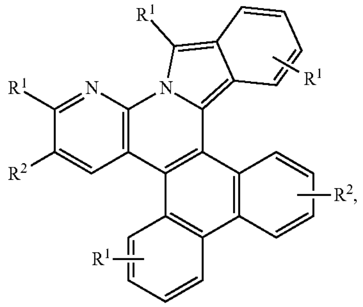
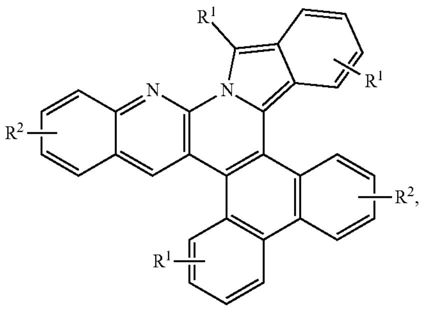
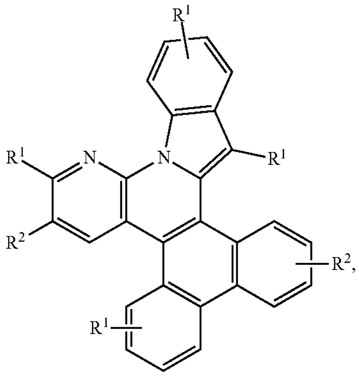
or
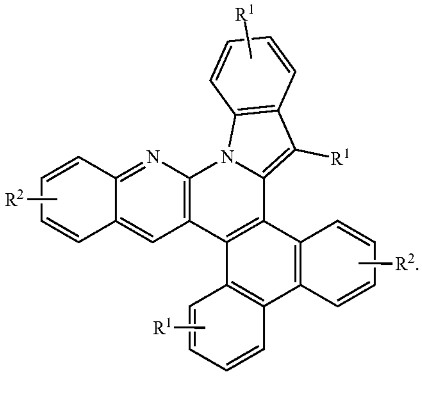

3. The compound of claim 1, wherein
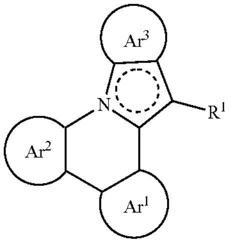
or
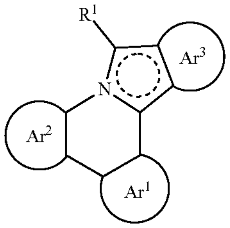
represents:
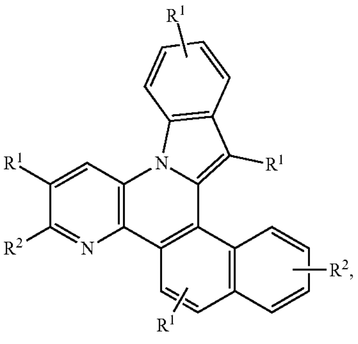
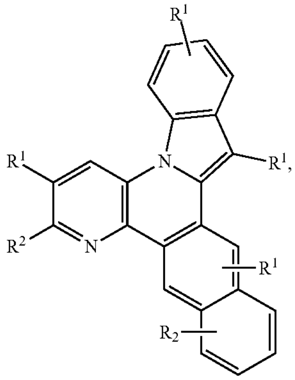
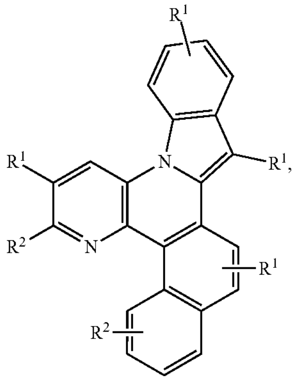
-continued
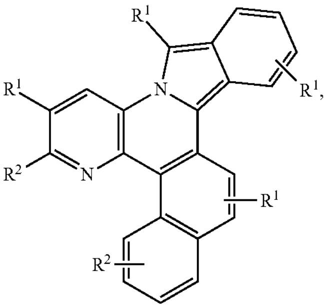
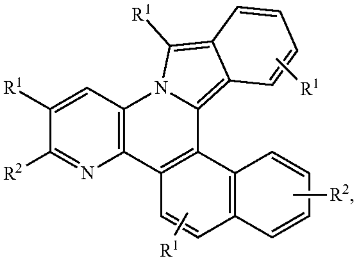
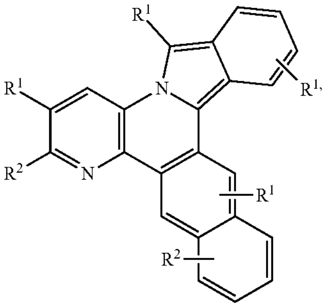
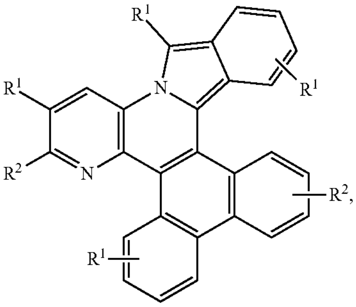
or
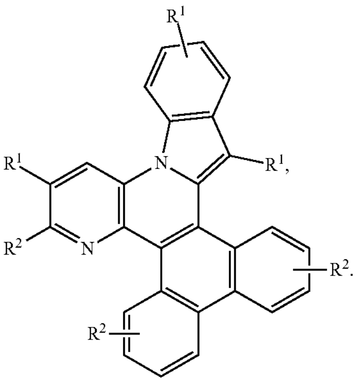

4. The compound of claim 1, wherein
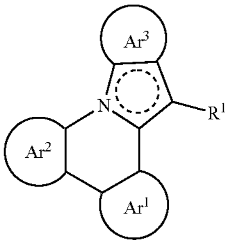
or
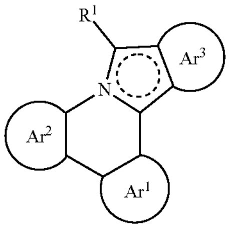
represents:
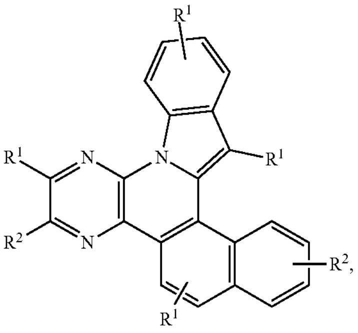
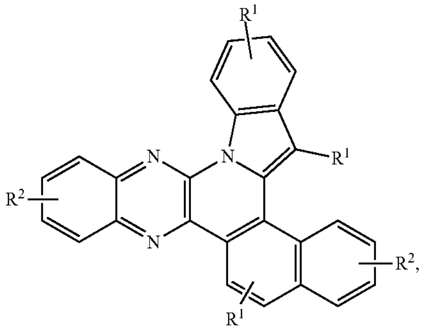
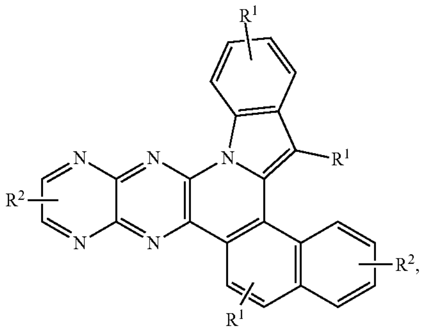
-continued
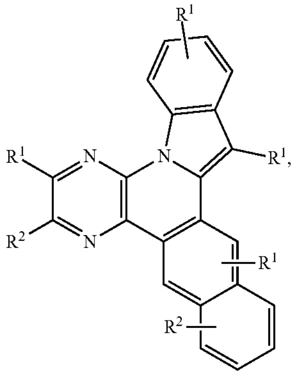
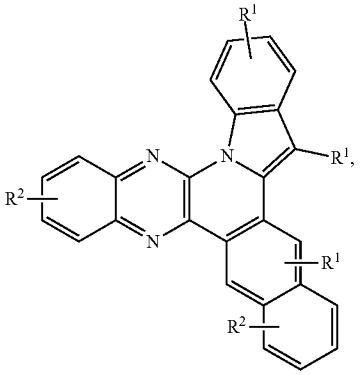
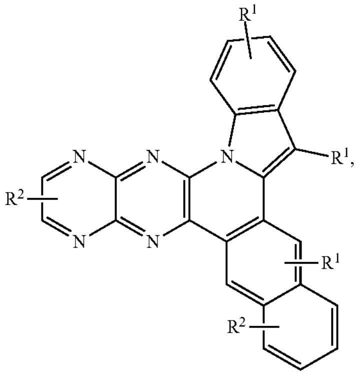
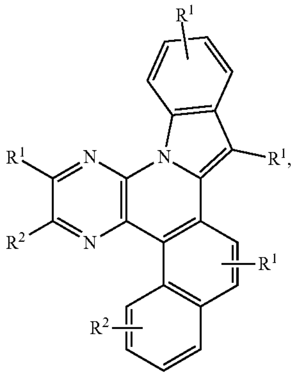

-continued
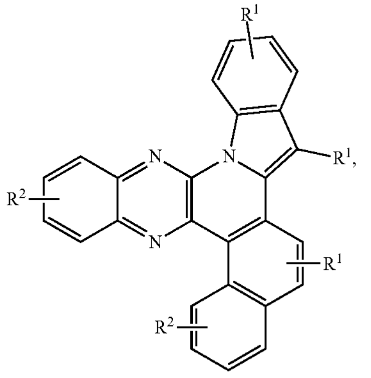
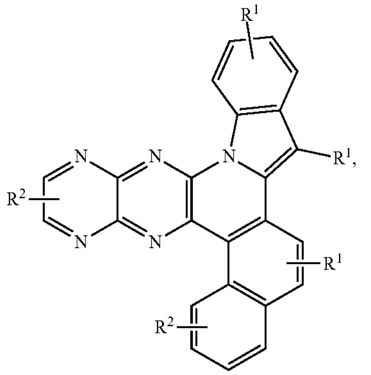
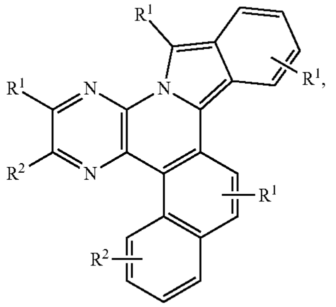
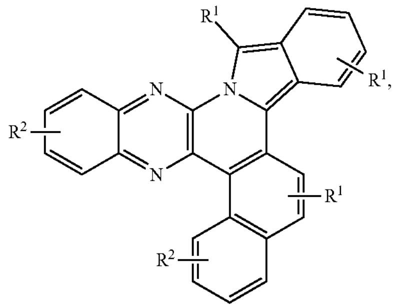
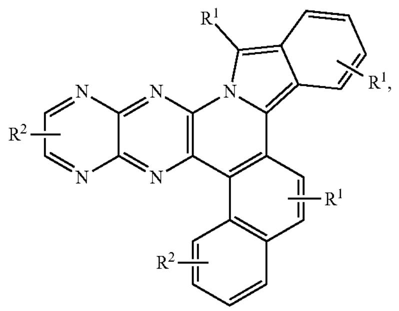
-continued
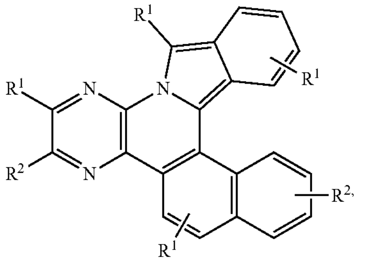
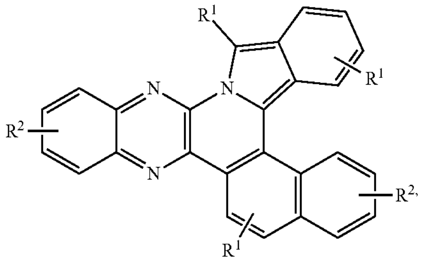
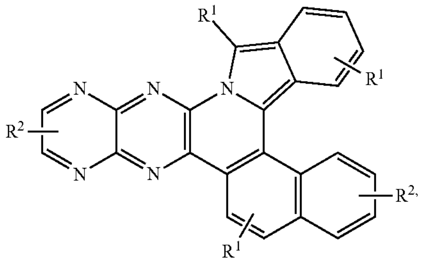
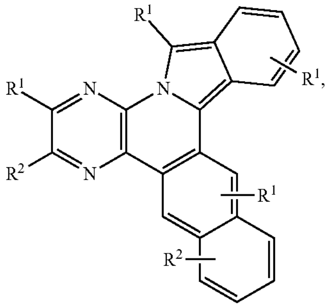
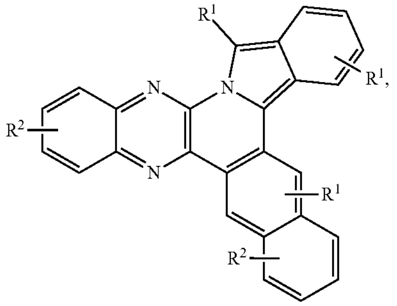
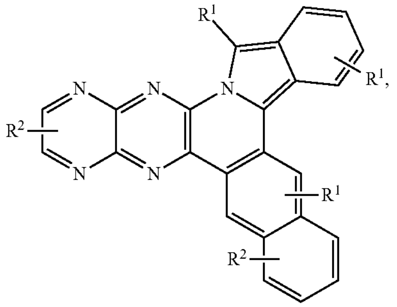

-continued
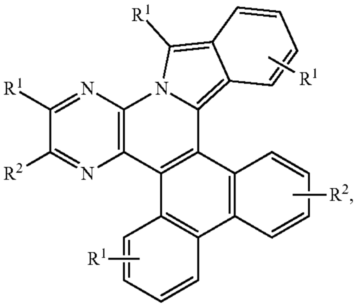
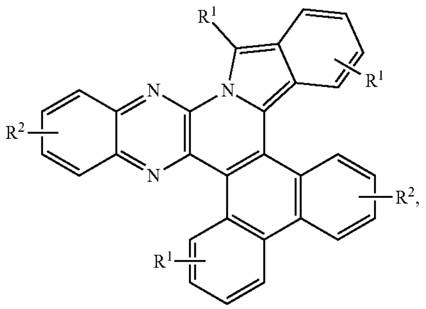
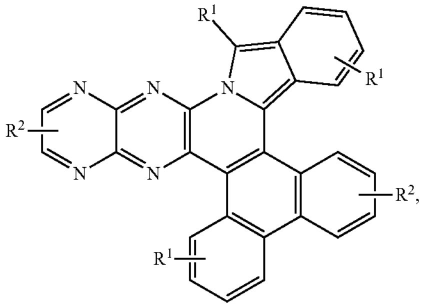
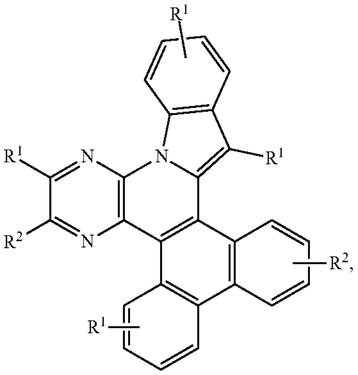
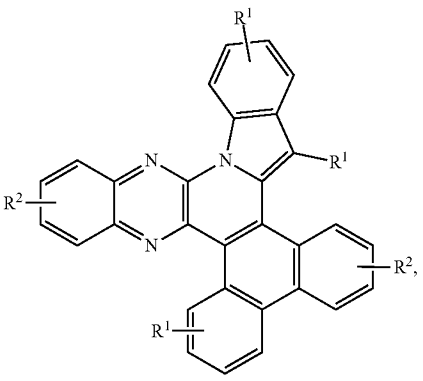
or
-continued
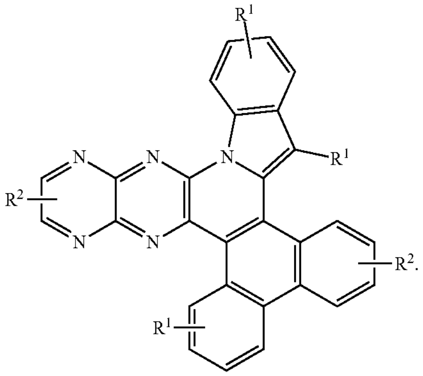
5. The compound of claim 1, wherein
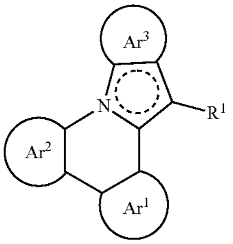
or
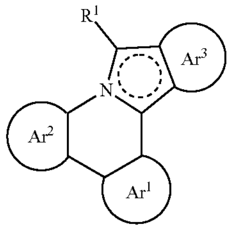
represents:
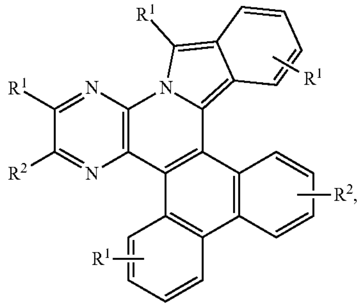
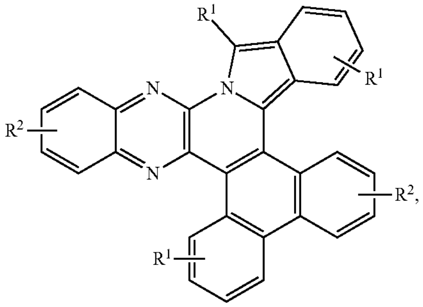

-continued
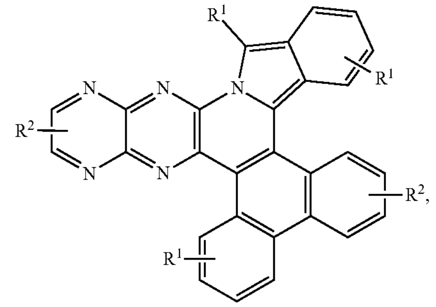
,
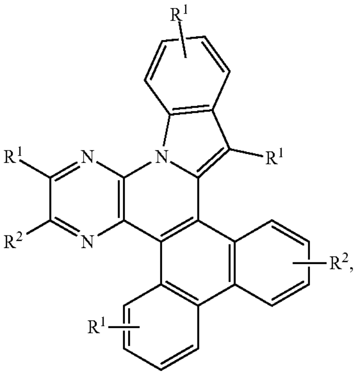
,
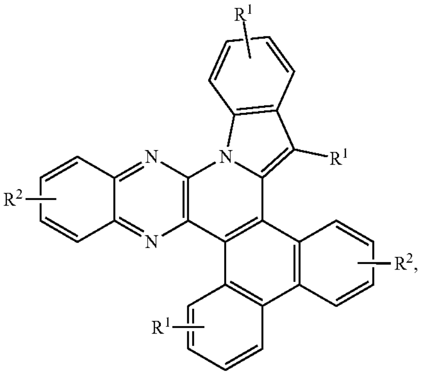
, or
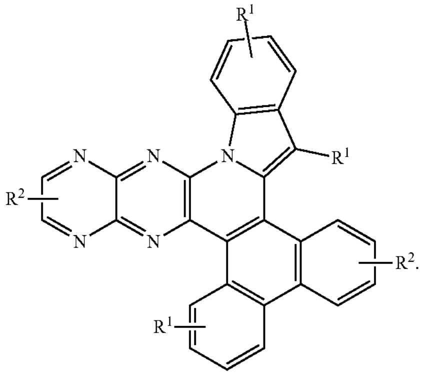
.
6. The compound of claim 1, wherein the compound is selected from the group consisting of:
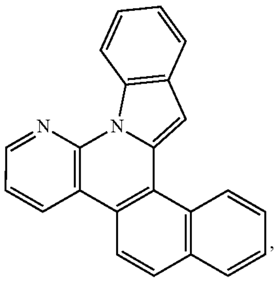
,
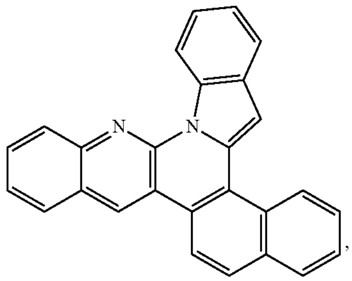
,
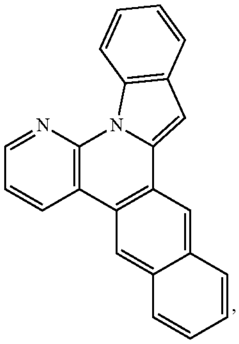
,
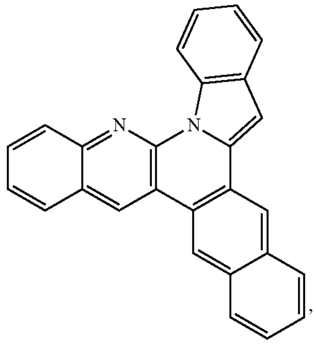
,
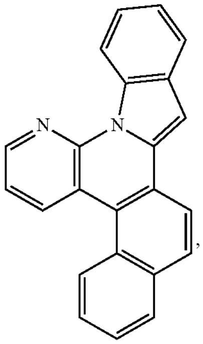
,
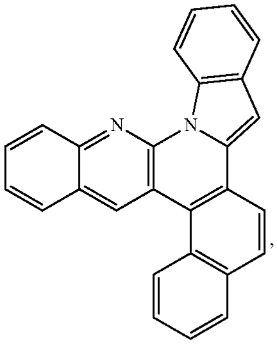
,
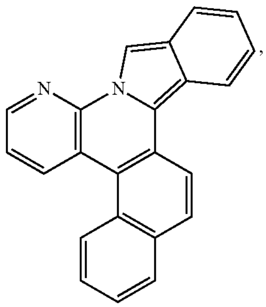
, -continued
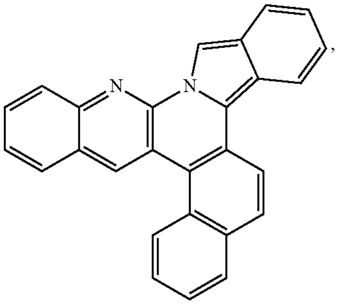
,
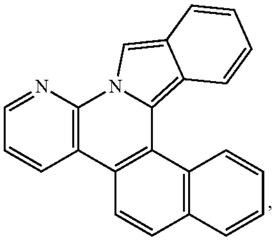
,
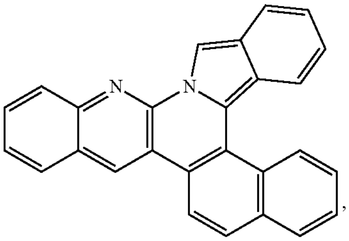
,
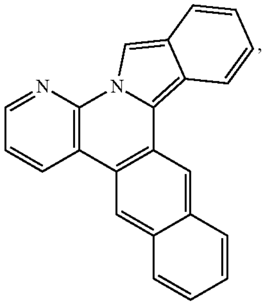
,
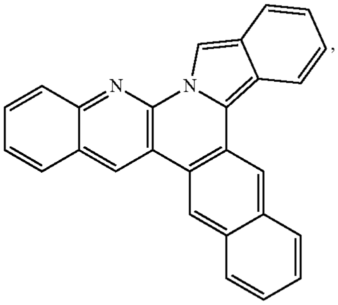
,
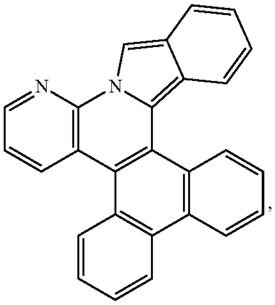
,
-continued
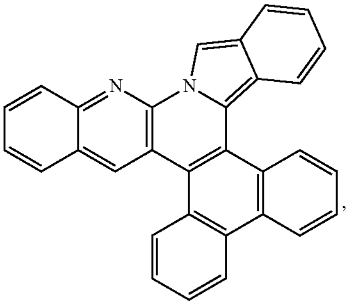
,
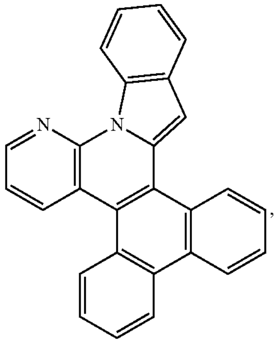
,
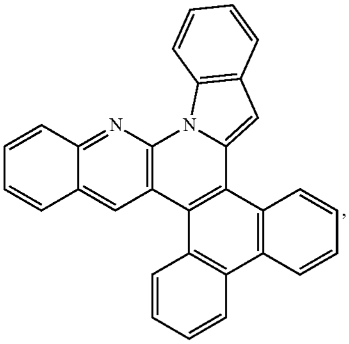
,
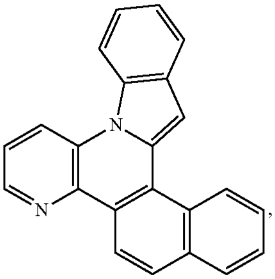
,
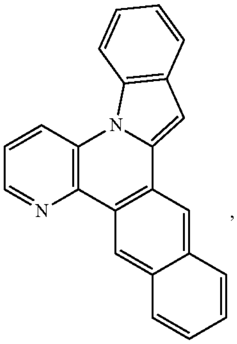
,
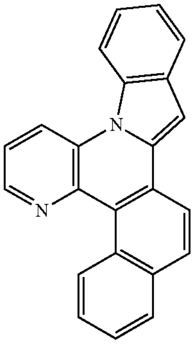
,
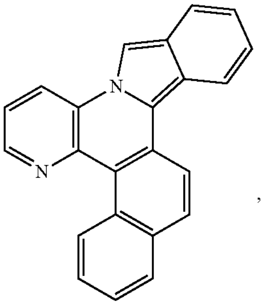
, -continued
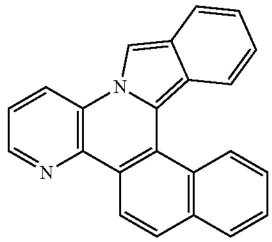
,
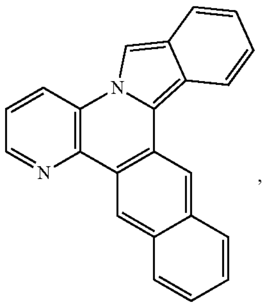
,
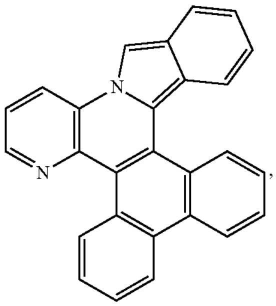
,
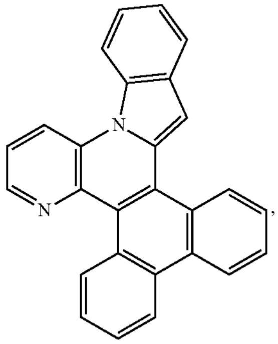
,
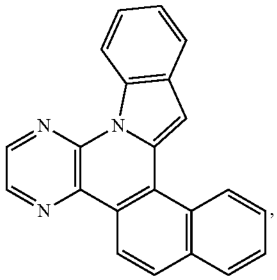
,
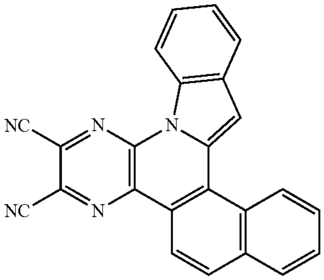
,
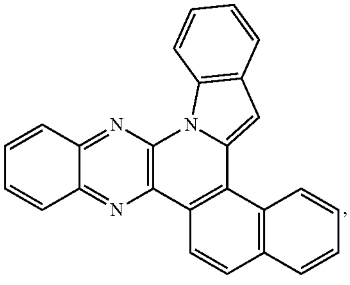
,
-continued
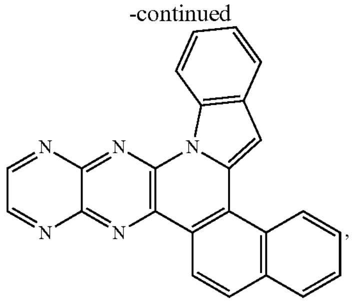
,
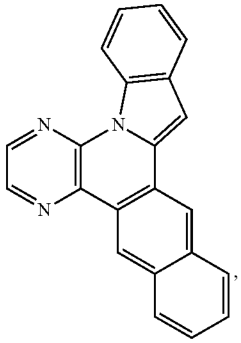
,
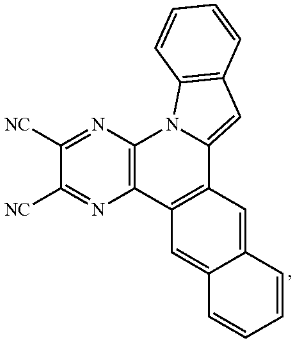
,
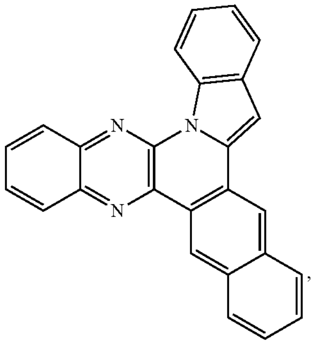
,
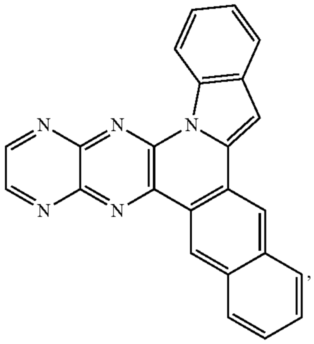
,
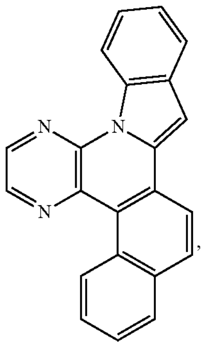
,
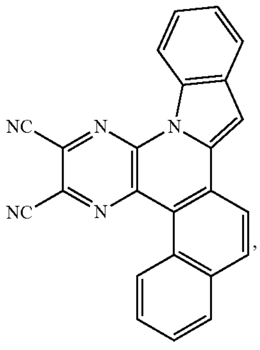
, -continued
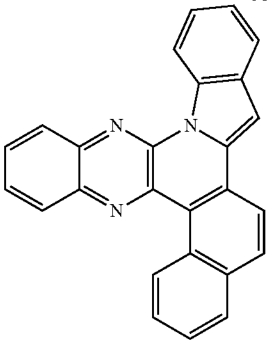,
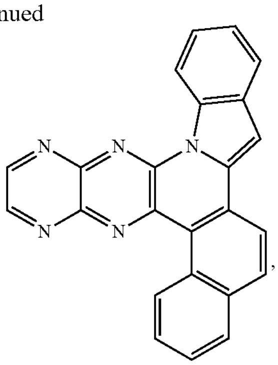,
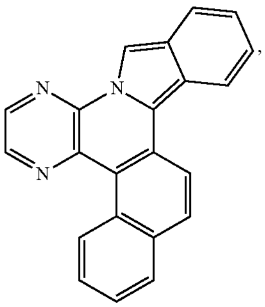,
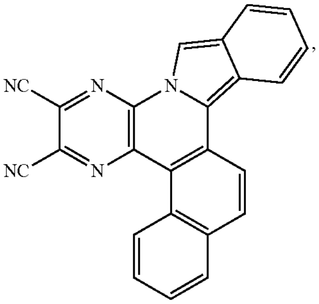,
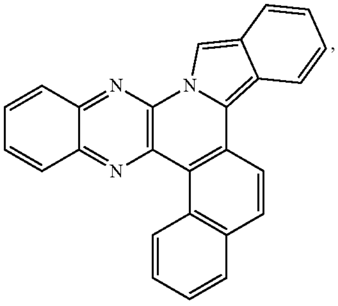,
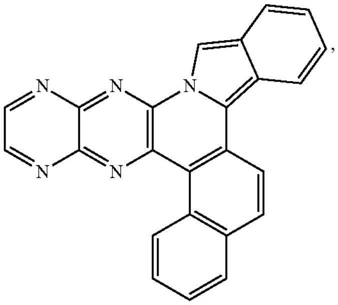,
-continued
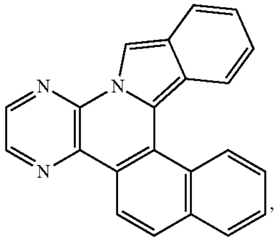,
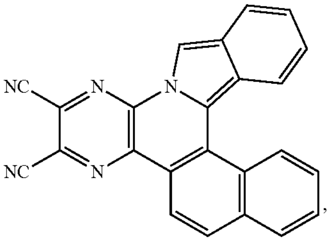,
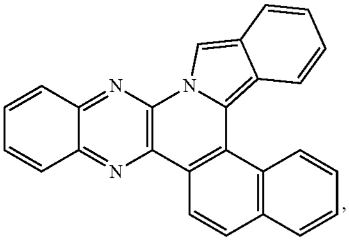,
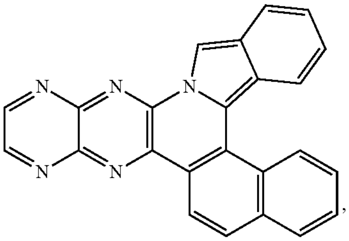,
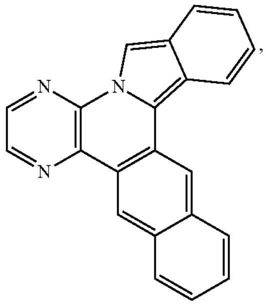,
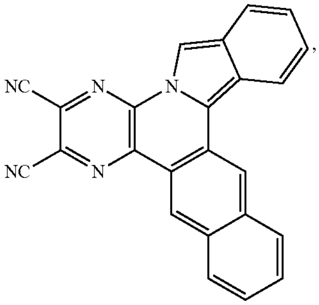, -continued
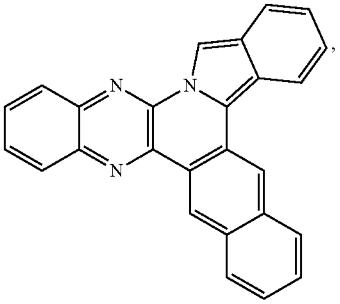
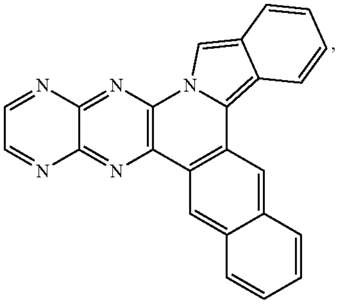
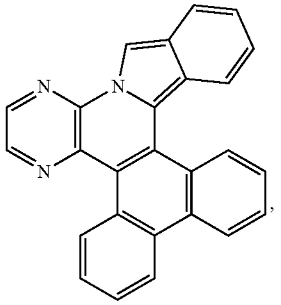
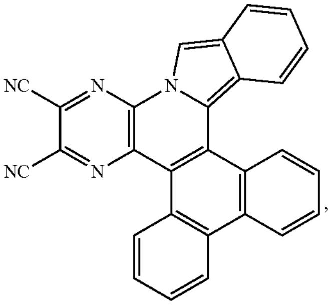
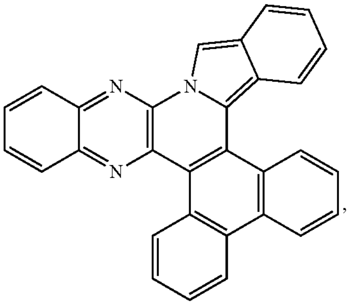
-continued
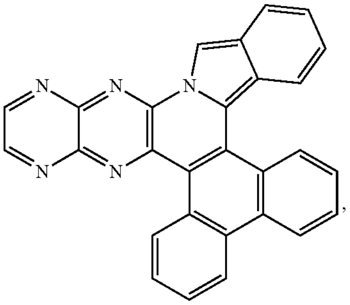
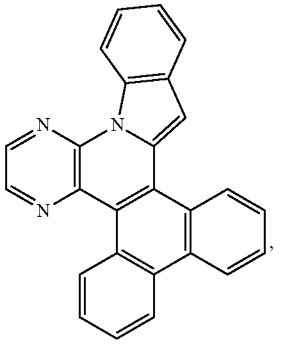
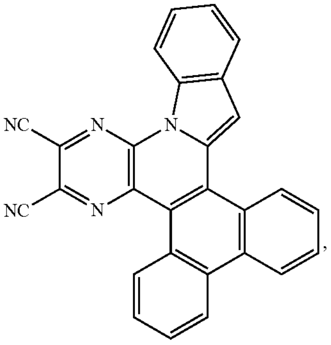
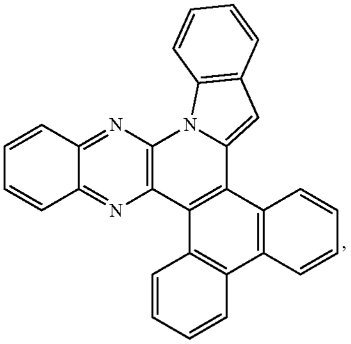
and
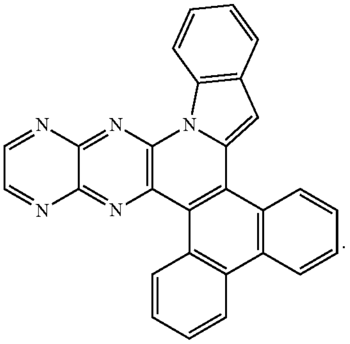

7. A light emitting diode comprising the compound of claim 1.

8. A light emitting diode comprising the compound of claim 6.

9. A light emitting device comprising the light emitting diode of claim 7.

10. A light emitting device comprising the light emitting diode of claim 8.

* * * * *